US011083776B2

(12) United States Patent
Flinspach et al.

(10) Patent No.: US 11,083,776 B2
(45) Date of Patent: *Aug. 10, 2021

(54) PROTOXIN-II VARIANTS AND METHODS OF USE

(71) Applicant: JANSSEN BIOTECH, INC., Horsham, PA (US)

(72) Inventors: Mack Flinspach, San Diego, CA (US); Alan Wickenden, San Diego, CA (US); Ross Fellows, San Diego, CA (US); Qinghao Xu, San Diego, CA (US); Andrew Piekarz, San Diego, CA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,750

(22) Filed: Nov. 4, 2019

(65) Prior Publication Data

US 2020/0054712 A1 Feb. 20, 2020

Related U.S. Application Data

(63) Continuation of application No. 15/090,328, filed on Apr. 4, 2016, now Pat. No. 10,463,714.

(60) Provisional application No. 62/142,069, filed on Apr. 2, 2015.

(51) Int. Cl.
| | |
|---|---|
| *A61K 38/17* | (2006.01) |
| *A61K 47/64* | (2017.01) |
| *A61K 47/60* | (2017.01) |
| *C07K 14/435* | (2006.01) |
| *A61K 38/00* | (2006.01) |

(52) U.S. Cl.
CPC .......... *A61K 38/1767* (2013.01); *A61K 47/60* (2017.08); *A61K 47/643* (2017.08); *C07K 14/43518* (2013.01); *A61K 38/00* (2013.01); *C07K 2319/21* (2013.01); *C07K 2319/30* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,309,989 A | 1/1982 | Fahim | |
| 4,767,402 A | 8/1988 | Kost et al. | |
| 6,103,495 A | 8/2000 | Mehta et al. | |
| 6,521,427 B1 | 2/2003 | Evans | |
| 6,670,127 B2 | 12/2003 | Evans | |
| 7,998,980 B2 | 8/2011 | Moran et al. | |
| 9,102,751 B2 | 8/2015 | Flinspach et al. | |
| 9,102,757 B2 | 8/2015 | Chen et al. | |
| 9,624,280 B2 | 4/2017 | Flinspach et al. | |
| 10,463,714 B2 | 11/2019 | Flinspach et al. | |
| 2003/0148273 A1 | 8/2003 | Dong et al. | |
| 2007/0212685 A1 | 9/2007 | MacDonald et al. | |
| 2011/0065647 A1 | 3/2011 | Meir et al. | |
| 2011/0124711 A1 | 5/2011 | Sah et al. | |
| 2011/0217714 A1 | 9/2011 | Makrigiorgos | |
| 2012/0185956 A1 | 7/2012 | Gingras | |
| 2013/0296247 A1 | 11/2013 | Park et al. | |
| 2014/0335514 A1 | 11/2014 | Arnold | |
| 2015/0087596 A1 | 3/2015 | Eckert et al. | |
| 2015/0099705 A1 | 4/2015 | Flinspach et al. | |
| 2016/0257726 A1 | 9/2016 | Flinspach et al. | |

FOREIGN PATENT DOCUMENTS

| | | |
|---|---|---|
| AU | 2013262630 A3 | 12/2014 |
| AU | 2014329454 B2 | 1/2019 |
| BR | 112016007062 A2 | 12/2017 |
| CA | 2873860 A1 | 11/2013 |
| CN | 101979411 A | 2/2011 |
| CN | 102859003 A | 1/2013 |
| CN | 103635593 A | 3/2014 |
| CN | 104768568 A | 7/2015 |
| CN | 2013825986 A | 7/2015 |
| CN | 105793277 A | 7/2016 |
| CN | 108220406 A | 6/2018 |
| EP | 2852397 A4 | 3/2016 |
| EP | 3052519 A1 | 8/2016 |
| JP | 2015518836 A | 7/2015 |
| JP | 2016519872 A | 7/2016 |
| JP | 2016-533710 A | 11/2016 |
| JP | 2016533710 A | 11/2016 |
| JP | 2018-512123 A | 5/2018 |
| JP | 2018512123 A | 5/2018 |
| WO | 9853847 A1 | 12/1998 |
| WO | 2006116156 A3 | 11/2006 |
| WO | 2007109324 A3 | 9/2007 |
| WO | 2008088422 A3 | 2/2009 |
| WO | 2010028089 A2 | 3/2010 |
| WO | 2010104115 A1 | 9/2010 |
| WO | 2012/004664 A2 | 1/2012 |
| WO | 2012004664 A2 | 1/2012 |

(Continued)

OTHER PUBLICATIONS

Australian Office Action issued in Application No. 2016226443 dated Oct. 25, 2019, 3 pages.

Frank Bosmans et al., "Four Novel Tarantula Toxins as Selective Modulators of Voltage-Gated Sodium Channel Subtypes", Molecular Pharmacology, vol. 62, No. 2, (2006), pp. 419-429.

Stephen C. Cannon et al., "Sodium channels gone wild: resurgent current from neuronal and muscle channelopathies", The Journal of Clinical Investigation, vol. 120, No. 1, (2010), pp. 80-84.

James J. Cox et al., "An SCN9A channelopathy causes congenital inability to experience pain", Nature PublishingGroup, vol. 444, (2006), pp. 894-898.

(Continued)

*Primary Examiner* — Adam Weidner
(74) *Attorney, Agent, or Firm* — Ditthavong, Steiner & Mlotkowski

(57) ABSTRACT

The present invention relates to Protoxin-II variants, polynucleotides encoding them, and methods of making and using the foregoing.

24 Claims, 35 Drawing Sheets

Specification includes a Sequence Listing.

(56) References Cited

FOREIGN PATENT DOCUMENTS

| WO | 2013173706 A2 | 11/2013 |
|---|---|---|
| WO | 2014/016673 A1 | 1/2014 |
| WO | 2014165277 A2 | 10/2014 |
| WO | 2015051216 A1 | 4/2015 |
| WO | 2016140859 A1 | 9/2016 |
| WO | 2016161100 A1 | 10/2016 |

OTHER PUBLICATIONS

Roman Cregg et al., "Pain channelopathies", The Journal of Physiology, vol. 588, No. 11, (2010), pp. 1897-1904.

David M. Dirig et al., "Characterization of variables defining hindpaw withdrawal latency evoked by radiant thermal stimuli", Journal of Neuroscience Methods, No. 76, (1997), pp. 183-191.

Mark Estacion et al., "A Sodium Channel Gene SCN9A Polymorphism That Increases Nociceptor Excitability", Annals of Neurology, vol. 66, No. 6, (2009), pp. 862-866.

Sultan Ahmad et al., "A stop codon mutation in SCN9A causes lack of pain sensation", Human Molecular Genetics, vol. 16, No. 17, (2007), pp. 2114-2121.

Caroline R. Fertleman et al., "SCN9A Mutations in Paroxysmal Clinical Study Extreme Pain Disorder: Allelic Variants Underlie Distinct Channel Defects and Phenotypes", Neuron 52, (2006), pp. 767-774.

Goldberg YP et al., "Loss-of-function mutations in the Nav1.7 gene underlie congenital indifference to pain in multiple human populations", Clinical Genetics, (2007), pp. 311-319.

Dagmar Hackel et al.,"Transient opening of the perineurial barrier for analgesic drug delivery", PNAS, (2012) pp. 2018-2027.

K. Hargreaves et al., "A new and sensitive method for measuring thermal nociception in cutaneous hyperalgesia", Elsevier, (1998), pp. 77-88.

Christian A. Hubner, "Ion channel diseases", Human Molecular Genetics, vol. 11, No. 2, (2002), pp. 2435-2445.

Julie K. Klint et al., "Spider-venom peptides that target voltage-gated sodium channels: Pharmacological tools and potential therapeutic leads", Toxicon, 60, (2012), pp. 478-491.

E. Legroux-Crespel et al., "Traitement de l'erythermalgie familiale par l;association lidocaine-mexiletine", Articles Scientifiques, (2003), vol. 130, pp. 429-433.

Richard E. Middleton et al., "Two Tarantula Peptides Inhibit Activation of Multiple Sodium Channels", Biochemistry, (2002), pp. 14734-14747.

Michael S. Minett et al., "Distinct Nav1.7-dependent pain sensations require different sets of sensory and sympathetic neurons", Nature communications, (2012), pp. 1-9.

Yukiko Muroi et al.,"Selective silencing of NaV1.7 decreases excitability and conduction in vagal sensory neurons", The Journal of Physiology, 589.23, (2011), pp. 5663-5676.

Nassar et al., "Nociceptor-specific gene deletion reveals a major role for Nav1.7 (PN1) in acute and inflammatory pain", PNAS, vol. 101, No. 34, (2004), pp. 12706-12711.

Oi et al., "Isolation of specific peptides that home to dorsal root ganglion neurons in mice", Neuroscience Letters, 434, (2008), pp. 266-272.

Peng et al., "Function and Solution Structure of Huwentoxin-IV, a Potent Neuronal Tetrodotoxin (TTX)-sensitive Sodium Channel Antagonist from Chinese Bird Spider Selenocosmia huwena", The Journal of Biological Chemistry, vol. 277, No. 49, Issue of Dec. 2002, pp. 47564-47671.

Reimann et al., "Pain perception is altered by a nucleotide polymorphism in SCN9A", PNAS, vol. 107, No. 11, (2010), pp. 5148-5153.

Schmalhofer et al., "ProTx-II, a Selective Inhibitor of NaV1.7 Sodium Channels, Blocks Action Potential Propagation in Nociceptors", Molecular Pharmacology, vol. 74, No. 6, (2008), pp. 1476-1484.

Sockolosky et al., "Engineering neonatal Fc receptor-mediated recycling and transcytosis in recombinant proteins by short terminal peptide extensions", PNAS, vol. 109, No. 40, (2012), pp. 16095-16100.

Tfelt-Hansen et al., "Inherited Cardiac Diseases Caused by Mutations in the Nav1.5 Sodium Channel", Journal of Cardiovascular Electrophysiology, vol. 21, No. 1, (2010), pp. 107-115.

Hagman, "Sterilization", Pharmaceutical Manufacturing, Lippincott Williams & Wilkins, Baltimore, MD (2005) Chapters 40, pp. 776-801.

Vargas-Alarcon et al., "A SCN9A gene-encoded dorsal root ganglia sodium channel polymorphism associated with severe fibromyalgia", BMC Musculoskeletal Disorders, (2012),13:23, pp. 5 pages.

Whitney et al., "Fluorescent peptides highlight peripheral nerves during surgery in mice", nature biotechnology, vol. 29, No. 4, (2011), pp. 352-358.

Yang et al., "Mutations in SCN9A, encoding a sodium channel alpha subunit, in patients with primary erythermalgia", J Med Genet, (2004), 41, pp. 171-174.

Yogeeswari et al., "Ion Channels as Important Targets for Antiepileptic Drug Desgin", Current Drug Targets, (2004), 5, pp. 589-602.

Dib-Hajj et al., "The NaV1.7 sodium channel: from molecule to man" Nature Reviews Neuroscience, vol. 14, (2013), pp. 49-62.

Park et al., "Studies Examining the Relationship between the Chemical Structure of Protoxin II and Its Activity on Voltage Gated Sodium Channels", Journal of Medicinal Chemistry, 57, (2014), pp. 6623-6631.

Berjanskii et al., "Predictor: A Web Server for Predicting Protein Torsion Angle Restraints", Nucleic Acids Research, vol. 34, pp. W63-W69 (2006).

Bodenhausen et al., "Natural Abundance Nitrogen-15 NMR by Enhanced Heteronuclear Spectroscopy", Chemical Physics Letters, (1980), vol. 69, pp. 185-189.

Chen et al., "Synthesis, Folding and Bioactivity Analysis of K27A-HWTX-IV: A mutant of the TTX-sensitive Sodium Channel Inhibitor, Huwentoxin-IV", Jour Nat Scie Hunan Naun Univ, 2003, vol. 26, pp. 2-7.

Clare et al., "Voltage-gated sodium channels as therapeutic targets", Therapeutic Focus, (2000), vol. 5, No. 11, pp. 506-520.

Delaglio et al., "NMRPipe: A multidimensional spectral processing system based on UNIX pipes", Journal of Biomolecular NMR, (1995), vol. 6, pp. 277-293.

Dib-Hajj et al., "Sodium Channels in Normal and Pathological Pain", Annual Review Neuroscience, (2010), vol. 33, pp. 325-347.

Guntert et al., "Torsion Angle Dynamics for NMR Structure Calculation with the New Program DYANA", JMB, (1997), vol. 273, 283-298.

Hubner et al., "Ion Channel Diseases", Human Molecular Genetics, (2002), vol. 11, No. 20, pp. 2435-2445.

Humphrey et al., "VMD: Visual Molecular Dynamics", Journal of Molecular Graphics, (1996), vol. 14, pp. 22-38.

Jeener et al., "Investiagtion of exchange processes by two-dimensional NMR spectroscopy", J. Chem. Phys., (1979), vol. 71, No. 11, pp. 4546-4553.

Jiang et al., "Molecular diversification based on analysis of expressed sequence tags from the venom glands of the Chinese bird spider Ornithoctonus huwena", Toxicon, (2008), vol. 51, pp. 1479-1489.

Liu et al., "Isolation and characterization of hainantoxin-IV, a novel antagonist of tetrodotoxin-sensitive sodium channels from the Chinese bird spider Selenocosmia hainana", Cellular and Molecular Life Sciences, (2003), vol. 60 (5), pp. 972-978.

Liu, "Screening of peptide-based modulators of voltage-gated sodium channels using QPatch", (2012).

Mackerell et al., "Extending the Treatment of Backbone Energetics in Protein Force Fields: Limitations of Gas-Phase Quantum Mechanics in Reproducing Protein Conformational Distributions in Molecular Dynamics Simulations", J Comput Chem, (2004), vol. 25, pp. 1400-1415.

Middleton et al., "Two Tarantula Peptides Inhibit Activation of Multiple Sodium Channels", Biochemistry, (2002), vol. 41, No. 50, pp. 14734-14747.

(56) References Cited

OTHER PUBLICATIONS

Minassian et al., "Analysis of the structural and molecular basis of voltage-sensitive sodium channel inhibition by the spider toxin, Huwentoxin-IV (u-TRTX-Hh2a)", JBC, (2013), pp. 1-28.
Minett et al., "Pain without Nociceptors? Nav1.7-Independent Pain Mechanisms", Cell Reports, (2014), vol. 6, 301-302.
Phillips et al., "Scable Molecular Dynamics with NAMD", J Comput Chem, (2005), vol. 26, pp. 1781-1802.
Revell et al., "Potency optimization of Huwentoxin-IV on hNav1.7: A neurotoxin TTX-S sodium-channel antagonist from the venom of the Chinese bird-eating spider *Selenocosmia huwena*", Peptides, Elsevier, Amsterdam, NL, (2013), vol. 44, pp. 40-46, XP028551011.
Shih et al., "Functional Studies of Interaction Between Huwentoxin-IV and Voltage-Gated Sodium Channel Nav1.7", Biophysical Journal, (2012) vol. 102, No. 3(S1), pp. 324a.
Smith et al., "Molecular Interactions of the Gating Modifier Toxin, ProTx-II, with Nav1.5: implied existence of a novel toxin binding site coupled to activation", The American Society for Biochemistry and Molecular Biology, (2007), vol. 282, No. 17, pp. 12687-12697.
Spassov et al., "Introducing an Implicit Membrane in Generalized Born/Solvent Accessibility Continuum Solvent Models", J. Phys, Chem. B, (2002), vol. 106, pp. 8726-8738.
Wang et al., "Expression and characterization of Huwentoxin-XI (HWTX-XI) and its mutants", Chinese Journal of Biotechnology, (2011), vol. 27, pp. 262-268.
Xiao et al., "Tarantula Huwentoxin-IV Inhibits Neuronal Sodium Channels by Binding to Receptor Site 4 and Trapping the domain II Voltage Sensor in the Closed Configuration", The Journal of Biological Chemistry, Oct. 3, 2008, vol. 283, No. 40, pp. 27300-27313.
Xiao et al., "The Tarantual Toxins ProTx-II and Huwentoxin-IV Differentially Interact with Human Nav1.7 Voltage Sensors to Inhibit Channel Activation and Inactivation", Molecular Pharmacology, (2010), vol. 28, pp. 1124-1134.
Xiao et al. "Common Molecular Determinants of Tarantula Huwentoxin-IV Inhibition of NA+ Channel Voltage Sensors in Domains II and IV", The Journal of Biological Chemistry, (2011) vol. 286, No. 31, pp. 27301-27310.
Yang et al., "Discovery of a selective Nav1.7 inhibitor from centipede venom with analgesic efficacy exceeding morphine in rodent pain models", Proceedings of the National Academy of Science, (2013), vol. 110, pp. 17534-17539.
Zhang et al., "Structure/Function Characterization of u-Conotoxin KIIIA, an Analgesic, Nearly Irreversible Blocker of Mammalian Neuronal Sodium Channels", The Journal of Biological Chemistry, 2007, vol. 282, pp. 30699-30706.
Cheung et al., "Dangle: A Bayesian inferential method for predicting protein backbone dihedral angles and secondary structure", Journal of Magnetic Resonance, (2010), vol. 202, pp. 223-233.
European Search Report of European Application No. 13791454.5, dated Jan. 27, 2016.
Chinese Search Report of Chinese Application No. 201380025986.1 dated, Jan. 19, 2016.
Luo Xuan "A Study of the Interactive Mechanism between Huwentoxin-IV and Sodium Channel", Chinese Master's Theses Full Test Database, Medicine and Health Sciences, No. S1, pp. E079-E241,(2011).
International Search Report of International Application No. PCT/2013/041572 dated Dec. 4, 2013.
International Search Report of International Application No. PCT/US2016/025247 dated Jul. 12, 2016.
International Search Report of International Application No. PCT/US2014/058972 dated Mar. 26, 2015.
International Search Report of International Application No. PCT/US2016/019549 dated Aug. 30, 2016.
Genbank:ABY77745.1, "HWTX-IVb precursor [Haplopelma schmidti]", Protein—NCBI (2007).
Minassian et al., "Functional Studies of the Interaction Between Huwentoxin-IV and the Voltage-Gated Sodium Chanel NAv 1.7", Johnson & Johnson Pharmaceutical Research & Development, San Diego, CA (2011).
Office Action in related U.S. Appl. No. 14/399,088 dated Oct. 7, 2016.
Office Action in related U.S. Appl. No. 14/505,592 dated Mar. 16, 2016.
Office Action in related U.S. Appl. No. 14/505,592 dated Nov. 3, 2015.
Office Action in related U.S. Appl. No. 14/399,088 dated Dec. 24, 2015.
Kumer et al., "A Two-Dimensional Nuclear Overhauser Enhancement (2D NOE) Experiment for the Elucidation of Complete Proton-Proton Cross-Relaxation Networks in Biological Macromolecules", Biochemical and Biophysical Research Communications, vol. 95, No. 1, Jul. 16, 1980, pp. 1-6.
Muroi et al., "Selective Inhibition of Vagal Afferent Nerve Pathways Regulating Cough using Na 1.7 shrnA Silencing in Guinea Pig Nodose Ganglia", Am. J. Physiol regul Integr Comp Physiol, vol. 304, pp. R1017-R1023 (2013).
Examination report No. 1 issued in Australian Patent Application No. 2014329454 dated Jan. 4, 2018.
Office Action issued in U.S. Appl. No. 14/399,088 dated Jun. 15, 2018.
Office Action issued in U.S. Appl. No. 15/583,793 dated May 18, 2018.
Examination Report issued by the Government of Pakistan Intellectual Property Organization the Patent Office in Patent Application No. 129/2016 dated Apr. 25, 2018.
Notice of Reexamination issued in Chinese Patent Application No. 201380025986.1 dated May 8, 2018.
Invitation pursuant to Rule 137(4) EPC and Article 94(3) EPC issued in European Application No. 14790422.1-1120 dated May 17, 2018.
Communication pursuant to Article 94(3) EPC issued in European Application No. 13791454.5-1120 dated May 17, 2018.
M. Flinspach et al., "Insensitivity to pain induced by a potent selective closed-state Nav1.7 inhibitor", Scientific Reports, Jan. 3, 2017, pp. 1-16, vol. 7.
Justin K. Murray et al., "Engineering Potent and Selective Analogues of GpTx-1, a Tarantula Venom Peptide Antagonist of the Nav1.7 Sodium Channel", Journal of Medicinal Chemistry, 2015, pp. 2299-2314, vol. 58, American Chemical Society, ACS Publications.
Extended European Search Report issued in European Patent Application No. 16759288.0 dated Jul. 20, 2018.
Communication pursuant to Rules 70(2) and 70a(2) EPC issued in European Patent Application No. 16759288.0 dated Aug. 7, 2018.
English Translation of Notice of Reasons for Rejection issued in Japanese Patent Application No. 2016-519872, dated Aug. 28, 2018.
Communication pursuant to Article 94(3) EPC issued in European Application No. 14 790 422.1-1120 dated Sep. 10, 2018; 6 pages.
Examination report No. 2 issued in Australian Application No. 2014329454 dated Sep. 17, 2018; 2 pages.
English translation of Reexamination Decision No. 162864 issued by the Patent Reexamination Board of National Intellectual Property Administration, P.R. China in Chinese Application No. 201380025986.1 dated Oct. 23, 2018; 25 pages.
English translation of Decision of Rejection issued in Japanese Application No. 2015-512885 dated Oct. 30, 2018; 16 pages.
Examination Report issued by the Government of Pakistan Intellectual Property Organization the Patent Office in Patent Application No. 189/2016 dated Nov. 9, 2018; 2 pages.
Extended European Search Report issued in European Application No. 16774187.5 dated Nov. 15, 2018.
Communication pursuant to Rules 70(2) and 70a(2) EPC issued in European Application No. 16774187.5 dated Dec. 4, 2018.
Notice of Allowance issued in U.S. Appl. No. 14/399,088 dated Nov. 21, 2018.
Office Action issued in U.S. Appl. No. 15/583,793 dated Jan. 4, 2019.
English translation of Examination Report issued by the Patent Office of the Cooperation Council for the Arab States of the Gulf in Application No. GC 2016-30933 dated Jan. 10, 2019.
Examiner's Requisition issued in Canadian Patent Application No. 2,873,860 dated Feb. 8, 2019.

(56) References Cited

OTHER PUBLICATIONS

Communication pursuant to Article 94(3) EPC issued in European Patent Application No. 14 790 422.1-1120 dated Feb. 21, 2019.
Advisory Action issued in U.S. Appl. No. 15/583,793 dated Mar. 18, 2019.
English Translation of Notice of Reasons for Rejection issued in Japanese Patent Application No. 2016-519872 dated Apr. 2, 2019.
Advisory Action issued in U.S. Appl. No. 15/583,793 dated Apr. 12, 2019.
International Preliminary Report on Patentability; PCT/US2016/025247; dated Apr. 14, 2017.
International Preliminary Report on Patentability; PCT/US2016/019549; dated Sep. 5, 2017.
Notice of Allowance issued in U.S. Appl. No. 14/505,592, dated Aug. 9, 2016.
Notice of Allowance issued in U.S. Appl. No. 13/833,555, dated Feb. 27, 2015.
Gingras et al., Global Nav1.7 KO mice recapitulate phenotype of congenital indifference to pain reported in humans; American Pain Society Meeting Abstract 2013.
Remington's Pharmaceutical Sciences, 15th Edition. Edited under the direction of Arthur Osol and John E. Hoover. Mack Publishing Co., Easton, PA 18042, 1975.
Minassian et al., "Functional Studies of the Interaction Between Huwentoxin-IV and the Voltage-Gated Sodium Channel Nav1.7", Janssen—Pharmaceutical Companies of Johnson and Johnson, Janssen Research and Development, San Diego, CA, Poster.
Office Action issued in U.S. Appl. No. 15/583,793 dated Dec. 14, 2017.
Office Action issued in U.S. Appl. No. 13/833,555 dated Sep. 23, 2013.
Office Action issued in U.S. Appl. No. 13/833,555 dated Jan. 8, 2014.
Office Action issued in U.S. Appl. No. 13/833,555 dated Jul. 17, 2014.
Office Action issued in U.S. Appl. No. 13/833,555 dated Nov. 3, 2014.
International Patent Application No. PCT/US2016/019549 filed Feb. 25, 2016.
International Patent Application No. PCT/US2016/025247 filed Mar. 31, 2016.
U.S. Appl. No. 15/060,158, filed Mar. 3, 2016.
U.S. Appl. No. 13/833,555, filed Mar. 15, 2013.
European Communication pursuant to Article 94(3) EPC issued in corresponding EP Application No. 14 790 422.4-1410 dated May 4, 2017.
European Communication pursuant to Article 94(3) EPC, issued in European Patent Application No. 14 790 422.1-1410 dated Nov. 16, 2017.
Patent Examination Report No. 1 issued in corresponding Australian Patent Application No. 2013262630 dated Nov. 2, 2016.
English translation of First Office Action issued in corresponding Chinese Patent Application No. 201380025986.1 dated Jan. 27, 2016.
English translation of Second Office Action issued in corresponding Chinese Patent Application No. 201380025986.1 dated Sep. 26, 2016.
European Communication pursuant to Article 94(3) EPC; EP Application No. 13 791 454.5-1402; dated Jul. 11, 2017.
English translation of Notice of Reasons for Rejection issued in corresponding Japanese Patent Application No. 2015-512885 dated Mar. 14, 2017.
English translation of Notice of Reasons for Rejection issued in corresponding Japanese Patent Application No. 2015-512885 dated Dec. 12, 2017.
Deng Mei-chun, Life Science Research, vol. 17, No. 2 (Apr. 2013) pp. 111-115. (Abstract Only).
Cavanagh et al., Protein NMR Spectroscopy: Principles and Practice, 2nd Edition, 1995 Academic Press. (Description Only).
Bax et al., MLEV-17 based two-dimensional homonuclear magnetization transfer spectroscopy. Journal of Magnetic Resonance, vol. 65, (1985) pp. 355-360.
Chinese Office Action issued in Application No. 201480066344.0 dated Mar. 29, 2019, with English Translation, 19 pages.
Japanese Office Action issued in Application No. 2016-519872 dated Apr. 2, 2019, 6 pages.
International Search Report and Written Opinion of related International Application No. PCT/US2013/041572 dated Dec. 13, 2013.
International Preliminary Report on Patentability of related International Application No. PCT/US2013/041572 dated Nov. 1, 2014.
International Search Report and Written Opinion of International Application No. PCT/US2016/025247 dated Jul. 12, 2016.
International Search Report and Written Opinion of related International Application No. PCT/US2014/058972 dated Mar. 26, 2015.
International Preliminary Report on Patentability of related International Application No. PCT/US2014/058972 dated Apr. 5, 2016.
International Search Report and Written Opinion of related International Application No. PCT/US2016/019549 dated Aug. 30, 2016.
Notice of Allowance dated Dec. 23, 2016 from U.S. Appl. No. 14/505,592.
Office Action dated Mar. 13, 2017 from U.S. Appl. No. 14/399,088.
Schmalhofer, et al., "ProTx-II, a Selective Inhibitor of NaV1.7 Sodium Channels, Blocks Action Potential Propagation in Nociceptors" Molecular Pharmacology, 74:1476-1484, 2008.
Murray et al., "Engineering Potent and Selective Analogues of GpTx-1, a Tarantula Venom Peptide Antagonist of the NaV1.7 Sodium Channel" J. Med. Chem. 2015, 58, pp. 2299-2314.
Minassian et al., "Analysis of the Structural and Molecular Basis of Voltage-sensitive Sodium Channel Inhibition by the Spider Toxin Huwentoxin-IV (_-TRTXHh2a)" The Journal of Biological Chemistry vol. 288, No. 31, dated Aug. 2, 2013, pp. 22707-22720.
Office Action for the Taiwanese Patent Application No. 105110361, dated May 14, 2020, 16 pages.
Office Action for the Taiwanese Patent Application No. 105106183, dated May 14, 2020, 16 pages.
Translation of Notification of Defects for related Israeli Patent Application No. 254599, dated Dec. 17, 2019, 3 pages.
Translation of Notification of Defects for related Israeli Patent Application No. 254273, dated Dec. 18, 2019, 3 pages.
Office Action for related U.S. Appl. No. 16/673,750, dated Mar. 19, 2020, 36 pages.
Office Action for related Chinese Patent Application No. 201480066344.0, dated Jan. 22, 2020, 11 pages.
Office Action for related European Patent Application No. 16744187.5-1111, dated Mar. 2, 2020, 4 pages.
Notice of Reasons for Rejection for related Japanese Patent Application No. 2017-551164, dated Feb. 19, 2020, 14 pages.
Office Action for related U.S. Appl. No. 15/489,714, dated May 22, 2020.
Annex to EPO Form 2004, Communication pursuant to Rule 71(3) EPC; Communication under Rule 71(3) EPC for related European Patent Application No. 14 790 422.1-1118, dated Apr. 24, 2020, 906 pages.
Office Action for related Canadian Patent Application No. 2,882,123, dated Mar. 13, 2020, 3 pages.
Japanese Office Action for related Japanese Patent Application No. 2015-512885 dated Apr. 7, 2020, 6 Pages.
Canadian Office Action for related Canadian Patent Application No. 2873860 dated Apr. 27, 2020, 3 Pages.
European Office Action for related European Patent Application No. 16759288.0-1118 dated May 12, 2020, 6 Pages.
Notice of Reasons for Rejection for related Japanese Patent Application No. 2019-036383, dated Dec. 24, 2019, 4 pages.
Office Action for the related European Patent Application No. 13791454.5-1118, dated Jul. 28, 2020, 3 pages.
Office Action for the related Argentina Patent Application No. 20160100558 dated Jul. 7, 2020, 15 pages.
Flinspach et al., "Insensitivity to pain induced by a potent selective closed-state Nav1. 7 inhibitor. Scientific reports, 2017, vol. 7, No. 1, pp. 1-16."
Flinspach et al., U.S. Appl. No. 61/648,871, filed May 18, 2012.
Flinspach et al., U.S. Appl. No. 61/702,538, filed Sep. 18, 2012.

(56) References Cited

OTHER PUBLICATIONS

Flinspach et al., U.S. Appl. No. 61/886,100, filed Oct. 3, 2013.
Flinspach et al., U.S. Appl. No. 62/127,339, filed Mar. 3, 2015.
Xin et al., U.S. Appl. No. 62/142,669, filed Apr. 3, 2015.
Flinspach et al., U.S. Appl. No. 15/489,714, filed Apr. 17, 2017.
Flinspach et al., U.S. Appl. No. 15/090,328, filed Apr. 4, 2016.
Translation of Notification of Defects for related Israeli Patent Application No. 254599, dated Dec. 17, 2019, 3 page.
Office Action for related Chinese Patent Application No. 201680020883.X, dated Nov. 12, 2020, 12 pages.
Office Action for the related Japanese Patent Application No. 2017-551164, dated Sep. 29, 2020, 7 pages.
Preliminary Office Action for the related Brazilian Patent Application No. BR112017018834-1, dated Oct. 8, 2020, 5 pages.
Office Action for the related Canadian Patent Application No. 2926052, dated Oct. 6, 2020, 5 pages.
Preliminary Office Action for the related Brazilian Patent Application No. BR112017020896-2, dated Sep. 14, 2020, 5 pages.
Office Action for the related European Patent Application No. 16774187.5-1111, dated Sep. 14, 2020, 4 pages.
Office Action for the related Japanese Patent Application No. 2019-036383, dated Nov. 10, 2020, 16 pages.
Office Action for the related Pakistan Patent Application No. 189/2016, dated Nov. 5, 2020, 2 pages.
Chen et al., Synthesis, folding and bioactivity analysis of K27A-HWTX-IV: a mutant of the TTX-sensitive sodium channel inhibitor, Hu wentoxin-IV., Hunan Shifan Daxue Ziran Kexue Xuebao, 26(3) (2003), pp. 67-72, 6 pages.
Office Action for the related Argentina Patent Application No. 20160100893, dated Jul. 23, 2020, 6 pages.
Office Action for the related Chinese Patent Application No. 201680026028.X, dated Jul. 17, 2020, 27 pages.
Office Action for the related Japanese Patent Application No. 2017-546100, dated Jan. 12, 2021, 14 pages.
Office Action for the related Japanese Patent Application No. 2020-013560, dated Jan. 26, 2021, 7 pages.
Office Action for the related Taiwanese Patent Application No. 105106183, dated Jan. 12, 2021, 14 pages.
Office Action for the related Taiwanese Patent Application No. 105110361, dated Jan. 12, 2021, 15 pages.
Office Action for related Argentinian Patent Application No. 20160100893, dated Jan. 27, 2021, with online machine generated English Translation, 10 pages.
Office Action for related Australian Patent Application No. 2016242905, dated Mar. 18, 2021, 4 pages.

Figure 1.

| Residue numbering | -2 | -1 | 1 | 2 | 3 | 4 | 5 | 6 | 7 | 8 | 9 | 10 |
|---|---|---|---|---|---|---|---|---|---|---|---|---|
| Genus | X1 | X2 | X3 | C | X4 | X5 | W | X6 | Q | X7 | C | X8 |
| Diversity | (GAP-) | (PA-) | (SQARY) | C | (QRKAS) | (KSQR) | W | (MF) | Q | (TSRKQ) | C | (DT) |

| Residue numbering | 11 | 12 | 13 | 14 | 15 | 16 | 17 | 18 | 19 | 20 |
|---|---|---|---|---|---|---|---|---|---|---|
| Genus | X9 | X10 | X11 | X12 | C | C | X13 | X14 | F | X15 |
| Diversity | (SAR) | (ERNKTQ) | (RK) | (KQSA) | C | C | (EQD) | (GQ) | F | (VS) |

| Residue numbering | 21 | 22 | 23 | 24 | 25 | 26 | 27 | 28 | 29 | 30 |
|---|---|---|---|---|---|---|---|---|---|---|
| Genus | C | X16 | L | W | C | X17 | K | K | L | W |
| Diversity | C | (RT) | L | W | C | (KR) | K | K | L | W |

FIG. 2A

| Protein name | Protoxin-II variant name | Protein SEQ ID NO: | Selectivity * | Nav1.6 | | Nav1.7 | |
|---|---|---|---|---|---|---|---|
| | | | | $IC_{50}$ (nM) | SE** | $IC_{50}$ (nM) | SE** |
| NV1D12_5 | wild type | 2 | 28 | 62 | 3.8 | 2.2 | 1.3 |
| NV1G1153-NH-butyl | NV1D3034-NH-butyl | 118 | 509.6 | 501.9 | 826.2 | 1.0 | 0.8 |
| NV1G1153-NH-methyl | NV1D3034-NH-methyl | 119 | 467.1 | 563.3 | 408.9 | 1.2 | 1.3 |
| NV1G1818 | NV1D3368 | 122 | 257.4 | 1466.7 | 789.0 | 5.7 | 2.9 |
| NV1G1818-NH2 | NV1D3368-NH2 | 123 | 201.6 | 862.0 | 330.9 | 4.3 | 1.9 |
| NV1G1153 | NV1D3034 | 78 | 128.7 | 568.6 | 352.6 | 4.4 | 4.3 |
| NV1G1781 | NV1D3388 | 217 | 105.9 | 1196.2 | 977.0 | 11.3 | 11.2 |
| NV1G1137 | NV1D2974 | 129 | 87.9 | 617.9 | 528.1 | 7.0 | 6.1 |
| NV1G1750 | NV1D3586 | 324 | 73.3 | 894.606 | 429.0 | 12.2 | 9.4 |
| (-GP) N-Ac-NV1G1153-NH2 | (-GP) N-Ac-NV1D3034-NH2 | 121 | 67.1 | 164.6 | 130.5 | 2.5 | 1.3 |
| NV1G1267 | NV1D3044 | 150 | 66.7 | 308.4 | 264.7 | 4.6 | 2.8 |
| NV1G1750-NH2 | NV1D3586-NH2 | 325 | 66.4 | 98.5 | 107.4 | 1.5 | 0.2 |
| NV1G1728 | NV1D3541 | 281 | 65.0 | 1746.5 | 372.0 | 26.9 | 105.6 |
| NV1G1007 | NV1D2775 | 56 | 59.0 | 236.4 | 108.1 | 4.0 | 8.9 |
| NV1G1007-NH2 | NV1D2775-NH2 | 111 | 52.0 | 61.4 | 38.5 | 1.2 | 0.8 |
| NV1G1137-NH2 | NV1D2974-NH2 | 130 | 50.8 | 218.9 | 185.2 | 4.3 | 2.5 |

FIG. 2B

| Protein name | Protoxin-II variant name | Protein SEQ ID NO: | Selectivity * | Nav1.6 | | Nav1.7 | |
|---|---|---|---|---|---|---|---|
| | | | | $IC_{50}$ (nM) | se** | $IC_{50}$ (nM) | se** |
| (-GP) N-Ac-NV1G1137-NH2 | (-GP) N-Ac-NV1D2974-NH2 | 114 | 45.4 | 476.1 | 139.2 | 10.3 | 5.9 |
| NV1G1001 | NV1D2773 | 65 | 45.9 | 197.3 | 44.4 | 4.3 | 3.3 |
| NV1G1153-NH2 | NV1D3034-NH2 | 117 | 43.5 | 160.3 | 107.3 | 3.7 | 2.7 |
| NV1G1005 | NV1D2772 | 59 | 39.2 | 241.8 | 82.6 | 6.2 | 3.2 |
| NV1G1519 | NV1D3006 | 133 | 37.9 | 123.6 | 34.3 | 3.3 | 3.1 |
| NV1G1749 | NV1D3587 | 326 | 34.1 | 433.9 | 483.8 | 12.7 | 8.2 |
| NV1G1836 | NV1D3359 | 190 | 31.5 | 485.9 | 277.4 | 15.4 | 10.6 |

*IC50(Nav1.6)/IC50(Nav1.7)

**standard error

FIG. 3A

| Protein name | Protoxin-II variant name | SEQ ID NO: | Residue numbering (according to SEQ ID NO: 1) | | | | | | | | | | | |
|---|---|---|---|---|---|---|---|---|---|---|---|---|---|---|
| | | | -2 | -1 | 1 | 2 | 3 | 4 | 5 | 6 | 7 | 8 | 9 | 10 |
| | wild type | 2 | G | P | Y | C | Q | K | W | M | W | T | C | D |
| NV1G1153-NH-butyl | NV1D3034-NH-butyl | 118 | G | P | Q | C | Q | K | W | M | Q | T | C | D |
| NV1G1153-NH-methyl | NV1D3034-NH-methyl | 119 | G | P | Q | C | Q | K | W | M | Q | T | C | D |
| NV1G1818 | NV1D3368 | 122 | G | P | Q | C | Q | K | W | M | Q | T | C | D |
| NV1G1818-NH2 | NV1D3368-NH2 | 123 | G | P | Q | C | Q | K | W | M | Q | T | C | D |
| NV1G1153 | NV1D3034 | 78 | G | P | Q | C | Q | K | W | M | Q | T | C | D |
| NV1G1781 | NV1D3388 | 217 | G | P | Q | C | Q | K | W | M | Q | T | C | D |
| NV1G1137 | NV1D2974 | 129 | G | P | Q | C | Q | K | W | M | Q | T | C | D |
| NV1G1750 | NV1D3586 | 324 | G | P | Y | C | Q | K | W | M | Q | T | C | D |
| (-GP) N-Ac-NV1G1153-NH2 | (-GP) N-Ac-NV1D3034-NH2 | 121 | | | Q | C | Q | K | W | M | Q | T | C | D |
| NV1G1267 | NV1D3044 | 150 | G | P | Q | C | Q | K | W | M | Q | T | C | D |
| NV1G1750-NH2 | NV1D3586-NH2 | 325 | G | P | Y | C | Q | K | W | M | Q | T | C | D |
| NV1G1728 | NV1D3541 | 281 | G | P | A | C | Q | K | W | M | Q | T | C | D |
| NV1G1007 | NV1D2775 | 56 | G | P | Q | C | Q | K | W | M | Q | T | C | D |
| NV1G1007-NH2 | NV1D2775-NH2 | 111 | G | P | Q | C | Q | K | W | M | Q | T | C | D |
| NV1G1137-NH2 | NV1D2974 | 130 | G | P | Q | C | Q | K | W | M | Q | T | C | D |
| (-GP) N-Ac-NV1G1137-NH2 | (-GP) N-Ac-NV1D2974-NH2 | 114 | | | Q | C | Q | K | W | M | Q | T | C | D |
| NV1G1001 | NV1D2773 | 53 | G | P | S | C | Q | K | W | M | Q | T | C | D |
| NV1G1153-NH2 | NV1D3034-NH2 | 117 | G | P | Q | C | Q | K | W | M | Q | T | C | D |
| NV1G1005 | NV1D2772 | 59 | G | P | R | C | Q | K | W | M | Q | T | C | D |
| NV1G1519 | NV1D3006 | 133 | G | P | Q | C | Q | K | W | M | Q | T | C | D |
| NV1G1749 | NV1D3587 | 326 | G | P | A | C | Q | K | W | M | Q | T | C | D |
| NV1G1836 | NV1D3359 | 190 | G | P | Q | C | Q | K | W | M | Q | S | C | D |
| Diversity | | | G | P | (YQASR) | C | Q | K | W | M | Q | (TS) | C | D |
| Genus sequence | | 405 | G | P | X1 | C | Q | K | W | M | Q | X2 | C | D |

FIG. 3B

| Protein name | Protoxin-II variant name | SEQ ID NO: | Residue numbering (according to SEQ ID NO: 1) | | | | | | | | | |
|---|---|---|---|---|---|---|---|---|---|---|---|---|
| | | | 11 | 12 | 13 | 14 | 15 | 16 | 17 | 18 | 19 | 20 |
| | wild type | 2 | S | E | R | K | C | C | E | G | M | V |
| NV1G1153-NH-butyl | NV1D3034-NH-butyl | 118 | R | E | R | K | C | C | E | G | F | V |
| NV1G1153-NH-methyl | NV1D3034-NH-methyl | 119 | R | E | R | K | C | C | E | G | F | V |
| NV1G1818 | NV1D3368 | 122 | R | T | R | K | C | C | E | G | F | V |
| NV1G1818-NH2 | NV1D3368-NH2 | 123 | R | T | R | K | C | C | E | G | F | V |
| NV1G1153 | NV1D3034 | 78 | R | E | R | K | C | C | E | G | F | V |
| NV1G1781 | NV1D3308 | 217 | R | E | R | K | C | C | Q | G | F | V |
| NV1G1137 | NV1D2974 | 129 | A | E | R | K | C | C | E | G | F | S |
| NV1G1750 | NV1D3586 | 324 | A | N | R | K | C | C | E | G | F | S |
| (-GP) N-Ac-NV1G1153-NH2 | (-GP) N-Ac-NV1D3034-NH2 | 121 | R | E | R | K | C | C | E | G | F | V |
| NV1G1267 | NV1D3044 | 150 | R | N | R | K | C | C | E | G | F | V |
| NV1G1750-NH2 | NV1D3586-NH2 | 325 | A | N | R | K | C | C | E | G | F | S |
| NV1G1728 | NV1D3541 | 281 | R | N | R | K | C | C | E | G | F | V |
| NV1G1097 | NV1D2775 | 56 | A | E | R | K | C | C | E | G | F | V |
| NV1G1097-NH2 | NV1D2775-NH2 | 111 | A | E | R | K | C | C | E | G | F | V |
| NV1G1137-NH2 | NV1D2974-NH2 | 130 | A | E | R | K | C | C | E | G | F | S |
| (-GP) N-Ac-NV1G1137-NH2 | (-GP) N-Ac-NV1D2974-NH2 | 114 | A | E | R | K | C | C | E | G | F | S |
| NV1G1001 | NV1D2773 | 65 | A | E | R | K | C | C | E | G | F | V |
| NV1G1153-NH2 | NV1D3034-NH2 | 117 | R | E | R | K | C | C | E | G | F | V |
| NV1G1095 | NV1D2772 | 59 | A | E | R | K | C | C | E | G | F | V |
| NV1G1519 | NV1D3306 | 133 | A | R | R | K | C | C | E | G | F | V |
| NV1G1749 | NV1D3587 | 326 | A | N | R | K | C | C | E | G | F | S |
| NV1G1836 | NV1D3259 | 190 | R | E | R | K | C | C | E | G | F | V |
| Diversity | | | (SRA) | (ETN) | R | K | C | C | (EQ) | G | F | (VS) |
| Genus sequence | | 405 | X3 | X4 | R | K | C | C | X5 | G | F | X6 |

FIG. 3C

| Protein name | Protoxin-II variant name | SEQ ID NO: | Residue numbering (according to SEQ ID NO: 1) | | | | | | | | | |
|---|---|---|---|---|---|---|---|---|---|---|---|---|
| | | | 21 | 22 | 23 | 24 | 25 | 26 | 27 | 28 | 29 | 30 |
| | wild type | 2 | C | R | L | W | C | K | K | K | L | W |
| NV1G1153-NH-butyl | NV1D3034-NH-butyl | 118 | C | T | L | W | C | R | K | K | L | W |
| NV1G1153-NH-methyl | NV1D3034-NH-methyl | 119 | C | T | L | W | C | R | K | K | L | W |
| NV1G1818 | NV1D3368 | 122 | C | T | L | W | C | R | K | K | L | W |
| NV1G1818-NH2 | NV1D3368-NH2 | 123 | C | T | L | W | C | R | K | K | L | W |
| NV1G1153 | NV1D3034 | 78 | C | T | L | W | C | R | K | K | L | W |
| NV1G1781 | NV1D3388 | 217 | C | T | L | W | C | R | K | K | L | W |
| NV1G1137 | NV1D2974 | 129 | C | T | L | W | C | K | K | K | L | W |
| NV1G1750 | NV1D3586 | 324 | C | R | L | W | C | K | K | K | L | W |
| (-GP) N-Ac-NV1G1153-NH2 | (-GP) N-Ac-NV1D3034-NH2 | 121 | C | T | L | W | C | R | K | K | L | W |
| NV1G1267 | NV1D3044 | 150 | C | T | L | W | C | R | K | K | L | W |
| NV1G1750-NH2 | NV1D3586-NH2 | 325 | C | R | L | W | C | K | K | K | L | W |
| NV1G1728 | NV1D3541 | 281 | C | T | L | W | C | R | K | K | L | W |
| NV1G1087 | NV1D2775 | 56 | C | R | L | W | C | K | K | K | L | W |
| NV1G1087-NH2 | NV1D2775-NH2 | 131 | C | R | L | W | C | K | K | K | L | W |
| NV1G1137-NH2 | NV1D2974-NH2 | 130 | C | T | L | W | C | K | K | K | L | W |
| (-GP) N-Ac-NV1G1137-NH2 | (-GP) N-Ac-NV1D2974-NH2 | 114 | C | T | L | W | C | K | K | K | L | W |
| NV1G1051 | NV1D2773 | 65 | C | R | L | W | C | K | K | K | L | W |
| NV1G1153-NH2 | NV1D3034-NH2 | 117 | C | T | L | W | C | R | K | K | L | W |
| NV1G1005 | NV1D2732 | 59 | C | R | L | W | C | K | K | K | L | W |
| NV1G1519 | NV1D3006 | 133 | C | R | L | W | C | R | K | K | L | W |
| NV1G1749 | NV1D3587 | 326 | C | R | L | W | C | K | K | K | L | W |
| NV1G1836 | NV1D3369 | 190 | C | T | L | W | C | R | K | K | L | W |
| Diversity | | | C | (RT) | L | W | C | (KR) | K | K | L | W |
| Genus sequence | | 435 | C | X7 | L | W | C | X8 | K | K | L | W |

PROTOXIN-II VARIANTS AND METHODS OF USE

CROSS REFERENCE TO RELATED APPLICATIONS

This application is a continuation of U.S. application Ser. No. 15/090,328, filed on Apr. 4, 2016, and claims the benefit of priority under 35 U.S.C. § 119(e) to U.S. Provisional Application 62/142,069, filed Apr. 2, 2015, the contents of each are herein incorporated by reference in entirety.

FIELD OF THE INVENTION

The present invention relates to Protoxin-II variants, synthetic polynucleotides encoding them, and methods of making and using the foregoing.

BACKGROUND OF THE INVENTION

Voltage-gated sodium channels (VGSC) are present in all excitable cells including cardiac and skeletal muscle cells and central and peripheral neurons. In neuronal cells, sodium channels are responsible for amplifying sub-threshold depolarizations and generating the rapid upstroke of the action potential. As such, sodium channels are essential to the initiation and propagation of electrical signals in the nervous system. Aberrant sodium channel function is thought to underlie a variety of medical disorders (Hübner and Jentsch, Hum Mol Genet 11:2435-45, 2002), including epilepsy (Yogeeswari et al., Curr Drug Targets 5:589-602, 2004), arrhythmia (Tfelt-Hansen et al., J Cardiovasc Electrophysiol 21:107-15, 2010), myotonia (Cannon and Bean, J Clin Invest 120:80-3, 2010), and pain (Cregg et al., J Physiol 588:1897-904, 2010). Sodium channels are typically a complex of various subunits, the principle one being the pore-forming alpha-subunit, which is alone sufficient for function.

Nine known members of the family of voltage-gated sodium channel alpha subunits exist in humans, Nav1.1-Nav1.9. The Nav1.x subfamily can be pharmacologically subdivided into two groups, the tetrodotoxin (TTX)-sensitive and TTX-resistant. Nav1.7, (a.k.a. PN1 or hNE) is encoded by the SCN9A gene, is TTX-sensitive and is primarily expressed in peripheral sympathetic and sensory neurons. Nav1.7 accumulates at nerve fiber endings and amplifies small sub-threshold depolarizations and acts as a threshold channel that regulates excitability.

Nav1.7 function is implicated in various pain states, including acute, inflammatory and/or neuropathic pain. In man, gain of function mutations of Nav1.7 have been linked to primary erythermalgia (PE), a disease characterized by burning pain and inflammation of the extremities (Yang et al., J Med Genet 41:171-4, 2004), and paroxysmal extreme pain disorder (PEPD)(Fertleman et al., Neuron 52:767-74, 2006). Consistent with this observation, non-selective sodium channel blockers lidocaine, mexiletine and carbamazepine can provide symptomatic relief in these painful disorders (Legroux-Crespel et al., Ann Dermatol Venereol 130:429-33, 2003; Fertleman et al., Neuron 52:767-74, 2006).

Loss-of-function mutations of Nav1.7 in humans cause congenital indifference to pain (CIP), a rare autosomal recessive disorder characterized by a complete indifference or insensitivity to painful stimuli (Cox et al., Nature 444: 894-8, 2006; Goldberg et al, Clin Genet 71:311-9, 2007; Ahmad et al., Hum Mol Genet 16:2114-21, 2007).

Single nucleotide polymorphisms in the coding region of SCN9A have been associated with increased nociceptor excitability and pain sensitivity. For example, a polymorphism rs6746030 resulting in R1150W substitution in human Nav1.7 has been associated with osteoarthritis pain, lumbar discectomy pain, phantom pain, and pancreatitis pain (Reimann et al., Proc Natl Acad Sci USA 107:5148-53, 2010). DRG neurons expressing the R1150W mutant Nav1.7 display increased firing frequency in response to depolarization (Estacion et al., Ann Neurol 66:862-6, 2009). A disabling form of fibromyalgia has been associated with SCN9A sodium channel polymorphism rs6754031, indicating that some patients with severe fibromyalgia may have a dorsal root ganglia sodium channelopathy (Vargas-Alarcon et al., BMC Musculoskelet Disord 13:23, 2012).

In mice, deletion of the SCN9A gene in nociceptive neurons leads to reduction in mechanical and thermal pain thresholds and reduction or abolition of inflammatory pain responses (Nassar et al., Proc Natl Acad Sci USA 101: 12706-11, 2004). Ablating SCN9A in all sensory neurons abolished mechanical pain, inflammatory pain and reflex withdrawal responses to heat. Deleting SCN9A in both sensory and sympathetic neurons abolished mechanical, thermal and neuropathic pain, and recapitulated the pain-free phenotype seen in humans with Nav1.7 loss-of-function mutations (Minett et al., Nat Commun 3:791, 2012). Nav1.7 inhibitors or blockers may therefore be useful in the treatment of a wide range of pain associated with various disorders.

Spider venoms are known to contain a large number of sodium channel blocking peptides, including Huwentoxin-IV (HwTx-IV) (Peng et al., J Biol Chem 277:47564-71, 2002), Protoxin-I, Protoxin-II (Middleton et al., Biochemistry 41:14734-47, 2002) and Phrixotoxin-III (Bosmans et al., Mol Pharmacol 69:419-29, 2006). There is a need for identification of additional Nav1.7 blockers for treatment of a wide range of pain indications. In particular, there is a need for new Nav1.7 blockers with selectivity for Nav1.7 over other voltage gated sodium channel isoforms.

SUMMARY OF THE INVENTION

One embodiment of the invention is an isolated Protoxin-II variant that inhibits human Nav1.7 activity, wherein the Protoxin-II variant has at least one amino acid substitution selected from the group consisting of W7Q and W30L; wherein residue numbering is according to SEQ ID NO: 1.

Another embodiment of the invention is an isolated Protoxin-II variant, wherein the Protoxin-II variant inhibits human Nav1.7 activity with an $IC_{50}$ value of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, wherein the $IC_{50}$ value is measured using a veratridine-induced depolarization inhibition assay using fluorescence resonance energy transfer (FRET) in the presence of $25\times10^{-6}$ M 3-veratroylveracevine in HEK293 cells stably expressing human Nav1.7, wherein the Protoxin-II variant has a W7Q and/or a W30L substitution, wherein residue numbering is according to SEQ ID NO: 1.

Another embodiment of the invention is an isolated Protoxin-II variant comprising the amino acid sequence of SEQ ID NOs: 30, 40, 44, 52, 56, 56, 59, 65, 78, 109, 110, 111, 114, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 162, 165, 166, 167, 168, 169, 170, 171, 172, 173, 174, 175, 177, 178, 179, 180, 182, 183, 184, 185, 186, 189, 190, 193, 195, 197, 199, 206, 207, 208, 209, 210, 211, 212, 213, 214, 215, 216, 217, 218, 224, 226, 227, 231, 232, 243, 244, 245, 247, 249, 252, 255, 258, 261, 263, 264, 265, 266, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 332, 334, 335, 336, 337, 339, 340, 341, 342, 346, 351, 358, 359, 364, 366, 367, 368, 369, 370, 371, 408, 409, 410, 411, 412, 413, 414, 415, 416, 417, 418, 419, 420, 421, 422, 423, 424, 425, 426, 427, 428, 429, 430, 431, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735 or 736.

Another embodiment of the invention is an isolated Protoxin-II variant comprising the amino acid sequence that is 90%, 91%, 92%, 93%, 94%, 95%, 96%, 97%, 98% or 99% identical to the amino acid sequence of SEQ ID NO: 422 (GPYCQKWMQTCDSERKC-CEGMVCRLWCKKKLL-COOH); wherein the amino acid sequence has Q at position 7 and L at position 30, when residue numbering is according to SEQ ID NO: 1.

Another embodiment of the invention is an isolated fusion protein comprising the Protoxin-II variant of the invention conjugated to a half-life extending moiety.

Another embodiment of the invention is an isolated polynucleotide encoding the Protoxin-II variant of the invention.

Another embodiment of the invention is a vector comprising the isolated polynucleotide of the invention. Another embodiment of the invention is a host cell comprising the vector of the invention.

Another embodiment of the invention is a method of producing the isolated Protoxin-II variant of the invention, comprising culturing the host cell of the invention and recovering the Protoxin-II variant produced by the host cell.

Another embodiment of the invention is a pharmaceutical composition comprising the isolated Protoxin-II variant or fusion protein of the invention and a pharmaceutically acceptable excipient.

Another embodiment of the invention is a method of treating Nav1.7-mediated pain in a subject, comprising administering to a subject in need thereof an effective amount of the Protoxin-II variant or the fusion protein of the invention to treat the pain.

BRIEF DESCRIPTION OF THE DRAWINGS

FIG. 1 shows the genus amino acid sequence of Protoxin-II variants that inhibit Nav1.7 with an $IC_{50}$ value of 30 nM or less in a veratridine-induced depolarization inhibition assay. Residue numbering is according to wild-type Protoxin-II of SEQ ID NO: 1. Genus SEQ ID NO: 403.

FIG. 2A shows the IC50 values for Nav1.7 and Nav1.6 in a QPatch assay, and selectivity of each variant calculated by ratio of $IC_{50}$ (Nav1.6/$IC_{50}$ (Nav1.7) obtained in QPatch assay. SE: standard error. FIG. 2B is a continuation of FIG. 2A showing the $IC_{50}$ values for Nav1.7 and Nav1.6 in a QPatch assay, and selectivity of each variant calculated by ratio of $IC_{50}$ (Nav1.6/$IC_{50}$ (Nav1.7) obtained in QPatch assay for additional Protoxin-II variants.

FIG. 3A shows the sequences and the genus sequence of Protoxin-II variants that inhibit Nav1.7 with an $IC_{50}$ value of 30 nM or less in a veratridine-induced depolarization inhibition assay, and are over 30-fold selective over Nav1.6. Selectivity of each variant was calculated by ratio of $IC_{50}$ (Nav1.6)/$IC_{50}$ (Nav1.7) obtained in QPatch assay. Residue numbering is according to wild-type Protoxin-II of SEQ ID NO: 1. FIG. 3B is a continuation of FIG. 3A showing the sequences and the genus sequence of additional Protoxin-II variants that inhibit Nav1.7 with an $IC_{50}$ value of 30 nM or less in a veratridine-induced depolarization inhibition assay, and are over 30-fold selective over Nav1.6. Selectivity of each variant was calculated by ratio of $IC_{50}$ (Nav1.6)/$IC_{50}$ (Nav1.7) obtained in QPatch assay. Residue numbering is according to wild-type Protoxin-II of SEQ ID NO: 1. FIG. 3C is a continuation of FIG. 3B showing the sequences and the genus sequence of additional Protoxin-II variants that inhibit Nav1.7 with an $IC_{50}$ value of 30 nM or less in a veratridine-induced depolarization inhibition assay, and are over 30-fold selective over Nav1.6. Selectivity of each variant was calculated by ratio of $IC_{50}$ (Nav1.6)/$IC_{50}$ (Nav1.7) obtained in QPatch assay. Residue numbering is according to wild-type Protoxin-II of SEQ ID NO: 1.

DETAILED DESCRIPTION OF THE INVENTION

Figure 4A:
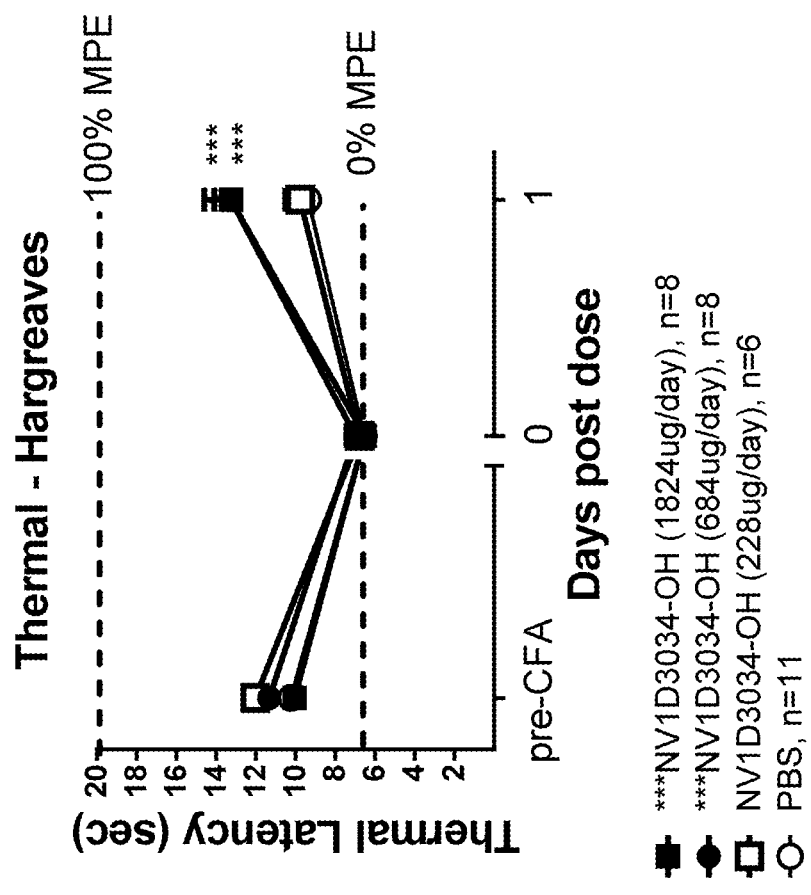
FIG. 4A shows efficacy of NV1D3034 (NV1D3034-OH) (SEQ ID NO: 78) against CFA-induced thermal hyperalgesia in mice, assessed by measurement of paw withdrawal latency in the Hargreaves test before (pre-CFA) and after CFA injection (0) and 1-day after peptide administration (1). ***$P<0.001$ vs. PBS, two-way ANOVA followed by Bonferroni's multiple comparison.

All publications, including but not limited to patents and patent applications, cited in this specification are herein incorporated by reference as though fully set forth.

As used herein and in the claims, the singular forms "a," "and," and "the" include plural reference unless the context clearly dictates otherwise.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins".

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence.

The term "vector" means a non-natural polynucleotide capable of being duplicated within a biological system or that can be moved between such systems. Vector polynucleotides typically contain a cDNA encoding a protein of interest and additional elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or a reconstituted biological system to direct the translation of a polypeptide encoded by a polynucleotide sequence present in the expression vector.

The term "variant" as used herein refers to a polypeptide or a polynucleotide that differs from wild type Protoxin-II polypeptide of SEQ ID NO: 1 or the polynucleotide encoding the wild type Protoxin-II having the sequence of SEQ ID NO: 107 by one or more modifications for example, substitutions, insertions or deletions of nucleotides or amino acids.

Throughout the specification, residues that are substituted in the Protoxin-II variants are numbered corresponding to their position in the wild-type Protoxin-II of SEQ ID NO: 1. For example, "Y1A" in the specification refers to the substitution of tyrosine at residue position that corresponds to the position 1 in the wild type Protoxin-II of SEQ ID NO:1 with alanine.

"Complementary DNA" or "cDNA" refers to a well-known synthetic polynucleotide that shares the arrangement of sequence elements found in native mature mRNA species with contiguous exons, with the intervening introns present in genomic DNA are removed. The codons encoding the initiator methionine may or may not be present in cDNA. cDNA may be synthesized for example by reverse transcription or synthetic gene assembly.

"Synthetic" or "non-natural" as used herein refers to a polynucleotide or a polypeptide molecule not present in nature.

"Nav1.7" (also referred to as hNE or PN1) or "hNav1.7" as used herein refers to the well-known human sodium channel protein type 9 subunit alpha having a sequence shown in GenBank accession number NP_002968.1 and in SEQ ID NO: 79.

The term "wild type Protoxin-II" or "wild type ProTx-II" as used herein refers to the tarantula *Thrixopelma pruriens* (Peruvian green velvet tarantula) toxin peptide having the amino acid sequence YCQKWMWTCDSERKC-CEGMVCRLWCKKKLW-COOH (SEQ ID NO: 1) as described in Middleton et al., Biochemistry 41(50):14734-47, 2002.

The term "recombinant Protoxin-II" or recombinant ProTx-II" as used herein refers to the recombinant Protoxin-II obtained from expression and subsequent cleavage of a Protoxin-II fusion protein having the sequence of GPYCQKWMWTCDSERKCCEGMVCRLWCKKKLW-OH as shown in SEQ ID NO: 2. Recombinant Protoxin-II incorporates a two amino acid N-terminal extension (residues G and P) when compared to the wild type Protoxin-II.

"Blocks human Nav1.7 activity" or "inhibits human Nav1.7 activity" as used herein refers to the ability of the Protoxin-II variant of the invention to reduce membrane depolarization induced by veratridine (3-veratroylveracevine) with an $IC_{50}$ value of about $1 \times 10^{-7}$ M or less in a veratridine-induced depolarization inhibition assay using fluorescence resonance energy transfer (FRET), where veratridine-induced depolarization is measured as a reduction in FRET signal using DISBAC2(3) ([bis-(1,3-diethylthiobarbituric acid) trimethine oxonol]) as an acceptor and PTS18 (trisodium 8-octadecyloxypyrene-1,3,6-trisulfonate) as a donor by exciting the donor at 390-420 nm and measuring FRET at 515-575 nm in a cell line stably expressing human Nav1.7. Ability of the Protoxin-II variants of the invention to block human Nav1.7 activity may also be measured using QPatch electrophysiology at single or several Protoxin-II variant concentrations according to protocol described in Example 3. The Protoxin-II variant of the invention blocks human Nav1.7 activity when it inhibits Nav1.7 currents measured using QPatch by at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when using the assay protocol described in Example 3.

"Veratridine-induced depolarization inhibition assay" as used herein refers to the assay described in Example 3.

"QPatch assay" or "QPatch electrophysiology assay" as used herein refers to the assay described in Example 3.

The term "substantially identical" as used herein means that the two Protoxin-II variant amino acid sequences being compared are identical or have "insubstantial differences". Insubstantial differences are substitutions of 1, 2, 3, 4, 5, 6, or 7 amino acids in the Protoxin-II variant amino acid sequence that do not adversely affect peptide properties. Amino acid sequences substantially identical to the Protoxin-II variants disclosed herein are within the scope of the application. In some embodiments, the sequence identity can be about 80%, 81%, 82%, 83%, 84%, 85%, 86%, 87%, 88%, 89%, 90%, 91%, 92%, 93%, 94%, 95%, 96%, 97%, 98%, 99% or higher. Percent identity can be determined for example by pairwise alignment using the default settings of the AlignX module of Vector NTI v. 9.0.0 (Invitrogen, Carslbad, Calif.). The protein sequences of the present invention may be used as a query sequence to perform a search against public or patent databases, for example, to identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings.

Abbreviations of natural amino acids are as used herein are shown in Table 1a.

TABLE 1

| Amino acid | Three letter code | One letter code |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides isolated Protoxin-II (ProTx-II) variant polypeptides that inhibit human Nav1.7 activity, polynucleotides encoding them, vectors, host cells, and methods of using the polynucleotides and polypeptides of the invention. The polypeptides of the invention inhibit depolarization/currents resulting from Nav1.7 activation, and therefore may be useful in the treatment of various conditions associated with pain and conditions associated with sensory or sympathetic neuron dysfunction.

The variants of the invention are potent inhibitors of Nav1.7. The current invention is based, at least in part, on the finding that certain residue substitutions in Protoxin-II enhance selectivity, synthetic yield and/or homogeneity without adversely affecting the potency of the generated Protoxin-II variants, specifically W7 and M19, and additionally residues Y1 and S11, and further additionally residues E12, R22 and (residue numbering according to SEQ ID NO: 1). For example, substitutions at positions W7 and W30 enhance the Protoxin-II variant folding and improve yield. Substitutions at positions S11, E12, K14, E17, G18, L29 and W30 improve selectivity of the resulting Protoxin-II variants to Nav1.7.

One embodiment of the invention disclosed herein, including in the numbered embodiments listed below is an isolated Protoxin-II variant, wherein the Protoxin-II variant inhibits human Nav1.7 activity with an $IC_{50}$ value of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, wherein the $IC_{50}$ value is measured using a veratridine-induced depolarization inhibition assay using fluorescence resonance energy transfer (FRET) in the presence of $25\times10^{-6}$ M 3-veratroylveracevine in HEK293 cells stably expressing human Nav1.7.

Another embodiment of the invention disclosed herein, including in the numbered embodiments listed below is an isolated Protoxin-II variant, wherein the Protoxin-II variant inhibits human Nav1.7 activity with an $IC_{50}$ value of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, wherein the $IC_{50}$ value is measured using a veratridine-induced depolarization inhibition assay using fluorescence resonance energy transfer (FRET) in the presence of $25\times10^{-6}$ M 3-veratroylveracevine in HEK293 cells stably expressing human Nav1.7, wherein the Protoxin-II variant has at least one amino acid substitution selected from the group consisting of W7Q and W30L; wherein residue numbering is according to SEQ ID NO: 1.

Another embodiment of the invention of the invention disclosed herein, including in the numbered embodiments listed below is an isolated Protoxin-II variant that inhibits human Nav1.7 activity, wherein the Protoxin-II variant has at least one amino acid substitution selected from the group consisting of W7Q and W30L; wherein residue numbering is according to SEQ ID NO: 1.

In some embodiments disclosed herein, including in the numbered embodiments listed below, the Protoxin-II variant has a W7Q substitution.

In some embodiments disclosed herein, including in the numbered embodiments listed below, the Protoxin-II variant has a W30L substitution.

In some embodiments disclosed herein, including in the numbered embodiments listed below, the Protoxin-II variant has a W7Q and a W30L substitution.

In some embodiments disclosed herein, including in the numbered embodiments listed below, the Protoxin-II variant inhibits Nav1.7 activity by at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when the Nav1.7 activity is measured using QPatch assay according to protocol described in Example 3.

In some embodiments disclosed herein, including in the numbered embodiments listed below, the Protoxin-II variant has a substitution at one or more residue positions Y1, W7, S11, E12, K14, E17, G18, R22, L29 and W30, when residue numbering is according to SEQ ID NO: 1.

Substitutions at position Y1 improve potency to human Nav1.7

Substitutions at position W7 improve Protoxin-II variant folding and protein yield.

Substitutions at position S11 improve selectivity to human Nav1.7.

Substitutions at position E12 improve selectivity to human Nav1.7.

Substitutions at position K14 improve selectivity to human Nav1.7.

Substitutions at position E17 improve selectivity to human Nav1.7.

Substitutions at position G18 improve selectivity to human Nav1.7.

Substitutions at position L29 improve selectivity to human Nav1.7.

Substitutions at position W30 improve Protoxin-II variant folding and protein yield and selectivity to Nav1.7.

Another embodiment of the invention disclosed herein, including in the numbered embodiments listed below is an isolated Protoxin-II variant comprising the sequence YCQKWMQTCDSERKCCEGMVCRLWCKKKLW-COOH (SEQ ID NO: 424); wherein residue Y1, S11, E12, K14, E17, G18, L29 and/or W30 is substituted with any other amino acid shown in Table 1 or a non-natural amino acid, optionally having an N-terminal extension or a C-terminal extension.

Another embodiment of the invention disclosed herein, including in the numbered embodiments listed below is an isolated Protoxin-II variant comprising the sequence YCQKWMQTCDSERKCCEGMVCRLWCKKKLL-COOH (SEQ ID NO: 425); wherein residue Y1, S11, E12, K14, E17, G18, M19, L29 and/or W30 is substituted with any other amino acid shown in Table 1 or a non-natural amino acid, optionally having an N-terminal extension or a C-terminal extension.

In some embodiments, the Protoxin-II variant of the invention described herein, including in the numbered embodiments listed below, contains at least one a non-natural amino acid.

Non-natural amino acids include amino β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-NaI); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); α-2-thienylalanine (Thi); methionine sulfoxide (MSO); N(omega)-methyl-L-arginine; N(omega), N(omega)-dimethyl-L-arginine (asymmetrical); 4-guanidino-L-phenylalanine; L-Lys(N-epsilon-(N-alpha-Palmitoyl-L-gamma-glutamyl); L-asparagyl-4-aminobutane; L-glutamyl-4-aminobutane; homoarginine (hArg); N-acetyl lysine (AcLys); 2,3-diaminobutyric acid (Dab); 2,4-diaminobutyric acid (Dbu); p-aminophenylalanine (Phe(pNH$_2$)); N-methyl valine (MeVal); homocysteine (hCys) and homoserine (hSer); 4-bromophenylalanine (Phe(4-Br)); 5-bromotryphophan (Trp(5-Br)); 3-chlorotyrosine (Tyr(3-Cl)) or beta-chloroalanine.

Another embodiment of the invention disclosed herein, including in the numbered embodiments listed below is an isolated Protoxin-II variant comprising the sequence $X_1X_2X_3CX_4X_5WX_6QX_7CX_8X_9X_{10}X_{11}X_{12}$
$CCX_{13}X_{14}X_{15}X_{16}CX_{17}LWCX_{18}KKLX_{19}$ (SEQ ID NO: 432), $X_1$ is G, P, A or deleted;
$X_2$ is P, A or deleted;
$X_3$ is S, Q, A, R or Y;
$X_4$ is Q, R, K, A, S or Y;
$X_5$ is K, S, Q or R;
$X_6$ is M or F;
$X_7$ is T, S, R, K or Q;
$X_8$ is D, T, or asparagyl-4-aminobutane;
$X_9$ is S, A, R, I or V;
$X_{10}$ is E, R, N, K, T, Q, Y or glutamyl-4-aminobutane;
$X_{11}$ is R or K;
$X_{12}$ is K, Q, S, A or F;
$X_{13}$ is E, Q, D, L, N, or glutamyl-4-aminobutane;
$X_{14}$ is G, Q or P;
$X_{15}$ is M or F;
$X_{16}$ is V or S;
$X_{17}$ is R, T or N-omega methyl-L-arginine; and
$X_{18}$ is K or R; and
$X_{19}$ is W or L,
optionally having an N-terminal extension or a C-terminal extension.

Another embodiment of the invention disclosed herein, including in the numbered embodiments listed below is an isolated Protoxin-II variant comprising the sequence $X_1X_2X_3CQKWMQTCDX_4X_5RX_6CCX_7X_8$
$X_9VCRLWCKKKX_{10}X_{11}$ (SEQ ID NO: 737);

wherein
$X_1$ is G, P, A or deleted;
$X_2$ is P, A or deleted;
$X_3$ is S, Q, A, R or Y;
$X_4$ is S, A, R, I or V;
$X_5$ is E, R, N, K, T, Q, Y or glutamyl-4-aminobutane;
$X_6$ is K, Q, S, A or F;
$X_7$ is E, Q, D, L, N or glutamyl-4-aminobutane;
$X_8$ is G, Q or P;
$X_9$ is M or F;
$X_{10}$ is L, V; and
$X_{11}$ is W or L.

In some embodiments disclosed herein, including in the numbered embodiments listed below, the Protoxin-II variant inhibits human Nav1.7 activity with an IC$_{50}$ value of about $1 \times 10^{-7}$ M or less, wherein the IC$_{50}$ value is measured using a veratridine-induced depolarization inhibition assay using fluorescence resonance energy transfer (FRET) in the presence of $25 \times 10^{-6}$ M 3-veratroylveracevine in HEK293 cells stably expressing human Nav1.7.

In some embodiments disclosed herein, including in the numbered embodiments listed below, the Protoxin-II variant inhibits Nav1.7 activity by at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when the Nav1.7 activity is measured using QPatch assay according to protocol described in Example 3.

In some embodiments disclosed herein, including in the numbered embodiments listed below, the N-terminal extension comprises the amino acid sequences of SEQ ID NOs: 372, 373, 374, 375, 376, 377, 378, 379, 380, 381, 382, 383, 384 or 385.

In some embodiments disclosed herein, including in the numbered embodiments listed below, the C-terminal extension comprises the amino acid sequence of SEQ ID NOs: 374, 386, 387, 388, 389, 390, 391, 392, 393, 394, 395, 396 or 397.

In some embodiments disclosed herein, including in the numbered embodiments listed below, the N-terminal and/or the C-terminal extension is conjugated to the Protoxin-II variant via a linker.

In some embodiments disclosed herein, including in the numbered embodiments listed below, the linker comprises the amino acid sequence of SEQ ID NOs: 383, 392, 398, 399, 400, 401 or 402.

In some embodiments disclosed herein, including in the numbered embodiments listed below, the N-terminal extension consists of the amino acid sequences of SEQ ID NOs: 372, 373, 374, 375, 376, 377, 378, 379, 380, 381, 382, 383, 384 or 385.

In some embodiments disclosed herein, including in the numbered embodiments listed below, the C-terminal extension consists of the amino acid sequence of SEQ ID NOs: 374, 386, 387, 388, 389, 390, 391, 392, 393, 394, 395, 396 or 397.

In some embodiments disclosed herein, including in the numbered embodiments listed below, the linker consists of the amino acid sequence of SEQ ID NOs: 383, 392, 398, 399, 400, 401 or 402.

Another embodiment of the invention disclosed herein, including in the numbered embodiments listed below is an isolated Protoxin-II variant comprising the sequence $$X_1X_2X_3CX_4X_5WX_6QX_7CX_8X_9X_{10}X_{11}X_{12}CCX_{13}X_{14}FX_{15}CX_{16}LWCX_{17}KKLW$$ (SEQ ID NO: 403), wherein $X_1$ is G, P, A or deleted;
$X_2$ is P, A or deleted;
$X_3$ is S, Q, A, R or Y;
$X_4$ is Q, R, K, A or S;
$X_5$ is K, S, Q or R;
$X_6$ is M or F;
$X_7$ is T, S, R, K or Q;
$X_8$ is D or T;
$X_9$ is S, A or R;
$X_{10}$ is E, R, N, K, T or Q;
$X_{11}$ is R or K;
$X_{12}$ is K, Q, S or A;
$X_{13}$ is E, Q or D;
$X_{14}$ is G or Q;
$X_{15}$ is V or S;
$X_{16}$ is R or T; and
$X_{17}$ is K or R;
optionally having an N-terminal extension or a C-terminal extension,
wherein the polypeptide inhibits human Nav1.7 activity with an $IC_{50}$ value of about $1 \times 10^{-7}$ M or less,
wherein the $IC_{50}$ value is measured using a veratridine-induced depolarization inhibition assay using fluorescence resonance energy transfer (FRET) in the presence of $25 \times 10^{-6}$ M 3-veratroylveracevine in HEK293 cells stably expressing human Nav1.7.

The Protoxin-II variants of the invention disclosed herein, including in the numbered embodiments listed below are potent Nav1.7 inhibitors. Recombinant Protoxin-II (SEQ ID NO: 2) has an $IC_{50}$ value of about $4 \times 10^{-9}$ M for human Nav1.7 in a veratridine-induced depolarization inhibition assay measuring decline in FRET (fluorescence resonance energy transfer) in cells stably expressing Nav1.7 using FLIPR® Tetra instrument (Molecular Devices) using experimental details described in Example 3. A Protoxin-II variant is "a potent" Nav1.7 inhibitor when the $IC_{50}$ value in the assay described above and in Experiment 3 is about $30 \times 10^{-9}$ M or less i.e. within 10 fold of recombinant Protoxin-II. For clarity, an $IC_{50}$ of $30 \times 10^{-9}$ M is identical to $IC_{50}$ of $3.0 \times 10^{-8}$ M.

The Protoxin-II variant polypeptides of the invention disclosed herein, including in the numbered embodiments listed below may be produced by chemical synthesis, such as solid phase peptide synthesis, on an automated peptide synthesizer. Alternatively, the polypeptides of the invention may be obtained from polynucleotides encoding the polypeptides by the use of cell-free expression systems such as reticulocyte lysate based expression systems, or by recombinant expression systems. Those skilled in the art will recognize other techniques for obtaining the polypeptides of the invention. In an exemplary method, the Protoxin-II variants of the invention are generated by expressing them as human serum albumin (HSA) fusion proteins utilizing a glycine-rich linker such as $(GGGGS)_4$ (SEQ ID NO:80) or $(GGGGS)_6$ (SEQ ID NO: 81) coupled to a protease cleavable linker such as a recognition sequence for HRV3C protease (Recombinant type 14 3C protease from human rhinovirus) LEVLFQGP (HRV3C linker) (SEQ ID NO: 82), and cleaving the expressed fusion proteins with the HRV3C protease to release the recombinant Protoxin-II variant peptides. Hexahistidine (SEQ ID NO: 108) or other tags may be used to facilitate purification using well known methods.

Protoxin-II variants of the invention disclosed herein, including in the numbered embodiments listed below may be purified using methods described herein. In an exemplary method, Protoxin-II variants of the invention expressed as HSA fusion proteins and cleaved with HRV3C protease may be purified using sold phase extraction (SPE) as described herein.

Generation of the Protoxin-II variants disclosed herein, including in the numbered embodiments listed below optionally having N-terminal and/or C-terminal extensions, and Protoxin-II variant fusion proteins is typically achieved at the nucleic acid level. The polynucleotides may be synthesized using chemical gene synthesis according to methods described in U.S. Pat. Nos. 6,521,427 and 6,670,127, utilizing degenerate oligonucleotides to generate the desired variants, or by standard PCR cloning and mutagenesis. Libraries of variants may be generated by standard cloning techniques to clone the polynucleotides encoding the Protoxin-II variants into the vector for expression.

The Protoxin-II variants of the invention disclosed herein, including in the numbered embodiments listed below may incorporate additional N- and/or C-terminal amino acids when compared to the wild type Protoxin-II of SEQ ID NO: 1, for example resulting from cloning and/or expression schemes. For example, cleavage from HSA after expression of the variant as HSA-linker-HRV3C cleavable peptide-Protoxin-II variant fusion protein may result in the incorporation of additional two residues to the N-terminus of each Protoxin-II variant, such as G and P.

The Protoxin-II variants of the invention disclosed herein, including in the numbered embodiments listed below are tested for their ability to inhibit human Nav1.7 using methods described herein. An exemplary assay is a veratridine-induced depolarization inhibition assay measuring decline in FRET (fluorescence resonance energy transfer) in cells stably expressing Nav1.7. Another exemplary assay employs electrophysiological recordings to measure changes in Nav1.7-mediated currents using well known patch clamp techniques and as described herein.

Another embodiment of the invention is an isolated Protoxin-II variant disclosed herein, including in the numbered embodiments listed below comprising the amino acid sequence of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 109, 110, 111, 112, 113, 114, 115, 116, 117, 118, 119, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 35, 357, 358, 359, 360, 361, 362, 363, 364, 365, 366, 367, 368 369, 370, 371, 408, 409, 410, 411, 412, 413, 414, 415, 416, 417, 418, 419, 420, 421, 422, 423, 424, 425, 426, 427, 428, 429, 430, 431, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735 or 736.

The Protoxin-II variants of the invention disclosed herein, including in the numbered embodiments listed below may inhibit human Nav1.7 with an $IC_{50}$ value of about $1\times10^{-7}$ M or less, about $1\times10^{-8}$ M about $1\times10^{-9}$ or less, about $1\times10^{-10}$ M or less, about $1\times10^{-11}$ M or less, or about $1\times10^{-12}$ M or less. Exemplary variants demonstrating the range of $IC_{50}$ values are variants having amino acid sequences shown in SEQ ID NOs: 30, 40, 44, 52, 56, 59, 65, 78, 109, 110, 111, 117, 118, 119, 120, 121, 122, 123, 124, 125, 126, 127, 128, 129, 131, 132, 133, 134, 135, 136, 137, 138, 139, 140, 141, 142, 143, 144, 145, 146, 147, 148, 149, 150, 151, 152, 153, 154, 155, 156, 157, 158, 159, 162, 165, 166, 167, 168, 169, 170, 171, 172, 173, 174, 175, 177, 178, 179, 180, 182, 183, 184, 185, 186, 189, 190, 193, 195, 197, 199, 206, 207, 208, 209, 210, 211, 212, 213, 214, 215, 216, 217, 218, 224, 226, 227, 231, 232, 243, 244, 245, 247, 249, 252, 255, 258, 261, 263, 264, 265, 266, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 332, 334, 335, 336, 337, 339, 340, 341, 342, 346, 351, 358, 359, 364, 366, 367, 368, 408, 409, 410, 411, 412, 413, 414, 415, 416, 417, 418, 419, 420, 421, 422, 423, 424, 425, 426, 427, 428, 429, 430 or 431.

In some embodiments disclosed herein, including in the numbered embodiments listed below, the Protoxin-II variant inhibits Nav1.7 activity by at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when the Nav1.7 activity is measured using QPatch assay according to protocol described in Example 3. Exemplary variants inhibiting Nav1.7 activity by at least 25% in a QPatch assay are variants having amino acid sequences shown in SEQ ID NOs: 109, 133, 408, 409, 410, 412, 419, 420, 421, 422, 423, 423, 424, 425, 426, 427, 427, 428, 429, 430, 431, 431, 434, 436, 437, 438, 439, 440, 441, 442, 444, 446, 447, 448, 450, 452, 453, 455, 456, 459, 460, 461, 462, 463, 464, 465, 466, 468, 469, 470, 471, 473, 474, 476, 477, 478, 479, 480, 482, 483, 485, 486, 487, 490, 491, 492, 494, 495, 496, 497, 498, 499, 500, 502, 504, 505, 507, 508, 510, 511, 512, 514, 516, 517, 518, 519, 521, 522, 523, 524, 526, 529, 531, 532, 533, 537, 546, 554, 557, 559, 560, 561, 562, 563, 566, 571, 579, 588, 589, 590, 591, 592, 593, 594, 595, 596, 597, 598, 599, 600, 601, 602, 603, 604, 605, 606, 607, 608, 609, 610, 611, 621, 622, 632, 633, 634, 635, 636, 637, 638, 639, 670, 671, 672, 673, 674, 675, 676, 677, 678, 679, 680, 681, 682, 683, 684 and 685.

Table 2, Table 3, Table 14, Table 18 and Table 2 show the sequences of select Protoxin-II variants.

TABLE 2

| Protein name | Protoxin-II variant peptide name | SEQ ID NO: | Protein amino acid sequence |
|---|---|---|---|
| | wild type | 1 | YCQKWMWTCDSERKCCEGMVCRLWCKKKLW-COOH |
| | NV1D12 | 2 | GPYCQKWMWTCDSERKCCEGMVCRLWCKKKLW-COOH |
| | NV1D748 | 3 | GPACQKWMWTCDSERKCCEGMVCRLWCKKKLW-COOH |
| | NV1D751 | 4 | GPQCQKWMWTCDSERKCCEGMVCRLWCKKKLW-COOH |
| | NV1D2292 | 5 | GPRCQKWMWTCDSERKCCEGMVCRLWCKKKLW-COOH |
| | NV1D750 | 6 | GPSCQKWMWTCDSERKCCEGMVCRLWCKKKLW-COOH |
| | NV1D1328 | 7 | GPYCQKWFWTCDSERKCCEGMVCRLWCKKKLW-COOH |
| | NV1D774 | 8 | GPYCQKWMQTCDSERKCCEGMVCRLWCKKKLW-COOH |
| | NV1D786 | 9 | GPYCQKWMWTCDAERKCCEGMVCRLWCKKKLW-COOH |
| | NV1D2300 | 10 | GPYCQKWMWTCDRERKCCEGMVCRLWCKKKLW-COOH |

TABLE 2-continued

| Protein name | Protoxin-II variant peptide name | SEQ ID NO: | Protein amino acid sequence |
|---|---|---|---|
| | NV1D791 | 11 | GPYCQKWMWTCDSKRKCCEGMVCRLWCKKKLW-COOH |
| | NV1D1332 | 12 | GPYCQKWMWTCDSNRKCCEGMVCRLWCKKKLW-COOH |
| | NV1D2512 | 13 | GPYCQKWMWTCDSERKCCEGFVCRLWCKKKLW-COOH |
| | NV1D1336 | 14 | GPYCQKWMWTCDSERKCCEGLVCRLWCKKKLW-COOH |
| | NV1D1337 | 15 | GPYCQKWMWTCDSERKCCEGMVCTLWCKKKLW-COOH |
| | NV1D2308 | 16 | GPYCQKWMWTCDSERKCCEGMVCRLWCRKKLW-COOH |
| NV1G953 | NV1D2670 | 17 | GPACQKWMQTCDSERKCCEGMVCRLWCKKKLW-COOH |
| NV1G951 | NV1D2674 | 18 | GPACQKWMWTCDAERKCCEGMVCRLWCKKKLW-COOH |
| NV1G909 | NV1D2664 | 19 | GPACQKWMWTCDSERKCCEGFVCRLWCKKKLW-COOH |
| NV1G963 | NV1D2671 | 20 | GPQCQKWMQTCDSERKCCEGMVCRLWCKKKLW-COOH |
| NV1G949 | NV1D2675 | 21 | GPQCQKWMWTCDAERKCCEGMVCRLWCKKKLW-COOH |
| NV1G977 | NV1D2665 | 22 | GPQCQKWMWTCDSERKCCEGFVCRLWCKKKLW-COOH |
| NV1G957 | NV1D2668 | 23 | GPRCQKWMQTCDSERKCCEGMVCRLWCKKKLW-COOH |
| NV1G965 | NV1D2672 | 24 | GPRCQKWMWTCDAERKCCEGMVCRLWCKKKLW-COOH |
| NV1G973 | NV1D2662 | 25 | GPRCQKWMWTCDSERKCCEGFVCRLWCKKKLW-COOH |
| NV1G975 | NV1D2669 | 26 | GPSCQKWMQTCDSERKCCEGMVCRLWCKKKLW-COOH |
| NV1G971 | NV1D2673 | 27 | GPSCQKWMWTCDAERKCCEGMVCRLWCKKKLW-COOH |
| NV1G995 | NV1D2663 | 28 | GPSCQKWMWTCDSERKCCEGFVCRLWCKKKLW-COOH |
| NV1G961 | NV1D2676 | 29 | GPYCQKWMQTCDAERKCCEGMVCRLWCKKKLW-COOH |
| NV1G911 | NV1D2666 | 30 | GPYCQKWMQTCDSERKCCEGFVCRLWCKKKLW-COOH |
| | NV1D2816 | 31 | GPACQKWFQTCDSERKCCEGMVCRLWCKKKLW-COOH |
| NV1G905 | NV1D2735 | 32 | GPACQKWMQTCDSERKCCEGFVCRLWCKKKLW-COOH |
| NV1G919 | NV1D2739 | 33 | GPACQKWMWTCDAERKCCEGFVCRLWCKKKLW-COOH |
| NV1G979 | NV1D2731 | 34 | GPACQKWMQTCDAERKCCEGMVCRLWCKKKLW-COOH |
| | NV1D2810 | 35 | GPQCQKWFQTCDSERKCCEGMVCRLWCKKKLW-COOH |
| NV1G1099 | NV1D2732 | 36 | GPQCQKWMQTCDAERKCCEGMVCRLWCKKKLW-COOH |
| NV1G1011 | NV1D2740 | 37 | GPQCQKWMWTCDAERKCCEGFVCRLWCKKKLW-COOH |
| | NV1D2819 | 38 | GPRCQKWFWTCDAERKCCEGMVCRLWCKKKLW-COOH |
| NV1G1105 | NV1D2729 | 39 | GPRCQKWMQTCDAERKCCEGMVCRLWCKKKLW-COOH |
| NV1G1013 | NV1D2733 | 40 | GPRCQKWMQTCDSERKCCEGFVCRLWCKKKLW-COOH |
| | NV1D2814 | 41 | GPSCQKWFQTCDSERKCCEGMVCRLWCKKKLW-COOH |
| | NV1D2820 | 42 | GPSCQKWFWTCDAERKCCEGMVCRLWCKKKLW-COOH |
| NV1G983 | NV1D2730 | 43 | GPSCQKWMQTCDAERKCCEGMVCRLWCKKKLW-COOH |
| NV1G1003 | NV1D2734 | 44 | GPSCQKWMQTCDSERKCCEGFVCRLWCKKKLW-COOH |
| NV1G1009 | NV1D2738 | 45 | GPSCQKWMWTCDAERKCCEGFVCRLWCKKKLW-COOH |
| | NV1D2851 | 46 | GPYCQKWFKTCDAERKCCEGMVCRLWCKKKLW-COOH |
| | NV1D2850 | 47 | GPYCQKWFQTCDAERKCCEGMVCRLWCKKKLW-COOH |
| NV1G987 | NV1D2667 | 48 | GPYCQKWMWTCDAERKCCEGFVCRLWCKKKLW-COOH |

TABLE 2-continued

| Protein name | Protoxin-II variant peptide name | SEQ ID NO: | Protein amino acid sequence |
|---|---|---|---|
| | NV1D2867 | 49 | GPACQKWFQTCDAERKCCEGMVCRLWCKKKLW-COOH |
| | NV1D2881 | 50 | GPACQKWFQTCDSERKCCEGFVCRLWCKKKLW-COOH |
| | NV1D2882 | 51 | GPACQKWFQTCDSERKCCEGLVCRLWCKKKLW-COOH |
| NV1G899 | NV1D2774 | 52 | GPACQKWMQTCDAERKCCEGFVCRLWCKKKLW-COOH |
| NV1G1077 | NV1D2902 | 53 | GPACQKWMQTCDAERKCCEGLVCRLWCKKKLW-COOH |
| | NV1D2861 | 54 | GPQCQKWFQTCDAERKCCEGMVCRLWCKKKLW-COOH |
| | NV1D2870 | 55 | GPQCQKWFQTCDSERKCCEGLVCRLWCKKKLW-COOH |
| NV1G1007 | NV1D2775 | 56 | GPQCQKWMQTCDAERKCCEGFVCRLWCKKKLW-COOH |
| NV1G1067 | NV1D2893 | 57 | GPQCQKWMQTCDAERKCCEGLVCRLWCKKKLW-COOH |
| | NV1D2887 | 58 | GPRCQKWFWTCDAERKCCEGFVCRLWCKKKLW-COOH |
| NV1G1005 | NV1D2772 | 59 | GPRCQKWMQTCDAERKCCEGFVCRLWCKKKLW-COOH |
| NV1G1061 | NV1D2896 | 60 | GPRCQKWMQTCDAERKCCEGLVCRLWCKKKLW-COOH |
| | NV1D2877 | 61 | GPSCQKWFQTCDSERKCCEGFVCRLWCKKKLW-COOH |
| | NV1D2878 | 62 | GPSCQKWFQTCDSERKCCEGLVCRLWCKKKLW-COOH |
| | NV1D2889 | 63 | GPSCQKWFWTCDAERKCCEGFVCRLWCKKKLW-COOH |
| | NV1D2889 | 64 | GPSCQKWFWTCDAERKCCEGFVCRLWCKKKLW-COOH |
| NV1G1001 | NV1D2773 | 65 | GPSCQKWMQTCDAERKCCEGFVCRLWCKKKLW-COOH |
| | NV1D2890 | 66 | GPSCQKWFWTCDAERKCCEGLVCRLWCKKKLW-COOH |
| NV1G1109 | NV1D2899 | 67 | GPSCQKWMQTCDAERKCCEGLVCRLWCKKKLW-COOH |
| | NV1D2905 | 68 | GPYCQKWFQTCDAERKCCEGFVCRLWCKKKLW-COOH |
| | NV1D2906 | 69 | GPYCQKWFQTCDAERKCCEGFVCRLWCKKKLW-COOH |
| | NV1D2921 | 70 | GPACQKWFQTCDAERKCCEGFVCRLWCKKKLW-COOH |
| | NV1D2922 | 71 | GPACQKWFQTCDAERKCCEGLVCRLWCKKKLW-COOH |
| | NV1D2909 | 72 | GPQCQKWFQTCDAERKCCEGFVCRLWCKKKLW-COOH |
| | NV1D2910 | 73 | GPQCQKWFQTCDAERKCCEGLVCRLWCKKKLW-COOH |
| | NV1D2913 | 74 | GPRCQKWFQTCDAERKCCEGFVCRLWCKKKLW-COOH |
| | NV1D2914 | 75 | GPRCQKWFQTCDAERKCCEGLVCRLWCKKKLW-COOH |
| | NV1D2917 | 76 | GPSCQKWFQTCDAERKCCEGFVCRLWCKKKLW-COOH |
| | NV1D2918 | 77 | GPSCQKWFQTCDAERKCCEGLVCRLWCKKKLW-COOH |
| NV1G1153 | NV1D3034 | 78 | GPQCQKWMQTCDRERKCCEGFVCTLWCRKKLW-COOH |

TABLE 3

| Protein name | Protoxin-II variant peptide name | SEQ ID NO: | Protein amino acid sequence |
|---|---|---|---|
| (-GP) NV1G1001 | (-GP) NV1D2773 | 109 | SCQKWMQTCDAERKCCEGFVCRLWCKKKLW-COOH |
| (-GP) NV1G1001-NH-Me | (-GP) NV1D2773-NH2 | 110 | SCQKWMQTCDAERKCCEGFVCRLWCKKKLW-NH2 |

TABLE 3-continued

| Protein name | Protoxin-II variant peptide name | SEQ ID NO: | Protein amino acid sequence |
|---|---|---|---|
| NV1G1007-NH2 | NV1D2775-NH2 | 111 | GPQCQKWMQTCDAERKCCEGFVCRLWCKKKLW-NH2 |
| NV1G1107-NH2 | NV1D2890-NH2 | 112 | GPSCQKWFWTCDAERKCCEGLVCRLWCKKKLW-NH2 |
| NV1G1137 | NV1D2974 | 113 | GPQCQKWMQTCDAERKCCEGFSCTLWCKKKLW-COOH |
| (-GP) N-Ac-NV1G1137-NH2 | (-GP) N-Ac-NV1D2974-NH2 | 114 | Ac-QCQKWMQTCDAERKCCEGFSCTLWCKKKLW-NH2 |
| (-GP) N-Ac-NV1G1137- | (-GP) N-Ac-NV1D2974 | 115 | Ac-QCQKWMQTCDAERKCCEGFSCTLWCKKKLW-COOH |
| NV1G1153 | NV1D3034 | 116 | GPQCQKWMQTCDRERKCCEGFVCTLWCRKKLW-COOH |
| NV1G1153-NH2 | NV1D3034-NH2 | 117 | GPQCQKWMQTCDRERKCCEGFVCTLWCRKKLW-NH2 |
| NV1G1153-NH-butyl | NV1D3034-NH-butyl | 118 | GPQCQKWMQTCDRERKCCEGFVCTLWCRKKLW-NH-butyl |
| NV1G1153-NH-methyl | NV1D3034-NH-methyl | 119 | GPQCQKWMQTCDRERKCCEGFVCTLWCRKKLW-NH-methyl |
| (-GP) N-Ac-NV1G1153 | (-GP) N-Ac-NV1D3034 | 120 | Ac-QCQKWMQTCDRERKCCEGFVCTLWCRKKLW-COOH |
| (-GP) N-Ac-NV1G1153-NH2 | (-GP) N-Ac-NV1D3034-NH2 | 121 | Ac-QCQKWMQTCDRERKCCEGFVCTLWCRKKLW-NH2 |
| NV1G1818 | NV1D3368 | 122 | GPQCQKWMQTCDRTRKCCEGFVCTLWCRKKLW-COOH |
| NV1G1818-NH2 | NV1D3368-NH2 | 123 | GPQCQKWMQTCDRTRKCCEGFVCTLWCRKKLW-NH2 |
| NV1G1147 | NV1D2969 | 124 | GPSCQKWMQTCDAERKCCEGFSCRLWCKKKLW-COOH |
| NV1G1145 | NV1D2970 | 125 | GPSCQKWMQTCDAERKCCEGFVCTLWCKKKLW-COOH |
| NV1G1143 | NV1D2971 | 126 | GPSCQKWMQTCDAERKCCEGFSCTLWCKKKLW-COOH |
| NV1G1141 | NV1D2972 | 127 | GPQCQKWMQTCDAERKCCEGFSCRLWCKKKLW-COOH |
| NV1G1139 | NV1D2973 | 128 | GPQCQKWMQTCDAERKCCEGFVCTLWCKKKLW-COOH |
| NV1G1137 | NV1D2974 | 129 | GPQCQKWMQTCDAERKCCEGFSCTLWCKKKLW-COOH |
| NV1G1137-NH2 | NV1D2974-NH2 | 130 | GPQCQKWMQTCDAERKCCEGFSCTLWCKKKLW-NH2 |
| NV1G1517 | NV1D3004 | 131 | GPQCQKWMQTCDRERKCCEGFVCRLWCKKKLW-COOH |
| NV1G1515 | NV1D3005 | 132 | GPQCQKWMQTCDANRKCCEGFVCRLWCKKKLW-COOH |
| NV1G1519 | NV1D3006 | 133 | GPQCQKWMQTCDARRKCCEGFVCRLWCKKKLW-COOH |
| NV1G1513 | NV1D3007 | 134 | GPQCQKWMQTCDAERKCCEGFVCRLWCRKKLW-COOH |
| NV1G1523 | NV1D3012 | 135 | GPQCQKWMQTCDRNRKCCEGFVCRLWCKKKLW-COOH |
| NV1G1525 | NV1D3013 | 136 | GPQCQKWMQTCDRRRKCCEGFVCRLWCKKKLW-COOH |

TABLE 3-continued

| Protein name | Protoxin-II variant peptide name | SEQ ID NO: | Protein amino acid sequence |
|---|---|---|---|
| NV1G1255 | NV1D3014 | 137 | GPQCQKWMQTCDRERKCCEGFVCTLWCKKKLW-COOH |
| NV1G1187 | NV1D3015 | 138 | GPQCQKWMQTCDRERKCCEGFVCRLWCRKKLW-COOH |
| NV1G1257 | NV1D3016 | 139 | GPQCQKWMQTCDANRKCCEGFVCTLWCKKKLW-COOH |
| NV1G1221 | NV1D3017 | 140 | GPQCQKWMQTCDARRKCCEGFVCTLWCKKKLW-COOH |
| NV1G1521 | NV1D3018 | 141 | GPQCQKWMQTCDANRKCCEGFVCRLWCRKKLW-COOH |
| NV1G1531 | NV1D3019 | 142 | GPQCQKWMQTCDARRKCCEGFVCRLWCRKKLW-COOH |
| NV1G1239 | NV1D3020 | 143 | GPQCQKWMQTCDAERKCCEGFVCTLWCRKKLW-COOH |
| NV1G1583 | NV1D3030 | 144 | GPQCQKWMQTCDRNRKCCEGFVCTLWCKKKLW-COOH |
| NV1G1527 | NV1D3031 | 145 | GPQCQKWMQTCDRRRKCCEGFVCTLWCKKKLW-COOH |
| NV1G1511 | NV1D3032 | 146 | GPQCQKWMQTCDRNRKCCEGFVCRLWCRKKLW-COOH |
| NV1G1509 | NV1D3033 | 147 | GPQCQKWMQTCDRRRKCCEGFVCRLWCRKKLW-COOH |
| NV1G1231 | NV1D3035 | 148 | GPQCQKWMQTCDANRKCCEGFVCTLWCRKKLW-COOH |
| NV1G1211 | NV1D3036 | 149 | GPQCQKWMQTCDARRKCCEGFVCTLWCRKKLW-COOH |
| NV1G1267 | NV1D3044 | 150 | GPQCQKWMQTCDRNRKCCEGFVCTLWCRKKLW-COOH |
| NV1G1269 | NV1D3045 | 151 | GPQCQKWMQTCDRRRKCCEGFVCTLWCRKKLW-COOH |
| NV1G1215 | NV1D3048 | 152 | GPQCQKWMQTCDAKRKCCEGFVCRLWCKKKLW-COOH |
| NV1G1593 | NV1D3050 | 153 | GPQCQKWMQTCDRKRKCCEGFVCRLWCKKKLW-COOH |
| NV1G1263 | NV1D3051 | 154 | GPQCQKWMQTCDAKRKCCEGFVCTLWCKKKLW-COOH |
| NV1G1585 | NV1D3052 | 155 | GPQCQKWMQTCDAKRKCCEGFVCRLWCRKKLW-COOH |
| NV1G1623 | NV1D3056 | 156 | GPQCQKWMQTCDRKRKCCEGFVCTLWCKKKLW-COOH |
| NV1G1613 | NV1D3057 | 157 | GPQCQKWMQTCDRKRKCCEGFVCRLWCRKKLW-COOH |
| NV1G1259 | NV1D3058 | 158 | GPQCQKWMQTCDAKRKCCEGFVCTLWCRKKLW-COOH |
| NV1G1265 | NV1D3062 | 159 | GPQCQKWMQTCDRKRKCCEGFVCTLWCRKKLW-COOH |
| NV1G1273 | NV1D3109 | 160 | GPQCQKWMWTCDARRKCCEGFVCTLWCRKKLW-COOH |
| NV1G1225 | NV1D3121 | 161 | GPQCQKWMWTCDRKRKCCEGFVCTLWCRKKLW-COOH |

TABLE 3-continued

| Protein name | Protoxin-II variant peptide name | SEQ ID NO: | Protein amino acid sequence |
| --- | --- | --- | --- |
| NV1G1886 | NV1D3249 | 162 | GPAAAAAQCQKWMQTCDAERKCCEGFVCRLWCKKKLW-COOH |
| NV1G1633 | NV1D3251 | 163 | GPAPAPAQCQKWMQTCDAERKCCEGFVCRLWCKKKLW-COOH |
| NV1G1631 | NV1D3252 | 164 | GPQCQKWMQTCDAERKCCEGFVCRLWCKKKLWAPAPA-COOH |
| NV1G1885 | NV1D3254 | 165 | GPQCQKWMQTCDAERKCCEGFVCRLWCKKKLWGGGGG-COOH |
| NV1G1884 | NV1D3256 | 166 | GPCCNCSSKWCRDHSRCCGRGSAPAPAPAPAPGSQCQKWMQTCDAERKCCEGFVCRLWCKKKLW-COOH |
| NV1G1881 | NV1D3257 | 167 | GPQCQKWMQTCDAERKCCEGFVCRLWCKKKLWGSAPAPAPAPAPGSCCNCSSKWCRDHSRCC-COOH |
| NV1G1879 | NV1D3259 | 168 | GPQCQKWMQTCDAERKCCEGFVCRLWCKKKLWGSAPAPAPAPAPAPAPAPGSCCNCSSKWCRDHSRCCGR-COOH |
| NV1G1883 | NV1D3260 | 169 | GPCCNCSSKWCRDHSRCCGRGSAPAPAPAPAPAPAPAPAPGSQCQKWMQTCDAERKCCEGFVCRLWCKKKLW-COOH |
| NV1G1880 | NV1D3261 | 170 | GPQCQKWMQTCDAERKCCEGFVCRLWCKKKLWGSAPAPAPAPAPAPAPAPGSCCNCSSKWCRDHSRCC-COOH |
| NV1G1882 | NV1D3262 | 171 | GPCCNCSSKWCRDHSRCCGSAPAPAPAPAPAPAPAPAPGSQCQKWMQTCDAERKCCEGFVCRLWCKKKLW-COOH |
| NV1G1776 | NV1D3339 | 172 | GPQCRKWMQTCDRERKCCEGFVCTLWCRKKLW-COOH |
| NV1G1775 | NV1D3340 | 173 | GPQCKKWMQTCDRERKCCEGFVCTLWCRKKLW-COOH |
| NV1G1768 | NV1D3341 | 174 | GPQCTKWMQTCDRERKCCEGFVCTLWCRKKLW-COOH |
| NV1G1777 | NV1D3342 | 175 | GPQCAKWMQTCDRERKCCEGFVCTLWCRKKLW-COOH |
| NV1G1770 | NV1D3344 | 176 | GPQCEKWMQTCDRERKCCEGFVCTLWCRKKLW-COOH |
| NV1G1767 | NV1D3345 | 177 | GPQCSKWMQTCDRERKCCEGFVCTLWCRKKLW-COOH |
| NV1G1769 | NV1D3346 | 178 | GPQCRWMQTCDRERKCCEGFVCTLWCRKKLW-COOH |
| NV1G1774 | NV1D3347 | 179 | GPQCTWMQTCDRERKCCEGFVCTLWCRKKLW-COOH |
| NV1G1771 | NV1D3348 | 180 | GPQCAWMQTCDRERKCCEGFVCTLWCRKKLW-COOH |
| NV1G1778 | NV1D3349 | 181 | GPQCDWMQTCDRERKCCEGFVCTLWCRKKLW-COOH |
| NV1G1773 | NV1D3350 | 182 | GPQCEWMQTCDRERKCCEGFVCTLWCRKKLW-COOH |
| NV1G1779 | NV1D3351 | 183 | GPQCQWMQTCDRERKCCEGFVCTLWCRKKLW-COOH |
| NV1G1772 | NV1D3352 | 184 | GPQCSWMQTCDRERKCCEGFVCTLWCRKKLW-COOH |

TABLE 3-continued

| Protein name | Protoxin-II variant peptide name | SEQ ID NO: | Protein amino acid sequence |
| --- | --- | --- | --- |
| NV1G1868 | NV1D3353 | 185 | GPQCQKWMQRCDRERKCCEGFVCTLWCRKKLW-COOH |
| NV1G1824 | NV1D3354 | 186 | GPQCQKWMQKCDRERKCCEGFVCTLWCRKKLW-COOH |
| NV1G1863 | NV1D3356 | 187 | GPQCQKWMQDCDRERKCCEGFVCTLWCRKKLW-COOH |
| NV1G1826 | NV1D3357 | 188 | GPQCQKWMQECDRERKCCEGFVCTLWCRKKLW-COOH |
| NV1G1810 | NV1D3358 | 189 | GPQCQKWMQQCDRERKCCEGFVCTLWCRKKLW-COOH |
| NV1G1836 | NV1D3359 | 190 | GPQCQKWMQSCDRERKCCEGFVCTLWCRKKLW-COOH |
| NV1G1834 | NV1D3360 | 191 | GPQCQKWMQTCRRERKCCEGFVCTLWCRKKLW-COOH |
| NV1G1829 | NV1D3361 | 192 | GPQCQKWMQTCKRERKCCEGFVCTLWCRKKLW-COOH |
| NV1G1820 | NV1D3362 | 193 | GPQCQKWMQTCTRERKCCEGFVCTLWCRKKLW-COOH |
| NV1G1828 | NV1D3363 | 194 | GPQCQKWMQTCARERKCCEGFVCTLWCRKKLW-COOH |
| NV1G1827 | NV1D3365 | 195 | GPQCQKWMQTCQRERKCCEGFVCTLWCRKKLW-COOH |
| NV1G1857 | NV1D3366 | 196 | GPQCQKWMQTCSRERKCCEGFVCTLWCRKKLW-COOH |
| NV1G1823 | NV1D3367 | 197 | GPQCQKWMQTCDRQRKCCEGFVCTLWCRKKLW-COOH |
| NV1G1818 | NV1D3368 | 198 | GPQCQKWMQTCDRTRKCCEGFVCTLWCRKKLW-COOH |
| NV1G1811 | NV1D3369 | 199 | GPQCQKWMQTCDREKKCCEGFVCTLWCRKKLW-COOH |
| NV1G1853 | NV1D3370 | 200 | GPQCQKWMQTCDRETKCCEGFVCTLWCRKKLW-COOH |
| NV1G1817 | NV1D3371 | 201 | GPQCQKWMQTCDREAKCCEGFVCTLWCRKKLW-COOH |
| NV1G1814 | NV1D3372 | 202 | GPQCQKWMQTCDREDKCCEGFVCTLWCRKKLW-COOH |
| NV1G1831 | NV1D3374 | 203 | GPQCQKWMQTCDREQKCCEGFVCTLWCRKKLW-COOH |
| NV1G1819 | NV1D3375 | 204 | GPQCQKWMQTCDRESKCCEGFVCTLWCRKKLW-COOH |
| NV1G1859 | NV1D3376 | 205 | GPQCQKWMQTCDRERRCCEGFVCTLWCRKKLW-COOH |
| NV1G1825 | NV1D3377 | 206 | GPQCQKWMQTCDRERTCCEGFVCTLWCRKKLW-COOH |
| NV1G1821 | NV1D3378 | 207 | GPQCQKWMQTCDRERACCEGFVCTLWCRKKLW-COOH |
| NV1G1835 | NV1D3379 | 208 | GPQCQDWMQTCDRERDCCEGFVCTLWCRKKLW-COOH |
| NV1G1815 | NV1D3380 | 209 | GPQCQEWMQTCDRERECCEGFVCTLWCRKKLW-COOH |

TABLE 3-continued

| Protein name | Protoxin-II variant peptide name | SEQ ID NO: | Protein amino acid sequence |
|---|---|---|---|
| NV1G1833 | NV1D3381 | 210 | GPQCQKWMQTCDRERQCCEGFVCTLWCRKKLW-COOH |
| NV1G1812 | NV1D3382 | 211 | GPQCQKWMQTCDRERSCCEGFVCTLWCRKKLW-COOH |
| NV1G1782 | NV1D3383 | 212 | GPQCQKWMQTCDRERKCCRGFVCTLWCRKKLW-COOH |
| NV1G1783 | NV1D3384 | 213 | GPQCQKWMQTCDRERKCCKGFVCTLWCRKKLW-COOH |
| NV1G1785 | NV1D3385 | 214 | GPQCQKWMQTCDRERKCCTGFVCTLWCRKKLW-COOH |
| NV1G1784 | NV1D3386 | 215 | GPQCQKWMQTCDRERKCCAGFVCTLWCRKKLW-COOH |
| NV1G1780 | NV1D3387 | 216 | GPQCQKWMQTCDRERKCCDGFVCTLWCRKKLW-COOH |
| NV1G1781 | NV1D3388 | 217 | GPQCQKWMQTCDRERKCCQGFVCTLWCRKKLW-COOH |
| NV1G1786 | NV1D3389 | 218 | GPQCQKWMQTCDRERKCCSGFVCTLWCRKKLW-COOH |
| NV1G1851 | NV1D3390 | 219 | GPQCQKWMQTCDRERKCCERFVCTLWCRKKLW-COOH |
| NV1G1852 | NV1D3391 | 220 | GPQCQKWMQTCDRERKCCEKFVCTLWCRKKLW-COOH |
| NV1G1854 | NV1D3392 | 221 | GPQCQKWMQTCDRERKCCETFVCTLWCRKKLW-COOH |
| NV1G1860 | NV1D3393 | 222 | GPQCQKWMQTCDRERKCCEAFVCTLWCRKKLW-COOH |
| NV1G1789 | NV1D3394 | 223 | GPQCQKWMQTCDRERKCCEDFVCTLWCRKKLW-COOH |
| NV1G1787 | NV1D3396 | 224 | GPQCQKWMQTCDRERKCCEQFVCTLWCRKKLW-COOH |
| NV1G1856 | NV1D3397 | 225 | GPQCQKWMQTCDRERKCCESFVCTLWCRKKLW-COOH |
| NV1G1855 | NV1D3398 | 226 | GPQCQKWMQTCDRERKCCEGFSCTLWCRKKLW-COOH |
| NV1G1788 | NV1D3399 | 227 | GPQCQKWMQTCDRERKCCEGFTCTLWCRKKLW-COOH |
| NV1G1849 | NV1D3400 | 228 | GPQCQKWMQTCDRERKCCEGFQCTLWCRKKLW-COOH |
| NV1G1795 | NV1D3401 | 229 | GPQCQKWMQTCDRERKCCEGFVCTLWCRRKLW-COOH |
| NV1G1803 | NV1D3403 | 230 | GPQCQKWMQTCDRERKCCEGFVCTLWCRAKLW-COOH |
| NV1G1807 | NV1D3408 | 231 | GPQCQKWMQTCDRERKCCEGFVCTLWCRKRLW-COOH |
| NV1G1806 | NV1D3409 | 232 | GPQCQKWMQTCDRERKCCEGFVCTLWCRKTLW-COOH |
| NV1G1805 | NV1D3410 | 233 | GPQCQKWMQTCDRERKCCEGFVCTLWCRKALW-COOH |
| NV1G1809 | NV1D3413 | 234 | GPQCQKWMQTCDRERKCCEGFVCTLWCRKQLW-COOH |

TABLE 3-continued

| Protein name | Protoxin-II variant peptide name | SEQ ID NO: | Protein amino acid sequence |
|---|---|---|---|
| NV1G1850 | NV1D3414 | 235 | GPQCQKWMQTCDRERKCCEGFVCTLWCRKSLW-COOH |
| NV1G1793 | NV1D3419 | 236 | GPQCQKWMQTCDRERKCCEGFVCTLWCRKKLD-COOH |
| NV1G1822 | NV1D3423 | 237 | GPQCQKWMQTCRRRKCCEGFVCTLWCRKKLW-COOH |
| NV1G1813 | NV1D3424 | 238 | GPQCQKWMQTCKRKRKCCEGFVCTLWCRKKLW-COOH |
| NV1G1840 | NV1D3425 | 239 | GPQCQKWMQTCRRRDKCCEGFVCTLWCRKKLW-COOH |
| NV1G1848 | NV1D3426 | 240 | GPQCQKWMQTCKRKDKCCEGFVCTLWCRKKLW-COOH |
| NV1G1841 | NV1D3427 | 241 | GPQCQKWMQTCRRREKCCEGFVCTLWCRKKLW-COOH |
| NV1G1844 | NV1D3428 | 242 | GPQCQKWMQTCKRKEKCCEGFVCTLWCRKKLW-COOH |
| NV1G1842 | NV1D3430 | 243 | GPQCQDWMQTCDRERKCCKGFVCTLWCRKKLW-COOH |
| NV1G1846 | NV1D3431 | 244 | GPQCQEWMQTCDRERKCCKGFVCTLWCRKKLW-COOH |
| NV1G1843 | NV1D3432 | 245 | GPQCQEWMQTCDRERKCCRGFVCTLWCRKKLW-COOH |
| NV1G1892 | NV1D3439 | 246 | GPQCQKWMQTCDRERKCCEGFVCTLWCRKKLG-COOH |
| NV1G1916 | NV1D3465 | 247 | GPQCQKFMQTCDRERKCCEGFVCTLWCRKKLW-COOH |
| NV1G1922 | NV1D3466 | 248 | GPQCQKWMQTCDEERKCCEGFVCTLWCRKKLW-COOH |
| NV1G1915 | NV1D3467 | 249 | GPQCQKWMQTCDRERKCCGGFVCTLWCRKKLW-COOH |
| NV1G1924 | NV1D3470 | 250 | GPQCQKWMQTCDRERKCCEGLVCTLWCRKKLW-COOH |
| NV1G1709 | NV1D3510 | 251 | GPQCQKWMQTCDRERKCCEGFVCTLWCRKKLWAPAPASPGARAF-COOH |
| NV1G1681 | NV1D3511 | 252 | GPQCQKWMQTCDRERKCCEGFVCTLWCRKKLWSPGARAF-COOH |
| NV1G1693 | NV1D3512 | 253 | GPQCQKWMQTCDRERKCCEGFVCTLWCRKKLWAPAPAPAPDGPWRKM-COOH |
| NV1G1705 | NV1D3513 | 254 | GPQCQKWMQTCDRERKCCEGFVCTLWCRKKLWAPAPADGPWRKM-COOH |
| NV1G1689 | NV1D3514 | 255 | GPQCQKWMQTCDRERKCCEGFVCTLWCRKKLWDGPWRKM-COOH |
| NV1G1711 | NV1D3515 | 256 | GPQCQKWMQTCDRERKCCEGFVCTLWCRKKLWAPAPAPAPAPFGQKASS-COOH |
| NV1G1685 | NV1D3516 | 257 | GPQCQKWMQTCDRERKCCEGFVCTLWCRKKLWAPAPAFGQKASS-COOH |
| NV1G1697 | NV1D3517 | 258 | GPQCQKWMQTCDRERKCCEGFVCTLWCRKKLWFGQKASS-COOH |
| NV1G1695 | NV1D3518 | 259 | GPQCQKWMQTCDRERKCCEGFVCTLWCRKKLWAPAPAPAPAPQRFVTGHFGGLYPANG-COOH |

TABLE 3-continued

| Protein name | Protoxin-II variant peptide name | SEQ ID NO: | Protein amino acid sequence |
|---|---|---|---|
| NV1G1701 | NV1D3519 | 260 | GPQCQKWMQTCDRERKCCEGFVCTLWCRKKLWAPAPAQRFVTGHFGGLYPANG-COOH |
| NV1G1691 | NV1D3520 | 261 | GPQCQKWMQTCDRERKCCEGFVCTLWCRKKLWQRFVTGHFGGLYPANG-COOH |
| NV1G1679 | NV1D3521 | 262 | GPQCQKWMQTCDRERKCCEGFVCTLWCRKKLWAPAPAPAPAPRRRRRRRRRR-COOH |
| NV1G1683 | NV1D3523 | 263 | GPQCQKWMQTCDRERKCCEGFVCTLWCRKKLWRRRRRRRRRRR-COOH |
| NV1G1707 | NV1D3524 | 264 | GPQCQKWMQTCDRERKCCEGFVCTLWCRKKLWAPAPAPAPAPYGRKKRRQRRR-COOH |
| NV1G1713 | NV1D3525 | 265 | GPQCQKWMQTCDRERKCCEGFVCTLWCRKKLWAPAPAYGRKKRRQRRR-COOH |
| NV1G1687 | NV1D3526 | 266 | GPQCQKWMQTCDRERKCCEGFVCTLWCRKKLWYGRKKRRQRRR-COOH |
| NV1G1699 | NV1D3527 | 267 | GPQCQKWMQTCDRERKCCEGFVCTLWCRKKLWAPAPAPAPAP-COOH |
| NV1G1675 | NV1D3528 | 268 | GPQCQKWMQTCDRERKCCEGFVCTLWCRKKLWAPAPA-COOH |
| NV1G1754 | NV1D3529 | 269 | GPRCQKWMQTCDAKRKCCEGFVCTLWCRKKLW-COOH |
| NV1G1748 | NV1D3530 | 270 | GPSCQKWMQTCDAKRKCCEGFVCTLWCRKKLW-COOH |
| NV1G1747 | NV1D3531 | 271 | GPYCQKWMQTCDAKRKCCEGFVCTLWCRKKLW-COOH |
| NV1G1752 | NV1D3532 | 272 | GPACQKWMQTCDAKRKCCEGFVCTLWCRKKLW-COOH |
| NV1G1722 | NV1D3533 | 273 | GPQCQKWMQTCDAKRKCCEGFSCTLWCRKKLW-COOH |
| NV1G1744 | NV1D3534 | 274 | GPRCQKWMQTCDAKRKCCEGFSCTLWCRKKLW-COOH |
| NV1G1742 | NV1D3535 | 275 | GPSCQKWMQTCDAKRKCCEGFSCTLWCRKKLW-COOH |
| NV1G1723 | NV1D3536 | 276 | GPYCQKWMQTCDAKRKCCEGFSCTLWCRKKLW-COOH |
| NV1G1745 | NV1D3537 | 277 | GPACQKWMQTCDAKRKCCEGFSCTLWCRKKLW-COOH |
| NV1G1757 | NV1D3538 | 278 | GPRCQKWMQTCDRNRKCCEGFVCTLWCRKKLW-COOH |
| NV1G1762 | NV1D3539 | 279 | GPSCQKWMQTCDRNRKCCEGFVCTLWCRKKLW-COOH |
| NV1G1763 | NV1D3540 | 280 | GPYCQKWMQTCDRNRKCCEGFVCTLWCRKKLW-COOH |
| NV1G1728 | NV1D3541 | 281 | GPACQKWMQTCDRNRKCCEGFVCTLWCRKKLW-COOH |
| NV1G1730 | NV1D3542 | 282 | GPQCQKWMQTCDRNRKCCEGFSCTLWCRKKLW-COOH |
| NV1G1760 | NV1D3543 | 283 | GPRCQKWMQTCDRNRKCCEGFSCTLWCRKKLW-COOH |
| NV1G1727 | NV1D3544 | 284 | GPSCQKWMQTCDRNRKCCEGFSCTLWCRKKLW-COOH |

TABLE 3-continued

| Protein name | Protoxin-II variant peptide name | SEQ ID NO: | Protein amino acid sequence |
|---|---|---|---|
| NV1G1729 | NV1D3545 | 285 | GPYCQKWMQTCDRNRKCCEGFSCTLWCRKKLW-COOH |
| NV1G1867 | NV1D3546 | 286 | GPACQKWMQTCDRNRKCCEGFSCTLWCRKKLW-COOH |
| NV1G1759 | NV1D3547 | 287 | GPRCQKWMQTCDRERKCCEGFVCTLWCRKKLW-COOH |
| NV1G1758 | NV1D3548 | 288 | GPSCQKWMQTCDRERKCCEGFVCTLWCRKKLW-COOH |
| NV1G1766 | NV1D3549 | 289 | GPYCQKWMQTCDRERKCCEGFVCTLWCRKKLW-COOH |
| NV1G1761 | NV1D3550 | 290 | GPACQKWMQTCDRERKCCEGFVCTLWCRKKLW-COOH |
| NV1G1726 | NV1D3551 | 291 | GPRCQKWMQTCDRERKCCEGFSCTLWCRKKLW-COOH |
| NV1G1721 | NV1D3552 | 292 | GPSCQKWMQTCDRERKCCEGFSCTLWCRKKLW-COOH |
| NV1G1765 | NV1D3553 | 293 | GPYCQKWMQTCDRERKCCEGFSCTLWCRKKLW-COOH |
| NV1G1764 | NV1D3554 | 294 | GPACQKWMQTCDRERKCCEGFSCTLWCRKKLW-COOH |
| NV1G1732 | NV1D3555 | 295 | GPRCQKWMQTCDAERKCCEGFSCTLWCKKKLW-COOH |
| NV1G1862 | NV1D3556 | 296 | GPYCQKWMQTCDAERKCCEGFSCTLWCKKKLW-COOH |
| NV1G1751 | NV1D3558 | 297 | GPRCQKWMQTCDANRKCCEGFSCTLWCKKKLW-COOH |
| NV1G1866 | NV1D3559 | 298 | GPSCQKWMQTCDANRKCCEGFSCTLWCKKKLW-COOH |
| NV1G1865 | NV1D3560 | 299 | GPYCQKWMQTCDANRKCCEGFSCTLWCKKKLW-COOH |
| NV1G1716 | NV1D3561 | 300 | GPACQKWMQTCDANRKCCEGFSCTLWCKKKLW-COOH |
| NV1G1724 | NV1D3562 | 301 | GPRCQKWMQTCDARRKCCEGFSCTLWCKKKLW-COOH |
| NV1G1717 | NV1D3563 | 302 | GPSCQKWMQTCDARRKCCEGFSCTLWCKKKLW-COOH |
| NV1G1743 | NV1D3564 | 303 | GPYCQKWMQTCDARRKCCEGFSCTLWCKKKLW-COOH |
| NV1G1720 | NV1D3565 | 304 | GPACQKWMQTCDARRKCCEGFSCTLWCKKKLW-COOH |
| NV1G1735 | NV1D3566 | 305 | GPRCQKWMQTCDAERKCCEGFVCTLWCKKKLW-COOH |
| NV1G1734 | NV1D3568 | 306 | GPACQKWMQTCDAERKCCEGFVCTLWCKKKLW-COOH |
| NV1G1741 | NV1D3569 | 307 | GPRCQKWMQTCDARRKCCEGFVCTLWCKKKLW-COOH |
| NV1G1719 | NV1D3570 | 308 | GPSCQKWMQTCDARRKCCEGFVCTLWCKKKLW-COOH |
| NV1G1718 | NV1D3571 | 309 | GPYCQKWMQTCDARRKCCEGFVCTLWCKKKLW-COOH |

TABLE 3-continued

| Protein name | Protoxin-II variant peptide name | SEQ ID NO: | Protein amino acid sequence |
|---|---|---|---|
| NV1G1725 | NV1D3572 | 310 | GPACQKWMQTCDARRKCCEGFVCTLWCKKKLW-COOH |
| NV1G1869 | NV1D3573 | 311 | GPRCQKWMQTCDANRKCCEGFVCTLWCKKKLW-COOH |
| NV1G1755 | NV1D3574 | 312 | GPSCQKWMQTCDANRKCCEGFVCTLWCKKKLW-COOH |
| NV1G1756 | NV1D3575 | 313 | GPYCQKWMQTCDANRKCCEGFVCTLWCKKKLW-COOH |
| NV1G1746 | NV1D3576 | 314 | GPACQKWMQTCDANRKCCEGFVCTLWCKKKLW-COOH |
| NV1G1733 | NV1D3577 | 315 | GPRCQKWMQTCDAERKCCEGFSCRLWCKKKLW-COOH |
| NV1G1738 | NV1D3578 | 316 | GPYCQKWMQTCDAERKCCEGFSCRLWCKKKLW-COOH |
| NV1G1737 | NV1D3579 | 317 | GPACQKWMQTCDAERKCCEGFSCRLWCKKKLW-COOH |
| NV1G1740 | NV1D3580 | 318 | GPRCQKWMQTCDARRKCCEGFSCRLWCKKKLW-COOH |
| NV1G1864 | NV1D3581 | 319 | GPSCQKWMQTCDARRKCCEGFSCRLWCKKKLW-COOH |
| NV1G1739 | NV1D3582 | 320 | GPYCQKWMQTCDARRKCCEGFSCRLWCKKKLW-COOH |
| NV1G1870 | NV1D3583 | 321 | GPACQKWMQTCDARRKCCEGFSCRLWCKKKLW-COOH |
| NV1G1715 | NV1D3584 | 322 | GPRCQKWMQTCDANRKCCEGFSCRLWCKKKLW-COOH |
| NV1G1753 | NV1D3585 | 323 | GPSCQKWMQTCDANRKCCEGFSCRLWCKKKLW-COOH |
| NV1G1750 | NV1D3586 | 324 | GPYCQKWMQTCDANRKCCEGFSCRLWCKKKLW-COOH |
| NV1G1750-NH2 | NV1D3586-NH2 | 325 | GPYCQKWMQTCDANRKCCEGFSCRLWCKKKLW-NH2 |
| NV1G1749 | NV1D3587 | 326 | GPACQKWMQTCDANRKCCEGFSCRLWCKKKLW-COOH |
| NV1G1871 | NV1D3772 | 327 | GPQCQKWMQTCDRERKCCEGFVCTLWCRKKLWSHSNTQTLAKAPEHTG-COOH |
| NV1G1839 | NV1D3774 | 328 | GPSHSNTQTLAKAPEHTGAPAPAPAPAPAPAPAPAPAPCQKWMQTCDRERKCCEGFVCTLWCRKKLW-COOH |
| NV1G1877 | NV1D3775 | 329 | GPSHSNTQTLAKAPEHTGAPAPAPAPAPQCQKWMQTCDRERKCCEGFVCTLWCRKKLW-COOH |
| NV1G1872 | NV1D3777 | 330 | GPSHSNTQTLAKAPEHTGQCQKWMQTCDRERKCCEGFVCTLWCRKKLW-COOH |
| NV1G1941 | NV1D3782 | 331 | GPQCQKWMQTCDRERKCCEGFVCTLWCRKKAW-COOH |
| NV1G1990 | NV1D3788 | 332 | GPAAAAAQCQKWMQTCDRERKCCEGFVCTLWCRKKLW-COOH |
| NV1G1991 | NV1D3789 | 333 | GPAPAPAQCQKWMQTCDRERKCCEGFVCTLWCRKKLW-COOH |
| NV1G1989 | NV1D3791 | 334 | GPQCQKWMQTCDRERKCCEGFVCTLWCRKKLWAAAAA-COOH |

TABLE 3-continued

| Protein name | Protoxin-II variant peptide name | SEQ ID NO: | Protein amino acid sequence |
|---|---|---|---|
| NV1G1993 | NV1D3792 | 335 | GPQCQKWMQTCDRERKCCEGFVCTLWCRKKLWGGGGG-COOH |
| NV1G1967 | NV1D3793 | 336 | GPCCNCSSKWCRDHSRCCGRGSAPAPAPAPAPAPAPAPAPAPGSQCQKWMQTCDRERKCCEGFVCTLWCRKKLW-COOH |
| NV1G1969 | NV1D3795 | 337 | GPCCNCSSKWCRDHSRCCGSAPAPAPAPAPAPAPAPAPAPGSQCQKWMQTCDRERKCCEGFVCTLWCRKKLW-COOH |
| NV1G1974 | NV1D3796 | 338 | GPCCNCSSKWCRDHSRCCGSAPAPAPAPAPGSQCQKWMQTCDRERKCCEGFVCTLWCRKKLW-COOH |
| NV1G1950 | NV1D3797 | 339 | GPQCQKWMQTCDRERKCCEGFVCTLWCRKKLWGSAPAPAPAPAPAPAPAPAPGSCCNCSSKWCRDHSRCC-COOH |
| NV1G1948 | NV1D3798 | 340 | GPQCQKWMQTCDRERKCCEGFVCTLWCRKKLWGSAPAPAPAPAPAPAPAPAPGSCCNCSSKWCRDHSRCCGR-COOH |
| NV1G2057 | NV1D3799 | 341 | GPQCQKWMQTCDRERKCCEGFVCTLWCRKKLWGSAPAPAPAPAPGSCCNCSSKWCRDHSRCC-COOH |
| NV1G1954 | NV1D3800 | 342 | GPQCQKWMQTCDRERKCCEGFVCTLWCRKKLWGSAPAPAPAPAPGSCCNCSSKWCRDHSRCCGR-COOH |
| NV1G1956 | NV1D3801 | 343 | GPSPGARAFAPAPAPAPAPQCQKWMQTCDRERKCCEGFVCTLWCRKKLW-COOH |
| NV1G1961 | NV1D3802 | 344 | GPSPGARAFAPAPAQCQKWMQTCDRERKCCEGFVCTLWCRKKLW-COOH |
| NV1G1960 | NV1D3803 | 345 | GPSPGARAFQCQKWMQTCDRERKCCEGFVCTLWCRKKLW-COOH |
| NV1G1977 | NV1D3804 | 346 | GPDGPWRKMAPAPAPAPAPQCQKWMQTCDRERKCCEGFVCTLWCRKKLW-COOH |
| NV1G1982 | NV1D3805 | 347 | GPDGPWRKMAPAPAQCQKWMQTCDRERKCCEGFVCTLWCRKKLW-COOH |
| NV1G1984 | NV1D3806 | 348 | GPDGPWRKMQCQKWMQTCDRERKCCEGFVCTLWCRKKLW-COOH |
| NV1G1985 | NV1D3808 | 349 | GPFGQKASSAPAPAQCQKWMQTCDRERKCCEGFVCTLWCRKKLW-COOH |
| NV1G1983 | NV1D3809 | 350 | GPFGQKASSQCQKWMQTCDRERKCCEGFVCTLWCRKKLW-COOH |
| NV1G1973 | NV1D3810 | 351 | GPQRFVTGHFGGLYPANGAPAPAPAPAPQCQKWMQTCDRERKCCEGFVCTLWCRKKLW-COOH |
| NV1G1976 | NV1D3811 | 352 | GPQRFVTGHFGGLYPANGAPAPAQCQKWMQTCDRERKCCEGFVCTLWCRKKLW-COOH |
| NV1G1980 | NV1D3812 | 353 | GPQRFVTGHFGGLYPANGQCQKWMQTCDRERKCCEGFVCTLWCRKKLW-COOH |
| NV1G1952 | NV1D3813 | 354 | GPRRRRRRRRRRAPAPAPAPAPQCQKWMQTCDRERKCCEGFVCTLWCRKKLW-COOH |
| NV1G1957 | NV1D3814 | 355 | GPRRRRRRRRRRAPAPAQCQKWMQTCDRERKCCEGFVCTLWCRKKLW-COOH |
| NV1G1981 | NV1D3815 | 356 | GPRRRRRRRRRRQCQKWMQTCDRERKCCEGFVCTLWCRKKLW-COOH |

TABLE 3-continued

| Protein name | Protoxin-II variant peptide name | SEQ ID NO: | Protein amino acid sequence |
|---|---|---|---|
| NV1G1959 | NV1D3818 | 357 | GPYGRKKRRQRRRQCQKWMQTCDRERKCCEGFVCTLWCRKKLW-COOH |
| NV1G1986 | NV1D3819 | 358 | GPAPAPAPAPAPAPQCQKWMQTCDRERKCCEGFVCTLWCRKKLW-COOH |
| NV1G1968 | NV1D3822 | 359 | GPGWCGDPGATCGKLRLYCCSGFCDSYTKTCKDKSSAGGGGSAPAPAPAPAPAPAPAPAPAPAPAPAPAPAPGGGGSQCQKWMQTCDRERKCCEGFVCTLWCRKKLW-COOH |
| NV1G1945 | NV1D3823 | 360 | GPQCQKWMQTCDRERKCCEGFVCTLWCRKKLWGGGGSAPAPAPAPAPAPAPAPAPAPAPAPAPAPGGGGSGWCGDPGATCGKLRLYCCSGFCDSYTKTCKDKSSA-COOH |
| NV1G1972 | NV1D3824 | 361 | GPGWCGDPGATCGKLRLYCCSGFCDAYTKTCKDKSSAGGGGSAPAPAPAPAPAPAPAPAPAPAPAPAPAPAPGGGGSQCQKWMQTCDRERKCCEGFVCTLWCRKKLW-COOH |
| NV1G1946 | NV1D3825 | 362 | GPQCQKWMQTCDRERKCCEGFVCTLWCRKKLWGGGGSAPAPAPAPAPAPAPAPAPAPAPAPAPAPGGGGSGWCGDPGATCGKLRLYCCSGFCDAYTKTCKDKSSA-COOH |
| NV1G1970 | NV1D3826 | 363 | GPGWCGDPGATCGKLRLYCCSGFCDCYTKTCKDKSSAGGGGSAPAPAPAPAPAPAPAPAPAPAPAPAPAPAPGGGGSQCQKWMQTCDRERKCCEGFVCTLWCRKKLW-COOH |
| NV1G1949 | NV1D3828 | 364 | GPQCQKWMQTCDRERKCCEGFVCTLWCRKKLWGSGGGSAPAPAPAPAPAPAPAPAPAPAPGGGGSGSCCNCSSKWCRDHSRCCGR-COOH |
| NV1G1951 | NV1D3829 | 365 | GPQCQKWMQTCDRERKCCEGFVCTLWCRKKLWGSGGGSAPAPAPAPAPAPAPAPAPAPAPGGGGSGSCCNCSSKWCRDHSRCC-COOH |
| NV1G1971 | NV1D3830 | 366 | GPCCNCSSKWCRDHSRCCGRGSGGGGSAPAPAPAPAPAPAPAPAPAPGGGGSGSQCQKWMQTCDRERKCCEGFVCTLWCRKKLW-COOH |
| NV1G1975 | NV1D3832 | 367 | GPCRTIGPSVCAPAPAPAPAPAPAPAPAPQCQKWMQTCDRERKCCEGFVCTLWCRKKLW-COOH |
| NV1G1978 | NV1D3833 | 368 | GPCRTIGPSVCAPAPAPAPAPQCQKWMQTCDRERKCCEGFVCTLWCRKKLW-COOH |
| NV1G1979 | NV1D3834 | 369 | GPCRTIGPSVCAPAPAQCQKWMQTCDRERKCCEGFVCTLWCRKKLW-COOH |
| NV1G2043 | NV1D3835 | 370 | GPCRTIGPSVCQCQKWMQTCDRERKCCEGFVCTLWCRKKLW-COOH |
| NV1G1955 | NV1D3838 | 371 | GPQCQKWMQTCDRERKCCEGFVCTLWCRKKLWAPAPACRTIGPSVC-COOH |

In some embodiments disclosed herein, including in the numbered embodiments listed below, the isolated Protoxin-II variant inhibits human Nav1.7 activity with an IC$_{50}$ value of about $3 \times 10^{-8}$ M or less.

In some embodiments disclosed herein, including in the numbered embodiments listed below, the isolated Protoxin-II variant inhibits human Nav1.7 activity with an IC$_{50}$ value of between about $3 \times 10^{-8}$ M to about $\times 10^{-9}$ M.

Another embodiment of the invention disclosed herein, including in the numbered embodiments listed below is an isolated Protoxin-II variant comprising the amino acid sequence
GPQCX$_1$X$_2$WX$_3$QX$_4$CX$_5$X$_6$X$_7$X$_8$X$_9$CCX$_{10}$X$_{11}$X$_{12}$X$_{13}$CX$_{14}$LWCX$_{15}$KKLL (SEQ ID NO: 433), wherein
X$_1$ is Q, R, K, A or S;
X$_2$ is K, S, Q or R;
X$_3$ is M or F;
X$_4$ is T, S, R, K or Q;
X$_5$ is D or T;
X$_6$ is S, A or R;
X$_7$ is E, R, N, K, T or Q;
X$_8$ is R or K;
X$_9$ is K, Q, S or A;
X$_{10}$ is E, Q or D;
X$_{11}$ is G or Q;
X$_{12}$ is F or M;
X$_{13}$ is V or S;
X$_{14}$ is R or T; and
X$_{15}$ is K or R.

Exemplary Protoxin-II variants that inhibit human Nav1.7 activity with an IC$_{50}$ value of about 30×10$^{-9}$ M or less are variants comprising the amino acid sequences of SEQ ID NOs: 56, 78, 111, 114, 117, 118, 119, 122, 123, 129, 130, 131, 132, 133, 134, 135, 136, 138, 139, 140, 141, 142, 145, 146, 147, 149, 150, 151, 152, 153, 154, 156, 158, 159, 165, 172, 173, 175, 177, 178, 183, 184, 185, 186, 189, 190, 193, 197, 199, 207, 210, 211, 216, 217, 224, 266, 273, 282, 335, 408, 409, 410, 422, 424, 425, 426, 427 and 428.

In some embodiments disclosed herein, including in the numbered embodiments listed below, the isolated Protoxin-II variant selectively inhibits human Nav1.7. The Protoxin-II variants of the invention may be more selective towards Nav1.7 when compared to the recombinant Protoxin-II (SEQ ID NO: 2). In the QPatch electrophysiology assay, recombinant Protoxin-II has an IC$_{50}$ of about 2.2×10$^{-9}$ M for Nav1.7 and an IC$_{50}$ of about 62×10$^{-9}$ M for Nav1.6, and therefore the ratio of IC$_{50}$ for Nav1.6 to IC$_{50}$ for Nav1.7 about 28 fold. "Selectivity" or "selective" or "more selective" or "selectively blocks" or "selectively inhibits" when used herein refers to a Protoxin-II variant that has a ratio of IC$_{50}$ for Nav1.6 to IC$_{50}$ for Nav1.7 (IC$_{50}$(Nav1.6)/IC$_{50}$(Nav1.7)) equal or over about 30. IC$_{50}$ for Nav1.6 may be assayed in a QPatch electrophysiology assay using cell lines stably expressing Nav1.6 using similar methods to those described for Nav1.7.

Residue positions in Protoxin-II that can be mutagenized to improve selectivity include residues 7, 11, 12, 14, 17, 18 and 19, and optionally residues 1, 20, 22 and 26 (residue numbering according to SEQ ID NO: 1). Exemplary substitutions to improve selectivity are Y1Q, W7Q, S11R, S11A, E12T, M19F, V20S, R22T, and K26R. Exemplary Protoxin-II variants with improved selectivity are variants of SEQ ID NOs: 56, 59, 65, 78, 111, 114, 117, 118, 119, 121, 122, 123, 129, 130, 133, 150, 190, 217, 281, 324, 325 or 326.

Another embodiment of the invention disclosed herein, including in the numbered embodiments listed below is an isolated Protoxin-II variant comprising the sequence GPX$_1$CQKWMQX$_2$CDX$_3$X$_4$RKCCX$_5$GFX$_6$CX$_7$LWCX$_8$KKLW (SEQ ID NO: 405);

wherein
X$_1$ is Y, Q, A, S or R;
X$_2$ is T or S;
X$_3$ is S, R or A;
X$_4$ is E, T or N;
X$_5$ is E or Q;
X$_6$ is V or S;
X$_7$ is R or T; and
X$_8$ is K or R;

wherein the Protoxin-II variant inhibits human Nav1.7 activity with an IC$_{50}$ value of about 3×10$^{-8}$ M or less, and selectively inhibits human Nav1.7.

In some embodiments disclosed herein, including in the numbered embodiments listed below, the isolated Protoxin-II variant comprises the sequence

GPQCQKWMQX$_1$CDX$_2$X$_3$RKCCX$_4$GFX$_5$CX$_6$LWCX$_8$KKLW (SEQ ID NO:406);

wherein
X$_1$ is T or S;
X$_2$ is S, R or A;
X$_3$ is E, T or N;
X$_4$ is E or Q;
X$_5$ is V or S;
X$_6$ is R or T; and
X$_7$ is K or R.

Another embodiment of the invention disclosed herein, including in the numbered embodiments listed below is an isolated Protoxin-II variant comprising the amino acid sequence that is 90%, 91%, 92%, 93%, 94%, 95%, 96%, 97%, 98% or 99% identical to the amino acid sequence of SEQ ID NO: 422 (GPYCQKWMQTCDSERKC-CEGMVCRLWCKKKLL-COOH); wherein
the amino acid sequence has Q at position 7 and L at position 30, when residue numbering is according to SEQ ID NO: 1; and
the polypeptide inhibits human Nav1.7 activity.
Protoxin-II variants having substitutions W7Q and W30L have improved folding, yield and selectivity when compared to the wild type Protoxin-II.

Another embodiment of the invention disclosed herein, including in the numbered embodiments listed below is an isolated Protoxin-II variant comprising the amino acid sequence that is 90%, 91%, 92%, 93%, 94%, 95%, 96%, 97%, 98% or 99% identical to the amino acid sequence of SEQ ID NO: 78 (GPQCQKWMQTCDRERKC-CEGFVCTLWCRKKLW-COOH); wherein
the amino acid sequence has Q at position 1, Q at position 7 and F at position 19, when residue numbering is according to SEQ ID NO: 1;
the polypeptide inhibits human Nav1.7 activity with an IC$_{50}$ value of about 30×10$^{-9}$ M or less, wherein the IC$_{50}$ value is measured using a veratridine-induced depolarization inhibition assay using fluorescence resonance energy transfer (FRET) in the presence of 25×10$^{-6}$ M 3-veratroylveracevine in HEK293 cells stably expressing human Nav1.7; and
the polypeptide selectively inhibits Nav1.7.

In some embodiments disclosed herein, including in the numbered embodiments listed below, the isolated Protoxin-II variant has a carboxylic acid, amide, methylamide or butylamide group at the C-terminus. C-terminal modifications may be generated via routine synthetic methods.

Another embodiment of the invention disclosed herein, including in the numbered embodiments listed below is an isolated fusion protein comprising the Protoxin-II variant of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 109, 110, 111, 112, 113, 114, 115, 116, 117, 118, 119, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 35, 357, 358, 359, 360, 361, 362, 363, 364, 365, 366, 367, 368 369, 370, 371, 408, 409, 410, 411, 412, 413, 414, 415, 416, 417, 418, 419, 420, 421, 422, 423, 424, 425, 426, 427, 428, 429, 430, 431, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735 or 736. Such second polypeptides may be well known leader or secretory signal sequences, or synthetic sequences resulting for example from cloning steps, or tags such as hexahistidine tag (SEQ ID NO: 108). Such second polypeptide may be a half-life extending moiety. In one embodiment, the isolated fusion protein comprises the Protoxin-II variant of the invention conjugated to a half-life extending moiety.

Exemplary half-life extending moieties that may be used include well known human serum albumin, transthyretin (TTR), a thyroxine-binding globulin (TGB), albumin-binding domains, or an Fc or fragments thereof. Biologically suitable polymers or copolymers may also be used, for example ethylene glycol or polyethylene glycol (PEG) molecules, such as PEG5000 or PEG20000, dextran, polylysine, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, octane, or carbohydrates (dextran, cellulose, oligo- or polysaccharides). Exemplary moieties that can improve biodistribution include polyamination (putrescine, spermine, or spermidine etc.), halogenation (chlorine, bromine, fluorine, iodine), and glycosylation. These moieties may be direct fusions with the Protoxin-II variant polypeptides and may be generated by standard cloning and expression techniques. Alternatively, well known chemical coupling methods may be used to attach the moieties to recombinantly produced Protoxin-II variants of the invention. Alternatively, moieties can be incorporated as non-coded amino acids during solid phase peptide synthesis.

In another embodiment of the invention disclosed herein, including in the numbered embodiments listed below, the half-life extending moiety of the fusion protein of the invention is human serum albumin, variants of human serum albumin, albumin binding domain (ABD), or polyethylene glycol (PEG).

In another embodiment disclosed herein, including in the numbered embodiments listed below, the half-life extending moiety of is conjugated to the Protoxin-II variant via a linker. Suitable linkers are well known and include linkers having the sequence shown in SEQ ID NOs: 80 or 81.

Exemplary fusion proteins incorporating Protoxin-II variants of the invention are those having the polypeptide sequence of SEQ ID NOs: 83, 85, 87, 89, 91, 93, 95, 97, 99, 101 or 103.

Protoxin-II variants of the invention disclosed herein, including in the numbered embodiments listed below incorporating additional moieties may be compared for functionality by several well-known assays. For example, pharmacokinetic properties of Protoxin-II variants coupled to PEG may be evaluated in well known in vivo models.

Additional Protoxin-II variants and Protoxin-II variant fusion proteins are within the scope of the invention. Additional substitutions to the Protoxin-II variants of the invention can be made as long as the resulting variant or the fusion protein retains similar characteristics when compared to the parent peptide. Exemplary modifications are for example conservative substitutions that will result in Protoxin-II variants with similar characteristics to those of the parent molecules. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the Protoxin-II variants that involve substitutions of amino acid residues between different classes of amino acids to improve properties of the Protoxin-II variants and Protoxin-II variant fusion proteins. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement takes place can readily be tested in the same manner.

Another embodiment of the invention is an isolated family 3 spider venom cysteine knot peptide comprising at least one substitution at a position corresponding to position W7 and/or W30 of SEQ ID NO: 1. Family 3 spider toxins include 14 toxins with conserved C-terminal region, including, in addition to Protoxin-II, κ-TRTX-Gr2b, κ-TRTX-Gr2c, κ-TRTX-Ps1a, κ-TRTX-Ps1b, β-TRTX-Gr1b, κ-TRTX-Cj2a, κ-TRTX-Cj2b, κ-TRTX-Ec2c, β-TRTX-Gr1a, κ-TRTX-Ec2b, κ-TRTX-Ec2a and β/κ-TRTX-Cj2a and those shown in FIG. 14. Substitutions at positions W7 and/or W30 are expected to improve folding of the family 3 spider venom cysteine knot peptides.

Another embodiment of the invention disclosed herein, including in the numbered embodiments listed below is an isolated synthetic polynucleotide comprising a polynucleotide encoding the Protoxin-II variant of the invention.

Certain exemplary synthetic polynucleotides are disclosed herein, however, other synthetic polynucleotides which, given the degeneracy of the genetic code or codon preferences in a given expression system, encode the Protoxin-II variants and Protoxin-II variant fusion proteins of the invention are also within the scope of the invention.

Exemplary synthetic polynucleotides are for example polynucleotide sequences shown in SEQ ID NOs: 84, 86, 88, 90, 92, 94, 96, 98, 100, 102 and 104, which encode the Protoxin-II variant fusion proteins of the invention. Those skilled in the art can readily identify the polynucleotide segments in the fusion proteins that encode the Protoxin-II variant itself. The synthetic polynucleotide sequences encoding the Protoxin-II variants or fusion proteins of the invention can be operably linked to one or more regulatory elements, such as a promoter and enhancer, that allow expression of the nucleotide sequence in the intended host cell. The synthetic polynucleotide may be a cDNA.

The polynucleotides of the invention may be produced by chemical synthesis such as solid phase polynucleotide synthesis on an automated polynucleotide synthesizer.

Alternatively, the polynucleotides of the invention may be produced by other techniques such as PCR based duplication, vector based duplication, or restriction enzyme based DNA manipulation techniques. Techniques for producing or obtaining polynucleotides of known sequences are well known.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or well-known tag sequences such as a hexa-histidine (SEQ ID NO: 108) or a HA tag which facilitate the purification of fused polypeptides.

Another embodiment of the invention disclosed herein, including in the numbered embodiments listed below is a vector comprising the polynucleotide of the invention. Such vectors may be plasmid vectors, viral vectors, vectors for baculovirus expression, transposon based vectors or any other vector suitable for introduction of the polynucleotide of the invention into a given organism or genetic background by any means. For example, polynucleotides encoding the Protoxin-II variants or the Protoxin-II variant fusion proteins of the invention are inserted into an expression vector and may be operably linked to control sequences in the expression vector to ensure efficient expression, such as signal sequences, promoters (e.g. naturally associated or heterologous promoters), enhancer elements, and transcription termination sequences, and are chosen to be compatible with the host cell chosen to express the Protoxin-II variant or the Protoxin-II variant fusion protein of the invention. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. For expression in a yeast cell, a suitable promoter is a constitutive promoter such as an ADH1 PGK1, ENO or PYK1 promoter and the like, or a regulatable promoter such as a GAL1 or GAL10 promoter. Selection of the appropriate vector and promoter is well within the level of ordinary skill in the art.

Large numbers of suitable vectors and promoters are known to those of skill in the art; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

An exemplary vector for expression of the Protoxin-II variants or Protoxin-II variant fusion proteins is a vector having ampicillin-resistance selection marker, CMV promoter, CMV intron, signal peptide, neomycin resistance, f1 origin of replication, SV40 polyadenylation signal, and cDNA encoding the Protoxin-II variant or the Protoxin-II variant fusion protein of the invention.

Another embodiment of the invention disclosed herein, including in the numbered embodiments listed below is a host cell comprising the vector of the invention. The term "host cell" refers to a cell into which a vector has been introduced. It is understood that the term host cell is intended to refer not only to the particular subject cell but also to the progeny of such a cell. Because certain modifications may occur in succeeding generations due to either mutation or environmental influences, such progeny may not be identical to the parent cell, but are still included within the scope of the term "host cell" as used herein.

Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species, are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Introduction of a polynucleotide, such as a vector, into a host cell can be effected by methods well known to those skilled in the art. Exemplary methods are calcium phosphate transfection, DEAE-Dextran mediated transfection, microinjection, cationic lipid-mediated transfection and electroporation.

Another embodiment of the invention disclosed herein, including in the numbered embodiments listed below is a method for producing the Protoxin-II variant of the invention comprising the steps of providing a host cell of the invention; and culturing the host cell under conditions sufficient for the expression of at least one Protoxin-II variant of the invention.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention disclosed herein, including in the numbered embodiments listed below, the expression of the Protoxin-II variant can be confirmed using a variety of well-known methods. For example, expression of a polypeptide can be confirmed using detection reagents, such as using SDS-PAGE or HPLC.

Another aspect of the invention is a method of modulating the activity of Nav1.7 in a biological tissue, the method comprising contacting the biological tissue expressing Nav1.7 with a Nav1.7-modulating amount of the Protoxin-II variant of the invention.

Methods of Treatment

Protoxin-II variants of the invention disclosed herein, including in the numbered embodiments listed below may be utilized in any therapy where it is desired to treat, reduce or alleviate symptoms of pain or other disorders of sensory or sympathetic neuron dysfunction.

Pain treated with the Protoxin-II variants of the invention disclosed herein, including in the numbered embodiments listed below may be any type of pain, such as chronic pain, acute pain, neuropathic pain, nociceptive pain, visceral pain, back pain, pain associated with inflammatory conditions, post-operative pain, thermal pain or pain associated with disease and degeneration.

Pain treated with the Protoxin-II variants of the invention disclosed herein, including in the numbered embodiments listed below may be Nav1.7-mediated pain.

Nav1.7-mediated pain as used herein refers to pain resulting at least partially from increased Nav1.7 channel activity.

The methods of the invention may be used to treat an animal patient belonging to any classification. Examples of such animals include mammals such as humans, rodents, dogs, cats and farm animals.

The pain and/or Nav1.7-mediated pain may result from one or more causes, such as peripheral neuropathy, central neuropathy, nerve compression or entrapment syndromes such as carpal tunnel syndrome, tarsus tunnel syndrome, ulnar nerve entrapment, compression radiculopathy, lumbar spinal stenosis, sciatic nerve compression, spinal root compression, intercostal neuralgia, compression radiculopathy and radicular lower back pain, spinal root lesions, neuritis, autoimmune diseases, general inflammation, chronic inflammatory conditions, arthritis, rheumatic diseases, lupus, osteoarthritis, general gastrointestinal disorders, colitis, gastric ulceration, duodenal ulcers, inflammatory bowel disorders, irritable bowel syndrome, pain associated with diarrhea, inflammatory eye disorders, inflammatory or unstable bladder disorders, psoriasis, skin complaints with inflammatory components, sunburn, carditis, dermatitis, myositis, neuritis, collagen vascular diseases, inflammatory pain and associated hyperalgesia and allodynia, neuropathic pain and associated hyperalgesia and allodynia, multiple sclerosis, demyelinating diseases, diabetes, diabetic neuropathy pain, causalgia, pain resulting from amputation or abscess, phantom limb pain, fracture pain, bone injury, direct trauma, HIV infection, acquired immune deficiency syndrome ("AIDS"), small pox infection, herpes infection, exposure to toxins or other foreign particles or molecules, invasive cancer, cancer, chemotherapy, radiotherapy, hormonal therapy, burns, congenital defect, dental pain, gout pain, fibromyalgias, encephalitis, chronic alcoholism, hypothyroidism, uremia and vitamin deficiencies, trigeminal neuralgia, stroke, thalamic pain syndrome, general headache, migraine, cluster headache, tension headache, mixed-vascular and non-vascular syndromes, sympathetically maintained pain, deafferentation syndromes, asthma, epithelial tissue damage or dysfunction, disturbances of visceral motility at respiratory, genitourinary, gastrointestinal or vascular regions, wounds, burns, allergic skin reactions, pruritis, vasomotor or allergic rhinitis, or bronchial disorders, dysmenorrhoea, pain during labor and delivery, dyspepsia, gastroesophageal reflux, pancreatitis, and visceralgia.

Other disorders of sensory or sympathetic neuron dysfunction that may be alleviated by the Protoxin-II variants of the invention include itch, cough and asthma. In mice, global deletion of the SCN9A gene leads to complete insensitivity to histamine-induced itch (Gingras et al., American Pain Society Meeting Abstract 2013 and U.S. Pat. Publ. No. 2012/0185956). This finding suggests that peptide Nav1.7 blockers may have utility in the treatment of itch, which may arise from various sources, such as dermatological or inflammatory disorders; or inflammatory disorders such as renal or hepatobiliary disorders, immunological disorders, medication reactions and unknown/idiopathic conditions, including dermatitis, psoriasis, eczema, insect sting or bite. Nav1.7 is also expressed in sensory nerves innervating the airways (Muroi et al., J Physiol. 2011 Dec. 1; 589(Pt 23):5663-76; Muroi et al., Am J Physiol Regul Integr Comp Physiol. 2013 Apr. 10), suggesting that peptide Nav1.7 blockers may be beneficial in the treatment of cough e.g., acute or chronic cough, or cough caused by irritation from gastroesophageal reflux disease, and inflammatory diseases of the airways such as asthma and allergy-related immune responses, bronchospasm, chronic obstructive pulmonary disease, chronic bronchitis, emphysema, and hiccups (hiccoughs, singultus). Silencing Nav1.7 in vivo in nodose ganglia of guinea pigs using shRNA nearly abolished the cough reflex induced by mechanical probing (Muroi et al., Am J Physiol Regul Integr Comp Physiol. 2013 Apr. 10).

One aspect of the invention is a method of alleviating or treating itch, cough or asthma in a subject by administering a therapeutically effective amount of the Protoxin-II variant of the invention disclosed herein, including in the numbered embodiments listed below to a subject in need thereof for a time sufficient to alleviate the itch, cough or asthma.

Another aspect of the invention is a method of alleviating or treating Nav1.7-mediated itch, Nav1.7-mediated cough or Nav1.7-mediated asthma in a subject by administering a therapeutically effective amount of the Protoxin-II variant of the invention disclosed herein, including in the numbered embodiments listed below to a subject in need thereof for a time sufficient to alleviate the itch, cough or asthma.

Nav1.7-mediated itch as used herein refers to itch resulting at least partially from increased Nav1.7 channel activity.

Nav1.7-mediated cough as used herein refers to cough resulting at least partially from increased Nav1.7 channel activity.

Nav1.7-mediated asthma as used herein refers to asthma resulting at least partially from increased Nav1.7 channel activity.

Protoxin-II variants of the invention disclosed herein, including in the numbered embodiments listed below may be tested for their effect in reducing or alleviating pain and/or Nav1.7-mediated pain using animal models described herein, and models such as the rat spinal nerve ligation (SNL) model of neuropathic pain, carageenan induced allodynia model, the Freund's complete adjuvant (CFA)-induced allodynia model, the thermal injury model, the formalin model and the Bennett Model, and other models as described in U.S. Pat. Appl. No. 2011/0124711 and U.S. Pat. No. 7,998,980. Carageenan induced allodynia and CFA-induced allodynia are models of inflammatory pain. The Bennett model provides an animal model for chronic pain including post-operative pain, complex regional pain syndrome, and reflex sympathetic dystrophy.

Any of the foregoing animal models may be used to evaluate the efficacy of Protoxin-II variants of the invention inhibitor in treating pain and/or NAv1.7-mediated pain. The efficacy of the Protoxin-II variants of the invention may be compared to a no treatment or placebo control. Additionally or alternatively, efficacy may be evaluated in comparison to one or more known pain-relieving medicaments.

The present invention provides methods of treating Nav1.7-mediated pain using the Protoxin-II variants of the invention disclosed herein, including in the numbered embodiments listed below. It has been discovered in the pending application by the inventors (U.S. Patent Application No. 61/781,276) that administration of Nav1.7 blocking peptides are efficacious in treating and/or alleviating pain in various animal models of pain, contrary to what was disclosed and suggested in the literature. While peptide inhibitors of Nav1.7 have been shown to be potent and/or selective towards Nav1.7 in in vitro cell culture models using overexpressed Nav1.7 or on isolated neurons in which the blood-nerve barrier is subverted through desheathing or hypertonic saline injection, they have so far proven non-efficacious in in vivo animal models of pain, where the lack of efficacy has been reported to result from the inability of the peptides to pass the blood-nerve barrier. Several publications describe lack of efficacy of Nav1.7 blocking peptides in animal models of pain or in isolated nerves. For example Hackel et al., Proc Natl Acad Sci 109:E2018-27, 2012, describes the inability of ProTx-II to inhibit action potential firing in isolated nerves unless the perineural barrier, which provides a diffusion barrier in this model, is compromised. ProTx-II was found non-efficacious in rodent models of acute and inflammatory pain; a likely explanation stated the inability of ProTx-II to cross the blood-nerve barrier (Schmalhofer et al., Mol Pharmacol 74:1476-1484, 2008). It has been proposed that Nav1.7 peptide toxin blockers have poor oral bioavailability and they are difficult to deliver to nerve endings, implying that their use as therapeutic agents remain limited (Dib-Hajj et al., Nature Rev Neuroscience 14, 49-62, 2013).

Nav1.7 is expressed in the peripheral nervous system e.g., in nociceptive dorsal root ganglions (DRG), most notably in nociceptive small-diameter DRG neurons, in particular in peripheral terminals in the skin, with little representation in the brain. Nav1.7 distribution (e.g. sensory ending) and physiology predispose it to a major role in transmitting painful stimuli.

One embodiment of the invention is a method of treating Nav1.7-mediated pain by administering a therapeutically effective amount of the Protoxin-II variant of the invention disclosed herein, including in the numbered embodiments listed below to a subject in need thereof for a time sufficient to treat the Nav1.7-mediated pain.

The Protoxin-II variants of the invention disclosed herein, including in the numbered embodiments listed below may be utilized in any therapy where it is desired to treat Nav1.7-mediated pain or other disorders of sensory or sympathetic neuron dysfunction. "Treat" or "treatment" of pain is meant to include partially or completely to prevent, stop, inhibit, reduce, or delay the perception of pain.

In some embodiments, the Nav1.7-mediated pain is chronic pain, acute pain, neuropathic pain, nociceptive pain, visceral pain, back pain, post-operative pain, thermal pain, phantom limb pain, or pain associated with inflammatory conditions, primary erythemalgia (PE), paraoxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis, or pain associated with disease and degeneration.

Neuropathic pain includes for example painful diabetic neuropathy (PDN), post-herpetic neuropathy (PHN) or trigeminal neuralgia (TN). Other causes of neuropathic pain include spinal cord injuries, multiple sclerosis, phantom limb pain, post-stroke pain and HIV-associated pain. Conditions such as chronic back pain, osteoarthritis and cancer may also result in the generation of neuropathic-related pain and thus are potentially suitable for treatment with the Protoxin-II variants of the invention.

In another embodiment, the Nav1.7-mediated pain is associated with primary erythemalgia (PE), paraoxysmal extreme pain disorder (PEPD), osteoarthritis, rheumatoid arthritis, lumbar discectomy, pancreatitis or fibromyalgia.

In the methods of the invention, the Protoxin-II variants of the invention may be conjugated to a second polypeptide to form a fusion protein. Such fusion proteins are for example the well-known Fc fusions or fusions to human serum albumin to extend half-life of the peptide inhibitors. The conjugation may be a direct conjugation via a linker, such as a glycine-serine rich linker. Such linkers are well known in the art. The Protoxin-II variants of the invention incorporating additional moieties may be compared for their Nav1.7 blocking ability and efficacy in treatment or reducing pain using well known methods and those described herein.

Other disorders of sensory or sympathetic neuron dysfunction that can be treated with the Protoxin-II variants of the invention, including asthma, cough, heart-burn, itch, dermatitis, bladder instability, and Reynaud's disease.

Pharmaceutical Compositions

The Protoxin-II variants of the invention disclosed herein, including in the numbered embodiments listed below may be formulated in a pharmaceutically acceptable vehicle or carrier. One embodiment of the invention is a pharmaceutical composition comprising the isolated Protoxin-II variant of the invention and a pharmaceutically acceptable excipient.

A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. These solutions are sterile and generally free of particulate matter, and may be sterilized by conventional, well-known sterilization techniques (e.g., filtration). The compositions may contain pharmaceutically acceptable excipients as required to approximate physiological conditions, such as pH adjusting and buffering agents, stabilizing, thickening, lubricating and coloring agents, etc. Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41).

In the methods of the invention, the Protoxin-II variants of the invention may be administered by peripheral administration. "Peripheral administration" or "administered peripherally" means introducing an agent into a subject outside of the central nervous system. Peripheral administration encompasses any route of administration other than direct administration to the spine or brain.

Peripheral administration can be local or systemic. Local administration may be used to concentrate the therapeutic to the site of action, such as local administration to joints, surgical wounds, sites of injury/trauma, peripheral nerve fibers, various organs (GI, urogenital, etc) or inflamed tissues. Systemic administration results in delivery of a pharmaceutical composition to essentially the entire peripheral nervous system of the subject and may also result in delivery to the central nervous system depending on the properties of the composition.

Routes of peripheral administration encompass, without limitation, topical administration, intravenous, subcutaneous, intra-muscular, intra-articular or other injection, and implanted mini-pumps or other extended release devices or formulations.

Compounds may also be administered directly to the central nervous system e.g., intrathecal or intracisternal administration. Continuous intrathecal administration can be achieved via the use of implanted spinal drug pumps.

Pharmaceutical compositions of the invention include formulations involving the Protoxin-II variants of the invention in sustained- or controlled-delivery formulations. These formulations may be achieved through use of for example injectable microspheres, bio-erodible particles, microemulsions, nanoparticles, nanocapsules, macroemulsions, polymeric compounds (such as polyesters, polyamino acids, hydrogels, poly(lactic acid), polyglycolic acid or ethylene vinylacetate copolymers), beads or liposomes, hyaluronic acid or implantable drug delivery devices.

The Protoxin-II variants of the invention disclosed herein, including in the numbered embodiments listed below may be prepared for use for parenteral (subcutaneous, intramuscular or intravenous), intracerebral (intra-parenchymal), intrathecal, intra-articular, intracerebroventricular, intramuscular, intra-ocular, intra-arterial, intraportal, or intralesional routes; by sustained release systems or by implantation devices, or any other administration, particularly in the form of liquid solutions or suspensions; for buccal or sublingual administration such as in the form of tablets or capsules; or intranasally such as in form of powders, nasal drops or aerosols or certain agents; transdermally in a form of a gel, ointment, lotion, cream or dusting powder, suspension or patch delivery system with chemical enhancers to either modify the skin structure or to increase the drug concentration in the transdermal patch, or with agents that enable the application of formulations containing proteins and peptides onto the skin (Int. Pat. Publ. No. WO98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402). The composition also may be administered locally via implantation of a membrane, sponge or another appropriate material onto which the desired molecule has been absorbed or encapsulated.

In certain embodiments, where an implantation device is used, the device may be implanted into any suitable tissue or organ, and delivery of the desired molecule may be via diffusion, timed-release bolus, or continuous administration.

The concentration of the Protoxin-II variants of the invention or other peptide inhibitors of Nav1.7 in such pharmaceutical formulation can vary widely, for example from about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, or between 2% to 5%, up to as much as 15%, 20%, 30%, 40%, 50%, 60% or 70% by weight and will be selected primarily based on fluid volumes, viscosities and other factors, according to the particular mode of administration selected. The Protoxin-II variants of the invention can be lyophilized for storage and reconstituted in a suitable vehicle prior to use. This technique has been shown to be effective with conventional protein preparations. Lyophilization and reconstitution techniques are well known in the art.

An exemplary pharmaceutical compositions of the present invention may comprise Tris buffer of about pH 7.0-8.5, or acetate buffer of about pH 4.0-5.5, and may further include sorbitol, sucrose, Tween-20 and/or a suitable substitute thereof.

The appropriate therapeutically effective amount may be determined readily by those skilled in the art. A therapeutically effective amount refers to an amount or dosage sufficient to produce a desired result, i.e. to partially or completely prevent, stop, inhibit, reduce, or delay the perception of pain associated with any painful medical condition. The therapeutically effective amount may vary depending on the specific vehicle and the Protoxin-II variants of the invention selected, and is also dependent on a variety of factors and conditions related to the subject to be treated and the severity of the pain. For example, factors such as age, weight and health of the subject to be administered with the pharmaceutical compositions of the invention as well as dose response curves and toxicity data obtained in preclinical animal work could be among those considered. A determined dose may, if necessary, be repeated at appropriate time intervals selected as appropriate by a physician or other person skilled in the relevant art (e.g. nurse, veterinarian, or veterinary technician) during the treatment period. The determination of an effective amount or a therapeutically effective amount for a given agent is well within the ability of those skilled in the art.

Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of a Protoxin-II variant of the invention. Similarly, a pharmaceutical composition of the invention for intravenous infusion could be made up to contain about 250 ml of sterile Ringer's solution, and about 1 mg to about 30 mg or about 5 mg to about 25 mg of the Protoxin-II variants of the invention. Actual methods for preparing parenterally administrable compositions are well known and are described in more detail in, for example, "Remington's Pharmaceutical Science", 15th ed., Mack Publishing Company, Easton, Pa.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1) An isolated Protoxin-II variant comprising the sequence $X_1X_2X_3CX_4X_5WX_6QX_7CX_8X_9X_{10}X_{11}X_{12}CCX_{13}X_{14}FX_{15}CX_{16}LWCX_{17}KKLW$ (SEQ ID NO: 403), wherein $X_1$ is G, P, A or deleted;
$X_2$ is P, A or deleted;
$X_3$ is S, Q, A, R or Y;
$X_4$ is Q, R, K, A or S;
$X_5$ is K, S, Q or R;
$X_6$ is M or F;
$X_7$ is T, S, R, K or Q;
$X_8$ is D or T;
$X_9$ is S, A or R;
$X_{10}$ is E, R, N, K, T or Q;
$X_{11}$ is R or K;
$X_{12}$ is K, Q, S or A;
$X_{13}$ is E, Q or D;
$X_{14}$ is G or Q;
$X_{15}$ is V or S;
$X_{16}$ is R or T; and
$X_{17}$ is K or R;
optionally having an N-terminal extension or a C-terminal extension,
wherein the polypeptide inhibits human Nav1.7 activity with an $IC_{50}$ value of about $1 \times 10^{-7}$ M or less,
wherein the $IC_{50}$ value is measured using a veratridine-induced depolarization inhibition assay using fluorescence resonance energy transfer (FRET) in the presence of $25 \times 10^{-6}$ M 3-veratroylveracevine in HEK293 cells stably expressing human Nav1.7.

2) The Protoxin-II variant of claim 1, wherein the N-terminal extension comprises the amino acid sequence of SEQ ID NOs: 372, 373, 374, 375, 376, 377, 378, 379, 380, 381, 382, 383, 384 or 385.

3) The Protoxin-II variant of claim 1 or 2, wherein the C-terminal extension comprises the amino acid sequence of SEQ ID NOs: 374, 386, 387, 388, 389, 390, 391, 392, 393, 394, 395, 396 or 397.

4) The Protoxin-II variant of claim 2 or 3, wherein the N-terminal and/or the C-terminal extension is conjugated to the Protoxin-II variant via a linker.

5) The Protoxin-II variant of claim 4, wherein the linker comprises the amino acid sequence of SEQ ID NOs: 383, 392, 398, 399, 400, 401 or 402.

6) The isolated Protoxin-II variant of any of the claim 1-5, comprising the amino acid sequence of SEQ ID NOs: 30, 40, 44, 52, 56, 56, 59, 65, 78, 109, 110, 111, 114, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 162, 165, 166, 167, 168, 169, 170, 171, 172, 173, 174, 175, 177, 178, 179, 180, 182, 183, 184, 185, 186, 189, 190, 193, 195, 197, 199, 206, 207, 208, 209, 210, 211, 212, 213, 214, 215, 216, 217, 218, 224, 226, 227, 231, 232, 243, 244, 245, 247, 249, 252, 255, 258, 261, 263, 264, 265, 266, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 332, 334, 335, 336, 337, 339, 340, 341, 342, 346, 351, 358, 359, 364, 366, 367, or 368.

7) The isolated Protoxin-II variant of any of the claims 1-6, that inhibits human Nav1.7 activity with an $IC_{50}$ value of about $3 \times 10^{-8}$ M or less.

8) The isolated Protoxin-II variant of claim 7 that inhibits human Nav1.7 activity with an $IC_{50}$ value of between about $3 \times 10^{-8}$ M to about $1 \times 10^{-9}$ M.

9) The isolated Protoxin-II variant of claim 7 or 8 comprising the amino acid sequence $GPQCX_1X_2WX_3QX_4CX_5X_6X_7X_8X_9CCX_{10}X_{11}FX_{12}CX_{13}LWCX_{14}KKLW$ (SEQ ID NO:404), wherein $X_1$ is Q, R, K, A or S;
$X_2$ is K, S, Q or R;
$X_3$ is M or F;
$X_4$ is T, S, R, K or Q;
$X_5$ is D or T;
$X_6$ is S, A or R;
$X_7$ is E, R, N, K, T or Q;
$X_8$ is R or K;
$X_9$ is K, Q, S or A;
$X_{10}$ is E, Q or D;
$X_{11}$ is G or Q;
$X_{12}$ is V or S;
$X_{13}$ is R or T; and
$X_{14}$ is K or R.

10) The isolated Protoxin-II variant of claim 9, comprising the amino acid sequence of SEQ ID NOs: 56, 78, 111, 114, 117, 118, 119, 122, 123, 129, 130, 131, 132, 133, 134, 135, 136, 138, 139, 140, 141, 142, 145, 146, 147, 149, 150, 151, 152, 153, 154, 156, 158, 159, 165, 172, 173, 175, 177, 178, 183, 184, 185, 186, 189, 190, 193, 197, 199, 207, 210, 211, 216, 217, 224, 266, 273, 282 or 335.

11) The isolated Protoxin-II variant of any of the claims 1-10, wherein the variant selectively inhibits human Nav1.7.

12) The isolated Protoxin-II variant of claim 11, comprising the sequence $GPX_1CQKWMQX_2CDX_3X_4RKCCX_5GFX_6CX_7LWCX_8KKLW$ (SEQ ID NO: 405); wherein $X_1$ is Y, Q, A, S or R;
$X_2$ is T or S;
$X_3$ is S, R or A;
$X_4$ is E, T or N;
$X_5$ is E or Q;
$X_6$ is V or S;
$X_7$ is R or T; and
$X_8$ is K or R.

13) The isolated Protoxin-II variant of claim 12, comprising the amino acid sequence of SEQ ID NOs: 56, 59, 65, 78, 111, 114, 117, 118, 119, 121, 122, 123, 129, 130, 133, 150, 190, 217, 281, 324, 325 or 326.

14) The isolated Protoxin-II variant of claim 12, comprising the sequence GPQCQKWMQX$_1$CDX$_2$X$_3$RKCCX$_4$GFX$_5$CX$_6$LWCX$_8$KKLW (SEQ ID NO: 406); wherein
X$_1$ is T or S;
X$_2$ is S, R or A;
X$_3$ is E, T or N;
X$_4$ is E or Q;
X$_5$ is V or S;
X$_6$ is R or T; and
X$_7$ is K or R.

15) An isolated Protoxin-II variant comprising the amino acid sequence that is 90%, 91%, 92%, 93%, 94%, 95%, 96%, 97%, 98% or 99% identical to the amino acid sequence of SEQ ID NO: 78 (GPQCQKWMQTC-DRERKCCEGFVCTLWCRKKLW-COOH), wherein
 a) the amino acid sequence has Q at position 1, Q at position 7 and F at position 19, when residue numbering is according to SEQ ID NO: 1;
 b) the polypeptide inhibits human Nav1.7 activity with an IC$_{50}$ value of about 30×10$^{-9}$ M or less, wherein the IC$_{50}$ value is measured using a veratridine-induced depolarization inhibition assay using fluorescence resonance energy transfer (FRET) in the presence of 25×10$^{-6}$ M 3-veratroylveracevine in HEK293 cells stably expressing human Nav1.7; and
 c) the polypeptide selectively inhibits Nav1.7.

16) The isolated Protoxin-II variant of any of the claims 1-15, having a free C-terminal carboxylic acid, amide, methylamide or butylamide group.

17) An isolated fusion protein comprising the Protoxin-II variant of any of the claims 1-16 conjugated to a half-life extending moiety.

18) The fusion protein of claim 17, wherein the half-life extending moiety is human serum albumin (HSA), albumin binding domain (ABD), Fc or polyethylene glycol (PEG).

19) An isolated polynucleotide encoding the Protoxin-II variant of claim 12 or 15.

20) A vector comprising the isolated polynucleotide of claim 19.

21) A host cell comprising the vector of claim 20.

22) A method of producing the isolated Protoxin-II variant, comprising culturing the host cell of claim 21 and recovering the Protoxin-II variant produced by the host cell.

23) A pharmaceutical composition comprising the isolated Protoxin-II variant of claim 1, 6, 12, 13 or 15 and a pharmaceutically acceptable excipient.

24) A method of treating Nav1.7-mediated pain in a subject, comprising administering to a subject in need thereof an effective amount of the Protoxin-II variant of any of the claims 1-16 to treat the pain.

25) The method of claim 24, wherein pain is chronic pain, acute pain, neuropathic pain, cancer pain, nociceptive pain, visceral pain, back pain, post-operative pain, thermal pain, phantom limb pain, or pain associated with inflammatory conditions, primary erythemalgia (PE), paraoxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis.

26) The method of claim 24, wherein the Protoxin-II variant is administered peripherally.

27) The method of claim 24, wherein the Protoxin-II variant is administered locally to a joint, spinal cord, surgical wound, sites of injury or trauma, peripheral nerve fibers, urogenital organs, or inflamed tissues.

28) The method of claim 24, wherein the subject is a human.

29) The Protoxin-II variant of any of the claims 1-16 for use in treating pain in a subject in need thereof.

30) The Protoxin-II variant for use according to claim 29, wherein pain is chronic pain, acute pain, neuropathic pain, cancer pain, nociceptive pain, visceral pain, back pain, post-operative pain, thermal pain, phantom limb pain, or pain associated with inflammatory conditions, primary erythemalgia (PE), paraoxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis.

31) The Protoxin-II variant for use according to claim 29 or 30, wherein the Protoxin-II variant is administered peripherally.

32) The Protoxin-II variant for use according to claim 29, 30 or 31, wherein the Protoxin-II variant is administered locally to a joint, spinal cord, surgical wound, sites of injury or trauma, peripheral nerve fibers, urogenital organs, or inflamed tissues.

The present invention will now be described with reference to the following specific, non-limiting examples.

Example 1: Design and Generation of Protoxin-II Variants

A Protoxin-II single position limited amino acid substitution scanning library was designed to assess to what degree selectivity, peptide yield, and homogeneity can be improved.

Protoxin-II variants were designed as HRV3C protease cleavable HSA fusion proteins in the following format from N- to C-terminus: 6×His-HSA-linker-HRV3C cleavable peptide-Protoxin-II variant ("6×His" disclosed as SEQ ID NO: 108); linker being (GGGGSGGGGSGGGGSGGGGS; SEQ ID NO: 80, HSA having the sequence of SEQ ID NO: 106, HRV3C cleavable peptide having the sequence of SEQ ID NO: 82). Each Protoxin-II variant, after cleavage from HSA had a residual N-terminal GP from the cleavage site.

The variants were characterized in membrane depolarization assays using FLIPR® Tetra as described in Example 3 veratridine-induced depolarization inhibition assay, and in whole cell patch clamp experiments using the QPatch assay as described in Example 3.

Combinatorial libraries were designed to test for additive effects of select single position hits in an attempt to generate Nav1.7 antagonists with further improved potency and selectivity profile compared to the native peptide.

Construction of the Expression Vectors

The designed Protoxin-II variant genes were generated using synthetic gene assembly technology as described in U.S. Pat. No. 6,521,427. The amino acid sequences of the designed peptide variants were back-translated to DNA sequences using human high-frequency codons. The DNA sequence of each variant gene, together with a portion of vector DNA including the DNA cloning sites, was synthesized as multiple oligonucleotides, some of which contained degenerate codons, and assembled into full-length DNA fragments. The assembled DNA fragments were amplified by PCR and PCR products were subsequently cloned as a pool. Pooled PCR products were digested with the appropriate restriction enzymes and cloned into the designed expression vector in such a manner as to fuse each toxin variant gene to the signal peptide and the fusion partner (6×His-HSA-linker-HRV3C cleavable peptide ("6×His" disclosed as SEQ ID NO: 108) contained in the vector. Standard molecular biology techniques were used to identify a positive clone for each designed variant. The plasmid DNA from these positive clones was purified and sequence confirmed before expressing the Protoxin-II peptide variant fusion proteins using standard methods.

Protein Expression

HEK 293-F cells were maintained in 293 Freestyle™ media (Invitrogen Cat #12338) and split when the cell concentration was between 1.5 and $2.0 \times 10^{-6}$ cells per ml. The cells were grown in suspension, shaking at 125 RPM in a humidified incubator set at 37° C. and 8% $CO_2$. HEK 293F cells were transiently transfected using a DNA/lipid complex after they were diluted to $1.0 \times 10^{-6}$ cells per ml. To generate the complex, 1.25 µg DNA per ml of transfection was diluted in 1.0 ml of OptiPro media (Invitrogen Cat #12309) and 1.25 ml of Freestyle™ Max transfection reagent (Invitrogen Cat #16447) was diluted in 1.0 ml of OptiPro media. The DNA and Max transfection reagent were mixed together and incubated for 10 minutes at room temperature before adding to the cells. Transfected cells were placed in a humidified incubator set at 37° C. and 8% $CO_2$ for 4 days shaking at 125 RPM. The supernatant was separated from the cells by centrifugation at 5,000×g for 10 minutes and filtered through a 0.2 µm filter (Corning; Cat #431153), then concentrated 10 and 50 fold using an Amicon Ultra Concentrator 10K (Cat # UFC901096), and centrifuging for approximately 10 minutes at 3,750×g.

Example 2: Purification of Protoxin-II Variants

Protoxin-II variants were expressed as HSA fusion proteins as indicated in Example 1 and the Protoxin-II variant peptides were cleaved with HRV3C protease prior to purification. Two methodologies were tested for efficient purification of the Protoxin-II variants.

Protein Purification
Purification of Protoxin-II Variants by RP-HPLC

The secreted proteins were purified from the expression supernatants via IMAC using 1 ml HisTrap HP columns (GE Healthcare Cat #17-5247-01). The chromatography method was run using an AKTA Xpress and protein was eluted from the column using a step gradient of Imidazole. Peak fractions were pooled and digested overnight with HRV 3C protease (1 µg protease/150 µg fusion).

Cleaved peptide-fusion pools were further purified using a Dionex HPLC system with a reverse phase Phenomenex Luna 5 µm C18(2) column (Cat #00B-4252-P0-AX). Samples were eluted from the column with a 0-68% Acetonitrile (0.05% TFA) linear gradient. Elution fractions were pooled, lyophilized overnight and reconstituted in HEPES buffered saline, pH 7.4 (10 mM HEPES, 137 mM NaCl, 5.4 mM KCl, 5 mM glucose, 2 mM $CaCl_2$), 1 mM $MgCl_2$).

Table 4 shows yields of Protoxin-II variants purified by RP-HPLC. The average mg yield/L was 0.01615.

TABLE 4

| Protoxin-II Variant Peptide ID | yield (mg) | Protoxin-II Variant Peptide ID | yield (mg) |
|---|---|---|---|
| NV1D816 | 0.0008 | NV1D2496 | 0.0006 |
| NV1D2511 | 0.0009 | NV1D2503 | 0.0030 |
| NV1D2513 | 0.0034 | NV1D766 | 0.0054 |
| NV1D2504 | 0.0071 | NV1D770 | 0.0040 |
| NV1D2260 | 0.0129 | NV1D772 | 0.0015 |
| NV1D2498 | 0.0079 | NV1D792 | 0.0016 |
| NV1D2499 | 0.0076 | NV1D815 | 0.0008 |
| NV1D2512 | 0.0061 | NV1D768 | 0.0060 |
| NV1D2267 | 0.0095 | NV1D2508 | 0.0017 |
| NV1D2507 | 0.0000 | NV1D2501 | 0.0008 |
| NV1D2509 | 0.0000 | NV1D2296 | 0.0018 |
| NV1D2305 | 0.0001 | NV1D2292 | 0.0059 |
| NV1D815 | 0.0021 | NV1D750 | 0.0023 |
| NV1D2506 | 0.0001 | NV1D748 | 0.0036 |
| NV1D2505 | 0.0006 | NV1D774 | 0.0050 |
| NV1D812 | 0.0001 | NV1D786 | 0.0036 |
| NV1D2510 | 0.0009 | NV1D855 | 0.0008 |
| NV1D769 | 0.0031 | NV1D2312 | 0.0011 |
| NV1D2497 | 0.0038 | NV1D1410 | 0.0074 |
| NV1D2500 | 0.0004 | NV1D1415 | 0.0128 |
| NV1D767 | 0.0004 | NV1D751 | 0.0033 |
| NV1D2502 | 0.0002 | | |

Purification of Protoxin-II Variants by Solid Phase Extraction (SPE)

The secreted proteins were purified from the expression supernatants via IMAC using 1 ml HisTrap HP columns (GE Healthcare Cat #17-5247-01). The chromatography method was run using an AKTA Xpress and protein was eluted from the column using a step gradient of Imidazole. Peak fractions were pooled and digested overnight with HRV3C protease (1 µg protease/150 µg fusion). The cleaved sample was loaded into a 50 kDa molecular weight cut off centrifugal filter unit (Millipore UFC805096) and cleaved peptide collected in the filtrate fraction.

Peptide pools were loaded onto a 96-well solid phase extraction block (Agilent Bond Elut Plexa A3969030) for further purification, desalting, and concentration. Blocks were used in conjunction with a vacuum manifold (Whatman).

Peptide samples were loaded and washed in 0.05% TFA in water and eluted with a step gradient of acetonitrile with 0.05% TFA in water. Elution fractions were then lyophilized overnight and reconstituted in HEPES buffered saline, pH 7.4 (10 mM HEPES, 137 mM NaCl, 5.4 mM KCl, 5 mM glucose, 2 mM $CaCl_2$, 1 mM $MgCl_2$) Peptides were reconstituted in supplemented HEPES buffered saline, pH 7.4 (10 mM HEPES, 137 mM NaCl, 5.4 mM KCl, 5 mM glucose, 2 mM $CaCl_2$, 1 mM $MgCl_2$) and absorbance was measured at 280 nm. Concentration values were then calculated using each sample's extinction coefficient. 2 µg of each peptide were loaded onto an Invitrogen NuPAGE® Novex® Bis-Tris Gel 15 well gel and run in MES buffer non-reduced.

Samples were analyzed on Agilent 1100 HPLC using 4-80% acetonitrile in 0.05% TFA linear gradient with a Phenomenex Luna C18(2) analytical column (Cat #00A-4041-B0). Concentrations of all peptides were normalized and 10 µl of each were injected for a total of 1.3 µg per sample. Absorbance at 220 nm was monitored and chromatograms analyzed were using Chromeleon software.

Table 5 shows yields (mg) of Protoxin-II variants purified by SPE. The average mg yield/L was 0.05353.

The benefits of the SPE purification process are ease and throughput of purification since samples are processed in parallel in a 96-well block rather than serially on RP-HPLC, and improvement in yield. There was, on average, more than 3-fold higher yield (mg/L) for variants purified by SPE versus RP-HPLC.

TABLE 5

| Protoxin-II Variant Peptide ID | yield (mg) | Protoxin-II Variant Peptide ID | yield (mg) |
|---|---|---|---|
| NV1D12 | 0.0054 | NV1D2734 | 0.0602 |
| NV1D2659 | 0.0234 | NV1D2772 | 0.2050 |
| NV1D2664 | 0.0060 | NV1D2775 | 0.2225 |
| NV1D2666 | 0.0225 | NV1D2738 | 0.0512 |
| NV1D2708 | 0.0721 | NV1D2740 | 0.0373 |
| NV1D2725 | 0.0144 | NV1D2733 | 0.1913 |
| NV1D2739 | 0.0053 | NV1D788 | 0.0000 |
| NV1D2765 | 0.0097 | NV1D757 | 0.0021 |
| NV1D2748 | 0.0995 | NV1D791 | 0.0007 |
| NV1D2771 | 0.0103 | NV1D2310 | 0.0011 |
| NV1D2770 | 0.0121 | NV1D2308 | 0.0014 |
| NV1D2778 | 0.0644 | NV1D778 | 0.0019 |
| NV1D2782 | 0.0202 | NV1D2294 | 0.0000 |
| NV1D2756 | 0.0466 | NV1D856 | 0.0047 |
| NV1D2759 | 0.0218 | NV1D2309 | 0.0023 |
| NV1D2712 | 0.0558 | NV1D846 | 0.0020 |
| NV1D12 | 0.0127 | NV1D2896 | 0.0504 |
| NV1D2673 | 0.0625 | NV1D2913 | 0.0203 |
| NV1D2662 | 0.0433 | NV1D2910 | 0.0253 |
| NV1D2669 | 0.2661 | NV1D2893 | 0.0569 |
| NV1D2665 | 0.0389 | NV1D2909 | 0.0195 |
| NV1D2731 | 0.2547 | NV1D2917 | 0.0339 |
| NV1D2767 | 0.0238 | NV1D2914 | 0.0201 |
| NV1D2730 | 0.2566 | NV1D2922 | 0.0554 |
| NV1D2766 | 0.0198 | NV1D2902 | 0.0061 |
| NV1D2667 | 0.0050 | NV1D2889 | 0.0022 |
| NV1D2769 | 0.0142 | NV1D2887 | 0.0025 |
| NV1D2719 | 0.0675 | NV1D2878 | 0.0272 |
| NV1D2776 | 0.0633 | NV1D2877 | 0.0129 |
| NV1D2663 | 0.0344 | NV1D2851 | 0.0029 |
| NV1D2709 | 0.1841 | NV1D2850 | 0.0026 |
| NV1D2720 | 0.0538 | NV1D2820 | 0.0020 |
| NV1D12 | 0.0095 | NV1D2819 | 0.0015 |
| NV1D2773 | 0.1921 | NV1D2814 | 0.0163 |
| NV1D2810 | 0.0086 | NV1D2918 | 0.0256 |
| NV1D2732 | 0.0262 | NV1D2921 | 0.0533 |
| NV1D757 | 0.0026 | NV1D2905 | 0.0126 |
| NV1D791 | 0.0206 | NV1D2906 | 0.0189 |
| NV1D2310 | 0.0085 | NV1D2881 | 0.0207 |
| NV1D2308 | 0.0179 | NV1D2882 | 0.0223 |
| NV1D778 | 0.0094 | NV1D2869 | 0.0038 |
| NV1D856 | 0.0247 | NV1D2870 | 0.0187 |
| NV1D2309 | 0.0035 | NV1D2867 | 0.0147 |
| NV1D846 | 0.0043 | NV1D2888 | 0.0045 |
| NV1D2889 | 0.0107 | NV1D2816 | 0.0133 |
| NV1D2887 | 0.0061 | NV1D2885 | 0.0025 |
| NV1D2861 | 0.0469 | NV1D2974 | 0.0418 |
| NV1D2729 | 0.1101 | NV1D2972 | 0.1089 |
| NV1D2890 | 0.0088 | NV1D2971 | 0.0407 |
| NV1D2899 | 0.0402 | NV1D2970 | 0.0557 |
| NV1D2804 | 0.0044 | NV1D2969 | 0.0799 |

Example 3: Characterization of Protoxin-II Variants

Select Protoxin-II variants were characterized in membrane depolarization and whole cell patch clamp assays to assess their potency and selectivity towards Nav1.7.

Veratridine-Induced Depolarization Inhibition Assay

The ability of the generated peptides to inhibit membrane depolarization induced by the Nav1.7 agonist veratridine (3-Veratroylveracevine; Biomol, Catalog # NA125) was measured with a veratridine-induced depolarization inhibition assay measuring decline in FRET (fluorescence resonance energy transfer) assay on a fluorescent resonance image plate reader (FLIPR® Tetra; Molecular Devices) using DISBAC2(3) (Invitrogen, K1018) as an electron acceptor and PTS18 (Trisodium 8-octadecyloxypyrene-1,3,6-trisulfonate) (Sigma) as a donor by exciting the donor at 390-420 nm and measuring FRET at 515-575 nm.

HEK293 cells stably expressing human Nav1.7 were cultured in DMEM/F-12 media (1:1), supplemented with 10% fetal bovine serum, 1% penicillin/streptomycin, 400 μg/mL geneticin and 100 μM NEAAs (all reagents from Invitrogen). 50 μL of harvested cells were plated at 25,000 cells/well into poly-lysine coated 384-well black clear bottom plates. The plates were incubated at room temperature (RT) for 15 min followed by an overnight incubation at 37° C. All incubations were done in the dark unless otherwise stated. The next day, the wells were washed 4 times with assay buffer (137 mM NaCl, 4 mM KCl, 2 mM $MgCl_2$, 2 mM $CaCl_2$, 5 mM Glucose, 10 mM HEPES, pH 7.4), and resuspended in 25 μL of assay buffer. 2× stock (6 μM) of the PTS18 dye was prepared by suspending the dye in 10% pluronic F127 in DMSO at 1:1 (v/v ratio). 25 μL of the 2×PTS18 stock was added into the wells and the cells were stained for 30 min at RT, after which the dye was washed off with the assay buffer. Peptides were suspended at 3× their final concentration in the assay buffer containing 10 μM DISBAC2(3) and 400 μM VABSC-1 to suppress background fluorescence (Sigma, cat #201987). 25 μL/well of the suspended peptides were added into each well, and incubated for 60 minutes at RT. Depolarization was induced by 25 μM final concentration of veratridine (by adding 25 μL/well of 75 μM (3×) stock solution), and the reduction in the mean intensity of FRET dye fluorescence was measured 30-100 seconds after adding the agonist. A 1.3× dilution of each measured peptide occurred after adding veratridine by convention, the concentration at the beginning of the veratridine-induced depolarization inhibition assay is reported.

Concentration-response curves of synthetic Protoxin-II (Peptide International) were constructed in each experimental series and were used as controls. Fluorescence counts for each well were converted to % response by normalizing the signal to the difference between negative control (response to agonist veratridine alone) and positive control (response to veratridine in the presence of 10 μM tetracaine) values. For measurements, "spatial uniformity correction" (all fluorescence traces are normalized to the average initial starting intensity) and "subtract bias value" (subtract the initial starting intensity from each trace) were turned on in FLIPR® Tetra. Each data point represented the response in an individual well. All individual data points were used in a non-linear least-squares fitting procedure to find the best fit to a Hill function using Origin (Microcal). $IC_{50}$ values were extracted from the resultant fitted curve. The mean responses of the positive (P) and negative (N) controls were used to calculate the % response in a well as follows: % response=100*(N−R)/(N−P).

Assay plates were accepted if the potency of control antagonists for that day were within ±0.5 log units of their historical mean.

QPatch Assay

HEK293 cells stably expressing human Nav1.5 (SEQ ID NO: 105), Nav1.7 (SEQ ID NO: 79) or Nav1.6 (SEQ ID NO: 407) were cultured in DMEM/F-12 media (1:1), supplemented with 10% fetal bovine serum, 1% penicillin/streptomycin, 400 μg/mL Geneticin and 100 μM NEAAs (all reagents from Invitrogen). Cells were maintained at 37° C. and in 5% $CO_2$ and assayed upon reaching ~50-90% confluency. CHO cells stably expressing human Nav1.6 in a tetracycline-inducible manner (SEQ ID NO: 407) were cultured in HAMs F12, supplemented with 10% fetal bovine serum, 1% penicillin/streptomycin, 10 μg/mL Blasticidin and 400 μg/mL Zeocin. Cells were maintained at 37° C. and in 5% CO2, and assayed upon reaching ~50-90% confluency. Nav1.6 expression was induced with 1 μg/ml of tetracycline, 24-48 h prior to an experiment.

Before testing in QPatch HT (Sophion), cells were first dissociated using 0.05% trypsin (5 min at 37° C.), resuspended in CHO-S-SFM media (Life Technologies) and gently triturated to break up cell clumps. Cell density was adjusted to 1-2×10⁶/mL with the same media and cells were the transferred to a cell "hotel" in QPatch HT and used in experiments for several hours. For giga-ohm seal formation and whole-cell patch clamp recording, the extracellular solution contained 137 mM NaCl, 5.4 mM KCl, 1 mM MgCl$_2$, 2 mM CaCl$_2$, 5 mM glucose, and 10 mM HEPES, pH=7.4 and osmolarity=315 mOsm. The intracellular solution contained 135 mM CsF, 10 mM CsCl, 5 mM EGTA, 5 mM NaCl and 10 mM HEPES, pH=7.3 and osmolarity=290 mOsm. The voltage protocol used in the assay was as follows. From a holding potential of −75 mV (Nav1.7), −60 mV (Nav1.6), or −105 mV (Nav1.5) cells were first hyperpolarized to −120 mV for 2 sec and then depolarized to 0 mV for 5 ms before returning to the holding potential. This protocol was repeated once every 60 sec during liquid applications (see below). Cells were otherwise held at the holding potential when the above voltage protocol was not executed. Upon establishment of the whole-cell recording configuration, a total of five applications of the extracellular solution (all containing 0.1% bovine serum albumin (BSA) with or without test compound, except for the last application, which contained 1 μM TTX or 10 mM lidocaine as a positive control) were made on to cells being recorded. The first liquid application contained only the control buffer (5 μl). The voltage protocol was executed 10 times (for a total duration of 10 min) five sec after the application. The next three liquid applications (5 μl each) contained a test compound (same compound at the same concentration for all three applications) or control buffer (for control cells only). Five seconds after each of these applications, the voltage protocol was again executed 10 times (also once per min). The last application contained positive (composed of three 10 μl sub-applications, each separated by 2 sec), five seconds after which the same voltage protocol was executed twice to obtain the baseline current. Currents were sampled at 25 kHz and filtered at 5 kHz with an 8-pole Bessle filter. The series resistance compensation level was set at 80%. For each cell, the peak current amplitude at 0 mV for each current trace in the first four liquid applications was first subtracted from that of the last trace in the presence of positive control and then normalized to that of the last trace in the first (control buffer) application as % inhibition. To control for current rundown, this (% inhibition) value for each cell in the presence of a test compound was further normalized to the average % inhibition value for control (typically 5-6) cells in the same experiment. The mean of the last two such values in the last compound application (i.e., the corrected % inhibition value for each concentration of a test compound) were taken as the % inhibition value for each cell at the particular compound concentration tested. The % inhibition values for all cells tested at each compound concentration were averaged and used in concentration response calculations. All experiments were performed at room temperature (~22° C.). Data are expressed as mean±se. Wild type Protoxin-II was included in each experiment as a positive control. Data were accepted only if the potency of Protoxin-II was within ±0.5 log units of its historical mean.

IC$_{50}$ values for Nav1.7 for select Protoxin-II variants obtained using the veratridine-induced depolarization inhibition assay are shown in Table 6.

TABLE 6

| Protein ID | Protoxin-II Variant Peptide ID | Protoxin-II variant Peptide SEQ ID NO: | hNav1.7 Veratridine-Induced Depolarization Inhibition Assay IC$_{50}$ (nM) |
|---|---|---|---|
| NV1D12_5 | NV1D12 | 2 | 4.1 ± 3.6 |
| NV1G1045 | NV1D791 | 11 | 4.8 ± 0.4 |
| NV1D1332_1 | NV1D1332 | 12 | 6.7 ± 0.5 |
| NV1D1336_1 | NV1D1336 | 14 | 10.5 ± 1.2 |
| NV1D1337_1 | NV1D1337 | 15 | 10.3 ± 1.0 |
| NV1G1049 | NV1D2308 | 16 | 4.5 ± 0.4 |
| NV1G953 | NV1D2670 | 17 | 22.2 ± 3.3 |
| NV1G951 | NV1D2674 | 18 | 4.0 ± 0.2 |
| NV1G963 | NV1D2671 | 20 | 31.5 ± 6.4 |
| NV1G949 | NV1D2675 | 21 | 4.3 ± 0.3 |
| NV1G977 | NV1D2665 | 22 | 4.9 ± 0.4 |
| NV1G957 | NV1D2668 | 23 | 17.5 ± 2.6 |
| NV1G965 | NV1D2672 | 24 | 4.5 ± 0.3 |
| NV1G973 | NV1D2662 | 25 | 4.0 ± 0.4 |
| NV1G975 | NV1D2669 | 26 | 18.4 ± 5.7 |
| NV1G971 | NV1D2673 | 27 | 4.3 ± 0.5 |
| NV1G995 | NV1D2663 | 28 | 4.2 ± 0.4 |
| NV1G961 | NV1D2676 | 29 | 26.5 ± 2.9 |
| NV1G911 | NV1D2666 | 30 | 66.5 ± 36.7 |
| NV1G1133 | NV1D2816 | 31 | 667 ± 93.6 |
| NV1G905 | NV1D2735 | 32 | 60.0 ± 16.2 |
| NV1G979 | NV1D2731 | 34 | 20.7 ± 7.2 |
| NV1G1097 | NV1D2810 | 35 | 339 ± 5750 |
| NV1G1099 | NV1D2732 | 36 | 126 ± 26.9 |
| NV1G1011 | NV1D2740 | 37 | 3.6 ± 9.9 |
| NV1G1105 | NV1D2729 | 39 | 8.0 ± 0.9 |
| NV1G1013 | NV1D2733 | 40 | 7.5 ± 2.9 |
| NV1G1095 | NV1D2814 | 41 | 754 ± 51.3 |
| NV1G983 | NV1D2730 | 43 | 25.5 ± 4.3 |
| NV1G1003 | NV1D2734 | 44 | 13.4 ± 0.8 |
| NV1G1009 | NV1D2738 | 45 | 2.6 ± 0.2 |
| NV1G1129 | NV1D2867 | 49 | >1000 |
| NV1G1121 | NV1D2881 | 50 | 488 ± 72.2 |
| NV1G1123 | NV1D2882 | 51 | 857 ± 65.7 |
| NV1G899 | NV1D2774 | 52 | 50.5 ± 15.2 |
| NV1G1103 | NV1D2861 | 54 | >1000 |
| NV1G1127 | NV1D2870 | 55 | 784 ± 84.8 |
| NV1G1007 | NV1D2775 | 56 | 25.4 ± 2.0 |
| NV1G1067 | NV1D2893 | 57 | 75.5 ± 10.5 |
| NV1G1005 | NV1D2772 | 59 | 15.6 ± 1.8 |
| NV1G1061 | NV1D2896 | 60 | 80.3 ± 7.1 |
| NV1G1085 | NV1D2877 | 61 | 441 ± 73.3 |
| NV1G1083 | NV1D2878 | 62 | 680 ± 40.7 |
| NV1G1079 | NV1D2889 | 64 | 12.1 ± 1.5 |
| NV1G1001 | NV1D2773 | 65 | 18.8 ± 1.5 |
| NV1G1107 | NV1D2890 | 66 | 25.8 ± 4.2 |
| NV1G1109 | NV1D2899 | 67 | 33.3 ± 6.7 |
| NV1G1117 | NV1D2905 | 68 | 713 ± 87.3 |
| NV1G1119 | NV1D2906 | 69 | 940 ± 86.7 |
| NV1G1115 | NV1D2921 | 70 | 586 ± 71.7 |
| NV1G1075 | NV1D2922 | 71 | 204 ± 45.7 |
| NV1G1069 | NV1D2909 | 72 | 97.1 ± 10.1 |
| NV1G1065 | NV1D2910 | 73 | 441 ± 41.7 |
| NV1G1063 | NV1D2913 | 74 | 79.7 ± 9.3 |
| NV1G1073 | NV1D2914 | 75 | 135 ± 7.8 |
| NV1G1071 | NV1D2917 | 76 | 197 ± 48.3 |
| NV1G1113 | NV1D2918 | 77 | 983 ± 98.7 |
| NV1G1153 | NV1D3034 | 78 | 10.3 ± 2.1 |

Select Protoxin-II variants were tested for selectivity against human Nav1.5 using QPatch. IC$_{50}$ values for both Nav1.7 and Nav1.5 for select peptides obtained using QPatch are shown in Table 7.

TABLE 7

| Protein ID | Protoxin-II Variant Peptide ID | Protoxin-II variant Peptide SEQ ID NO: | hNav1.7 QPatch IC$_{50}$ (nM) | hNav1.5 IC$_{50}$ (nM) |
|---|---|---|---|---|
| NV1D12_5 | NV1D12 | 2 | 2.2 ± 1.3 | >1000 |
| NV1G899 | NV1D2774 | 52 | 18.7 ± 13.6 | >3000 |
| NV1G1007 | NV1D2775 | 56 | 4.0 ± 8.9 | >3000 |
| NV1G1005 | NV1D2772 | 59 | 6.2 ± 3.2 | >3000 |
| NV1G1001 | NV1D2773 | 65 | 4.3 ± 3.3 | >3000 |
| NV1G1153 | NV1D3034 | 78 | 4.3 ± 4.3 | >1000 |

Example 4. Generation and Characterization of Combinatorial Protoxin-II Variants Combinatorial libraries were designed to test for additive effects of select single position hits in an attempt to generate Nav1.7 antagonists with further improved potency and selectivity profile compared to the native peptide using several approaches.

A limited amino acid scan was conducted at all non-cysteine Protoxin-II positions using A, D, Q, R, K and S for diversification. In these experiments, Protoxin-II was expressed and tested as monovalent Fc fusion protein as described in Example 1. From this scan, substitutions Y1Q, W7Q, S11A, were identified that improved potency and/or selectivity of the resulting variants.

A full amino acid scan (excluding cys and trp) at positions M6 and M19 was also conducted. M19F substitution was identified from this scan that improved potency and/or selectivity of the resulting variants.

Protoxin-II/Huwentoxin-IV single position chimeras were designed bidirectionally. The purpose of this library was to obtain Protoxin-II variants that retained potency and selectivity profile of the wild type Protoxin-II and would achieve beneficial refolding properties associated with Huwentoxin-IV. Substitutions R22T and E12N were identified from this scan.

Peptide NV1G1153 was further engineered by diversifying position Y1 by a limited amino acid scan using R, K, T, A, D, E, Q and S, and by charge cluster engineering, where all sets of charged residues in the three-dimensional structure of the peptide (D10/E12, K4/E17, D10/E12/R13) were mutated.

N- and C-terminal extensions were introduced to select peptides, including NV1G1153 with the purpose of improving peptide distribution to the site of action and of improving half-life of the peptides without significantly increasing the molecular weight of the resulting peptide. The N- and C-terminal extensions that were used are shown in Table 8 and 9, respectively, and are described in Oi et. al., Neuroscience Letters 434, 266-272, 2008; Whitney et. al., Nature Biotechnology 2011 29:4, 352-356; Sockolosky et. al., (2012) 109:40, 16095-16100. Cell penetrating peptides HIV Tat and polyarginine were also used. Various linkers were used to couple the Protoxin-II variant to the N- and/or C-terminal extensions. The linkers used are shown in Table 10.

Protoxin-II variants from each campaign were tested for their potency and selectivity for Nav1.7 using methods described in Example 3. The amino acid sequences of the variants that inhibited Nav1.7 with an IC$_{50}$ value of 200 nM or less are shown in Table 3. Table 11 shows the amino acid substitutions in select variant when compared to the wild type Protoxin-II, and the IC$_{50}$ values for Nav1.7 inhibition in the veratridine-induced depolarization inhibition assay.

TABLE 8

N-terminal extension

| Amino acid sequence | SEQ ID NO: |
|---|---|
| GPAAAAA | 372 |
| GPAPAPA | 373 |
| GGGGG | 374 |
| GPCCNCSSKWCRDHSRCC | 375 |
| GPSPGARAF | 376 |
| GPDGPWRKM | 377 |
| GPFGQKASS | 378 |
| GPCRTIGPSVC | 379 |
| GPSHSNTQTLAKAPEHTG | 380 |
| GPQRFVTGHFGGLYPANG | 381 |
| GPGWCGDPGATCGKLRLYCCSGFCDSYTKTCKDKSSA | 382 |
| APAPAPAPAP | 383 |
| GPYGRKKRRQRRR | 384 |
| GPRRRRRRRRRRR | 385 |

TABLE 9

C-terminal extensions

| Amino acid sequence | SEQ ID NO: |
|---|---|
| CRTIGPSVC | 386 |
| YGRKKRRQRRR | 387 |
| GGGGG | 374 |
| DGPWRKM | 388 |
| CCNCSSKWCRDHSRCC | 389 |
| RRRRRRRRRR | 390 |
| SHSNTQTLAKAPEHTG | 391 |
| APAPA | 392 |
| AAAAA | 393 |
| FGQKASS | 394 |
| QRFVTGHFGGLYPANG | 395 |
| SPGARAF | 396 |
| GPGWCGDPGATCGKLRLYCCSGFCDAYTKTCKDKSSA | 397 |

TABLE 10

| Linkers | |
|---|---|
| Amino acid sequence | SEQ ID NO: |
| GSAPAPAPAPAPGS | 398 |
| GSAPAPAPAPAPAPAPAPAPAPGS | 399 |
| GGGGSAPAPAPAPAPAPAPAPAPAPAPAPAPAPAPAPAPGGGGS | 400 |
| APAPA | 392 |
| GSGGGGSAPAPAPAPAPAPAPAPAPAPGGGGSGS | 401 |
| APAPAPAPAP | 383 |
| APAPAPAPAPAPAPAPAPAP | 402 |

TABLE 11

| Protein name | Protoxin-II variant peptide name | Protein SEQ ID NO: | Substitutions | Nav1.7 $IC_{50}$ (nM) | SE |
|---|---|---|---|---|---|
| NV1G1728 | NV1D3541 | 281 | Y1A, W7Q, S11R, E12N, M19F, R22T, K26R | 9.4 | 1.2 |
| NV1G1870 | NV1D3583 | 321 | Y1A, W7Q, S11A, E12R, M19F, V20S | 13.1 | 1.57 |
| NV1G1752 | NV1D3532 | 272 | Y1A, W7Q, S11A, E12K, M19F, R22T, K26R | 17.3 | 2 |
| NV1G1749 | NV1D3587 | 326 | Y1A, W7Q, S11A, E12N, M19F, V20S | 18.3 | 2.6 |
| NV1G1725 | NV1D3572 | 310 | Y1A, W7Q, S11A, E12R, M19F, R22T | 19.8 | 2.2 |
| NV1G1745 | NV1D3537 | 277 | Y1A, W7Q, S11A, E12K, M19F, V20S, R22T, K26R | 21.4 | 4.1 |
| NV1G1720 | NV1D3565 | 304 | Y1A, W7Q, S11A, E12R, M19F, V20S, R22T | 23 | 2.8 |
| NV1G1761 | NV1D3550 | 290 | Y1A, W7Q, S11R, M19F, R22T, K26R | 25.8 | 2.7 |
| NV1G1746 | NV1D3576 | 314 | Y1A, W7Q, S11A, E12N, M19F, R22T | 26.7 | 5.2 |
| NV1G979 | NV1D2731 | 34 | Y1A, W7Q, S11A | 20.7 | 7.2 |
| NV1G953 | NV1D2670 | 17 | Y1A, W7Q | 22.2 | 3.3 |
| NV1G1519 | NV1D3006 | 133 | Y1Q, W7Q, S11A, E12R, M19F | 4.03 | 1.05 |
| NV1G1007-NH2 | NV1D2775-NH2 | 111 | Y1Q, W7Q, S11A, M19F | 5.06 | 0.473 |
| NV1G1517 | NV1D3004 | 131 | Y1Q, W7Q, S11R, M19F | 6.23 | 1.56 |
| (-GP) N-Ac-NV1G1137-NH2 | (-GP) N-Ac-NV1D2974-NH2 | 114 | Y1Q, W7Q, S11A, M19F, V20S, R22T | 6.43 | 1.06 |
| NV1G1776 | NV1D3339 | 172 | Y1Q, Q3R, W7Q, S11R, M19F, R22T, K26R | 6.57 | 0.675 |
| NV1G1153-NH-methyl | NV1D3034-NH-methyl | 119 | Y1Q, W7Q, S11R, M19F, R22T, K26R | 7.1 | 0.9 |
| (-GP) N-Ac-NV1G1153-NH2 | (-GP) N-Ac-NV1D3034-NH2 | 121 | Y1Q, W7Q, S11R, M19F, R22T, K26R | 7.63 | 1.04 |
| NV1G1523 | NV1D3012 | 135 | Y1Q, W7Q, S11R, E12N, M19F | 7.74 | 0.904 |
| NV1G1515 | NV1D3005 | 132 | Y1Q, W7Q, S11A, E12N, M19F | 7.83 | 1.38 |
| NV1G1187 | NV1D3015 | 138 | Y1Q, W7Q, S11R, M19F, K26R | 8.86 | 2.28 |
| NV1G1521 | NV1D3018 | 141 | Y1Q, W7Q, S11A, E12N, M19F, K26R | 9.79 | 2.91 |
| NV1G1267 | NV1D3044 | 150 | Y1Q, W7Q, S11R, E12N, M19F, R22T, K26R | 9.8 | 0.849 |
| NV1G1153 | NV1D3034 | 78 | Y1Q, W7Q, S11R, M19F, R22T, K26R | 10.3 | 2.14 |
| NV1G1836 | NV1D3359 | 190 | Y1Q, W7Q, T8S, S11R, M19F, R22T, K26R | 10.5 | 0.739 |
| NV1G1593 | NV1D3050 | 153 | Y1Q, W7Q, S11R, E12K, M19F | 10.8 | 1.3 |
| NV1G1215 | NV1D3048 | 152 | Y1Q, W7Q, S11A, E12K, M19F | 11.1 | 1.05 |
| NV1G1868 | NV1D3353 | 185 | Y1Q, W7Q, T8R, S11R, M19F, R22T, K26R | 11.2 | 1.25 |
| NV1G1525 | NV1D3013 | 136 | Y1Q, W7Q, S11R, E12R, M19F | 11.3 | 1.83 |
| NV1G1775 | NV1D3340 | 173 | Y1Q, Q3K, W7Q, S11R, M19F, R22T, K26R | 11.5 | 0.798 |
| NV1G1833 | NV1D3381 | 210 | Y1Q, W7Q, S11RK14Q, M19F, R22T, K26R | 12.2 | 1.56 |
| NV1G1153-NH2 | NV1D3034-NH2 | 117 | Y1Q, W7Q, S11R, M19F, R22T, K26R | 12.2 | 1 |
| NV1G1777 | NV1D3342 | 175 | Y1Q, Q3A, W7Q, S11R, M19F, R22T, K26R | 12.8 | 2.67 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1259 | NV1D3058 | 158 | Y1Q, W7Q, S11A, E12K, M19F, R22T, K26R | 12.9 | 1.29 |
| NV1G1511 | NV1D3032 | 146 | Y1Q, W7Q, S11R, E12N, M19F, K26R | 13 | 203 |
| NV1G1527 | NV1D3031 | 145 | Y1Q, W7Q, S11R, E12R, M19F, R22T | 13 | 1.36 |
| NV1G1265 | NV1D3062 | 159 | Y1Q, W7Q, S11R, E12K, M19F, R22T, K26R | 13.2 | 1.43 |
| NV1G1781 | NV1D3388 | 217 | Y1Q, W7Q, S11RE17Q, M19F, R22T, K26R | 13.5 | 1.14 |
| NV1G1824 | NV1D3354 | 186 | Y1Q, W7Q, T8K, S11R, M19F, R22T, K26R | 13.9 | 1.12 |
| NV1G1772 | NV1D3352 | 184 | Y1Q, K4S, W7Q, S11R, M19F, R22T, K26R | 14.2 | 2.01 |
| NV1G1509 | NV1D3033 | 147 | Y1Q, W7Q, S11R, E12R, M19F, K26R | 14.5 | 2.18 |
| NV1G1779 | NV1D3351 | 183 | Y1Q, K4Q, W7Q, S11R, M19F, R22T, K26R | 15.3 | 2.39 |
| NV1G1687 | NV1D3526 | 266 | Y1Q, W7Q, S11R, M19F, R22T, K26R | 15.4 | |
| NV1G1269 | NV1D3045 | 151 | Y1Q, W7Q, S11R, E12R, M19F, R22T, K26R | 15.6 | 1.39 |
| NV1G1623 | NV1D3056 | 156 | Y1Q, W7Q, S11R, E12K, M19F, R22T | 16.2 | 2.99 |
| NV1G1859 | NV1D3376 | 205 | Y1Q, W7Q, S11R, K14R, M19F, R22T, K26R | 16.3 | 2.53 |
| NV1G1153-NH-butyl | NV1D3034-NH-butyl | 118 | Y1Q, W7Q, S11R, M19F, R22T, K26R | 16.6 | 1.4 |
| NV1G1211 | NV1D3036 | 149 | Y1Q, W7Q, S11A, E12R, M19F, R22T, K26R | 17.2 | 1.55 |
| NV1G1885 | NV1D3254 | 165 | Y1Q, W7Q, S11A, M19F | 17.5 | 2.45 |
| NV1G1730 | NV1D3542 | 282 | Y1Q, W7Q, S11R, E12N, M19F, V20S, R22T, K26R | 17.7 | 2.5 |
| NV1G1263 | NV1D3051 | 154 | Y1Q, W7Q, S11A, E12K, M19F, R22T | 17.9 | 1.78 |
| NV1G1818 | NV1D3368 | 122 | Y1Q, W7Q, S11R, E12T, M19F, R22T, K26R | 17.9 | 1.89 |
| NV1G1153 (synthetic) | NV1D3034 | 116 | Y1Q, W7Q, S11R, M19F, R22T, K26R | 18 | 2.5 |
| NV1G1823 | NV1D3367 | 197 | Y1Q, W7Q, S11R, E12Q, M19F, R22T, K26R | 18.6 | 2.17 |
| NV1G1820 | NV1D3362 | 193 | Y1Q, W7Q, D10T, S11R, M19F, R22T, K26R | 20.1 | 2.32 |
| NV1G1811 | NV1D3369 | 199 | Y1Q, W7Q, S11R, R13K, M19F, R22T, K26R | 20.4 | 2.44 |
| NV1G1810 | NV1D3358 | 189 | Y1Q, W7Q, T8Q, S11R, M19F, R22T, K26R | 20.5 | 2.11 |
| NV1G1818-NH2 | NV1D3368-NH2 | 123 | Y1Q, W7Q, S11R, E12T, M19F, R22T, K26R | 20.5 | 2.8 |
| NV1G1137 (synthetic) | NV1D2974 | 129 | Y1Q, W7Q, S11A, M19F, V20S, R22T | 21.6 | 1.34 |
| NV1G1221 | NV1D3017 | 140 | Y1Q, W7Q, S11A, E12R, M19F, R22T | 21.9 | 2.48 |
| NV1G1722 | NV1D3533 | 273 | Y1Q, W7Q, S11A, E12K, M19F, V20S, R22T, K26R | 22.4 | 3.5 |
| NV1G1767 | NV1D3345 | 177 | Y1Q, Q3S, W7Q, S11R, M19F, R22T, K26R | 22.4 | 2.52 |
| NV1G1769 | NV1D3346 | 178 | Y1Q, K4R, W7Q, S11R, M19F, R22T, K26R | 23.2 | 3.39 |
| NV1G1780 | NV1D3387 | 216 | Y1Q, W7Q, S11R, E17D, M19F, R22T, K26R | 23.7 | 2.85 |
| NV1G1886 | NV1D3249 | 162 | Y1Q, W7Q, S11A, M19F | 24.1 | 11.5 |
| NV1G1812 | NV1D3382 | 211 | Y1Q, W7Q, S11R, K14S, M19F, R22T, K26R | 24.3 | 2.14 |
| NV1G1857 | NV1D3366 | 196 | Y1Q, W7Q, D10S, S11R, M19F, R22T, K26R | 24.6 | 3.8 |
| NV1G1821 | NV1D3378 | 207 | Y1Q, W7Q, S11R, K14A, M19F, R22T, K26R | 24.8 | 2.66 |
| NV1G1993 | NV1D3792 | 335 | Y1Q, W7Q, S11R, M19F, R22T, K26R | 25.3 | 2.8 |
| NV1G1007 | NV1D2775 | 56 | Y1Q, W7Q, S11A, M19F | 25.4 | 2 |
| NV1G1787 | NV1D3396 | 224 | Y1Q, W7Q, S11R, G18Q, M19F, R22T, K26R | 26.4 | 3.17 |
| NV1G1257 | NV1D3016 | 139 | Y1Q, W7Q, S11A, E12N, M19F, R22T | 26.6 | 3.1 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1153 (synthetic) | NV1D3034 | 116 | Y1Q, W7Q, S11R, M19F, R22T, K26R | 27.3 | 2.02 |
| NV1G1803 | NV1D3403 | 230 | Y1Q, W7Q, S11R, M19F, R22T, K26R, K27A | 28.3 | 1.97 |
| (-GP) N-Ac-NV1G1137 | N-Ac-NV1D2974 | 115 | Y1Q, W7Q, S11A, M19F, V20S, R22T | 28.6 | 2.23 |
| NV1G1531 | NV1D3019 | 142 | Y1Q, W7Q, S11A, E12R, M19F, K26R | 28.7 | 4.78 |
| NV1G1513 | NV1D3007 | 134 | Y1Q, W7Q, S11A, M19F, K26R | 29.6 | 9.17 |
| NV1G1991 | NV1D3789 | 333 | Y1Q, W7Q, S11R, M19F, R22T, K26R | 29.9 | 5.19 |
| NV1G1013 | NV1D2733 | 40 | Y1R, W7Q, M19F | 7.54 | 2.9 |
| NV1G1740 | NV1D3580 | 318 | Y1R, W7Q, S11A, E12R, M19F, V20S | 8.4 | 1.5 |
| NV1G1757 | NV1D3538 | 278 | Y1R, W7Q, S11R, E12N, M19F, R22T, K26R | 11.6 | 1.4 |
| NV1G1741 | NV1D3569 | 307 | Y1R, W7Q, S11A, E12R, M19F, R22T | 11.9 | 0.8 |
| NV1G1715 | NV1D3584 | 322 | Y1R, W7Q, S11A, E12N, M19F, V20S | 13.9 | 1.4 |
| NV1G1754 | NV1D3529 | 269 | Y1R, W7Q, S11A, E12K, M19F, R22T, K26R | 14.6 | 1.7 |
| NV1G1005 | NV1D2772 | 59 | Y1R, W7Q, S11A, M19F | 15.6 | 1.8 |
| NV1G1733 | NV1D3577 | 315 | Y1R, W7Q, S11A, M19F, V20S | 18.8 | 2.2 |
| NV1G1744 | NV1D3534 | 274 | Y1R, W7Q, S11A, E12K, M19F, V20S, R22T, K26R | 20.6 | 2.2 |
| NV1G1724 | NV1D3562 | 301 | Y1R, W7Q, S11A, E12R, M19F, V20S, R22T | 23.6 | 2.7 |
| NV1G1735 | NV1D3566 | 305 | Y1R, W7Q, S11A, M19F, R22T | 23.7 | 2.5 |
| NV1G1760 | NV1D3543 | 283 | Y1R, W7Q, S11R, E12N, M19F, V20S, R22T, K26R | 23.8 | 1.9 |
| NV1G1759 | NV1D3547 | 287 | Y1R, W7Q, S11R, M19F, R22T, K26R | 26.5 | 2.1 |
| NV1G1751 | NV1D3558 | 297 | Y1R, W7Q, S11A, E12N, M19F, V20S, R22T | 26.7 | 3.4 |
| NV1G1726 | NV1D3551 | 291 | Y1R, W7Q, S11R, M19F, V20S, R22T, K26R | 29.3 | 3.8 |
| NV1G1105 | NV1D2729 | 39 | Y1R, W7Q, S11A | 8 | 8.85E−01 |
| NV1G957 | NV1D2668 | 23 | Y1R, W7Q | 17.5 | 2.6 |
| (-GP) NV1G1001 | (-GP) NV1D2773 | 109 | Y1S, W7Q, S11A, M19F | 9.47 | 1.28 |
| (-GP) NV1G1001-NH-methyl | (-GP) NV1D2773-NH-methyl | 110 | Y1S, W7Q, S11A, M19F | 11.5 | 0.61 |
| NV1G1003 | NV1D2734 | 44 | Y1S, W7Q, M19F | 13.4 | 0.8 |
| NV1G1864 | NV1D3581 | 319 | Y1S, W7Q, S11A, E12R, M19F, V20S | 14.6 | 1.7 |
| NV1G1748 | NV1D3530 | 270 | Y1S, W7Q, S11A, E12K, M19F, R22T, K26R | 15.6 | 2.2 |
| NV1G1758 | NV1D3548 | 288 | Y1S, W7Q, S11R, M19F, R22T, K26R | 17.6 | 1.9 |
| NV1G1727 | NV1D3544 | 284 | Y1S, W7Q, S11R, E12N, M19F, V20S, R22T, K26R | 17.8 | 2.2 |
| NV1G1719 | NV1D3570 | 308 | Y1S, W7Q, S11A, E12R, M19F, R22T | 18.1 | 1.5 |
| NV1G1742 | NV1D3535 | 275 | Y1S, W7Q, S11A, E12K, M19F, V20S, R22T, K26R | 18.7 | 2.8 |
| NV1G1001 | NV1D2773 | 65 | Y1S, W7Q, S11A, M19F | 18.8 | 1.5 |
| NV1G1753 | NV1D3585 | 323 | Y1S, W7Q, S11A, E12N, M19F, V20S | 19.4 | 2.1 |
| NV1G1762 | NV1D3539 | 279 | Y1S, W7Q, S11R, E12N, M19F, R22T, K26R | 19.4 | 1.8 |
| NV1G1755 | NV1D3574 | 312 | Y1S, W7Q, S11A, E12N, M19F, R22T | 22.3 | 2.7 |
| NV1G1717 | NV1D3563 | 302 | Y1S, W7Q, S11A, E12R, M19F, V20S, R22T | 22.4 | 2.4 |
| NV1G1866 | NV1D3559 | 298 | Y1S, W7Q, S11A, E12N, M19F, V20S, R22T | 26.5 | 5.02 |
| NV1G1721 | NV1D3552 | 292 | Y1S, W7Q, S11R, M19F, V20S, R22T, K26R | 28.1 | 3.7 |
| NV1G975 | NV1D2669 | 26 | Y1S, W7Q | 18.4 | 5.7 |
| NV1G983 | NV1D2730 | 43 | Y1S, W7Q, S11A | 25.5 | 4.3 |
| NV1G1750-NH2 | NV1D3586-NH2 | 325 | W7Q, S11A, E12N, M19F, V20S | 4.23 | 0.33 |
| NV1G1747 | NV1D3531 | 271 | W7Q, S11A, E12K, M19F, R22T, K26R | 13 | 2.1 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1763 | NV1D3540 | 280 | W7Q, S11R, E12N, M19F, R22T, K26R | 16 | 1.5 |
| NV1G1739 | NV1D3582 | 320 | W7Q, S11A, E12R, M19F, V20S | 17.8 | 2.2 |
| NV1G1750 | NV1D3586 | 324 | W7Q, S11A, E12N, M19F, V20S | 20.5 | 2.2 |
| NV1G1718 | NV1D3571 | 309 | W7Q, S11A, E12R, M19F, R22T | 21 | 2.3 |
| NV1G1865 | NV1D3560 | 299 | W7Q, S11A, E12N, M19F, V20S, R22T | 27.2 | 3.42 |
| NV1G1766 | NV1D3549 | 289 | W7Q, S11R, M19F, R22T, K26R | 27.5 | 3.2 |
| NV1G961 | NV1D2676 | 29 | W7Q, S11A | 26.5 | 2.9 |
| NV1G951 | NV1D2674 | 18 | Y1A, S11A | 4.03 | 0.2 |
| NV1G1011 | NV1D2740 | 37 | Y1Q, S11A, M19F | 3.62 | 9.9 |
| NV1G977 | NV1D2665 | 22 | Y1Q, M19F | 4.9 | 0.4 |
| NV1G949 | NV1D2675 | 21 | Y1Q, S11A | 4.33 | 0.3 |
| NV1G973 | NV1D2662 | 25 | Y1R, M19F | 4.03 | 0.4 |
| NV1G965 | NV1D2672 | 24 | Y1R, S11A | 4.5 | 0.3 |
| NV1G1009 | NV1D2738 | 45 | Y1S, S11A, M19F | 2.57 | 0.2 |
| NV1G995 | NV1D2663 | 28 | Y1S, M19F | 4.19 | 0.4 |
| NV1G1107-NH2 | NV1D2890-NH2 | 112 | Y1S, M6F, S11A, M19L | 9.12 | 1.17 |
| NV1G971 | NV1D2673 | 27 | Y1S, S11A | 4.31 | 0.5 |
| NV1G1782 | NV1D3383 | 212 | Y1Q, W7Q, S11R, E17R, M19F, R22T, K26R, | 30.3 | 4.06 |
| NV1G1990 | NV1D3788 | 332 | Y1Q, W7Q, S11R, M19F, R22T, K26R, | 30.3 | 4.78 |
| (-GP) N-Ac-NV1G1153- | (-GP) N-Ac-NV1D3034 | 120 | Y1Q, W7Q, S11R, M19F, R22T, K26R | 30.4 | 2.96 |
| NV1G1786 | NV1D3389 | 218 | Y1Q, W7Q, S11R, E17S, M19F, R22T, K26R, | 30.8 | 4.48 |
| NV1G1147 | NV1D2969 | 124 | Y1S, W7Q, S11A, M19F, V20S | 31 | 6.15 |
| NV1G1764 | NV1D3554 | 294 | Y1A, W7Q, S11R, M19F, V20S, R22T, K26R | 31.4 | 3.3 |
| NV1G963 | NV1D2671 | 20 | Y1Q, W7Q | 31.5 | 6.4 |
| NV1G1835 | NV1D3379 | 208 | Y1Q, K4D, W7Q, S11R, M19F, R22T, K26R | 31.6 | 2.88 |
| NV1G1231 | NV1D3035 | 148 | Y1Q, W7Q, S11A, E12N, M19F, R22T, K26R | 32 | 4.9 |
| NV1G1743 | NV1D3564 | 303 | W7Q, S11A, E12R, M19F, V20S, R22T | 32.3 | 3.1 |
| NV1G1960 | NV1D3803 | 345 | Y1Q, W7Q, S11R, M19F, R22T, K26R | 32.3 | 5.33 |
| NV1G1924 | NV1D3470 | 250 | Y1Q, W7Q, S11R, M19L, R22T, K26R | 32.5 | 403 |
| NV1G1756 | NV1D3575 | 313 | W7Q, S11A, E12N, M19F, R22T | 33.2 | 3.9 |
| NV1G1109 | NV1D2899 | 67 | Y1S, W7Q, S11A, M19L | 33.3 | 6.7 |
| NV1G1818 | NV1D3368 | 122 | Y1Q, W7Q, S11R, E12T, M19F, R22T, K26R | 33.5 | 10.7 |
| NV1G1784 | NV1D3386 | 215 | Y1Q, W7Q, S11R, E17A, M19F, R22T, K26R | 33.6 | 4.71 |
| NV1G1141 | NV1D2972 | 127 | Y1Q, W7Q, S11A, M19F, V20S | 34.1 | 6.2 |
| NV1G1774 | NV1D3347 | 179 | Y1Q, K4T, W7Q, S11R, M19F, R22T, K26R | 34.2 | 5.99 |
| NV1G1881 | NV1D3257 | 167 | Y1Q, W7Q, S11A, M19F | 34.2 | 2.81 |
| NV1G1915 | NV1D3467 | 249 | Y1Q, W7Q, S11R, E17G, M19F, R22T, K26R | 34.5 | 4 |
| NV1G1984 | NV1D3806 | 348 | Y1Q, W7Q, S11R, M19F, R22T, K26R | 35.1 | 4.56 |
| NV1G1716 | NV1D3561 | 300 | Y1A, W7Q, S11A, E12N, M19F, V20S, R22T, | 35.6 | 5 |
| NV1G1255 | NV1D3014 | 137 | Y1Q, W7Q, S11R, M19F, R22T | 36.1 | 5.37 |
| NV1G1959 | NV1D3818 | 357 | Y1Q, W7Q, S11R, M19F, R22T, K26R | 36.3 | 204 |
| NV1G1825 | NV1D3377 | 206 | Y1Q, W7Q, S11R, K14T, M19F, R22T, K26R | 36.4 | 4.83 |
| NV1G1723 | NV1D3536 | 276 | W7Q, S11A, E12K, M19F, V20S, R22T, K26R | 37 | 5.4 |
| NV1G1732 | NV1D3555 | 295 | Y1R, W7Q, S11A, M19F, V20S, R22T, | 37.4 | 4.3 |
| NV1G1983 | NV1D3809 | 350 | Y1Q, W7Q, S11R, M19F, R22T, K26R | 38.9 | 4.81 |
| NV1G1982 | NV1D3805 | 347 | Y1Q, W7Q, S11R, M19F, R22T, K26R | 41.2 | 5.44 |
| NV1G1785 | NV1D3385 | 214 | Y1Q, W7Q, S11R, E17T, M19F, R22T, K26R | 41.5 | 6.5 |
| NV1G1583 | NV1D3030 | 144 | Y1Q, W7Q, S11R, E12N, M19F, R22T | 41.9 | 5.15 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1729 | NV1D3545 | 285 | W7Q, S11R, E12N, M19F, V20S, R22T, K26R | 42.8 | 4.6 |
| NV1G1007 | NV1D2775 | 56 | Y1Q, W7Q, S11A, M19F | 42.9 | 6.7 |
| NV1G1734 | NV1D3568 | 306 | Q1A, W7Q, S11A, M19F, R22T | 44 | 8.3 |
| NV1G1683 | NV1D3523 | 263 | Y1Q, W7Q, S11R, M19F, R22T, K26R | 44.7 | |
| NV1G1834 | NV1D3360 | 191 | Y1Q, W7Q, D10R, S11R, M19F, R22T, K26R | 45.2 | 3.79 |
| NV1G1795 | NV1D3401 | 229 | Y1Q, W7Q, S11R, M19F, R22T, K26R, K27R | 45.5 | 6.58 |
| NV1G1689 | NV1D3514 | 255 | Y1Q, W7Q, S11R, M19F, R22T, K26R | 46.4 | |
| NV1G2043 | NV1D3835 | 370 | Y1Q, W7Q, S11R, M19F, R22T, K26R | 46.4 | 4.09 |
| NV1G1783 | NV1D3384 | 213 | Y1Q, W7Q, S11R, E17K, M19F, R22T, K26R | 46.8 | 7.39 |
| NV1G1239 | NV1D3020 | 143 | Y1Q, W7Q, S11A, M19F, R22T, K26R | 47.2 | 7.84 |
| NV1G1788 | NV1D3399 | 227 | Y1Q, W7Q, S11R, M19F, V20T, R22T, K26R | 47.3 | 6.36 |
| NV1G899 | NV1D2774 | 52 | Y1A, W7Q, S11A, M19F | 50.5 | 15.2 |
| NV1G2057 | NV1D3799 | 341 | Y1Q, W7Q, S11R, M19F, R22T, K26R | 50.6 | 6.33 |
| NV1G1738 | NV1D3578 | 316 | W7Q, S11A, M19F, V20S, | 50.7 | 5.7 |
| NV1G1713 | NV1D3525 | 265 | Y1Q, W7Q, S11R, M19F, R22T, K26R | 52.3 | |
| NV1G1765 | NV1D3553 | 293 | W7Q, S11R, M19F, V20S, R22T, K26R | 52.4 | 10 |
| NV1G1916 | NV1D3465 | 247 | Y1Q, W5F, W7Q, S11R, M19F, R22T, K26R | 52.8 | 10.3 |
| NV1G1977 | NV1D3804 | 346 | Y1Q, W7Q, S11R, M19F, R22T, K26R | 53.6 | 6.27 |
| NV1G1879 | NV1D3259 | 168 | Y1Q, W7Q, S11A, M19F | 54.9 | 7.62 |
| NV1G1884 | NV1D3256 | 166 | Y1Q, W7Q, S11A, M19F | 55.7 | 10.5 |
| NV1G1986 | NV1D3819 | 358 | Y1Q, W7Q, S11R, M19F, R22T, K26R | 56 | 6.57 |
| NV1G1633 | NV1D3251 | 163 | Y1Q, W7Q, S11A, M19F | 56.1 | 13.9 |
| NV1G1880 | NV1D3261 | 170 | Y1Q, W7Q, S11A, M19F | 57 | 6.25 |
| NV1G1985 | NV1D3808 | 349 | Y1Q, W7Q, S11R, M19F, R22T, K26R | 57 | 6.74 |
| NV1G1849 | NV1D3400 | 228 | Y1Q, W7Q, S11R, M19F, V20Q, R22T, K26R | 57.3 | 9.52 |
| NV1G1883 | NV1D3260 | 169 | Y1Q, W7Q, S11A, M19F | 57.6 | 6.91 |
| NV1G1145 | NV1D2970 | 125 | Y1S, W7Q, S11A, M19F, R22T | 58 | 18.8 |
| NV1G1697 | NV1D3517 | 258 | Y1Q, W7Q, S11R, M19F, R22T, K26R | 58.5 | |
| NV1G1737 | NV1D3579 | 317 | Y1A, W7Q, S11A, M19F, V20S | 59.9 | 9.6 |
| NV1G1978 | NV1D3833 | 368 | Y1Q, W7Q, S11R, M19F, R22T, K26R | 60.3 | 9.57 |
| NV1G1954 | NV1D3800 | 342 | Y1Q, W7Q, S11R, M19F, R22T, K26R | 60.9 | 6.43 |
| NV1G1989 | NV1D3791 | 334 | Y1Q, W7Q, S11R, M19F, R22T, K26R | 61.8 | 8.66 |
| NV1G1815 | NV1D3380 | 209 | Y1Q, K4E, W7Q, S11R, M19F, R22T, K26R | 64 | 10.5 |
| NV1G1967 | NV1D3793 | 336 | Y1Q, W7Q, S11R, M19F, R22T, K26R | 64.6 | 8.19 |
| NV1G1869 | NV1D3573 | 311 | Y1R, W7Q, S11A, E12N, M19F, R22T | 64.7 | 50.7 |
| NV1G1872 | NV1D3777 | 330 | Y1Q, W7Q, S11R, M19F, R22T, K26R | 64.9 | 15.3 |
| NV1G1979 | NV1D3834 | 369 | Y1Q, W7Q, S11R, M19F, R22T, K26R | 65.5 | 7.59 |
| NV1G1827 | NV1D3365 | 195 | Y1Q, W7Q, D10Q, S11R, M19F, R22T, K26R | 66.1 | 10.1 |
| NV1G1768 | NV1D3341 | 174 | Y1Q, Q3T, W7Q, S11R, M19F, R22T, K26R | 66.2 | 9.32 |
| NV1G911 | NV1D2666 | 30 | W7Q, M19F | 66.5 | 36.7 |
| NV1G1856 | NV1D3397 | 225 | Y1Q, W7Q, S11R, G18S, M19F, R22T, K26R | 66.7 | 7.31 |
| NV1G1973 | NV1D3810 | 351 | Y1Q, W7Q, S11R, M19F, R22T, K26R | 66.9 | 7.04 |
| NV1G1855 | NV1D3398 | 226 | Y1Q, W7Q, S11R, M19F, V20S, R22T, K26R | 67.3 | 11 |
| NV1G1961 | NV1D3802 | 344 | Y1Q, W7Q, S11R, M19F, R22T, K26R | 68 | 8.23 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1846 | NV1D3431 | 244 | Y1Q, K4E, W7Q, S11R, E17K, M19F, R22T, K26R | 68.6 | 13.9 |
| NV1G1771 | NV1D3348 | 180 | Y1Q, K4A, W7Q, S11R, M19F, R22T, K26R | 70.6 | 15.9 |
| NV1G1691 | NV1D3520 | 261 | Y1Q, W7Q, S11R, M19F, R22T, K26R | 71.4 | |
| NV1G1681 | NV1D3511 | 252 | Y1Q, W7Q, S11R, M19F, R22T, K26R | 71.5 | |
| NV1G1968 | NV1D3822 | 359 | Y1Q, W7Q, S11R, M19F, R22T, K26R | 74.2 | 11.1 |
| NV1G1813 | NV1D3424 | 238 | Y1Q, W7Q, D10K, S11R, E12K, M19F, R22T, K26R | 75.2 | 12.2 |
| NV1G1067 | NV1D2893 | 57 | Y1Q, W7Q, S11A, M19L | 75.5 | 10.5 |
| NV1G1867 | NV1D3546 | 286 | Y1A, W7Q, S11R, E12N, M19F, V20S, R22T, K26R | 76 | 17.6 |
| NV1G1143 | NV1D2971 | 126 | Y1S, W7Q, S11A, M19F, V20S, R22T | 77.5 | 22.1 |
| NV1G1806 | NV1D3409 | 232 | Y1Q, W7Q, S11R, M19F, R22T, K26R, K28T | 79.1 | 11.3 |
| NV1G1061 | NV1D2896 | 60 | Y1R, W7Q, S11A, M19L | 80.3 | 7.13 |
| NV1G1793 | NV1D3419 | 236 | Y1Q, W7Q, S11R, M19F, R22T, K26R, W30D | 80.9 | 11.9 |
| NV1G1613 | NV1D3057 | 157 | Y1Q, W7Q, S11R, E12K, M19F, K26R | 83.4 | 16.6 |
| NV1G1585 | NV1D3052 | 155 | Y1Q, W7Q, S11A, E12K, M19F, K26R | 84.8 | 28.8 |
| NV1G1707 | NV1D3524 | 264 | Y1Q, W7Q, S11R, M19F, R22T, K26R | 84.9 | |
| NV1G1773 | NV1D3350 | 182 | Y1Q, K4E, W7Q, S11R, M19F, R22T, K26R | 85.6 | 14.4 |
| NV1G1949 | NV1D3828 | 364 | Y1Q, W7Q, S11R, M19F, R22T, K26R | 87.5 | 11 |
| NV1G1976 | NV1D3811 | 352 | Y1Q, W7Q, S11R, M19F, R22T, K26R | 87.7 | 15.7 |
| NV1G1956 | NV1D3801 | 343 | Y1Q, W7Q, S11R, M19F, R22T, K26R | 88.1 | 11.4 |
| NV1G1975 | NV1D3832 | 367 | Y1Q, W7Q, S11R, M19F, R22T, K26R | 88.4 | 12.3 |
| NV1G1839 | NV1D3774 | 328 | Y1Q, W7Q, S11R, M19F, R22T, K26R | 88.6 | 19.6 |
| NV1G1971 | NV1D3830 | 366 | Y1Q, W7Q, S11R, M19F, R22T, K26R | 88.6 | 9.88 |
| NV1G1882 | NV1D3262 | 171 | Y1Q, W7Q, S11A, M19F | 89.2 | 8.32 |
| NV1G1950 | NV1D3797 | 339 | Y1Q, W7Q, S11R, M19F, R22T, K26R | 91.1 | 13.5 |
| NV1G1828 | NV1D3363 | 194 | Y1Q, W7Q, D10A, S11R, M19F, R22T, K26R | 93.1 | 15.3 |
| NV1G1139 | NV1D2973 | 128 | Y1Q, W7Q, S11A, M19F, R22T | 93.9 | 19.5 |
| NV1G1842 | NV1D3430 | 243 | Y1Q, K4D, W7Q, S11R, E17K, M19F, R22T, K26R | 93.9 | 14.1 |
| NV1G1948 | NV1D3798 | 340 | Y1Q, W7Q, S11R, M19F, R22T, K26R | 94.5 | 17.8 |
| NV1G1807 | NV1D3408 | 231 | Y1Q, W7Q, S11R, M19F, R22T, K26R, K28R | 94.8 | 17.8 |
| NV1G1137 | NV1D2974 | 129 | Y1Q, W7Q, S11A, M19F, V20S, R22T | 95.7 | 16.2 |
| NV1G1843 | NV1D3432 | 245 | Y1Q, K4E, W7Q, S11R, E17R, M19F, R22T, K26R | 95.9 | 10.4 |
| NV1G1822 | NV1D3423 | 237 | Y1Q, W7Q, D10R, S11R, E12R, M19F, R22T, K26R | 99.5 | 9.45 |
| NV1G1862 | NV1D3556 | 296 | W7Q, S11A, M19F, V20S, R22T | 100 | 18.5 |
| NV1G1969 | NV1D3795 | 337 | Y1Q, W7Q, S11R, M19F, R22T, K26R | 100 | 14.5 |
| NV1G1980 | NV1D3812 | 353 | Y1Q, W7Q, S11R, M19F, R22T, K26R | 101 | 23.6 |
| NV1G1850 | NV1D3414 | 235 | Y1Q, W7Q, S11R, M19F, R22T, K26R, K28S | 102 | 19.4 |
| NV1G1981 | NV1D3815 | 356 | Y1Q, W7Q, S11R, M19F, R22T, K26R | 102 | 13.5 |
| NV1G1851 | NV1D3390 | 219 | Y1Q, W7Q, S11R, G18R, M19F, R22T, K26R | 108 | 15.5 |
| NV1G1922 | NV1D3466 | 248 | Y1Q, W7Q, S11E, M19F, R22T, K26R | 108 | 922 |
| NV1G1778 | NV1D3349 | 181 | Y1Q, K4D, W7Q, S11R, M19F, R22T, K26R | 109 | 16 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1972 | NV1D3824 | 361 | Y1Q, W7Q, S11R, M19F, R22T, K26R | 110 | 16.1 |
| NV1G1974 | NV1D3796 | 338 | Y1Q, W7Q, S11R, M19F, R22T, K26R | 110 | 19.6 |
| NV1G1826 | NV1D3357 | 188 | Y1Q, W7Q, T8E, S11R, M19F, R22T, K26R | 111 | 15.1 |
| NV1G1892 | NV1D3439 | 246 | Y1Q, W7Q, S11R, M19F, R22T, K26R, W30G | 112 | 13.2 |
| NV1G1819 | NV1D3375 | 204 | Y1Q, W7Q, S11R, R13S, M19F, R22T, K26R | 113 | 1270 |
| NV1G1805 | NV1D3410 | 233 | Y1Q, W7Q, S11R, M19F, R22T, K26R, K28A | 114 | 21.5 |
| NV1G1831 | NV1D3374 | 203 | Y1Q, W7Q, S11R, R13Q, M19F, R22T, K26R | 114 | 1600 |
| NV1G1693 | NV1D3512 | 253 | Y1Q, W7Q, S11R, M19F, R22T, K26R | 115.6 | |
| NV1G1854 | NV1D3392 | 221 | Y1Q, W7Q, S11R, G18T, M19F, R22T, K26R | 117 | 21.8 |
| NV1G1951 | NV1D3829 | 365 | Y1Q, W7Q, S11R, M19F, R22T, K26R | 122 | 13.3 |
| NV1G1860 | NV1D3393 | 222 | Y1Q, W7Q, S11R, G18A, M19F, R22T, K26R | 125 | 24.8 |
| NV1G1099 | NV1D2732 | 36 | Y1Q, W7Q, S11A | 126 | 26.9 |
| NV1G1705 | NV1D3513 | 254 | Y1Q, W7Q, S11R, M19F, R22T, K26R | 131.2 | |
| NV1G1848 | NV1D3426 | 240 | Y1Q, W7Q, D10K, S11R, E12K, R13D, M19F, R22T, K26R | 135 | 39.9 |
| NV1G1952 | NV1D3813 | 354 | Y1Q, W7Q, S11R, M19F, R22T, K26R | 139 | 30.1 |
| NV1G1631 | NV1D3252 | 164 | Y1Q, W7Q, S11A, M19F | 145 | 53 |
| NV1G1817 | NV1D3371 | 201 | Y1Q, W7Q, S11R, R13A, M19F, R22T, K26R | 151 | 33.7 |
| NV1G1789 | NV1D3394 | 223 | Y1Q, W7Q, S11R, G18D, M19F, R22T, K26R | 155 | 41.4 |
| NV1G1852 | NV1D3391 | 220 | Y1Q, W7Q, S11R, G18K, M19F, R22T, K26R | 157 | 23.1 |
| NV1G1709 | NV1D3510 | 251 | Y1Q, W7Q, S11R, M19F, R22T, K26R | 159 | |
| NV1G1840 | NV1D3425 | 239 | Y1Q, W7Q, D10R, S11R, E12R, R13D, M19F, R22T, K26R | 161 | 27.9 |
| NV1G1809 | NV1D3413 | 234 | Y1Q, W7Q, S11R, M19F, R22T, K26R, K28Q | 164 | 43.7 |
| NV1G1863 | NV1D3356 | 187 | Y1Q, W7Q, T8D, S11R, M19F, R22T, K26R | 167 | 32.2 |
| NV1G1699 | NV1D3527 | 267 | Y1Q, W7Q, S11R, M19F, R22T, K26R | 169.1 | |
| NV1G1844 | NV1D3428 | 242 | Y1Q, W7Q, D10K, S11R, E12K, R13E, M19F, R22T, K26R | 180 | 52.4 |
| NV1G1853 | NV1D3370 | 200 | Y1Q, W7Q, S11R, R13T, M19F, R22T, K26R | 181 | 25.1 |
| NV1G1946 | NV1D3825 | 362 | Y1Q, W7Q, S11R, M19F, R22T, K26R | 194 | 28.4 |

The wild-type Protoxin-II inhibits Nav1.7 with an IC$_{50}$ value of about 4 nM in veratridine-induced depolarization inhibition assay as described in Example 3. Variants retaining significant Nav1.7 potency were characterized further. FIG. 1 shows the sequence genus of generated Protoxin-II variants that inhibit Nav1.7 with an IC$_{50}$ value of 30 nM or less.

Select Protoxin-II variants were tested for their inhibition of Nav1.7 and for their selectivity against human Nav1.6 using QPatch. IC$_{50}$ values for both Nav1.7 and Nav1.6 for select peptides obtained using QPatch are shown in FIG. 2. These peptides inhibited Nav1.7 with an IC$_{50}$ of 30 nM or less, and were at least 30-fold selective over Nav1.7 when compared to Nav1.6.

The amino acid sequences of the peptides shown in FIG. 2 are shown in FIG. 3. All these peptides had W7Q and M19F substitutions when compared to the wild type Protoxin-II.

The Protoxin-II variants were expressed and purified as described in Example 1, or synthesized by standard solid phase synthesis methods. The yields of the recombinant or synthetic peptides were compared to the yields of the wild-type Protoxin-II. Table 12 shows that the yields of the select Protoxin-II variants were significantly higher than that of Protoxin-II, indicating improved folding properties of the variants. The scale of the solid-phase synthesis was 0.5 mmol.

TABLE 12

| | Solid phase synthesis | | | |
|---|---|---|---|---|
| Peptide | Total yield | Yield from Crude | Yield From Linear | Recombinant expression % active isomer |
| Protoxin-II | 52 mg | 2.7% | 7.3% | 54.0% |
| NV1D2775 | 84 mg | 4.5% | 18.7% | 89.1% |
| NV1D3034 | 149 mg | 8.0% | 21.0% | 85.2% |
| NV1D3368 | 83 mg | 4.0% | 24.0% | 93.8% |

Example 5. Protoxin-II Variants are Efficacious in In Vivo Models of Pain

Materials and Methods
Animals

Male C57Bl/6 mice (24-26 g), ordered from Charles River and housed individually, were used for this study.
Behavioral Tests Von Frey Test:

Mechanical (tactile) threshold was assessed by Von Frey Hairs following the Up-Down method (Dixon, 1980, Chaplan et al., 1994). 7 graded stimuli (von Frey filaments: 0.03, 0.07, 0.16, 0.4, 0.6, 1, 2 g; Stoelting, Wood Dale, Ill.) were used. Von Frey hairs were presented perpendicularly against the center plantar area (between toris) on a hindpaw. Sufficient force was applied to bend the filament slightly and held for 3 seconds. Per the Chaplan paper, a positive response can be either 1) a sharp withdrawal or 2) immediate flinching upon removal of the filament. See Chaplan et al for more details. Mice were acclimated to the wire mesh in the testing chamber for 30-60 minutes prior to testing.

Hargreaves Test:

A modified Hargreaves box was used to measure thermal paw withdrawal latency (PWL) (Hargreaves et al., 1988, Pain, 32:77-88; Dirig et al., 1997, J Neurosci. Methods, 76:183-191). This box consists of a chamber with a raised glass floor maintained at a constant temperature (27° C.). The thermal nociceptive stimulus originates from a projection bulb light beam below the glass surface. The light beam is aimed at the area between toris (center plantar). The "start" button will turn on the light and start the timer. Movements (such as a sudden withdrawal) of the stimulated paw will trigger the switch to turn off the light and stop the timer. The latency in seconds is displayed. If no movement occurs, the bulb will be turned off after 20 seconds (cutoff) to prevent tissue injury. The animals were allowed to habituate on the glass surface for 30-60 minutes before PWL measurement. Constant amperage was used throughout the study, which resulted in Pre-test paw withdrawal latencies between 8-12 seconds when averaged over 3 to 6 read-outs taken at least 5 minutes apart.

MPE % Calculation:

Percent maximum possible effect (MPE %)=$(T_1-T_0)/(Tc-T_0) \times 100\%$. $T_0$: threshold on day0 (post-CFA, pre-pump); $T_1$: threshold on day1 post pump implantation; Tc: cut-off of the test (20 s for the Hargreaves test and 2 g for the Von Frey test)

Hotplate Test:

Animals were placed on a 10"×10" metal plate surrounded by 4 Plexiglas walls (15 inches high). The plate was maintained at a temperature of either 50 or 55° C. The response latency (time when the animal first flinches or licks its hind paw, jumps, or vocalizes) was measured and the animal removed from the plate. Animals showing no response were removed from the plate after 40 s (50° C.) or 20 s (55° C.) to prevent any possible tissue damage. This trial was repeated 2-5 times every 15-60 minutes in a day.
Inflammatory Pain Models CFA Model:

Animals were anesthetized with isoflurane (4% induction and 2% maintenance) and 20 μL of 100% Complete Freund's Adjuvant (CFA; Sigma-Aldrich; Saint Louis, Mo.) was injected into the center plantar area on one hind paw using a 27 gauge needle attached to a 50 μL Hamilton syringe.

Figure 4B:
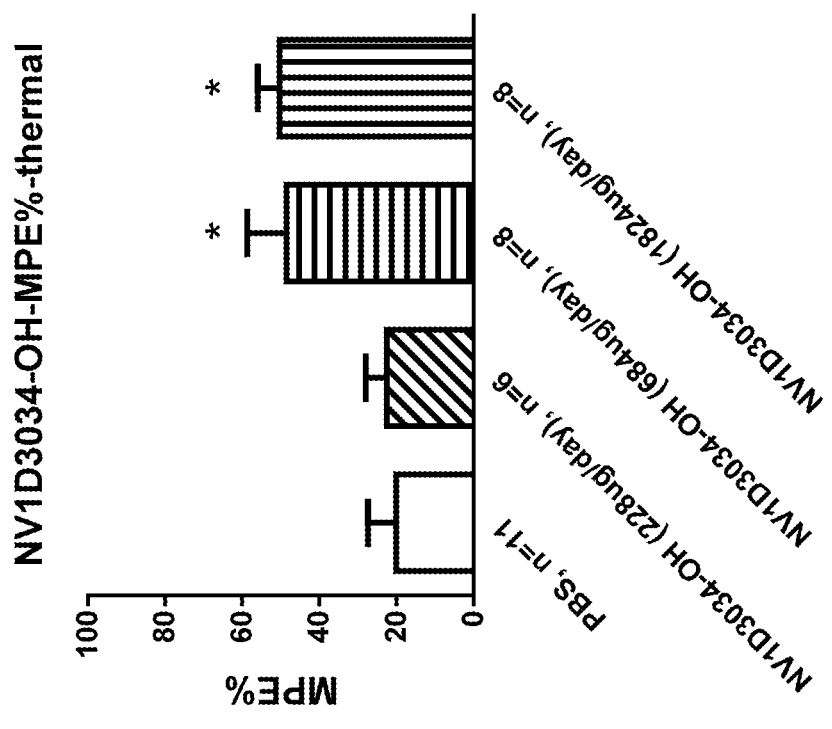
FIG. 4B shows efficacy of NV1D3034 (NV1D3034-OH) (SEQ ID NO: 78) in CFA-induced thermal hyperalgesia in mice, expressed as percent MPE (maximum possible effect) (MPE %) at each dose on day1 following peptide administration. *$P<0.05$ vs PBS, one-way ANOVA followed by Bonferroni's multiple comparison.
Figure 6A:
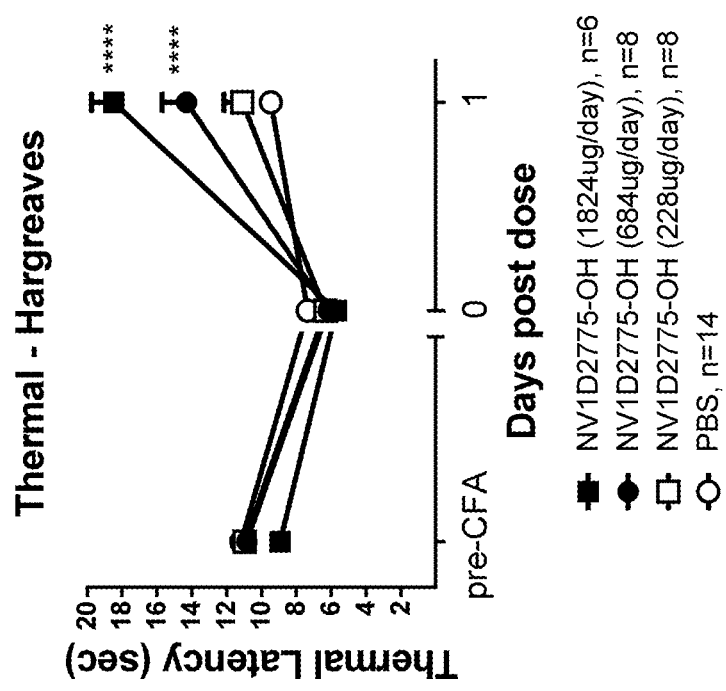
FIG. 6A shows efficacy of NV1D2775-OH (SEQ ID NO: 56) against CFA-induced thermal hyperalgesia in mice, assessed by measurement of paw withdrawal latency in the Hargreaves test before (pre-CFA) and after CFA injection (0) and 1-day after peptide administration (1). ****P<0.0001 vs. PBS, two-way ANOVA followed by Bonferroni's multiple comparison.

Carrageenan Model:

Animals were anesthetized with isoflurane (4% induction and 2% maintenance) and 25 μL of 2% Δ-carrageenan (Sigma-Aldrich; Saint Louis, Mo.) dissolved in normal saline was injected into the center plantar area on hind paws using an insulin syringe (BD; Franklin Lakes, N.J.).
Implantation of Mini Pumps Alzet micro-osmotic mini pumps (Durect Corporation Model 1003D and 2001D) were filled and primed per manufacturer's guide. Mice were anesthetized with isoflurane (5% induction; 2% maintenance). Their backs were shaved, wiped down with isopropyl alcohol and povidone iodine, and a small incision was made between the scapulae. Using a pair of forceps or hemostat, a small pocket was formed by spreading the subcutaneous connective tissues apart. The pump was inserted into the pocket with the flow moderator pointing away from the incision. The skin incision was then closed using 7 mm staples and the animals were allowed to recover in their home cages.
Data Analysis Data are represented as mean±s.e.m. Prism (Graphpad Software Inc., La Jolla, Calif.) was used for graphing and statistical analysis. For comparison of threshold values over time, a two-way ANOVA followed by Bonferroni's multiple comparison test was used with a significance level of p<0.05. Hotplate and MPE % data were analyzed by one-way ANOVA followed by Bonferroni's multiple comparison test.
Results Efficacy of variants NV1D3034-OH (NV1D3034-COOH), NV1D3368-OH (NV1D3368-COOH) and NV1D2775-OH (NV1D2775-COOH) was studied in the CFA model, a commonly used model of inflammatory pain. The injection of CFA in the hindpaw induced paw edema (not shown) and hypersensitivity to thermal stimuli (thermal hyperalgesia), as indicated by the lowered thermal latency in the injected paw on day0 (FIG. 6A). Thermal hyperalgesia was completely reversed by NV1D3034-OH at 684 and 1824 μg/day, when administered by a subcutaneous osmotic mini-pump (FIGS. 4A and 4B).

Figure 5A:
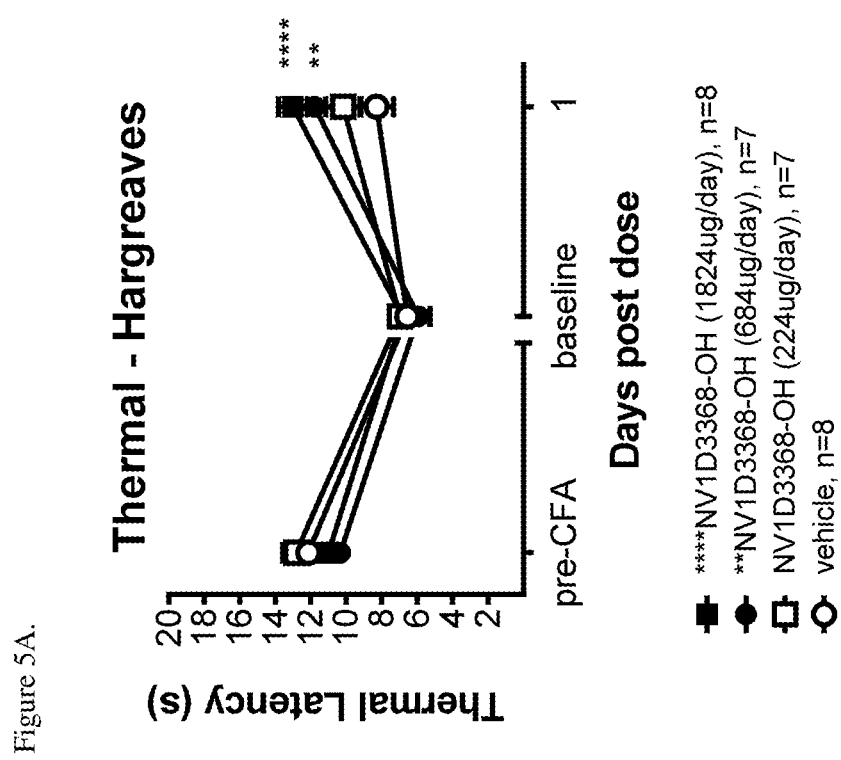
FIG. 5A shows efficacy of NV1D3368 (NV1D3368-OH) (SEQ ID NO: 198) against CFA-induced thermal hyperalgesia in mice, assessed by measurement of paw withdrawal latency in the Hargreaves test before (pre-CFA) and after CFA injection (0) and 1-day after peptide administration (1). $P<0.01$ and **$P<0.0001$ vs. PBS, two-way ANOVA followed by Bonferroni's multiple comparison
Figure 5B:
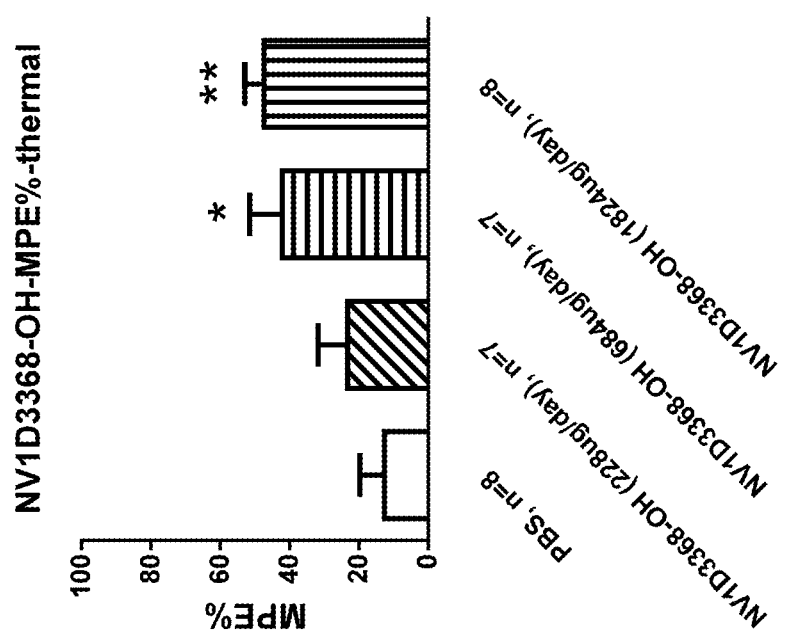
FIG. 5B shows efficacy of NV1D3368 (NV1D3368-OH) (SEQ ID NO: 198) in CFA-induced thermal hyperalgesia in mice, expressed as percent MPE (MPE %) at each dose on day1 following peptide administration. *P<0.05 and **P<0.01 vs PBS, one-way ANOVA followed by Bonferroni's multiple comparison.
Figure 6B:
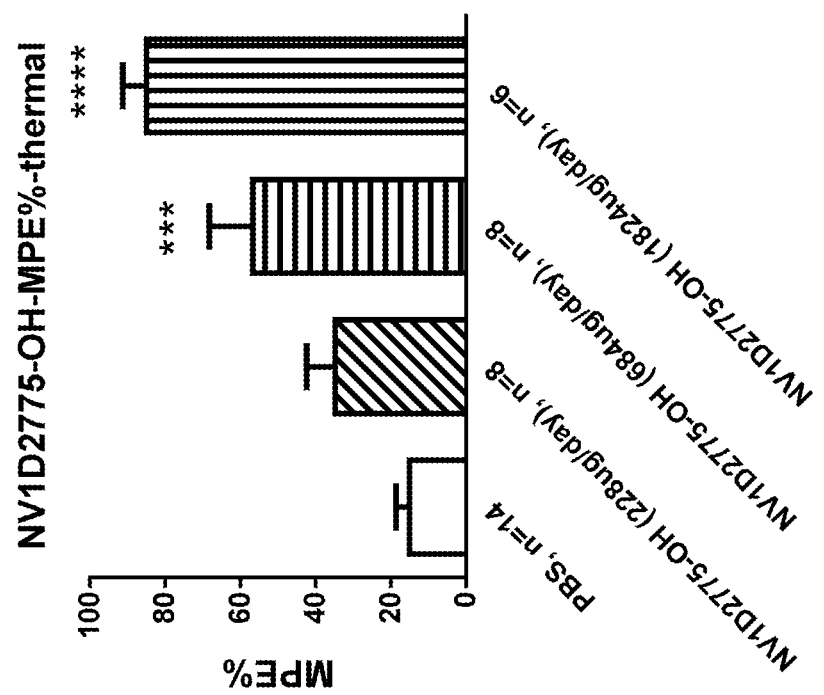
FIG. 6B shows efficacy of NV1D2775-OH (SEQ ID NO: 56) in CFA-induced thermal hyperalgesia in mice, expressed as percent MPE (MPE %) at each dose on day1 following peptide administration. *P<0.001 and **P<0.0001 vs PBS, one-way ANOVA followed by Bonferroni's multiple comparison.
Figure 6C:
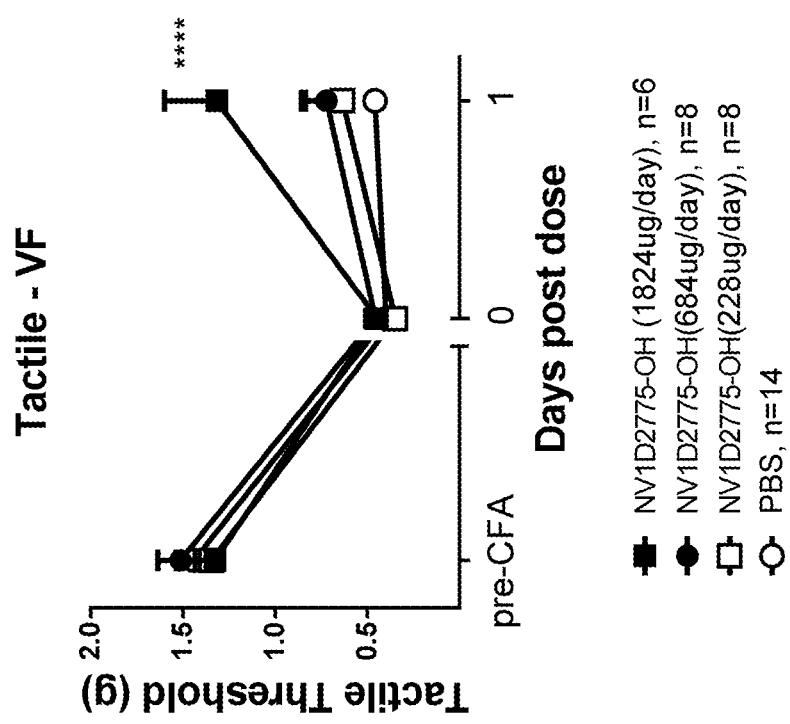
FIG. 6C shows efficacy of NV1D2775-OH (SEQ ID NO: 56) against CFA-induced tactile allodynia in mice. Tactile thresholds of hind paw before (pre-CFA) and after CFA (0) and 1-day after peptide administration (1). ****P<0.0001 vs. PBS, two-way ANOVA followed by Bonferroni's multiple comparison.
Figure 6D:
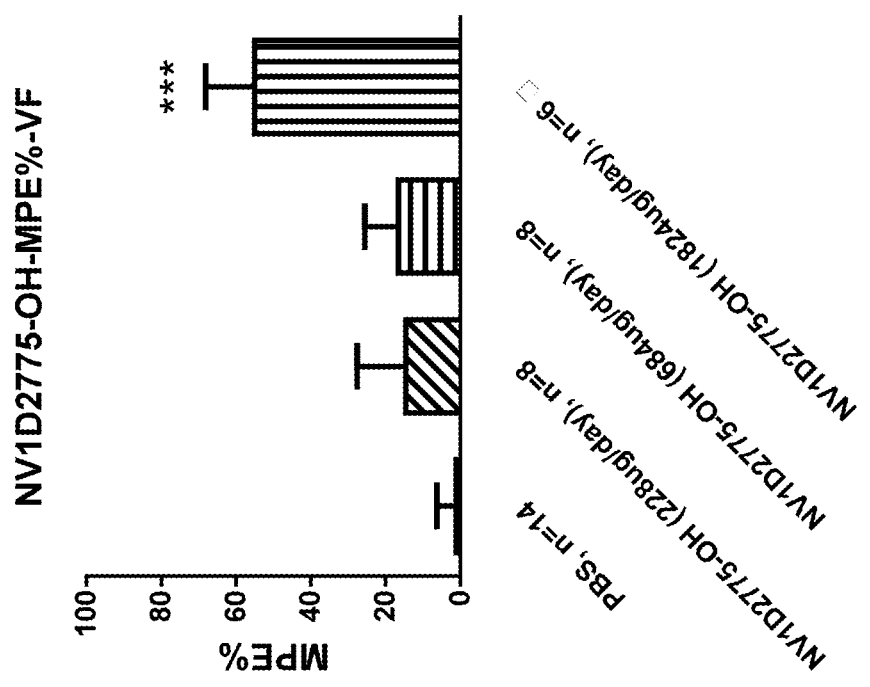
FIG. 6D shows efficacy of NV1D2775-OH (SEQ ID NO: 56) against CFA-induced tactile allodynia in mice, expressed as percent MPE (MPE %) on day1 following peptide. ***P<0.001 vs PBS, one-way ANOVA followed by Bonferroni's multiple comparison.
Figure 7A:
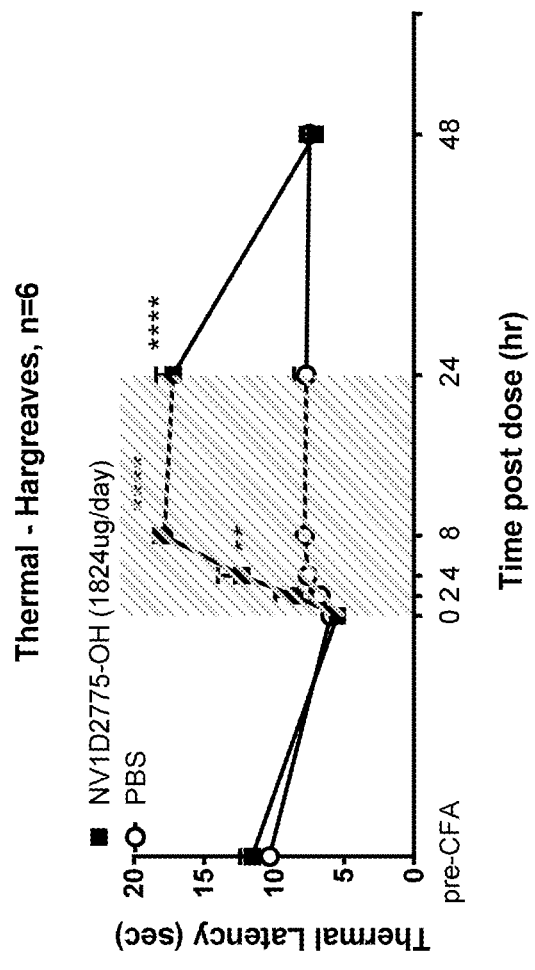
FIG. 7A shows time course of NV1D2775-OH mediated reversal of thermal hyperalgesia in the mouse CFA model as assessed by measurement of paw withdrawal latency in the Hargreaves test before and after CFA and at various time points post-peptide administration. **P<0.01 vs. PBS, two-way ANOVA followed by Bonferroni's multiple comparison. Shaded areas indicate compound delivery period (0-24 hr).
Figure 7B:
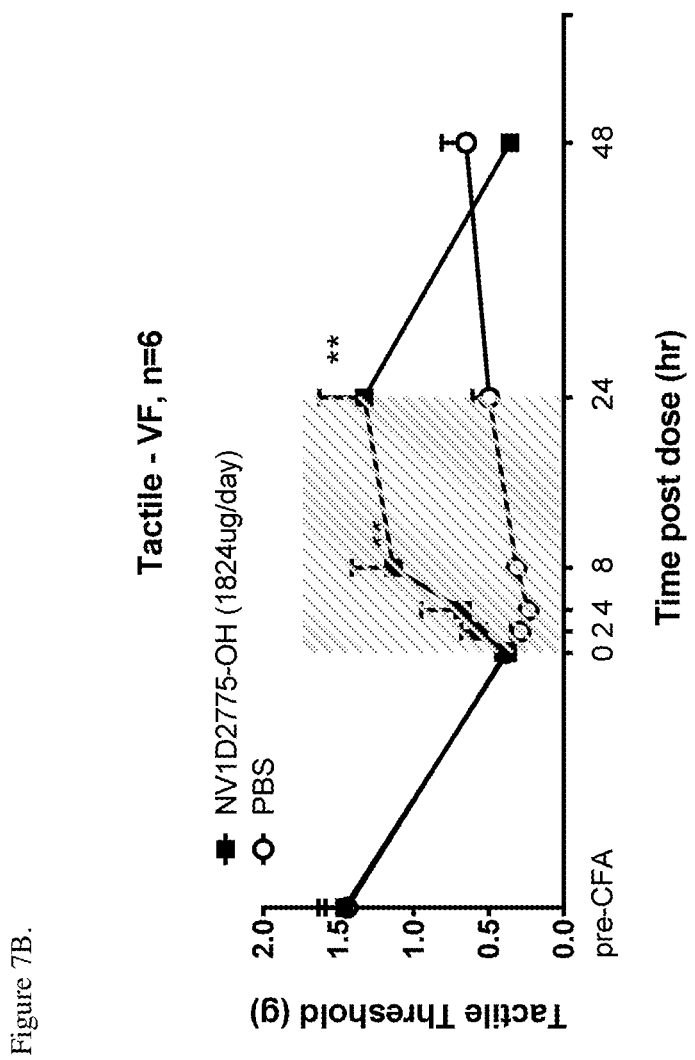
FIG. 7B shows time course of NV1D2775-OH mediated reversal of tactile allodynia in the mouse CFA model as assessed by measurement of tactile threshold before and after CFA and at various time points post-peptide administration. **P<0.01 vs. PBS, two-way ANOVA followed by Bonferroni's multiple comparison. Shaded areas indicate compound delivery period (0-24 hr).

NV1D3368-OH fully reversed CFA-induced thermal hyperalgesia at 684 and 1824 μg/day (FIGS. 5A and 5B). NV1D2775-OH demonstrated strong efficacy in the CFA model. Thermal latencies reached values close to the cut-off following NV1D2775 administration (FIGS. 6A and 6B, 1824 μg/day), suggesting a strong analgesia effect on top of the anti-hyperalgesia effect. In addition, NV1D2775-OH reversed CFA-induced tactile allodynia (FIGS. 6C and 6D, 1824 μg/day). The anti-hyperalgesic effect of NV1D2775-OH was seen as early as 4 hr post-pump implantation (FIG. 7A). The effect reached the maximum at 8 hr in both the thermal and tactile tests (FIGS. 7A and 7B), which was maintained at 24 hr. Thermal latency and tactile threshold returned the control level by 48 h post pump implantation (approximately 24 h after the pumps were predicted to be empty) (FIGS. 7A and 7B).

CFA-induced thermal hyperalgesia was readily reversed by two additional peptides, NV1D3368-amide (NV1D3368-NH$_2$) and NV1D3034-N-methylamide (NV1D3034-NHMe). Thermal MPE % from the experiments is summarized in Table 13.

TABLE 13

| Peptide | Dose (μg/day/mouse) | | | |
|---|---|---|---|---|
| | Vehicle (PBS) | 228 | 684 | 1824 |
| NV1D3034-OH | 20 ± 7 (11) | 22 ± 6 (6) | 48 ± 10* (8) | 50 ± 6* (8) |
| NV1D3368-OH | 13 ± 7 (8) | 23 ± 8 (7) | 42 ± 9* (7) | 47 ± 6** (8) |
| NV1D2775-OH | 15 ± 4 (20) | 35 ± 8 (8) | 57 ± 12*** (8) | 85 ± 6**** (12) |
| NV1D3368-NH$_2$ | 15 ± 13 (6) | 27 ± 4 (4) | 46 ± 9 (4) | 55 ± 15 (6) |
| NV1D3034-NHMe | 5 ± 25 (3) | | | 49 ± 17 (6) |

*$P < 0.05$,
**$P < 0.01$,
***$P < 0.001$ and
****$P < 0.0001$ vs. PBS, one-way ANOVA followed by Bonferroni's multiple comparison.

Figure 8:
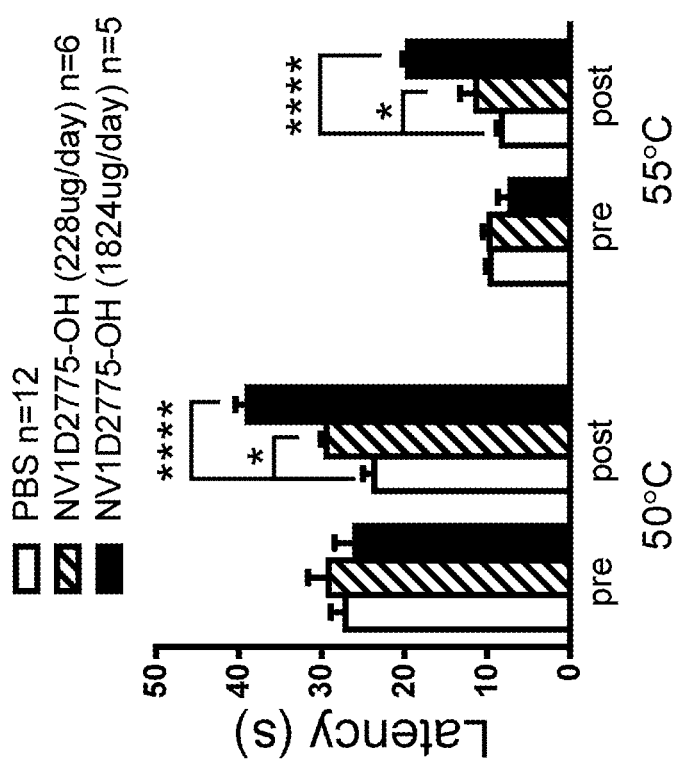
FIG. 8 shows that NV1D2775-OH produced significant analgesia in the mouse hotplate test. Thermal withdrawal latency was evaluated at 50 and 55° C. pre- and post-pump implantation. Pump implantation had no impact on the latency in the control PBS group. One day after pump, NV1D2775-OH treated-mice exhibited prolonged latency compared to the PBS group. *P<0.05 and ****P<0.0001 vs. PBS, one-way ANOVA followed by Bonferroni's multiple comparison.

NV1D2775-OH also exhibited strong, dose-dependent efficacy in the hotplate test (FIG. 8). Latencies at 50 and 55° C. reached values near cut-off following the administration of 1824 μg/day. At 228 μg/day, NV1D2775-OH produced a modest yet significant increase in the thermal latency, compared to the PBS control.

Figure 9:
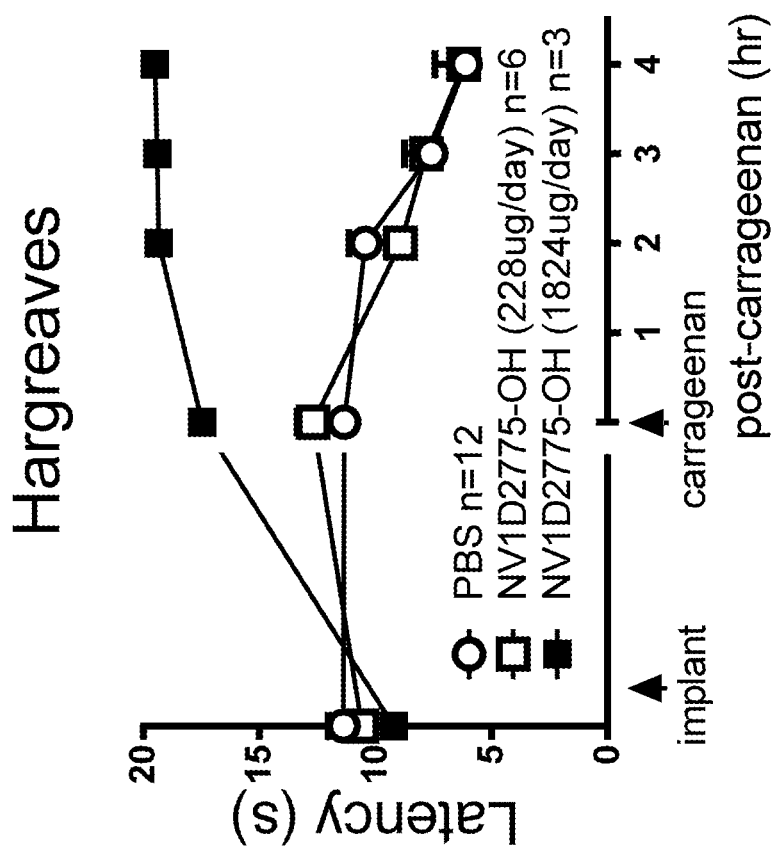
FIG. 9 shows that NV1D2775-OH pretreatment protected animals from carrageenan-induced thermal hyperalgesia in mice. Paw withdrawal latencies were measured pre- and on day1 post-pump before intraplantar carrageenan injection. Latencies were measured again at 2, 3 and 4 hr following carrageenan.

The efficacy of NV1D2775-OH was evaluated in another model of inflammatory pain, the carrageenan model. Animals were implanted with NV1D2775-OH or PBS pumps. Thermal withdrawal latencies were measured pre- and on day1 post-pump. A-carrageenan was injected into the hindpaws and thermal latencies were measured again on 2, 3 and 4 hr following carrageenan. NV1D2775-OH at 1824 μg/day produced significant analgesia (FIG. 9). Injection of Δ-carrageenan in the hindpaws induced inflammation (not shown) and lowered thermal paw withdrawal latency in the Hargreaves test over the 4 hr test-period (FIG. 9, PBS group). Animals pretreated with NV1D2775-OH at 1824 μg/day were fully protected from carrageenan-induced hyperalgesia.

Example 6. Generation and Characterization of Combinatorial Protoxin-II Variants An amino acid scanning library was generated for Protoxin-II. At every non-cysteine position in Protoxin-II (Tyr1, Gln3, Lys4, Trp5, Met6, Trp7, Thr8, Asp10, Ser11, Glu12, Arg13, Lys14, Glu17, Gly18, Met19, Val20, Arg22, Leu23, Trp24, Lys26, Lys27, Lys28, Leu29 and Trp30) the following residues were substituted in place of the native residue: Ala, Asp, Glu, Phe, Gly, His, Ile, Lys, Leu, Asn, Pro, Gln, Arg, Ser, Thr, Val, and Tyr.

Mutant peptides were expressed as recombinant fusions to human serum albumin and site-specifically enzymatically cleaved using HRV3C to generate Protoxin-II variants as described in Example 1. Each Protoxin-II variant, after cleavage from HSA had a residual N-terminal GP from the cleavage site. For each Protoxin-II variant, IC$_{50}$ values against human Nav1.7 were measured using veratridine-induced depolarization inhibition assay or Qpatch according to the protocols described in Example 3. Variants demonstrating IC$_{50}$≤100 nM for human Nav1.7 were counter-screened for selectivity against additional hNav channels using Qpatch electrophysiology. Selective hits were identified and used in the design of combinatorial peptide libraries which were produced using both recombinant expression and solid-phase peptide synthesis. Combinatorial variants were screened using the same strategy as detailed above.

Based on the results, positions that can be mutated to improve selectivity include Gln3, Ser11, Glu12, Lys14, Glu17, Gly18, Leu29 and Trp30 (residues numbering according to SEQ ID NO: 1).

Figure 10:
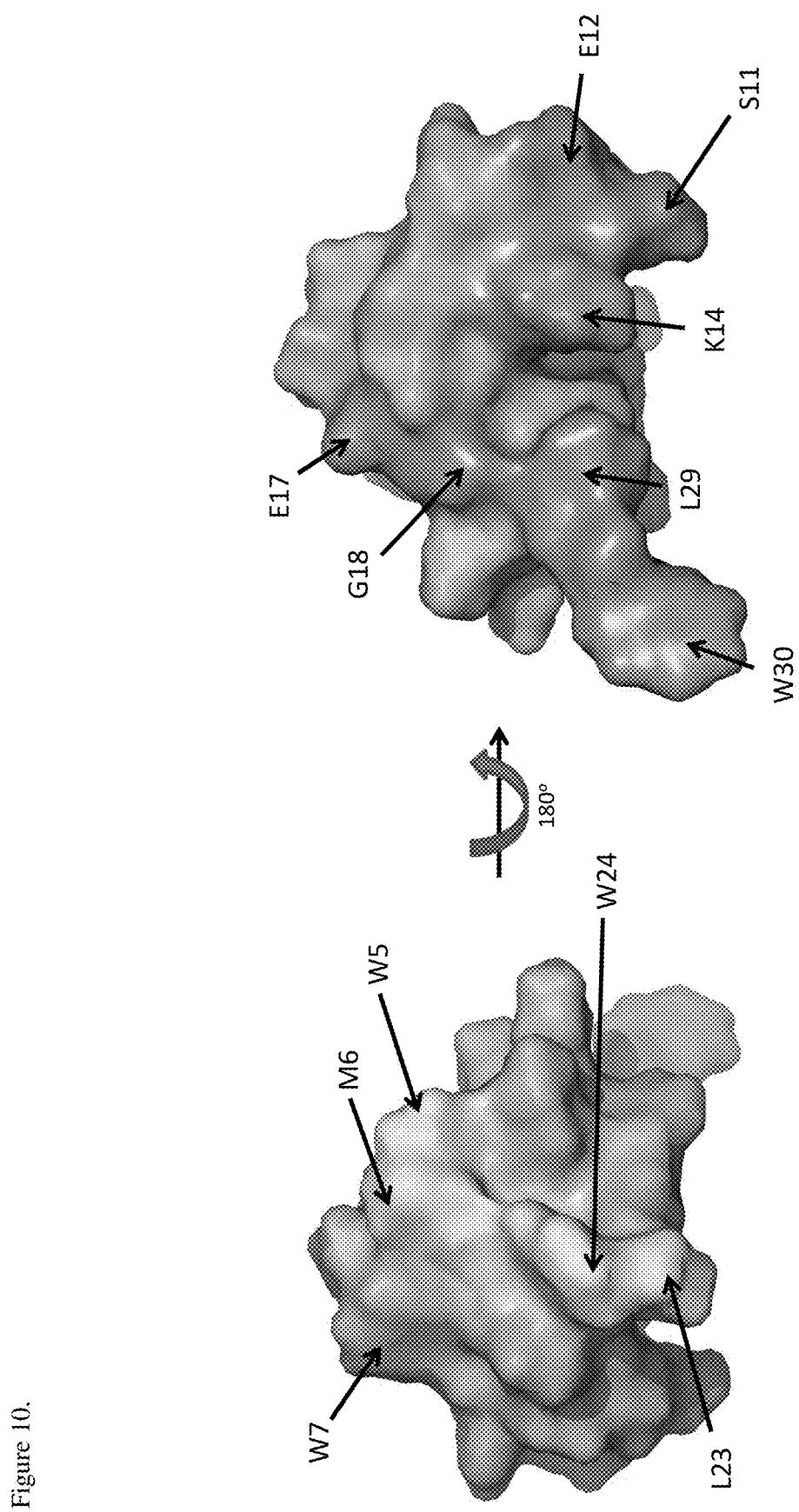
FIG. 10 shows the surface representation of the NMR structure of the wild type Protoxin-II. A hydrophobic face shown on left includes residues W5, M6, W7, L23 and W24. A selectivity face is shown on the right and includes residues S11, E12, K14, E17, G18, L29 and W30. Residue numbering according to SEQ ID NO: 1.
Figure 11A:
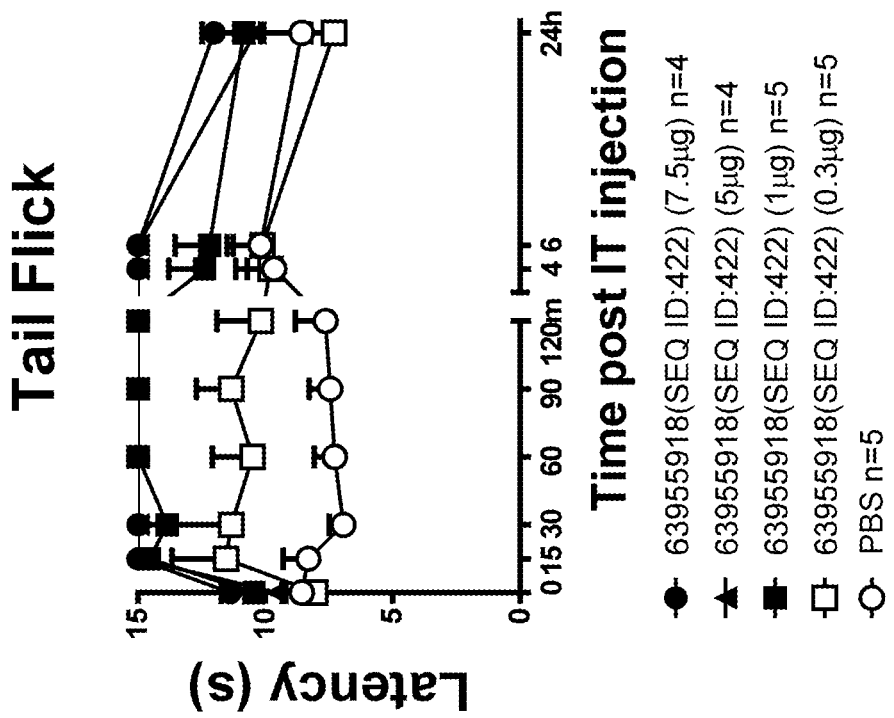
FIG. 11A shows efficacy of the Protoxin-II variant 63955918 SEQ ID NO: 422) after a single intrathecal (IT) administration in the rat tail flick test. Tail withdrawal latency to a thermal stimulus was measured at the indicated time post-peptide administration.
Figure 11B:
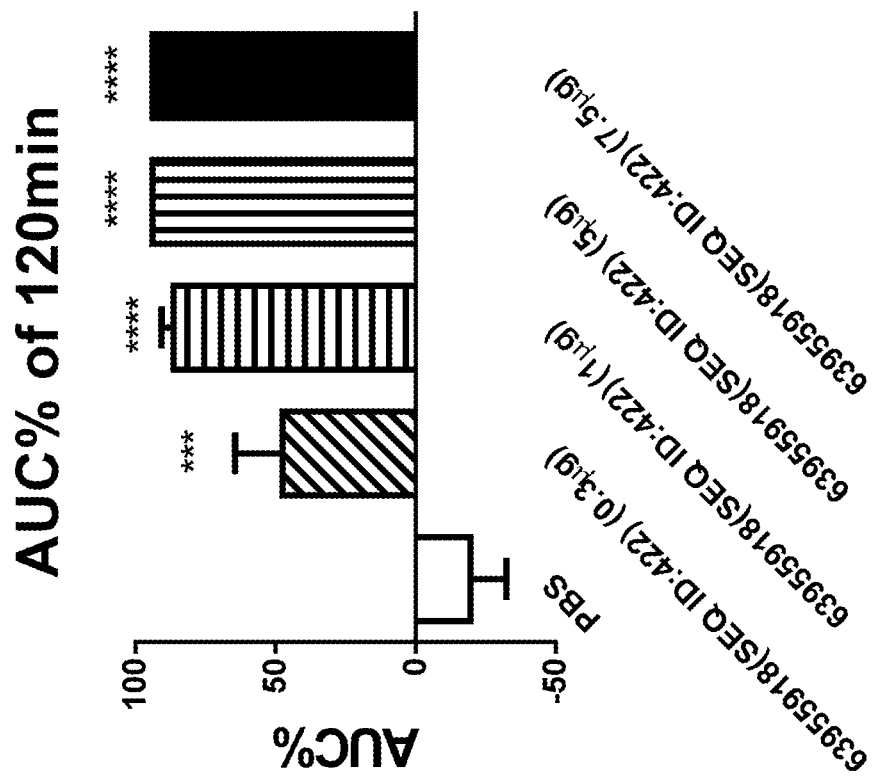
FIG. 11B shows efficacy of the Protoxin-II variant 63955918 SEQ ID NO: 422) in the rat tail flick test expressed as percent area under the curve (AUC %) in the first 120 min after a single intrathecal (IT) administration. *P<0.001 and **P<0.0001 vs PBS, one-way ANOVA followed by Bonferroni's multiple comparison.
Figure 11C:
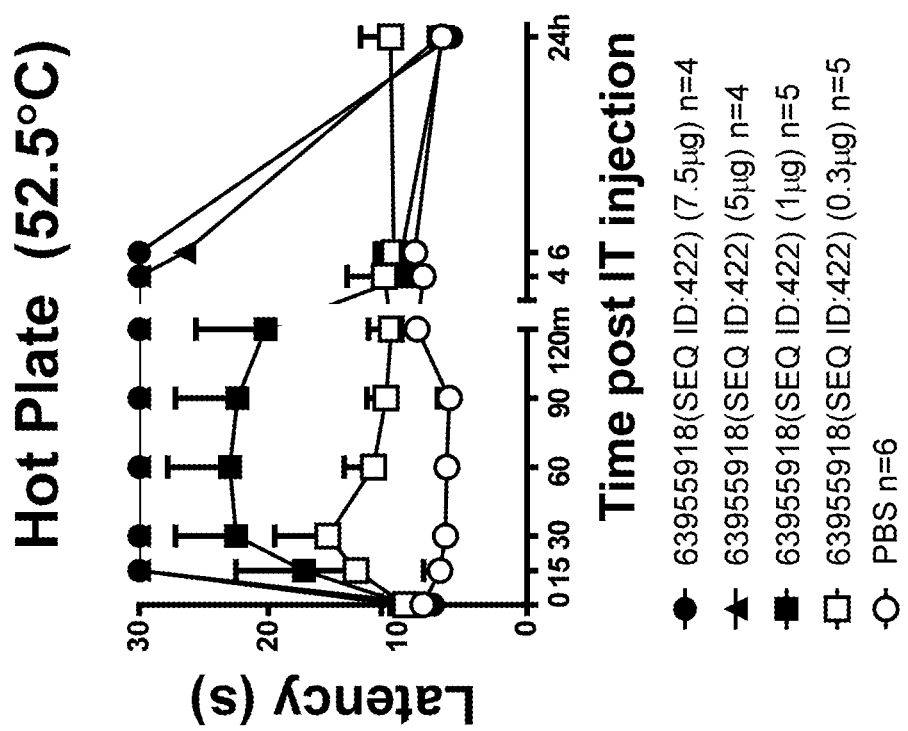
FIG. 11C shows efficacy of the Protoxin-II variant 63955918 SEQ ID NO: 422) after a single intrathecal (IT) administration in the rat hot plate test (52.5° C.). The latency of a nociceptive response on a hot plate was measured at the indicated time post-peptide administration.
Figure 11D:
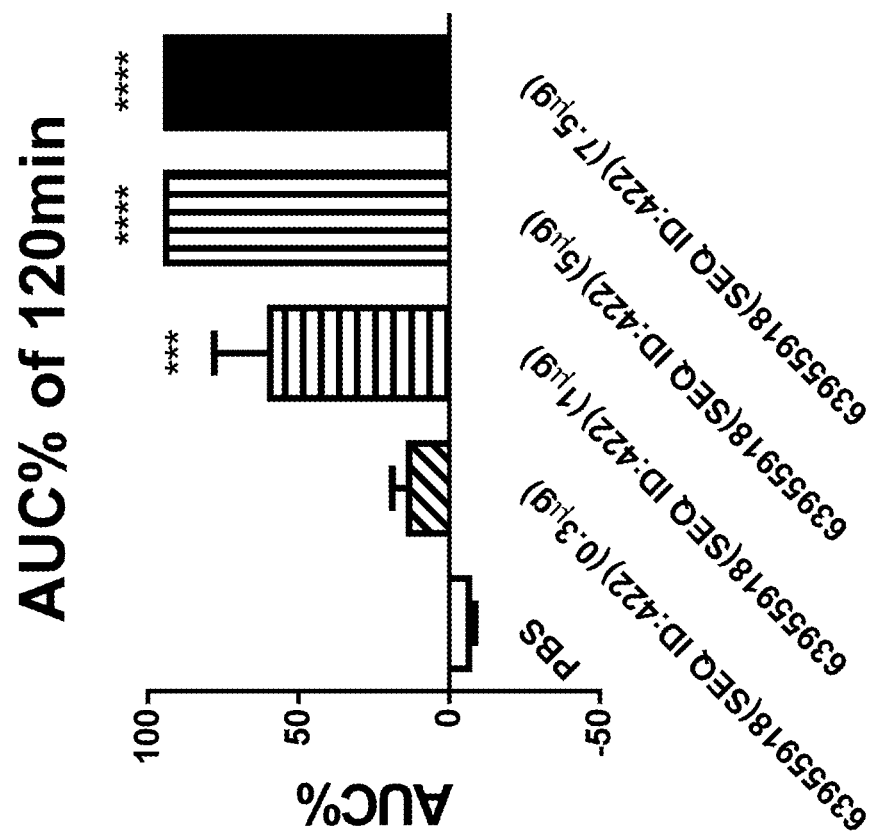
FIG. 11D shows efficacy of the Protoxin-II variant 63955918 SEQ ID NO: 422) in the hot plate test expressed as percent area under the curve (AUC %) in the first 120 min after a single intrathecal (IT) administration. *P<0.001 and **P<0.0001 vs PBS, one-way ANOVA followed by Bonferroni's multiple comparison.
Figure 11E:
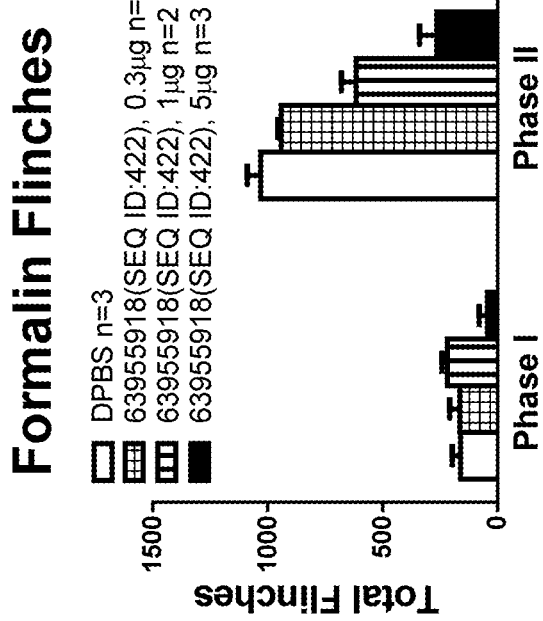
FIG. 11E shows efficacy of the Protoxin-II variant 63955918 SEQ ID NO: 422) in the rat formalin test. Injection of formalin into the rat hindpaw induced a bi-phasic flinching behavior. Total number of flinches in Phase I (0-10 min post formalin) and Phase II (11-60 min post formalin) was measured by an automated device. No statistics were performed in E) due to small group size.
Figure 12A:
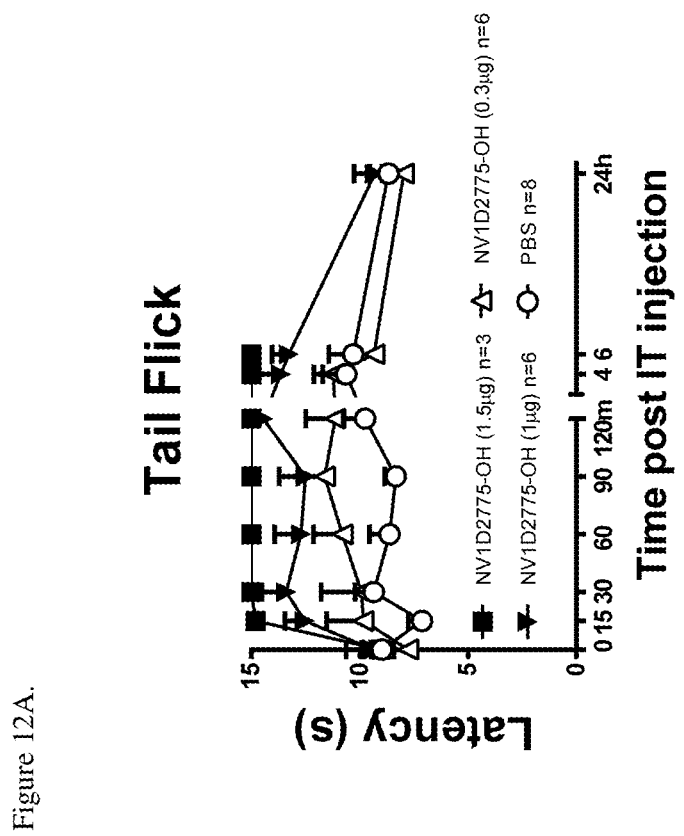
FIG. 12A shows efficacy of NV1D2775-OH after a single intrathecal (IT) administration in the rat tail flick test. Tail withdrawal latency to a thermal stimulus was measured at the indicated time post-peptide administration.
Figure 12B:
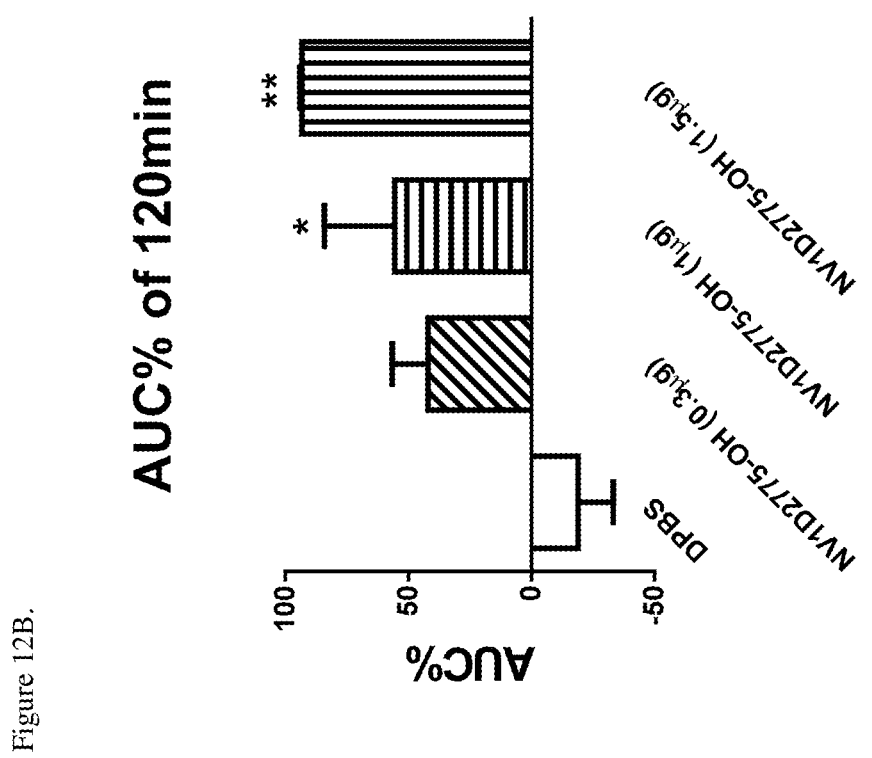
FIG. 12B shows efficacy of NV1D2775-OH in the rat tail flick test expressed as percent area under the curve (AUC %) in the first 120 min after a single intrathecal (IT) administration. *P<0.05 and **P<0.01 vs PBS, one-way ANOVA followed by Bonferroni's multiple comparison.
Figure 12C:
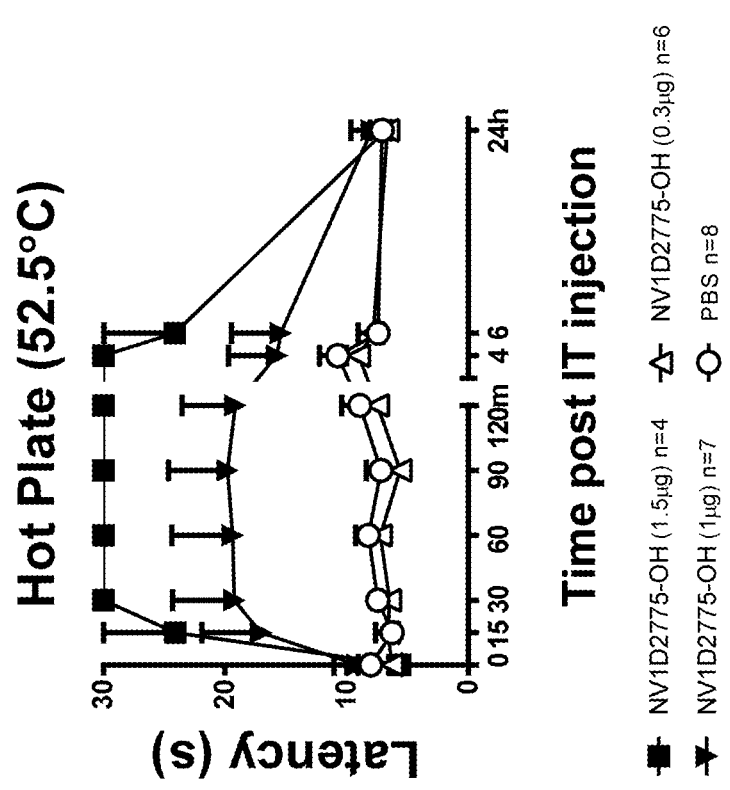
FIG. 12C shows efficacy of NV1D2775-OH after a single intrathecal (IT) administration in the rat hot plate test (52.5° C.). The latency of a nociceptive response on a hot plate was measured at the indicated time post-peptide administration.
Figure 12D:
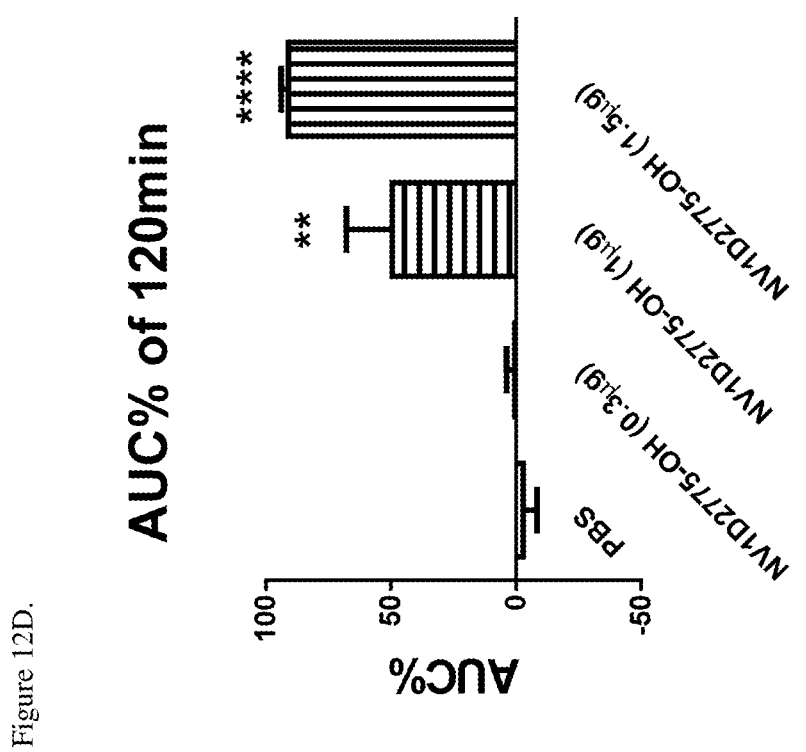
FIG. 12D shows efficacy of NV1D2775-OH in the rat hot plate test expressed as percent area under the curve (AUC %) in the first 120 min after a single intrathecal (IT) administration. P<0.01 and **P<0.0001 vs PBS, one-way ANOVA followed by Bonferroni's multiple comparison.
Figure 12E:
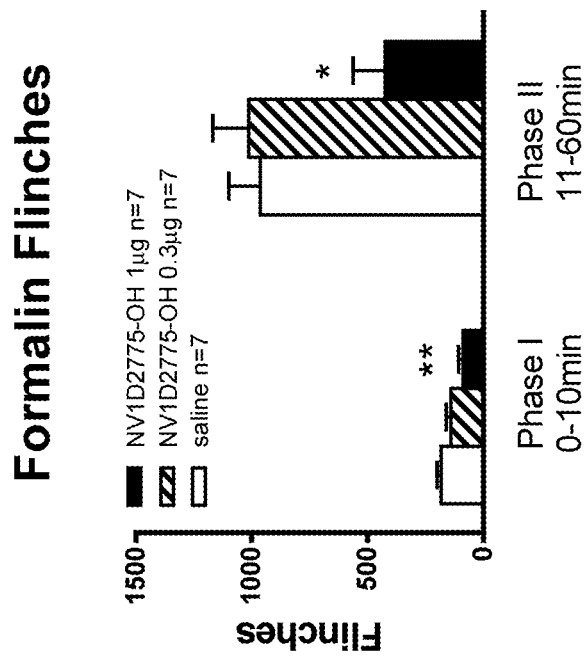
FIG. 12E shows efficacy of NV1D2775-OH in the formalin test. Injection of formalin into the rat hindpaw induced a bi-phasic flinching behavior. Total number of flinches in Phase I (0-10 min post formalin) and Phase II (11-60 min post formalin) was measured by an automated device. **P<0.01 vs PBS, phase I, *P<0.05 vs PBS, phase II, one-way ANOVA followed by Bonferroni's multiple comparison.
Figure 13A:
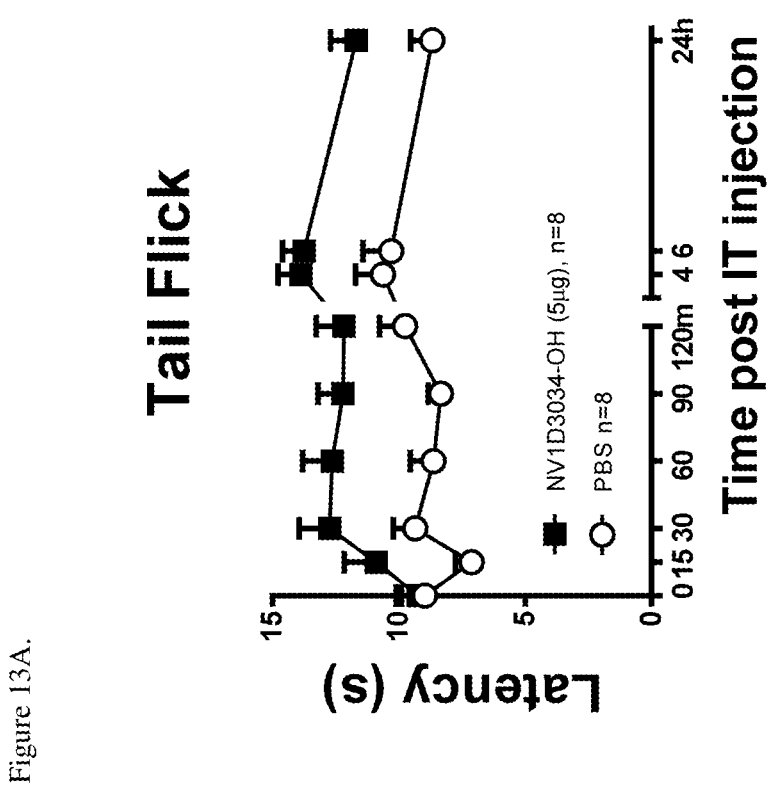
FIG. 13A shows efficacy of NV1D3034-OH after a single intrathecal (IT) administration in the rat tail flick test. Tail withdrawal latency to a thermal stimulus was measured at the indicated time post-peptide administration.
Figure 13B:
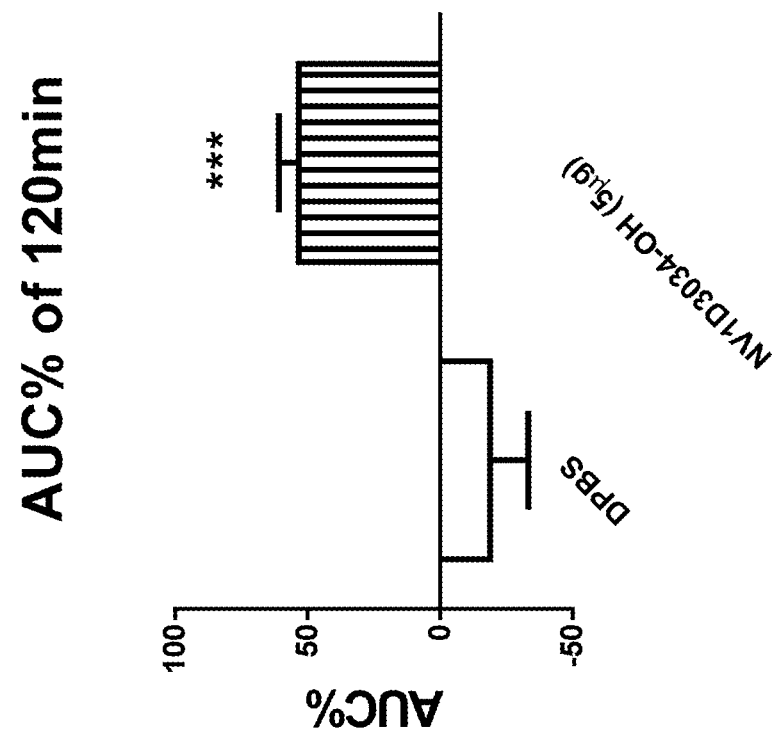
FIG. 13B shows efficacy of NV1D3034-OH in the rat tail flick test expressed as percent area under the curve (AUC %) in the first 120 min after a single intrathecal (IT) administration. ***P<0.005 vs PBS, t-test.
Figure 13C:
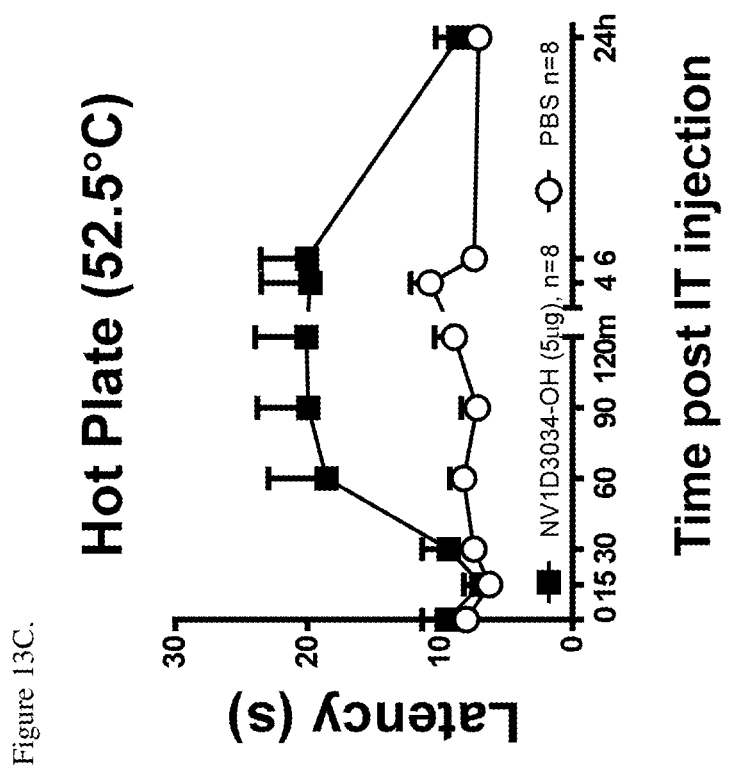
FIG. 13C shows efficacy of NV1D3034-OH after a single intrathecal (IT) administration in the rat hot plate test (52.5° C.). The latency of a nociceptive response on a hot plate was measured at the indicated time post-peptide administration.
Figure 13D:
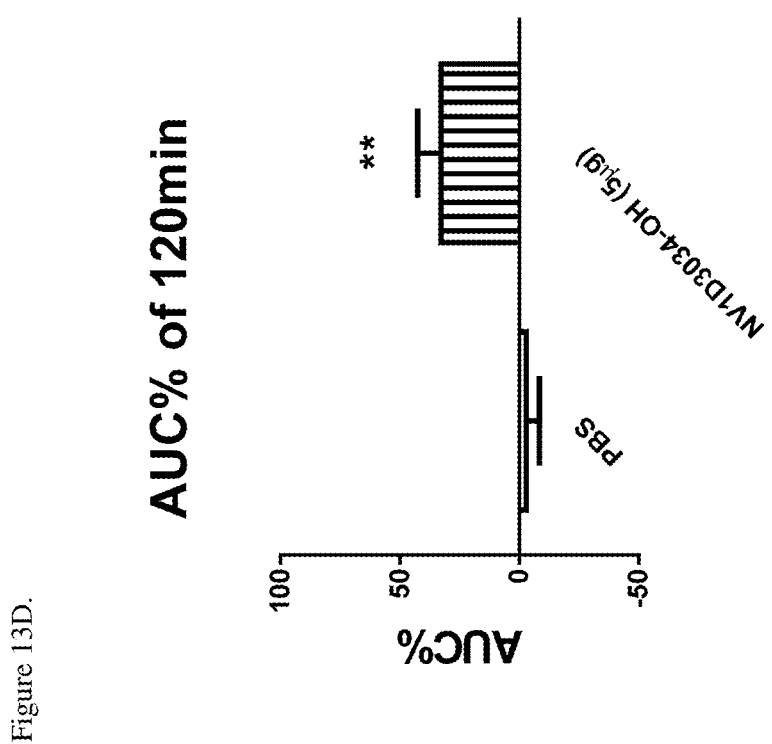
FIG. 13D shows efficacy of NV1D3034-OH in the rat hot plate test expressed as percent area under the curve (AUC %) in the first 120 min after a single intrathecal (IT) administration. **P<0.01 vs PBS, t-test.
Figure 13E:
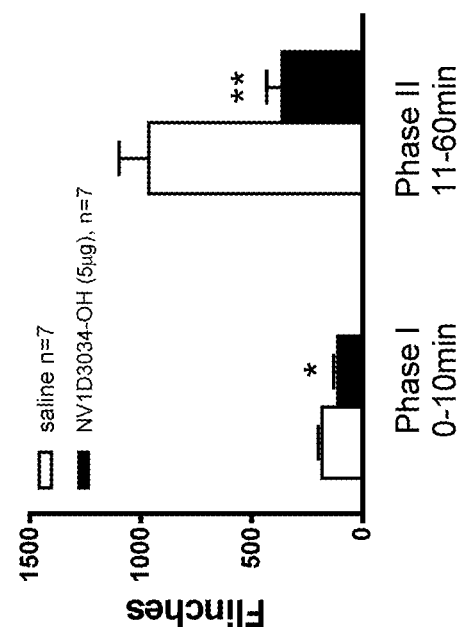
FIG. 13E shows efficacy of NV1D3034-OH in the rat formalin test. Injection of formalin into the rat hindpaw induced a bi-phasic flinching behavior. Total number of flinches in Phase I (0-10 min post formalin) and Phase II (11-60 min post formalin) was measured by an automated device. *P<0.05 vs PBS, phase I, **P<0.01 vs PBS, phase II, t-test.

The solution structure of Protoxin-II was determined by NMR and is shown in FIG. 10 as a surface representation. The left hand side of the Figure shows the previously described (Park et al., J. Med. Chem. 2014, 57:6623-6631) ring of Trp residues, W5/W7/W24, surrounding M6. On the opposite side of the molecule, using both mutagenesis and the NMR structure, a selectivity face was identified in this study on Protoxin-II consisting of multiple amino acid positions which can be mutated to improve selectivity for hNav1.7 over other sodium channel isoforms. The residues residing on the selectivity face include residues Ser11, Glu12, Lys14, Glu17, Gly18, Leu29 and Trp30 (residue numbering according to SEQ ID NO: 1). The identification of the selectivity face and multiple positions within responsible for selectivity towards Nav1.7 has not been described earlier.

Improved selectivity of Protoxin II variants with substitution at Ser11 is unexpected as it has been earlier demonstrated that mutation of Ser11 affect activity on multiple Nav channels, and therefore the residue was concluded not to play a role in Protoxin-II Nav1.7 selectivity (Park et al., J. Med. Chem. 2014, 57:6623-6631).

A key step in the synthetic production of Protoxin-II variants is the oxidative refolding of the linear peptide, where the disulfide pairings are formed. The RP-HPLC trace for native Protoxin-II purification following refolding revealed multiple peaks at differing retention times that were of correct mass but demonstrated differing levels of activity, indicative of a mixture of properly and improperly folded isomers of the peptide.

The relative abundance of the RP-HPLC major peak, and therefore the relative abundance of correctly folded peptide could be improved by making substitutions at various Protoxin-II positions. Mutation of Trp7 or Trp30 improved folding of the resulting Protoxin-II variant. Mutation of both Trp7 and Trp30 in combination further improved folding of the resulting Protoxin-II variant, and could rescue folding of difficult-to-refold Protoxin-II variants.

Production of combinatorial mutant peptides having one or more substitutions that improved selectivity (Gln3, Ser11, Glu12, Lys14, Glu17, Gly18, and Leu29) as well as mutations at Trp7 and Trp30 resulted in peptides with both improved selectivity and improved refolding properties. Protoxin-II belongs to a family 3 of inhibitory cysteine knot peptides (Klint et. al., Toxicon 60:478-491, 2012). Trp7 is conserved in all family 3 members, and substitutions at this position as well as at Trp5 and Met6 in Jingzhaotoxin-V, another family 3 inhibitory cysteine knot peptide, resulted in loss in potency, indicating that hydrophobic residues at positions 5, 6 and 7 in Jingzhaotoxin-V are essential to Jingzhaotoxin-V Nav1.7 inhibitory potency (Int. Pat. Publ. No. 2014/165277). Trp5/Met6/Trp7 is also conserved in Protoxin-II, and therefore it was unexpected that polar substitutions at Trp7 can be made without loss of Protoxin-II activity with significantly improved refolding properties. Substitutions at Trp30 were shown to simultaneously improve Nav1.7 selectivity and refolding properties of the variant peptide and were unexpected since individual advantageous substitutions typically only improve a single parameter.

Table 13 shows the amino acid sequences of the select generated Protoxin-II variants.

TABLE 14

| Protein Name | Substitution | Protein SEQ ID NO: | Amino acid sequence |
|---|---|---|---|
| NV1G2232 | W30L | 408 | GPYCQKWMWTCDSERKCCEGMVCRLWCKKKLL-COOH |
| NV1G2182 | W30F | 409 | GPYCQKWMWTCDSERKCCEGMVCRLWCKKKLF-COOH |
| NV1G2319 | W30Y | 410 | GPYCQKWMWTCDSERKCCEGMVCRLWCKKKLY-COOH |
| NV1G2329 | W30G | 411 | GPYCQKWMWTCDSERKCCEGMVCRLWCKKKLG-COOH |
| NV1G2129 | W30I | 412 | GPYCQKWMWTCDSERKCCEGMVCRLWCKKKLI-COOH |
| NV1G2291 | W30V | 413 | GPYCQKWMWTCDSERKCCEGMVCRLWCKKKLV-COOH |
| NV1G2156 | W7Y | 414 | GPYCQKWMYTCDSERKCCEGMVCRLWCKKKLW-COOH |
| NV1G2082 | W7E | 415 | GPYCQKWMETCDSERKCCEGMVCRLWCKKKLW-COOH |
| 63930841 | W7Q | 416 | GPYCQKWMQTCDSERKCCEGMVCRLWCKKKLW-COOH |
| 64087946 | (-GP) W7Q, S11A, M19F, V20S, R22Me, W30L | 417 | YCQKWMQTCDAERKCCEGFSC-(N-Me-Arg)-LWCKKKLL-COOH |
| 64053366 | (-GP) W7Q S11D W30L | 418 | YCQKWMQTCDDERKCCEGMVCRLWCKKKLL-COOH |
| 64053340 | (-GP) W7Q K14F W30L | 419 | YCQKWMQTCDSERFCCEGMVCRLWCKKKLL-COOH |
| 64053236 | W7Q K14F W30L | 420 | GPYCQKWMQTCDSERFCCEGMVCRLWCKKKLL-COOH |
| 64053223 | W7Q S11I W30L | 421 | GPYCQKWMQTCDIERKCCEGMVCRLWCKKKLL-COOH |
| 63955918 | W7Q W30L | 422 | GPYCQKWMQTCDSERKCCEGMVCRLWCKKKLL-COOH |
| 64053210 | W7Q E17N W30L | 423 | GPYCQKWMQTCDSERKCCNGMVCRLWCKKKLL-COOH |
| 64087907 | (-GP) W7Q | 424 | YCQKWMQTCDSERKCCEGMVCRLWCKKKLW-COOH |
| 64032488 | (-GP) W7Q W30L | 425 | YCQKWMQTCDSERKCCEGMVCRLWCKKKLL-COOH |
| 64053301 | W7Q S11V W30L | 426 | GPYCQKWMQTCDVERKCCEGMVCRLWCKKKLL-COOH |
| 64053275 | W7Q E17L W30L | 427 | GPYCQKWMQTCDSERKCCLGMVCRLWCKKKLL-COOH |
| 64053327 | (-GP) W7Q E17N W30L | 428 | YCQKWMQTCDSERKCCNGMVCRLWCKKKLL-COOH |

TABLE 14-continued

| Protein Name | Substitution | Protein SEQ ID NO: | Amino acid sequence |
|---|---|---|---|
| NV1G2324 | E17Y | 429 | GPYCQKWMWTCDSERKCCYGMVCR LWCKKKLW-COOH |
| NV1G2094 | E17I | 430 | GPYCQKWMWTCDSERKCCIGMVCRL WCKKKLW-COOH |
| NV1G1996 | E17L | 431 | GPYCQKWMWTCDSERKCCLGMVCRL WCKKKLW-COOH |

Select variants were characterized for their inhibition of Nav1.7 using veratridine-induced depolarization inhibition assay or Qpatch as described in Example 3. Table 15 shows the $IC_{50}$ values obtained. For some variants, only % inhibition (% blk; percent block of control) at a single concentration (10 nM or 30 nM) was recorded for Qpatch.

TABLE 15

| | | hNav1.7 | | | | |
|---|---|---|---|---|---|---|
| Protein | Protein | Veratridine-induced Depolarization Inhibition Assay | | QP | | |
| Name | SEQ ID NO: | IC50 (nM) | se* | IC50 (nM) | % blk** | se* |
| NV1G2232 | 408 | 16.7 | 1.32 | 5.0 | 56.5% @ 10 nM | 5.7 |
| NV1G2182 | 409 | 17.3 | 1.37 | 3.8 | 54.2% @ 10 nM | 5.4 |
| NV1G2319 | 410 | 20.7 | 2.3 | 9.7 | 43.2% @ 10 nM | 6.2 |
| NV1G2329 | 411 | 38 | 2.43E+00 | | | |
| NV1G2129 | 412 | 47.3 | 3.81 | | −6.5% @ 10 nM | 6.5 |
| NV1G2291 | 413 | 63.3 | 14.9 | | | |
| NV1G2156 | 414 | 90.5 | 6.88 | | | |
| NV1G2082 | 415 | 90.8 | 11.4 | | | |
| 63930841 | 416 | | | 20.9 | | |
| 64087946 | 417 | | | 23.8 | 20.7% @ 10 nM | 10.9 |
| 64053366 | 418 | | | | 22.1% @ 10 nM | 3.5 |
| 64053340 | 419 | | | | 26.8% @ 10 nM | 3.7 |
| 64053236 | 420 | | | | 28.0% @ 10 nM | 13.2 |
| 64053223 | 421 | | | | 33.0% @ 10 nM | 5.8 |
| 63955918 | 422 | | | 10.8 | 38.50% @ 10 nM | 4.5 |
| 64053210 | 423 | | | | 41.7% @ 10 nM | 6.2 |
| 64087907 | 424 | | | 7.1 | 45.1% @ 10 nM | 6.0 |
| 64032488 | 425 | | | 6.5 | 45.6% @ 10 nM | 4.6 |
| 64053301 | 426 | | | 10.7 | 45.83% @ 10 nM | 3.3 |
| 64053275 | 427 | | | 2.9 | 48.22% @ 10 nM | 5.2 |
| 64053327 | 428 | | | 7.9 | 51.9% @ 10 nM | 2.6 |
| NV1G2324 | 429 | | | | 57.5% @ 10 nM | 3.9 |
| NV1G2094 | 430 | | | | 63.2% @ 30 nM | 6.2 |
| NV1G1996 | 431 | | | 0.5 | 76.9% @ 10 nM | 2.3 |

*se; standard error
**% blk: % block
QP: QPatch

Select variants were tested against various human Nav1.x channels. Table 16 shows the results of those experiments. $IC_{50}$ values for each channel were measured using QPatch.

TABLE 16

| Protein | | Protein | $IC_{50}$ (nM) | | | |
|---|---|---|---|---|---|---|
| Name | Substitution | SEQ ID NO: | Nav1.1 | Nav1.2 | Nav1.4 | Nav1.6 |
| NV1G2232 | W30L | 408 | | | 3847.0 | 562.7 |
| NV1G2182 | W30F | 409 | | 239.6 | 732.2 | 253.1 |
| NV1G2319 | W30Y | 410 | | | 1704.0 | |
| 63930841 | W7Q | 416 | | | 543.1 | |

TABLE 16-continued

| Protein Name | Protein Substitution | SEQ ID NO: | IC$_{50}$ (nM) Nav1.1 | Nav1.2 | Nav1.4 | Nav1.6 |
|---|---|---|---|---|---|---|
| 64087946 | (-GP) W7Q, S11A, M19F, V20S, R22Me, W30L | 417 | | | 2586.0 | |
| 63955918 | W7Q W30L | 422 | | 1951.0 | 17000.0 | 1987.0 |
| 64087907 | (-GP) W7Q | 424 | | | 1460.0 | |
| 64032488 | (-GP) W7Q W30L | 425 | | 1336.0 | | 1842.0 |
| 64053301 | W7Q S11V W30L | 426 | 15340.0 | 19350.0 | 2244.0 | |
| 64053275 | W7Q E17L W30L | 427 | 3868.0 | 136.7 | 2219.0 | |
| 64053327 | (-GP) W7Q E17N W30L | 428 | 6391.0 | 6656.0 | 3867.0 | |

Protoxin-II variants were expressed and purified as described in Example 1, or synthesized by standard solid phase synthesis methods. The yields of the recombinant or synthetic peptides were compared to the yields of the wild-type Protoxin-II. Table 17 shows that the yields of the select Protoxin-II variants were significantly higher than that of Protoxin-II, indicating improved folding properties of the variants. The scale of the solid-phase synthesis was 0.1 mmol.

TABLE 17

| Protein name | Substitution | total yield (mg) |
|---|---|---|
| NV1D12 (Protoxin-II with N-terminal GP) | | 3.8 |
| 63930841 | W7Q | 14.4 |
| NV1G2232 | W30L | 14.5 |
| 63955918 | W7Q, W30L | 16.2 |
| NV1G1996 | E17L | 1.8 |
| 64053275 | E17L W7Q W30L | 13.0 |

Example 7. Protoxin-II Variants are Efficacious in In Vivo Models of Pain Following Intrathecal Administration Efficacy of select Protoxin-II variants in reducing pain after intrathecal administration was evaluated.

Peptides NV1D2775-OH, NV1D3034 and 63955918 were used in the studies. Animal models that measure acute thermal pain (tail flick and hot plate) and injury-induced pain (formalin flinching) were used.

Tail-Flick Test:

The animals were placed on a tail-flick device (Ugo Basile). The device has a focal infrared light heating area (diameter—5 mm). The tail (⅓-½ way from distal end) of the animal was placed on the focal heating area. The temperature of the heat source was adjusted to elicit a tail-flick within 10 seconds in animals treated with vehicle. A 15 second cut-off time was used to prevent tissue damage, as is standard in the literature. The time elapsed between the start of the heat stimulus and any avoidance response was measured automatically and recorded for the test groups.

Hot Plate Test:

Animals were placed on a 10"×10" metal plate surrounded by 4 Plexiglas walls (15 inches high). The plate was maintained at a temperature of 52.5° C. The response latency (time when the animal first flinches or licks its hind paw, jumps, or vocalizes) was measured and the animal removed from the plate. Animals showing no response were removed from the plate after 30 s to prevent any possible tissue damage.

Formalin Flinching:

Formalin-induced pain behavior (i.e. paw flinches) was measured using an automated "flinch response" measuring device manufactured by UCSD. The device detects any sudden movement of a metal band glued onto one hind paw of the animal using a motion sensor installed underneath the device floor. One-half to one hour prior to formalin injection, a small metal band was attached to the plantar surface of one hind paw using a small drop of cyanoacrylate and the animal was placed in the testing chamber to be acclimatized. Formalin (2.5%, 50 μL) was injected subcutaneously into the dorsum of the paw with the metal band. The animal was placed in the customized cylinder (25×10×20 cm, San Diego Instrument) immediately after intraplantar formalin injection. Paw flinches were recorded automatically.

In the acute thermal pain models, Protoxin-II variant 63955918 produced potent and prolonged analgesia as indicated by the elevated latency in the tail flick test (FIG. 11A and FIG. 11B) and hot plate test (FIG. 11C, FIG. 11D) after a single intrathecal administration. The significance and duration of the analgesia was dose-dependent.

Hindpaw formalin injection is a commonly used model for injury-induced pain. The injection induces a characteristic, bi-phasic flinching behavior, which indicates pain in test animals. As shown in FIG. 11E, animals pretreated with intrathecal injection of Protoxin-II variant 63955918 demonstrated less flinches in the formalin test, suggesting an inhibition of injury-induced pain.

Similarly, peptides NV1D2775-OH and NV1D3034 demonstrated significant efficacy in the tail flick, hot plate and formalin test (FIG. 12A, FIG. 12B, FIG. 12C, FIG. 12D, FIG. 12E, FIG. 13A, FIG. 13B, FIG. 13C, FIG. 13D, FIG. 13E) following a single intrathecal administration.

Example 8. Characterization of Additional Protoxin-II Variants

Additional Protoxin-II variants were designed and expressed using the strategies and methods described in Example 6, and characterized in FLPR Tetra and/or Qpatch according to the protocols described in Example 3.

Table 18 shows the amino acid sequence of the select generated Protoxin-II variants.

TABLE 18

| ID | Mutation | SEQ ID NO: | Sequence |
| --- | --- | --- | --- |
| NV1G2228 | E12R | 434 | GPYCQKWMWTCDSRRKCCEGMVCRLWCKKKLW-COOH |
| NV1G2072 | E12T | 435 | GPYCQKWMWTCDSTRKCCEGMVCRLWCKKKLW-COOH |
| NV1G2008 | S11N | 436 | GPYCQKWMWTCDNERKCCEGMVCRLWCKKKLW-COOH |
| NV1G1994 | T8F | 437 | GPYCQKWMWFCDSERKCCEGMVCRLWCKKKLW-COOH |
| NV TABLE 18-continued

| ID | Mutation | SEQ ID NO: | Sequence |
|---|---|---|---|
| NV1G2149 | T8L | 456 | GPYCQKWMWLCDSERKCCEGMVCRLWCKKKLW-COOH |
| NV1G2226 | V20I | 457 | GPYCQKWMWTCDSERKCCEGMICRLWCKKKLW-COOH |
| NV1G2286 | T8K | 458 | GPYCQKWMWKCDSERKCCEGMVCRLWCKKKLW-COOH |
| NV1G2128 | E12H | 459 | GPYCQKWMWTCDSHRKCCEGMVCRLWCKKKLW-COOH |
| NV1G2041 | K4E, E17R | 460 | GPYCQEWMWTCDSERKCCRGMVCRLWCKKKLW-COOH |
| NV1G2001 | T8G | 461 | GPYCQKWMWGCDSERKCCEGMVCRLWCKKKLW-COOH |
| NV1G2019 | K4E, W5F, M6L, E12T | 462 | GPYCQEFLWTCDSTRKCCEGMVCRLWCKKKLW-COOH |
| NV1G2002 | K14H | 463 | GPYCQKWMWTCDSERHCCEGMVCRLWCKKKLW-COOH |
| NV1G2225 | E17R | 464 | GPYCQKWMWTCDSERKCCRGMVCRLWCKKKLW-COOH |
| NV1G2012 | K14V | 465 | GPYCQKWMWTCDSERVCCEGMVCRLWCKKKLW-COOH |
| NV1G2020 | Y1S, M6F, A11R, E12T, M19L | 466 | GPSCQKWFWTCDRTRKCCEGLVCRLWCKKKLW-COOH |
| NV1G2334 | E17K | 467 | GPYCQKWMWTCDSERKCCKGMVCRLWCKKKLW-COOH |
| NV1G2025 | Y1Q, W7Q, S11A, E12T, M19F | 468 | GPQCQKWMQTCDATRKCCEGFVCRLWCKKKLW-COOH |
| NV1G2131 | E12Y | 469 | GPYCQKWMWTCDSYRKCCEGMVCRLWCKKKLW-COOH |
| NV1G1007 A11I, E12T | Y1Q, W7Q, S11I, E12T, M19F | 470 | GPQCQKWMQTCDITRKCCEGFVCRLWCKKKLW-COOH |
| NV1G2268 | Y1F | 471 | GPFCQKWMWTCDSERKCCEGMVCRLWCKKKLW-COOH |
| NV1G2332 | E17S | 472 | GPYCQKWMWTCDSERKCCSGMVCRLWCKKKLW-COOH |
| NV1G2010 | T8V | 473 | GPYCQKWMWVCDSERKCCEGMVCRLWCKKKLW-COOH |
| NV1G2053 | Y1T | 474 | GPTCQKWMWTCDSERKCCEGMVCRLWCKKKLW-COOH |
| NV1G1519 | Y1Q,W7QA [[S11I]] S11A, E12R, M19F | 133 | GPQCQKWMQTCDARRKCCEGFVCRLWCKKKLW-COOH |
| NV1G2253 | E12I | 475 | GPYCQKWMWTCDSIRKCCEGMVCRLWCKKKLW-COOH |
| NV1G2055 | E12L | 476 | GPYCQKWMWTCDSLRKCCEGMVCRLWCKKKLW-COOH |
| NV1G2338 | K4R | 477 | GPYCQRWMWTCDSERKCCEGMVCRLWCKKKLW-COOH |
| NV1G2030 | K14F | 478 | GPYCQKWMWTCDSERFCCEGMVCRLWCKKKLW-COOH |

TABLE 18-continued

| ID | Mutation | SEQ ID NO: | Sequence |
|---|---|---|---|
| NV1G2024 | Y1S, M6F, S11A, E12N, M19L | 479 | GPSCQKWFWTCDANRKCCEGLVCRLWCKKKLW-COOH |
| NV1G2004 | K14Y | 480 | GPYCQKWMWTCDSERYCCEGMVCRLWCKKKLW-COOH |
| NV1G2336 | M6L | 481 | GPYCQKWLWTCDSERKCCEGMVCRLWCKKKLW-COOH |
| NV1G2011 | E17F | 482 | GPYCQKWMWTCDSERKCCFGMVCRLWCKKKLW-COOH |
| NV1G2080 | W5Y | 483 | GPYCQKYMWTCDSERKCCEGMVCRLWCKKKLW-COOH |
| NV1G2288 | D10R | 484 | GPYCQKWMWTCRSERKCCEGMVCRLWCKKKLW-COOH |
| NV1G2142 | K14R | 485 | GPYCQKWMWTCDSERRCCEGMVCRLWCKKKLW-COOH |
| NV1G2232 | W30L | 408 | GPYCQKWMWTCDSERKCCEGMVCRLWCKKKLL-COOH |
| NV1G2193 | E12D | 486 | GPYCQKWMWTCDSDRKCCEGMVCRLWCKKKLW-COOH |
| NV1G2230 | S11D | 487 | GPYCQKWMWTCDDERKCCEGMVCRLWCKKKLW-COOH |
| NV1G2182 | W30F | 409 | GPYCQKWMWTCDSERKCCEGMVCRLWCKKKLF-COOH |
| NV1G1153 C-terminal palmitoyl-lysine | Y1Q, W7Q, S11R, M19F, R22T, K26R, addition of palmitoyl-lysine at position 33 | 488 | GPQCQKWMQTCDRERKCCEGFVCTLWCRKKLW-(palmitoyl-lysine)-COOH |
| NV1G2339 | T8A | 489 | GPYCQKWMWACDSERKCCEGMVCRLWCKKKLW-COOH |
| NV1G2016 | Y1S, M6F, S11R, M19L | 490 | GPSCQKWFWTCDRERKCCEGLVCRLWCKKKLW-COOH |
| NV1G2017 | Y1Q, K4E, W5F, M6L | 491 | GPQCQEFLWTCDSERKCCEGMVCRLWCKKKLW-COOH |
| NV1G2111 | E17N | 492 | GPYCQKWMWTCDSERKCCNGMVCRLWCKKKLW-COOH |
| NV1G2330 | R22S | 493 | GPYCQKWMWTCDSERKCCEGMVCSLWCKKKLW-COOH |
| NV1G2204 | E17T | 494 | GPYCQKWMWTCDSERKCCTGMVCRLWCKKKLW-COOH |
| NV1G2026 | Y1S, M6F, S11A, E12T, M19L | 495 | GPSCQKWFWTCDATRKCCEGLVCRLWCKKKLW-COOH |
| NV1G1007 with C-terminal 5x Gly | Y1Q, W7Q, S11A, M19F, addition of 5xGly at positions 31-35 | 496 | GPQCQKWMQTCDAERKCCEGFVCRLWCKKKLWGGGGG-COOH |
| NV1G2038 | L23F | 497 | GPYCQKWMWTCDSERKCC TABLE 18-continued

| ID | Mutation | SEQ ID NO: | Sequence |
|---|---|---|---|
| NV1G2021 | K4E, W5F, M6L, S11R, E12T | 499 | GPYCQEFLWTCDRTRKCCEGMVCRLWCKKK LW-COOH |
| NV1G2319 | W30Y | 410 | GPYCQKWMWTCDSERKCCEGMVCRLWCKKK LY-COOH |
| NV1G2100 | E12G | 500 | GPYCQKWMWTCDSGRKCCEGMVCRLWCKKK LW-COOH |
| NV1G2130 | Y1D | 501 | GPDCQKWMWTCDSERKCCEGMVCRLWCKKK LW-COOH |
| NV1G2081 | K4D | 502 | GPYCQDWMWTCDSERKCCEGMVCRLWCKKK LW-COOH |
| NV1G2252 | T8H | 503 | GPYCQKWMWHCDSERKCCEGMVCRLWCKKK LW-COOH |
| NV1G2040 | K26Y | 504 | GPYCQKWMWTCDSERKCCEGMVCRLWCYKK LW-COOH |
| NV1G2146 | G18P | 505 | GPYCQKWMWTCDSERKCCEPMVCRLWCKKK LW-COOH |
| NV1G1153-N-ethyl | Y1Q ,W7Q, S11R, M19F, R22T, K26R, C-terminal ethylamide | 506 | GPQCQKWMQTCDRERKCCEGFVCTLWCRKK LW-(ethylamide) |
| NV1G2098 | E17H | 507 | GPYCQKWMWTCDSERKCCHGMVCRLWCKKK LW-COOH |
| NV1G2191 | L29H | 508 | GPYCQKWMWTCDSERKCCEGMVCRLWCKKK HW-COOH |
| NV1G2333 | G18K | 509 | GPYCQKWMWTCDSERKCCEKMVCRLWCKKK LW-COOH |
| NV1G2224 | K14S | 510 | GPYCQKWMWTCDSERSCCEGMVCRLWCKKK LW-COOH |
| NV1G1001-N-ethyl | (-GP) Y1S, W7Q, S11A, M19F, C-terminal ethylamide | 511 | SCQKWMQTCDAERKCCEGFVCRLWCKKKL W-(ethylamide) |
| NV1G1996 | E17L | 431 | GPYCQKWMWTCDSERKCCLGMVCRLWCKKK LW-COOH |
| NV1G2337 | K14Q | 512 | GPYCQKWMWTCDSERQCCEGMVCRLWCKKK LW-COOH |
| NV1G2301 | V20T | 513 | GPYCQKWMWTCDSERKCCEGMTCRLWCKKK LW-COOH |
| NV1G2075 | K4T | 514 | GPYCQTWMWTCDSERKCCEGMVCRLWCKKK LW-COOH |
| NV1G2278 | R22N | 515 | GPYCQKWMWTCDSERKCCEGMVCNLWCKKK LW-COOH |
| NV1G2014 | W24H | 516 | GPYCQKWMWTCDSERKCCEGMVCRLHCKKK LW-COOH |
| NV1G2065 | Y1Q, W7Q, S11R, E12T, M19F | 517 | GPQCQKWMQTCDRTRKCCEGFVCRLWCKKK LW-COOH |
| NV1G2099 | L29V | 518 | GPYCQKWMWTCDSERKCCEGMVCRLWCKKK VW-COOH |
| NV1G1007 E17L | Y1Q, W7Q, S11A, E17L, M19F | 519 | GPQCQKWMQTCDAERKCCLGFVCRLWCKKK LW-COOH |

TABLE 18-continued

| ID | Mutation | SEQ ID NO: | Sequence |
|---|---|---|---|
| NV1G1007 G33 | Y1Q, W7Q, S11A, M19F, addition of Gly at position 33 | 520 | GPQCQKWMQTCDAERKCCEGFVCRLWCKKK LWG-COOH |
| 1007 A11I | Y1Q, W7Q, S11I, M19F | 521 | GPQCQKWMQTCDIERKCCEGFVCRLWCKKK LW-COOH |
| NV1G2221 | K27A | 522 | GPYCQKWMWTCDSERKCCEGMVCRLWCKAK LW-COOH |
| NV1G2097 | K14I | 523 | GPYCQKWMWTCDSERICCEGMVCRLWCKKK LW-COOH |
| NV1G2029 | W5L | 524 | GPYCQKLMWTCDSERKCCEGMVCRLWCKKK LW-COOH |
| NV1G2257 | S11V | 525 | GPYCQKWMWTCDVERKCCEGMVCRLWCKKK LW-COOH |
| NV1G1998 | V20H | 526 | GPYCQKWMWTCDSERKCCEGMHCRLWCKKK LW-COOH |
| NV1G2068 | R13Y | 527 | GPYCQKWMWTCDSEYKCCEGMVCRLWCKKK LW-COOH |
| NV1G1001 | Y1S, W7Q, S11A, M19F | 65 | GPSCQKWMQTCDAERKCCEGFVCRLWCKKK LW-COOH |
| NV1G2137 | V20K | 528 | GPYCQKWMWTCDSERKCCEGMKCRLWCKKK LW-COOH |
| NV1G2199 | S11H | 529 | GPYCQKWMWTCDHERKCCEGMVCRLWCKKK LW-COOH |
| NV1G2300 | K27G | 530 | GPYCQKWMWTCDSERKCCEGMVCRLWCKGK LW-COOH |
| NV1G2124 | R13H | 531 | GPYCQKWMWTCDSEHKCCEGMVCRLWCKKK LW-COOH |
| NV1G2254 | T8P | 532 | GPYCQKWMWPCDSERKCCEGMVCRLWCKKK LW-COOH |
| NV1G2239 | K4N | 533 | GPYCQNWMWTCDSERKCCEGMVCRLWCKKK LW-COOH |
| NV1G2255 | K4E, E17K | 534 | GPYCQEWMWTCDSERKCCKGMVCRLWCKKK LW-COOH |
| NV1G2256 | K14G | 535 | GPYCQKWMWTCDSERGCCEGMVCRLWCKKK LW-COOH |
| NV1G2095 | K14T | 536 | GPYCQKWMWTCDSERTCCEGMVCRLWCKKK LW-COOH |
| NV1G2220 | L29S | 537 | GPYCQKWMWTCDSERKCCEGMVCRLWCKKK SW-COOH |
| NV1G2154 | T8Q | 538 | GPYCQKWMWQCDSERKCCEGMVCRLWCKKK LW-COOH |
| NV1G2329 | W30G | 411 | GPYCQKWMWTCDSERKCCEGMVCRLWCKKK LG-COOH |
| NV1G2122 | R13K | 539 | GPYCQKWMWTCDSEKKCCEGMVCRLWCKKK LW-COOH |
| NV1G1007 C-terminal palmitoyl-lysine | Y1Q, W7Q, S11A, M19F, addition of palmitoyl-lysine at position 33 | 540 | GPQCQKWMQTCDAERKCCEGFVCRLWCKKK LW-(palmitoyl-lysine)-COOH |

TABLE 18-continued

| ID | Mutation | SEQ ID NO: | Sequence |
|---|---|---|---|
| NV1G2000 | R22Y | 541 | GPYCQKWMWTCDSERKCCEGMVCYLWCKKK LW-COOH |
| NV1G2009 | G18Y | 542 | GPYCQKWMWTCDSERKCCEYMVCRLWCKKK LW-COOH |
| NV1G2066 | K4E, W5F, M6L, K26R | 543 | GPYCQEFLWTCDSERKCCEGMVCRLWCRKK LW-COOH |
| NV1G2083 | W7S | 544 | GPYCQKWMSTCDSERKCCEGMVCRLWCKKK LW-COOH |
| NV1G2126 | K4G | 545 | GPYCQGWMWTCDSERKCCEGMVCRLWCKK KLW-COOH |
| NV1G2043 | (-GP) Y1Q, W7Q, S11R, M19F, R22T, K26R + N-term GPCRTIGPSVC | 370 | GPCRTIGPSVCQCQKWMQTCDRERKCCEGF VCTLWCRKKLW-COOH |
| NV1G2050 | W7R | 546 | GPYCQKWMRTCDSERKCCEGMVCRLWCKKK LW-COOH |
| NV1G2071 | K26T | 547 | GPYCQKWMWTCDSERKCCEGMVCRLWCTKK LW-COOH |
| NV1G2129 | W30I | 412 | GPYCQKWMWTCDSERKCCEGMVCRLWCKKK LI-COOH |
| NV1G2086 | R22V | 548 | GPYCQKWMWTCDSERKCCEGMVCVLWCKKK LW-COOH |
| NV1G2057 | Y1Q, W7Q, S11R, M19F, R22T, K26R + C-term GSAPAPAPAPAP GSCCNCSSKWCR DHSRCC | 341 | GPQCQKWMQTCDRERKCCEGFVCTLWCRKK LWGSAPAPAPAPAPGSCCNCSSKWCRDHSR CC-COOH |
| NV1G2093 | V20E | 549 | GPYCQKWMWTCDSERKCCEGMECRLWCKKK LW-COOH |
| NV1G1995 | D10F | 550 | GPYCQKWMWTCFSERKCCEGMVCRLWCKKK LW-COOH |
| NV1G2312 | K27H | 551 | GPYCQKWMWTCDSERKCCEGMVCRLWCKHK LW-COOH |
| NV1G2176 | K4S | 552 | GPYCQSWMWTCDSERKCCEGMVCRLWCKKK LW-COOH |
| NV1G2046 | K28N | 553 | GPYCQKWMWTCDSERKCCEGMVCRLWCKKN LW-COOH |
| NV1G2047 | W5E | 554 | GPYCQKEMWTCDSERKCCEGMVCRLWCKKK LW-COOH |
| NV1G2170 | V20R | 555 | GPYCQKWMWTCDSERKCCEGMRCRLWCKKK LW-COOH |
| NV1G2042 | T8E | 556 | GPYCQKWMWECDSERKCCEGMVCRLWCKKK LW-COOH |
| NV1G2117 | K14E | 557 | GPYCQKWMWTCDSERECCEGMVCRLWCKKK LW-COOH |
| NV1G1999 | R22G | 558 | GPYCQKWMWTCDSERKCCEGMVCGLWCKKK LW-COOH |
| NV1G2247 | K28V | 559 | GPYCQKWMWTCDSERKCCEGMVCRLWCKKV LW-COOH |
| NV1G2054 | D10R, E12R | 560 | GPYCQKWMWTCRSRRKCCEGMVCRLWCKKK LW-COOH |

TABLE 18-continued

| ID | Mutation | SEQ ID NO: | Sequence |
|---|---|---|---|
| NV1G1007 E17F | Y1Q, W7Q, S11A, E17F, M19F | 561 | GPQCQKWMQTCDAERKCCFGFVCRLWCKKK LW-COOH |
| NV1G2056 | D10V | 562 | GPYCQKWMWTCVSERKCCEGMVCRLWCKKK LW-COOH |
| NV1G1007 D33 | Y1Q, W7Q, S11A, M19F, addition of D at position 33 | 563 | GPQCQKWMQTCDMAERKCCEGFVCTLWCRK KLWD-COOH |
| NV1G2291 | W30V | 413 | GPYCQKWMWTCDSERKCCEGMVCRLWCKKK LV-COOH |
| NV1G2306 | K26S | 564 | GPYCQKWMWTCDSERKCCEGMVCRLWCSKK LW-COOH |
| NV1G2023 | Y1S, M6F, S11A, M19L, K26R | 565 | GPSCQKWFWTCDAERKCCEGLVCRLWCRKK LW-COOH |
| NV1G2133 | K28H | 566 | GPYCQKWMWTCDSERKCCEGMVCRLWCKKH LW-COOH |
| NV1G2070 | S11T | 567 | GPYCQKWMWTCDTERKCCEGMVCRLWCKKK LW-COOH |
| NV1G2317 | K28D | 568 | GPYCQKWMWTCDSERKCCEGMVCRLWCKKD LW-COOH |
| NV1G2116 | K27T | 569 | GPYCQKWMWTCDSERKCCEGMVCRLWCKTK LW-COOH |
| NV1G2174 | R22Q | 570 | GPYCQKWMWTCDSERKCCEGMVCQLWCKKK LW-COOH |
| NV1G2209 | K14N | 571 | GPYCQKWMWTCDSERNCCEGMVCRLWCKKK LW-COOH |
| NV1G2134 | W7H | 572 | GPYCQKWMHTCDSERKCCEGMVCRLWCKKK LW-COOH |
| NV1G2166 | K4P | 573 | GPYCQPWMWTCDSERKCCEGMVCRLWCKKK LW-COOH |
| NV1G2119 | Q3G | 574 | GPYCGKWMWTCDSERKCCEGMVCRLWCKKK LW-COOH |
| NV1G2285 | D10Q | 575 | GPYCQKWMWTCQSERKCCEGMVCRLWCKKK LW-COOH |
| NV1G2067 | Y1S, K4E, W5F, M6L, S11A, M19L | 576 | GPSCQEFLWTCDAERKCCEGLVCRLWCKKK LW-COOH |
| NV1G2299 | K27L | 577 | GPYCQKWMWTCDSERKCCEGMVCRLWCKLK LW-COOH |
| NV1G2316 | V20Y | 578 | GPYCQKWMWTCDSERKCCEGMYCRLWCKKK LW-COOH |
| NV1G2322 | L29N | 579 | GPYCQKWMWTCDSERKCCEGMVCRLWCKKK NW-COOH |
| NV1G2156 | W7Y | 414 | GPYCQKWMYTCDSERKCCEGMVCRLWCKKK LW-COOH |
| NV1G2082 | W7E | 415 | GPYCQKWMETCDSERKCCEGMVCRLWCKKK LW-COOH |
| NV1G2165 | D10A | 580 | GPYCQKWMWTCASERKCCEGMVCRLWCKKK LW-COOH |
| NV1G2201 | V20L | 581 | GPYCQKWMWTCDSERKCCEGMLCRLWCKKK LW-COOH |

TABLE 18-continued

| ID | Mutation | SEQ ID NO: | Sequence |
|---|---|---|---|
| NV1G2077 | Q3F | 582 | GPYCFKWMWTCDSERKCCEGMVCRLWCKKKLW-COOH |
| NV1G2173 | V20A | 583 | GPYCQKWMWTCDSERKCCEGMACRLWCKKKLW-COOH |
| NV1G2207 | S11Y | 584 | GPYCQKWMWTCDYERKCCEGMVCRLWCKKKLW-COOH |
| 64087946 | (-GP) W7Q, S11A, M19F, V20S, R22Me, W30L | 417 | YCQKWMQTCDAERKCCEGFSC-(N-Me-Arg)-LWCKKKLL-COOH |
| 64053366 | (-GP) W7Q S11D W30L | 418 | YCQKWMQTCDDERKCCEGMVCRLWCKKKLL-COOH |
| 64087868 | W7Q L29V | 585 | GPYCQKWMQTCDSERKCCEGMVCRLWCKKKVW-COOH |
| NV1G2266 | R13L | 586 | GPYCQKWMWTCDSELKCCEGMVCRLWCKKKLW-COOH |
| NV1G2287 | D10R, E12R, R13E | 587 | GPYCQKWMWTCRSREKCCEGMVCRLWCKKKLW-COOH |
| NV1G2041 | K4E/E17R | 588 | GPYCQEWMWTCDSERKCCRGMVCRLWCKKKLW-COOH |
| 64053340 | (-GP) W7Q K14F W30L | 419 | YCQKWMQTCDSERFCCEGMVCRLWCKKKLL-COOH |
| 64053236 | W7Q K14F W30L | 420 | GPYCQKWMQTCDSERFCCEGMVCRLWCKKKLL-COOH |
| 64087881 | D10, E12, E17 side chains and C-terminus derviatized with putrescine | 589 | GPQCQKWMQTC-(L-aspartyl-4-aminobutane)-A-(glutamyl-4 aminobutane)-RKCC-(glutamyl-4-aminobutane)-GFVCRLWCKKKLW-(putrescine) |
| NV1G2217 | T8I | 590 | GPYCQKWMWICDSERKCCEGMVCRLWCKKKLW-COOH |
| NV1G2183 | K4D, E17R | 591 | GPYCQDWMWTCDSERKCCRGMVCRLWCKKKLW-COOH |
| 64087894 | (-GP) W7Q, S11I, M19F | 592 | YCQKWMQTCDIERKCCEGFVCRLWCKKKLW-COOH |
| 64053223 | W7Q S11I W30L | 421 | GPYCQKWMQTCDIERKCCEGMVCRLWCKKKLL-COOH |
| NV1G2216 | K28T | 593 | GPYCQKWMWTCDSERKCCEGMVCRLWCKKTLW-COOH |
| NV1G2210 | D10G | 594 | GPYCQKWMWTCGSERKCCEGMVCRLWCKKKLW-COOH |
| NV1G2314 | G18H | 595 | GPYCQKWMWTCDSERKCCEHMVCRLWCKKKLW-COOH |
| 64032501 | (-GP) W7Q S11I | 596 | YCQKWMQTCDIERKCCEGMVCRLWCKKKLW-COOH |
| 63955918 | W7Q W30L | 422 | GPYCQKWMQTCDSERKCCEGMVCRLWCKKKLL-COOH |
| NV1G2088 | S11F | 597 | GPYCQKWMWTCDFERKCCEGMVCRLWCKKKLW-COOH |
| NV1G2289 | K27F | 598 | GPYCQKWMWTCDSERKCCEGMVCRLWCKFKLW-COOH |

TABLE 18-continued

| ID | Mutation | SEQ ID NO: | Sequence |
|---|---|---|---|
| 64053210 | W7Q E17N W30L | 423 | GPYCQKWMQTCDSERKCCNGMVCRLWCKKK LL-COOH |
| 64053210 | W7Q E17N W30L | 423 | GPYCQKWMQTCDSERKCCNGMVCRLWCKKK LL-COOH |
| 64087907 | (-GP) W7Q | 424 | YCQKWMQTCDSERKCCEGMVCRLWCKKKLW-COOH |
| 64032488 | (-GP) W7Q W30L | 425 | YCQKWMQTCDSERKCCEGMVCRLWCKKKL L-COOH |
| 63955931 | Y1Q, W7Q, S11A, M19F, R22N-omega-methyl-L-arginine | 599 | GPQCQKWMQTCDAERKCCEGFVC-(N-omega-methyl-L-arginine)-LWCKK KLW-COOH |
| 64053301 | W7Q S11V W30L | 426 | GPYCQKWMQTCDVERKCCEGMVCRLWCKKK LL-COOH |
| NV1G2243 | L29F | 600 | GPYCQKWMWTCDSERKCCEGMVCRLWCKKK FW-COOH |
| NV1G2227 | Q3S | 601 | GPYCSKWMWTCDSERKCCEGMVCRLWCKKK LW-COOH |
| 64053275 | W7Q E17L W30L | 427 | GPYCQKWMQTCDSERKCCLGMVCRLWCKKK LL-COOH |
| 64053275 | W7Q E17L W30L | 427 | GPYCQKWMQTCDSERKCCLGMVCRLWCKKK LL-COOH |
| 64087920 | Y1Q, W7Q, S11A, M19 (4-Cl-Phe) | 602 | GPQCQKWMQTCDAERKCCEG-(4-chloro-Phe)-VCRLWCKKKLW-COOH |
| 64053327 | (-GP) W7Q E17N W30L | 428 | YCQKWMQTCDSERKCCNGMVCRLWCKKKL L-COOH |
| NV1G2233 | E12Q | 603 | GPYCQKWMWTCDSQRKCCEGMVCRLWCKKK LW-COOH |
| NV1G2265 | Q3Y | 604 | GPYCYKWMWTCDSERKCCEGMVCRLWCKKK LW-COOH |
| NV1G2172 | K27V | 605 | GPYCQKWMWTCDSERKCCEGMVCRLWCKVK LW-COOH |
| NV1G2248 | E17V | 606 | GPYCQKWMWTCDSERKCCVGMVCRLWCKKK LW-COOH |
| NV1G2039 | S11I | 607 | GPYCQKWMWTCDIERKCCEGMVCRLWCKKK LW-COOH |
| NV1G2229 | G18R | 608 | GPYCQKWMWTCDSERKCCERMVCRLWCKKK LW-COOH |
| NV1G2099 | L29V | 609 | GPYCQKWMWTCDSERKCCEGMVCRLWCKKK VW-COOH |
| NV1G2324 | E17Y | 429 | GPYCQKWMWTCDSERKCCYGMVCRLWCKKK LW-COOH |
| NV1G2096 | K27I | 610 | GPYCQKWMWTCDSERKCCEGMVCRLWCKIK LW-COOH |
| NV1G2094 | E17I | 430 | GPYCQKWMWTCDSERKCCIGMVCRLWCKKK LW-COOH |
| NV1G1996 | E17L | 431 | GPYCQKWMWTCDSERKCCLGMVCRLWCKKK LW-COOH |
| NV1G2039 (-GP) | (-GP) S11I | 611 | YCQKWMWTCDIERKCCEGMVCRLWCKKKLW-COOH |

TABLE 18-continued

| ID | Mutation | SEQ ID NO: | Sequence |
|---|---|---|---|
| 63930854 | Y1Q, W7Q, S11I, E17L, M19F | 612 | GPQCQKWMQTCDIERKCCLGFVCRLWCKKK LW-COOH |
| 63909404 | Y1Q, W7Q, S11I, M19F, L29V | 613 | GPQCQKWMQTCDIERKCCEGFVCRLWCKKK VW-COOH |
| 63930880 | Y1Q, W7Q, S11A, E17L, M19F, L29V | 614 | GPQCQKWMQTCDAERKCCLGFVCRLWCKKK VW-COOH |
| 63909378 | Y1Q, W7Q, S11A, M19F, L29V | 615 | GPQCQKWMQTCDAERKCCEGFVCRLWCKKK VW-COOH |
| 63930841 | W7Q | 416 | GPYCQKWMQTCDSERKCCEGMVCRLWCKKK LW-COOH |
| NV1G714 | Y1Q | 616 | GPQCQKWMWTCDSERKCCEGMVCRLWCKKK LW-COOH |
| NV1G690 | Y1S | 617 | GPSCQKWMWTCDSERKCCEGMVCRLWCKKK LW-COOH |
| NV1G688 | Y1R | 618 | GPRCQKWMWTCDSERKCCEGMVCRLWCKKK LW-COOH |
| NV1G700 | S11A | 619 | GPYCQKWMWTCDAERKCCEGMVCRLWCKKK LW-COOH |
| NV1G692 | Y1A | 620 | GPACQKWMWTCDSERKCCEGMVCRLWCKKK LW-COOH |
| NV1G1051 | T8S | 621 | GPYCQKWMWSCDSERKCCEGMVCRLWCKKK LW-COOH |
| NV1G702 | S11R | 622 | GPYCQKWMWTCDRERKCCEGMVCRLWCKKK LW-COOH |
| NV1D1328_1 | M6F | 623 | GPYCQKWFWTCDSERKCCEGMVCRLWCKKK LW-COOH |
| NV1G694 | W7Q | 624 | GPYCQKWMQTCDSERKCCEGMVCRLWCKKK LW-COOH |
| NV1D1339_1 | L23T | 625 | GPYCQKWMWTCDSERKCCEGMVCRTWCKKK LW-COOH |
| NV1G698 | D10S | 626 | GPYCQKWMWTCSSERKCCEGMVCRLWCKKK LW-COOH |
| NV1G1055 | W30S | 627 | GPYCQKWMWTCDSERKCCEGMVCRLWCKKK LS-COOH |
| NV1G1635 | K14A | 628 | GPYCQKWMWTCDSERACCEGMVCRLWCKKK LW-COOH |
| NV1G224 | M19S | 629 | GPYCQKWMWTCDSERKCCEGSVCRLWCKKK LW-COOH |
| NV1G704 | V20S | 630 | GPYCQKWMWTCDSERKCCEGMSCRLWCKKK LW-COOH |
| NV1D1335_1 | K14D | 631 | GPYCQKWMWTCDSERDCCEGMVCRLWCKKK LW-COOH |
| NV1G1057 | K27R | 632 | GPYCQKWMWTCDSERKCCEGMVCRLWCKRK LW-COOH |
| NV1G217 | E12S | 633 | GPYCQKWMWTCDSSRKCCEGMVCRLWCKKK LW-COOH |
| NV1G225 | R22K | 634 | GPYCQKWMWTCDSERKCCEGMVCKLWCKKK LW-COOH |

TABLE 18-continued

| ID | Mutation | SEQ ID NO: | Sequence |
|---|---|---|---|
| NV1G696 | T8R | 635 | GPYCQKWMWRCDSERKCCEGMVCRLWCKKKLW-COOH |
| NV1D1331_1 | S11P | 636 | GPYCQKWMWTCDPERKCCEGMVCRLWCKKKLW-COOH |
| NV1G1047 | K28R | 637 | GPYCQKWMWTCDSERKCCEGMVCRLWCKKRLW-COOH |
| NV1G576 | M19Y | 638 | GPYCQKWMWTCDSERKCCEGYVCRLWCKKKLW-COOH |
| NV1G581 | M19F | 639 | GPYCQKWMWTCDSERKCCEGFVCRLWCKKKLW-COOH |
| NV1D1338_1 | L23R | 640 | GPYCQKWMWTCDSERKCCEGMVCRRWCKKKLW-COOH |
| NV1D1333_1 | R13N Protoxin-II | 641 | GPYCQKWMWTCDSENKCCEGMVCRLWCKKKLW-COOH |
| NV1G2349 | L2K (+GP) Protoxin-II | 642 | GPYCQKWMWTCDSERKCCEGMVCRKWCKKKLW-COOH |
| NV1G585 | M19R (+GP) Protoxin-II | 643 | GPYCQKWMWTCDSERKCCEGRVCRLWCKKKLW-COOH |
| 64151490 | W7Q Q30L R22Me(2) (+GP) Protoxin-II | 644 | GPYCQKWMQTCDSERKCCEGMVC-(N-omega,N-omega-dimethyl(asymmetric)-L-arginine)-LCKKKLL-COOH |
| NVQG587 | M19N (+GP) Protoxin-II | 645 | GPYCQKWMWTCDSERKCCEGNVCRLWCKKKLW-COOH |
| NV1G2352 | K4Q (+GP) Protoxin-II | 646 | GPYCQQWMWTCDSERKCCEGMVCRLWCKKKLW-COOH |
| NV1G2035 | G18N (+GP) Protoxin-II | 647 | GPYCQKWMWTCDSERKCCENMVCRLWCKKKLW-COOH |
| NV1G2351 | E17G (+GP) Protoxin-II | 648 | GPYCQKWMWTCDSERKCCGGMVCRLWCKKKLW-COOH |
| NV1G2346 | S11G (+GP) Protoxin-II | 649 | GPYCQKWMWTCDGERKCCEGMVCRLWCKKKLW-COOH |
| NV1G2341 | V20F (+GP) Protoxin-II | 650 | GPYCQKWMWTCDSERKCCEGMFCRLWCKKKLW-COOH |
| NV1G2342 | D10T (+GP) Protoxin-II | 651 | GPYCQKWMWTCTSERKCCEGMVCRLWCKKKLW-COOH |
| NV1G2348 | K28Q (+GP) Protoxin-II | 652 | GPYCQKWMWTCDSERKCCEGMVCRLWCKKQLW-COOH |
| NV1G1934 | S11E (+GP) Protoxin-II | 653 | GPYCQKWMWTCDEERKCCEGMVCRLWCKKKLW-COOH |
| NV1G2347 | K4H (+GP) Protoxin-II | 654 | GPYCQHWMWTCDSERKCCEGMVCRLWCKKKLW-COOH |
| NV1G584 | M19H (+GP) Protoxin-II | 655 | GPYCQKWMWTCDSERKCCEGHVCRLWCKKKLW-COOH |
| NV1G2033 | L23I (+GP) Protoxin-II | 656 | GPYCQKWMWTCDSERKCCEGMVCRIWCKKKLW-COOH |
| NV1G2343 | Q3R (+GP) Protoxin-II | 657 | GPYCRKWMWTCDSERKCCEGMVCRLWCKKKLW-COOH |
| NV1G2344 | Y1H (+GP) Protoxin-II | 658 | GPHCQKWMWTCDSERKCCEGMVCRLWCKKKLW-COOH |
| NV1G2345 | Y1G (+GP) Protoxin-II | 659 | GPGCQKWMWTCDSERKCCEGMVCRLWCKKKLW-COOH |

TABLE 18-continued

| ID | Mutation | SEQ ID NO: | Sequence |
|---|---|---|---|
| NV1G2034 | W24G(+GP) Protoxin-II | 660 | GPYCQKWMWTCDSERKCCEGMVCRLGCKKK LW-COOH |
| NV1G594 | M6K(+GP) Protoxin-II | 661 | GPYCQKWKWTCDSERKCCEGMVCRLWCKKK LW-COOH |
| NV1G1041 | S11Q(+GP) | 662 | GPYCQKWMWTCDQERKCCEGMVCRLWCKKK LW-COOH |

Select variants were characterized for their inhibition of Nav1.7 using veratridine-induced depolarization inhibition assay or Qpatch as described in Example 3. Table 19 shows the $IC_{50}$ values obtained. For some variants, only % inhibition (% blk; percent block of control) at single concentration (10 nM or 30 nM) was recorded for Qpatch. se; standard error.

TABLE 19

| | | hNav1.7 | | | | |
|---|---|---|---|---|---|---|
| | | Veratridine-induced Depolarization Inhibition Assay | | QP | | |
| Peptide ID | SEQ ID NO: | $IC_{50}$ (nM) | ± | $IC_{50}$ (nM) | se | % blk | se |
| NV1G2228 | 434 | 4.69 | 2.70E−01 | | | 59.8% @ 10 nM | 7.2 |
| NV1G2072 | 435 | 4.71 | 0.291 | | | 82.2% @ 10 nM | 2.5 |
| NV1G2008 | 436 | 5.6 | 0.6 | | | 57.1% @ 10 nM | 4.6 |
| NV1G1994 | 437 | 6.5 | 0.3 | 4.138 | | 69.1% @ 10 nM | 7.8 |
| NV1G2070 | 438 | 6.46 | 0.438 | 2.8889 | | 74.5% @ 10 nM | 4.6 |
| NV1G2074 | 439 | 6.48 | 0.482 | | | 71.3% @ 10 nM | 3.3 |
| NV1G2079 | 440 | 6.65 | 0.608 | | | 69.4% @ 10 nM | 3.2 |
| NV1G2073 | 441 | 6.73 | 0.572 | 4.6 | | 71.2% @ 10 nM | 3.9 |
| NV1G2076 | 442 | 6.93 | 0.764 | 2.77 | | 76.1% @ 10 nM | 2.2 |
| NV1G1864 S11I | 443 | 22.3 | 0.141 | | | 52.3% @ 10 nM | 7.8 |
| NV1G2039 | 444 | 7.15 | 0.579 | 2.586 | | 71.8% @ 10 nM | 0.8 |
| NV1G1007 W30tryptophanol | 445 | 13.3 | 1.17 | 1.4 | | 65.8% @ 10 nM | 2.9 |
| NV1G2238 | 446 | 7.47 | 5.84E−01 | | | 32.1% @ 10 nM | 9.8 |
| NV1G2198 | 447 | 7.49 | 0.856 | | | 37.6% @ 10 nM | 7.6 |
| NV1G2195 | 448 | 7.66 | 0.48 | | | 62.4% @ 10 nM | 2.4 |
| NV1G1153-N-methyl | 449 | 7.1 | 0.9 | 1.2 | 1.3 | 56.1% @ 30 nM | 7.9 |
| NV1G2007 | 450 | 8.4 | 1.1 | | | 46.5% @ 10 nM | 2.4 |
| NV1G2140 | 451 | 8.55 | 1.46 | | | | |
| NV1G2003 | 452 | 8.8 | 1.5 | | | 51.8% @ 10 nM | 5.1 |
| NV1G2236 | 453 | 9.12 | 7.75E−01 | | | 45.3% @ 10 nM | 4.3 |
| NV1G2164 | 454 | 9.37 | 0.507 | | | | |
| NV1G1864 E17L (−GP) | 455 | 9.38 | 5.32E−01 | | | 28.4% @ 10 nM | 18.2 |
| NV1G1001 | 109 | 9.47 | 1.28 | 2.6 | 1.4 | 50.9% @ 10 nM | 4.7 |
| NV1G2149 | 456 | 9.61 | 0.834 | | | 62.3% @ 10 nM | 4.6 |
| NV1G2226 | 457 | 9.71 | 7.19E−01 | | | 24.2% @ 10 nM | 6.0 |
| NV1G2286 | 458 | 9.85 | 0.923 | | | | |
| NV1G2128 | 459 | 9.94 | 0.945 | | | 63.8% @ 10 nM | 4.9 |
| NV1G2041 | 460 | 9.98 | 1.07 | 4.791 | | 53.4% @ 10 nM | 4.4 |
| NV1G2001 | 461 | 10.9 | 0.6 | | | 39.9% @ 10 nM | 5.6 |
| NV1G2019 | 462 | 11 | 0.787 | | | 44.2% @ 10 nM | 4.0 |
| NV1G2002 | 463 | 11.0 | 0.9 | | | 36.9% @ 10 nM | 5.8 |
| NV1G2225 | 464 | 11.2 | 7.85E−01 | | | 37.6% @ 10 nM | 8.1 |
| NV1G2012 | 465 | 11.3 | 0.7 | | | 35.8% @ 10 nM | 7.5 |
| NV1G2020 | 466 | 12 | 47.5 | | | 40.7% @ 10 nM | 17.9 |
| NV1G2334 | 467 | 12 | 5.52E−01 | | | | |
| NV1G2025 | 468 | 12.3 | 0.853 | 7.4 | | 73.9% @ 10 nM | 7.2 |
| NV1G2131 | 469 | 12.4 | 1.58 | | | 61.8% @ 10 nM | 2.8 |
| NV1G1007 A11I, E12T | 470 | 12.5 | 1.3 | | | 28.1% @ 10 nM | 18.0 |
| NV1G2268 | 471 | 12.5 | 0.861 | 1.8 | | 61.8% @ 10 nM | 2.7 |

TABLE 19-continued

| | | hNav1.7 | | | | | |
|---|---|---|---|---|---|---|---|
| | | Veratridine-induced Depolarization Inhibition Assay | | QP | | | |
| Peptide ID | SEQ ID NO: | IC$_{50}$ (nM) | ± | IC$_{50}$ (nM) | se | % blk | se |
| NV1G2332 | 472 | 12.5 | 7.44E−01 | | | | |
| NV1G2010 | 473 | 12.5 | 1.0 | | | 56.4% @ 30 nM | 3.8 |
| NV1G2053 | 474 | 12.5 | 33.3 | | | 73.1% @ 10 nM | 2.40 |
| NV1G1519 | 133 | 12.9 | 0.943 | | | 52.3% @ 10 nM | 7.9 |
| NV1G2253 | 475 | 13.5 | 0.695 | | | | |
| NV1G2055 | 476 | 14.6 | 8.58 | | | 73.5% @ 10 nM | 5.50 |
| NV1G2338 | 477 | 14.8 | 6.98E−01 | 2.4 | | 62.2% @ 10 nM | 4.7 |
| NV1G2030 | 478 | 15.2 | 1.3 | 9.291 | | 68.4% @ 30 nM | 4.3 |
| NV1G2024 | 479 | 15.5 | 1.76 | | | 78.1% @ 30 nM | 3.2 |
| NV1G2004 | 480 | 15.6 | 1.4 | | | 44.1% @ 30 nM | 5.9 |
| NV1G2336 | 481 | 15.8 | 1.14E+00 | | | | |
| NV1G2011 | 482 | 16.0 | 1.5 | | | 56.7% @ 30 nM | 8.8 |
| NV1G2080 | 483 | 16.1 | 1.81 | 13.43 | | 70.2% @ 30 nM | 4.6 |
| NV1G2288 | 484 | 16.3 | 1.52 | | | | |
| NV1G2142 | 485 | 16.4 | 0.834 | 5.3 | | 51.2% @ 10 nM | 2.9 |
| NV1G2232 | 408 | 16.7 | 1.32 | 5.0 | | 56.5% @ 10 nM | 5.7 |
| NV1G2193 | 486 | 16.8 | 1.23 | | | 43.3% @ 10 nM | 11.3 |
| NV1G2230 | 487 | 17 | 2.42 | 9.5 | | 41.3% @ 10 nM | 4.5 |
| NV1G2182 | 409 | 17.3 | 1.37 | 3.8 | | 54.2% @ 10 nM | 5.4 |
| NV1G1153 C-terminal palmitoyl-lysine | 488 | 29.1 | 0.125 | 5.3 | | 66.0% @ 10 nM | 5 |
| NV1G2339 | 489 | 18.1 | 1.35E+00 | | | | |
| NV1G2016 | 490 | 18.3 | 1.5 | | | 71.1% @ 30 nM | 5.6 |
| NV1G2017 | 491 | 18.4 | 1.47 | | | 38.9% @ 30 nM | 11.8 |
| NV1G2111 | 492 | 18.5 | 2.06 | 1.4 | | 57.3% @ 10 nM | 5.6 |
| NV1G2330 | 493 | 18.5 | 2.04E+00 | | | | |
| NV1G2204 | 494 | 18.8 | 0.578 | | | 49.0% @ 10 nM | 13.0 |
| NV1G2026 | 495 | 18.9 | 1.48 | | | 80.2% @ 30 nM | 2.2 |
| NV1G1007 with C-terminal 5x Gly | 496 | 18.9 | 1.2 | 3.9 | | 56.5% @ 10 nM | 6.8 |
| NV1G2038 | 497 | 18.9 | 1.46 | | | 64.8% @ 30 nM | 3.3 |
| NV1G2305 | 498 | 20.4 | 5.08 | 6.2 | | 41.5% @ 10 nM | 4.5 |
| NV1G2021 | 499 | 20.4 | 1.88 | 39.76 | | 60.5% @ 30 nM | 6.9 |
| NV1G2319 | 410 | 20.7 | 2.3 | 9.7 | | 43.2% @ 10 nM | 6.2 |
| NV1G2100 | 500 | 20.8 | 1.65 | | | 35.2% @ 10 nM | 10.8 |
| NV1G2130 | 501 | 21.2 | 2.48 | | | 20.9% @ 10 nM | 5.7 |
| NV1G2081 | 502 | 21.9 | 1.99 | | | 29.5% @ 30 nM | 10.5 |
| NV1G2252 | 503 | 22.2 | 1.54 | 2.9 | | 63.1% @ 10 nM | 6.5 |
| NV1G2040 | 504 | 22.7 | 2.17 | | | 55.5% @ 30 nM | 9.1 |
| NV1G2146 | 505 | 22.86 | 2.3 | 20.62 | | 53.1% @ 10 nM | 19.9 |
| NV1G1153-N-ethyl | 506 | 24 | 3.14 | 4.7 | 4.2 | 36.7% @ 10 nM | 16.7 |
| NV1G2098 | 507 | 24.1 | 5.44 | | | 48.4% @ 10 nM | 8.4 |
| NV1G2191 | 508 | 24.1 | 1.79 | | | 3.7% @ 10 nM | 7.8 |
| NV1G2333 | 509 | 24.3 | 2.00E+00 | | | | |
| NV1G2224 | 510 | 24.3 | 1.59 | 10.4 | | 34.5% @ 10 nM | 7.7 |
| NV1G1001-N-ethyl | 511 | 25.1 | 2.21 | 4.77 | | 74.3% @ 30 nM | 1.0 |
| NV1G1996 | 431 | 25.2 | 2.1 | 6.4 | 3.5 | 54.5% @ 30 nM | 8.4 |
| NV1G2337 | 512 | 25.6 | 1.10E+00 | 8.5 | | 48.0% @ 10 nM | 7.5 |
| NV1G2301 | 513 | 25.7 | 3.83 | | | | |
| NV1G2075 | 514 | 26.1 | 1.8 | | | 36.8% @30 nM | 10.7 |
| NV1G2278 | 515 | 26.3 | 3.34 | 1.5 | | 58.7% @ 10 nM | 5.45 |
| NV1G2014 | 516 | 27 | 3.43 | | | 36.4% @ 30 nM | 7.6 |
| NV1G2065 | 517 | 27 | 2.53 | | | 53% @ 10 nM | 2.6 |
| NV1G2099 | 518 | 27.9 | 2.54 | 3.4 | | 41.7% @ 10 nM | 10.1 |
| NV1G1007 E17L | 519 | 28.4 | 2 | 5.6 | | 31.9% @ 10 nM | 16.5 |
| NV1G1007 G33 | 520 | 29.1 | 2.11 | | | | |
| 1007 A11I | 521 | 29.3 | 2.8 | 9.6 | | 38.5% @ 10 nM | 5.4 |
| NV1G2221 | 522 | 29.3 | 1.89 | | | 31.3% @ 10 nM | 7.5 |
| NV1G2097 | 523 | 29.9 | 2.92 | | | 7.0% @ 10 nM | 12.2 |
| NV1G2029 | 524 | 30.1 | 6.29 | | | 50.8% @ 30 nM | 0.4 |
| NV1G2257 | 525 | 30.1 | 1.7 | 4.9 | | 50.9% @ 10 nM | 8.4 |
| NV1G1998 | 526 | 30.6 | 2.7 | | | 6.0% @ 30 nM | 5.0 |

TABLE 19-continued

| | | hNav1.7 | | | | | |
|---|---|---|---|---|---|---|---|
| | | Veratridine-induced Depolarization Inhibition Assay | | QP | | | |
| Peptide ID | SEQ ID NO: | IC$_{50}$ (nM) | ± | IC$_{50}$ (nM) | se | % blk | se |
| NV1G2068 | 527 | 30.7 | 3.11 | | | 24.0% @ 30 nM | 20.0 |
| NV1G1001 | 65 | 30.8 | 2.34 | | | 20.3% @ 10 nM | 8.6 |
| NV1G2137 | 528 | 30.9 | 6.08 | | | | |
| NV1G2199 | 529 | 31.7 | 1.72 | | | 29.6% @ 10 nM | 4.5 |
| NV1G2300 | 530 | 32.6 | 3.69 | | | | |
| NV1G2124 | 531 | 32.7 | 8.78 | | | 33.8% @ 10 nM | 9.1 |
| NV1G2254 | 532 | 32.8 | 3.85 | | | 34.1% @ 10 nM | 10.3 |
| NV1G2239 | 533 | 33.8 | 2.39 | 14.6 | | 42.2% @ 10 nM | 10.1 |
| NV1G2255 | 534 | 34.2 | 2.55 | | | | |
| NV1G2256 | 535 | 34.4 | 1.98 | 17.3 | | 27.7% @ 10 nM | 13.4 |
| NV1G2095 | 536 | 35 | 6.48 | | | 18.8% @ 10 nM | 7.2 |
| NV1G2220 | 537 | 36.7 | 3.86 | | | 8.4% @ 10 nM | 5.7 |
| NV1G2154 | 538 | 37.7 | 2.44 | | | 12.5% @ 10 nM | N/A |
| NV1G2329 | 411 | 38 | 2.43E+00 | | | | |
| NV1G2122 | 539 | 38.4 | 5.7 | | | 22.4% @ 10 nM | 10.5 |
| NV1G1007 C-terminal palmitoyl-lysine | 540 | 39.7 | 3.22 | | | | |
| NV1G2000 | 541 | 40.0 | 6.3 | | | | |
| NV1G2009 | 542 | 40.8 | 3.2 | | | | |
| NV1G2066 | 543 | 41.7 | 4.56 | | | | |
| NV1G2083 | 544 | 43 | 3.71 | | | | |
| NV1G2126 | 545 | 43.9 | 11.6 | | | 0.4% @ 10 nM | 9.4 |
| NV1G2043 | 370 | 46.4 | 4.09 | 58.7 | 36.5 | | |
| NV1G2050 | 546 | 46.7 | 6.26 | | | 49.1% @ 30 nM | 11.50 |
| NV1G2071 | 547 | 47 | 5.73 | | | | |
| NV1G2129 | 412 | 47.3 | 3.81 | | | −6.5% @ 10 nM | 6.5 |
| NV1G2086 | 548 | 47.3 | 5.5 | | | | |
| NV1G2057 | 341 | 50.6 | 6.33 | | | 22.2% @ 30 nM | 12.20 |
| NV1G2093 | 549 | 50.8 | 5.42 | | | | |
| NV1G1995 | 550 | 51.3 | 3.6 | | | | |
| NV1G2312 | 551 | 51.5 | 5.05 | | | | |
| NV1G2176 | 552 | 52.9 | 3.3 | | | | |
| NV1G2046 | 553 | 53.1 | 6.52 | | | 11.2% @ 30 nM | 11.5 |
| NV1G2047 | 554 | 53.7 | 4.23 | | | 40.3% @ 30 nM | 12.5 |
| NV1G2170 | 555 | 55.4 | 3.41 | | | | |
| NV1G2042 | 556 | 56.5 | 3.71 | | | | |
| NV1G2117 | 557 | 56.9 | 8.86 | | | 42.7% @ 30 nM | 13.0 |
| NV1G1999 | 558 | 57.1 | 18.2 | | | | |
| NV1G2247 | 559 | 57.7 | 8.37 | 9.9 | | 34.2% @ 10 nM | 6.4 |
| NV1G2054 | 560 | 57.8 | 7.98 | | | 33.0% @ 30 nM | 13.40 |
| NV1G1007 E17F | 561 | 59.5 | 4.12 | | | 6.1% @ 10 nM | 13.4 |
| NV1G2056 | 562 | 59.6 | 4.36 | | | 26.3% @ 30 nM | 16.10 |
| NV1G1007 D33 | 563 | 63 | 5.52 | | | 7.4% @ 10 nM | 10.2 |
| NV1G2291 | 413 | 63.3 | 14.9 | | | | |
| NV1G2306 | 564 | 64.4 | 4.75 | | | | |
| NV1G2023 | 565 | 66.2 | 9.12 | | | | |
| NV1G2133 | 566 | 68.9 | 11.7 | | | 28.6% @ 10 nM | 6.2 |
| NV1G2317 | 568 | 71.2 | 5.72 | | | | |
| NV1G2116 | 569 | 71.5 | 7.97 | | | 10.4% @ 30 nM | 20.9 |
| NV1G2174 | 570 | 72.7 | 6.86 | | | | |
| NV1G2209 | 571 | 77.8 | 6.33 | 13.7 | | 39.96% @ 10 nM | 7.6 |
| NV1G2134 | 572 | 78.3 | 7.06 | | | 9.9% @ 10 nM | 3.5 |
| NV1G2166 | 573 | 80.4 | 5.72 | | | | |
| NV1G2119 | 574 | 82.1 | 21.5 | | | | |
| NV1G2285 | 575 | 82.9 | 6.47 | | | | |
| NV1G2067 | 576 | 85.2 | 13 | | | | |
| NV1G2299 | 577 | 88.1 | 21.3 | | | | |
| NV1G2316 | 578 | 88.5 | 7.99 | | | | |
| NV1G2322 | 579 | 90 | 6.48 | | | 35.2% @ 10 nM | 4.1 |
| NV1G2156 | 414 | 90.5 | 6.88 | | | | |
| NV1G2082 | 415 | 90.8 | 11.4 | | | | |
| NV1G2165 | 580 | 91.6 | 6.58 | | | | |
| NV1G2201 | 581 | 94.8 | 5.67 | | | 13.957% @ 10 nM | 4.5 |
| NV1G2077 | 582 | 95.4 | 11.9 | | | | |
| NV1G2173 | 583 | 99.9 | 10.6 | | | | |
| NV1G2207 | 584 | | | | | 20.5% @ 10 nM | 4.8 |

TABLE 19-continued

| | | hNav1.7 | | | | |
|---|---|---|---|---|---|---|
| | | Veratridine-induced Depolarization Inhibition Assay | | QP | | |
| Peptide ID | SEQ ID NO: | IC$_{50}$ (nM) | ± | IC$_{50}$ (nM) | se | % blk | se |
| 64087946 | 417 | | | 23.8 | | 20.7% @ 10 nM | 10.9 |
| 64053366 | 418 | | | | | 22.1% @ 10 nM | 3.5 |
| 64087868 | 585 | | | 64.9 | | 22.9% @ 10 nM | 4.2 |
| NV1G2266 | 586 | | | | | 23.5% @ 10 nM | 6.2 |
| NV1G2287 | 587 | | | | | 24.8% @ 10 nM | 8.3 |
| 64053340 | 419 | | | | | 26.8% @ 10 nM | 3.7 |
| 64053236 | 420 | | | | | 28.0% @ 10 nM | 13.2 |
| 64087881 | 589 | | | | | 28.4% @ 10 nM | 5.4 |
| NV1G2217 | 590 | | | | | 29.4% @ 10 nM | 9.3 |
| NV1G2183 | 591 | | | | | 31.0% @ 10 nM | 7.7 |
| 64087894 | 592 | | | 9.4 | | 31.0% @ 10 nM | 3.8 |
| 64053223 | 421 | | | | | 33.0% @ 10 nM | 5.8 |
| NV1G2216 | 593 | | | | | 33.5% @ 10 nM | 7.0 |
| NV1G2210 | 594 | | | | | 34.3% @ 10 nM | 5.5 |
| NV1G2314 | 595 | | | | | 34.9% @ 10 nM | 7.5 |
| 64032501 | 596 | | | 9.3 | | 35.1% @ 10 nM | 6.3 |
| 63955918 | 422 | | | 10.8 | | 38.50% @ 10 nM | 4.5 |
| NV1G2088 | 597 | | | | | 41.4% @ 30 nM | 4.0 |
| NV1G2289 | 598 | | | 14.3 | | 41.4% @ 10 nM | 5.9 |
| 64053210 | 423 | | | | | 41.7% @ 10 nM | 6.2 |
| 64053210 | 423 | | | | | 41.7% @ 10 nM | 6.2 |
| 64087907 | 424 | | | 7.1 | | 45.1% @ 10 nM | 6.0 |
| 64032488 | 425 | | | 6.5 | | 45.6% @ 10 nM | 4.6 |
| 63955931 | 599 | | | 6.2 | | 45.66% @ 10 nM | 4.6 |
| 64053301 | 426 | | | 10.7 | | 45.83% @ 10 nM | 3.3 |
| NV1G2243 | 600 | | | | | 47.6% @ 10 nM | 4.8 |
| NV1G2227 | 601 | | | 8.1 | | 47.7% @ 10 nM | 6.3 |
| 64053275 | 427 | | | 2.9 | | 48.22% @ 10 nM | 5.2 |
| 64053275 | 427 | | | 2.9 | | 48.22% @ 10 nM | 5.2 |
| 64087920 | 602 | | | 2.6 | | 50.3% @ 10 nM | 8.9 |
| 64053327 | 428 | | | 7.9 | | 51.9% @ 10 nM | 2.6 |
| NV1G2233 | 603 | | | | | 52.8% @ 10 nM | 2.0 |
| NV1G2265 | 604 | | | | | 53.1% @ 10 nM | 7.0 |
| NV1G2172 | 605 | | | | | 54.4% @ 30 nM | 6.7 |
| NV1G2248 | 606 | | | 5.2 | | 54.8% @ 10 nM | 3.6 |
| NV1G2229 | 608 | | | | | 55.9% @ 10 nM | 7.0 |
| NV1G2324 | 429 | | | | | 57.5% @ 10 nM | 3.9 |
| NV1G2096 | 610 | | | | | 61.5% @ 30 nM | 22.8 |
| NV1G2094 | 430 | | | | | 63.2% @ 30 nM | 6.2 |
| NV1G2039 (−GP) | 611 | | | 1.9 | | 78.9% @ 10 nM | 2.5 |
| 63930854 | 612 | | | 5.1 | | | |
| 63909404 | 613 | | | 9.1 | | | |
| 63930880 | 614 | | | 12.2 | | | |
| 63909378 | 615 | | | 12.5 | | | |
| 63930841 | 416 | | | 20.9 | | | |
| NV1G714 | 616 | 1.3 | 1.4 | | | | |
| NV1G690 | 617 | 1.9 | 1.2 | | | | |
| NV1G688 | 618 | 2.2 | 0.4 | | | | |
| NV1G700 | 619 | 2.5 | 1.3 | | | | |
| NV1G692 | 620 | 2.8 | 1.4 | | | | |
| NV1G1051 | 621 | 5.0 | 3.0 | | | 38.6% @ 10 nM | 8.5 |
| NV1G702 | 622 | 5.5 | 4.0 | | | 62.8% @ 10 nM | 5.8 |
| NV1D1328_1 | 623 | 6.4 | 1.5 | | | | |
| NV1G694 | 624 | 24.1 | 23.5 | | | | |
| NV1D1339_1 | 625 | | | | | 21.5% @ 10 nM | 13.6 |
| NV1G698 | 626 | | | | | 22.8% @ 10 nM | |
| NV1G1055 | 627 | | | | | 22.9% @ 10 nM | 3.6 |
| NV1G1635 | 628 | | | | | 24.3% @ 10 nM | 10.0 |
| NV1G224 | 629 | | | | | 24.4% @ 20 nM | |
| NV1G704 | 630 | | | | | 24.8% @ 3 nM | 2.7 |
| NV1D1335_1 | 631 | | | | | 25.0% @ 10 nM | |
| NV1G1057 | 632 | | | | | 26.7% @ 10 nM | 5.4 |
| NV1G217 | 633 | | | | | 30.8% @ 10 nM | 2.7 |
| NV1G225 | 634 | | | | | 30.8% @ 10 nM | 5.9 |
| NV1G696 | 635 | | | | | 31.1% @ 10 nM | |
| NV1D1331_1 | 636 | | | | | 43.7% @ 10 nM | |
| NV1G1047 | 637 | | | | | 47.7% @ 10 nM | 6.5 |
| NV1G576 | 638 | | | | | 60.1% @ 10 nM | |
| NV1G581 | 639 | | | | | 60.2% @ 10 nM | 6.0 |
| NV1G2349 | 642 | | | | | 10.1% @ 10 nM | 7.9 |

TABLE 19-continued

| | | hNav1.7 | | | | |
|---|---|---|---|---|---|---|
| | | Veratridine-induced Depolarization Inhibition Assay | | QP | | |
| Peptide ID | SEQ ID NO: | $IC_{50}$ (nM) | ± | $IC_{50}$ (nM) | se | % blk | se |
| NV1G585 | 643 | | | | | 16.2% @ 10 nM | 13.1 |
| 64151490 | 644 | | | 32.5 | | 18.3% @ 10 nM | 20.5 |
| NV1G587 | 645 | | | | | 20.6% @ 10 nM | 12.8 |
| NV1G2352 | 646 | | | | | 23.4% @ 10 nM | 9.2 |
| NV1G2035 | 647 | | | | | 27.7% @ 10 nM | 6.7 |
| NV1G2351 | 648 | | | | | 28.9% @ 10 nM | 9.3 |
| NV1G2346 | 649 | | | | | 33.6% @ 10 nM | 12.4 |
| NV1G2341 | 650 | | | | | 35.8% @ 10 nM | 2.2 |
| NV1G2342 | 651 | | | | | 39.2% @ 10 nM | 13.0 |
| NV1G2348 | 652 | | | | | 41.7% @ 10 nM | 10.8 |
| NV1G1934 | 653 | | | | | 53.0% @ 10 nM | 6.1 |
| NV1G2347 | 654 | | | | | 56.3% @ 10 nM | 14.8 |
| NV1G584 | 655 | | | | | 56.4% @ 10 nM | 4.9 |
| NV1G2033 | 656 | | | | | 59.1% @ 10 nM | 3.6 |
| NV1G2343 | 657 | | | | | 59.6% @ 10 nM | 3.5 |
| NV1G2344 | 658 | | | | | 63% @ 10 nM | 3.8 |
| NV1G2345 | 659 | | | | | 64.8% @ 10 nM | 10.4 |
| NV1G2034 | 660 | | | | | 7.0% @ 10 nM | 3.6 |
| NV1G594 | 661 | | | | | | |
| NV1G1041 | 662 | | | | | | |

Example 9. Generation of Variants of 63955918

Protoxin-II variant 63955918 has W7Q and W30L substitutions when compared to the wild type Protoxin-II. As described in Example 6, mutation of both Trp7 and Trp30 alone or in combination improves folding of the resulting Protoxin-II variants, and could rescue folding of difficult-to-refold Protoxin-II variants.

Additional variants were generated onto the 63955918 backbone to evaluate possibility of further improving characteristics of the molecule. Some variants are also described in Examples 6 and 7.

The generated variants and their sequences are shown in Table 20.

TABLE 20

| ID | Mutations | SEQ ID NO: | Sequence |
|---|---|---|---|
| 64053366 | Protoxin-II W7Q S11D W30L (-GP) | 418 | YCQKWMQTCDDERKCCEGMVCRLWCKKKLL-COOH |
| 64053340 | Protoxin-II W7Q K14F W30L (-GP) | 419 | YCQKWMQTCDSERFCCEGMVCRLWCKKKLL-COOH |
| 64053236 | Protoxin-11 W7Q K14F W30L (+GP) | 420 | GPYCQKWMQTCDSERFCCEGMVCRLWCKKKLL-COOH |
| 64053223 | Protoxin-II W7Q S11I W30L (+GP) | 421 | GPYCQKWMQTCDIERKCCEGMVCRLWCKKKLL-COOH |
| 64053210 | Protoxin-11 W7Q E17N W30L (+GP) | 423 | GPYCQKWMQTCD5ERKCCNGMVCRLWCKKKLL-COOH |
| 64053301 | Protoxin-II W7Q S11V W30L (+GP) | 426 | GPYCQKWMQTCDVERKCCEGMVCRLWCKKKLL-COOH |
| 64053275 | Protoxin-11 W7Q E17L W30L (+GP) | 427 | GPYCQKWMQTCD5ERKCCLGMVCRLWCKKKLL-COOH |
| 64053327 | Protoxin-11 W7Q E17N W30L (-GP) | 428 | YCQKWMQTCD5ERKCCNGMVCRLWCKKKLL-COOH |

TABLE 20-continued

| ID | Mutations | SEQ ID NO: | Sequence |
|---|---|---|---|
| 64159108 | nerve labeling peptide-5xAP-Protoxin-II W7Q W30L | 663 | SHSNTQTLAKAPEHTGAPAPAPAPAPYCQKWMQTCD SERKCCEGMVCRLWCKKKLL-COOH |
| 64151477 | Protoxin-II W7Q W30L K14F E12Y N-methyl (-GP) | 664 | YCQKWMQTCD5YRFCCEGMVCRLWCKKKLL-NH-methyl |
| 64053288 | Protoxin-11 W7Q K4E E17R W30L (+GP) | 665 | GPYCQEWMQTCD5ERKCCRGMVCRLWCKKKLL-COOH |
| 64106666 | Protoxin-11 W7Q E17L W30L R22F(Guanidino) (-GP) | 666 | YCQKWMQTCDSERKCCLGMVC-(4-guanidino-L-phenylalanine)-LWCKKKLL-COOH |
| 64159134 | Protoxin-II W7Q W30L R22F(Guanidino) (-GP) | 667 | YCQKWMQTCD5ERKCCEGMVC-(4-guanidino-L-phenylalanine)-LWCKKKLL-COOH |
| 64106575 | Protoxin-11 W7Q E17L W30L S11V (-GP) | 668 | YCQKWMQTCDVERKCCLGMVCRLWCKKKLL-COOH |
| 64106627 | Protoxin-11 W7Q E17L W30L G18P (-GP) | 669 | YCQKWMQTCDSERKCCLPMVCRLWCKKKLL-COOH |
| 64106640 | Protoxin-II W7Q E17L W30L R22Me (-GP) | 670 | YCQKWMQTCDSERKCCLGMVC-(N-omega-methyl-L-arginine)-LWCKKKLL-COOH |
| 64106653 | Protoxin-II W7Q E17L W30L R22Me(2) (-GP) | 671 | YCQKWMQTCDSERKCCLGMVC-(N-omega,N-omega-dimethyl(asymmetric)-L-arginine)-LWCKKKLL-COOH |
| 64159121 | Protoxin-11 WW R22Me (+GP) | 672 | GPYCQKWMQTCDSERKCCEGMVC-(N-omega-methyl-L-arginine)-LWCKKKLL-COOH |
| 64106757 | Protoxin-11 W7Q W30L Q3Y (-GP) | 673 | YCYKWMQTCDSERKCCEGMVCRLWCKKKLL-COOH |
| 64106744 | Protoxin-11 W7Q W30L G18P (-GP) | 674 | YCQKWMQTCDSERKCCEPMVCRLWCKKKLL-COOH |
| 64106705 | Protoxin-II W7Q W30L E17L (-GP) | 675 | YCQKWMQTCDSERKCCLGMVCRLWCKKKLL-COOH |
| 64106718 | Protoxin-11 W7Q W30L E17Q (-GP) | 676 | YCQKWMQTCDSERKCCQGMVCRLWCKKKLL-COOH |
| 64170171 | Protoxin-11 W7Q W30L E17glutamyl-4-aminobutane (-GP) | 677 | YCQKWMQTCDSERKCC-(Glutamyl-4-amino-butane)-GMVCRLWCKKKLL-COOH |
| 64106731 | Protoxin-11 W7Q W30L E12Y (-GP) | 678 | YCQKWMQTCDSYRKCCEGMVCRLWCKKKLL-COOH |
| 64159082 | Protoxin-II W7Q W30L Leucinol (+GP) | 679 | GPYCQKWMQTCDSERKCCEGMVCRLWCKKKLL-OH |
| 64151503 | Protoxin-II W7Q W30L Tet1 | 680 | HLNILSTLWKYRGPYCQKWMQTCDSERKCCEGMVCRLWCKKKLL-COOH |

TABLE 20-continued

| ID | Mutations | SEQ ID NO: | Sequence |
|---|---|---|---|
| 64151438 | Protoxin-II W7Q W30L N-methyl (-GP) | 681 | YCQKWMQTCDSERKCCEGMVCRLWCKKKLL-NH-methyl |
| 64151464 | Protoxin-II W7Q W30L K14F N-methyl (-GP) | 682 | YCQKWMQTCDSERFCCEGMVCRLWCKKKLL-NH-methyl |
| 64170145 | Protoxin-11 W7Q W30L E12glutamyl-4-aminobutane (-GP) | 683 | YCQKWMQTCDS-(Glutamyl-4-aminobutane)-RKCCEGMVCRLWCKKKLL-COOH |
| 64170132 | Protoxin-11 W7Q W30L D10asparagyl-4-aminobutane (-GP) | 684 | YCQKWMQTC-(Asparagyl-4-aminobutane)-SER KCCEGMVCRLWCKKKLL-COOH |
| 64106601 | Protoxin-11 W7Q E17L W30L K14F (-GP) | 685 | YCQKWMQTCDSERFCCLGMVCRLWCKKKLL-COOH |

The variants were characterized as described above. Table 21 shows the $IC_{50}$ values and/or percent block (% blk) (% inhibition of currents in comparison to a control sample). Se: standard error.

TABLE 21

| Protein | SEQ | Nav1.7 Veratridine-induced Depolarization Inhibition Assay | | Nav1.7 QP | | | |
|---|---|---|---|---|---|---|---|
| ID | ID NO: | $IC_{50}$ (nM) | ± | $IC_{50}$ (nM) | se | % blk | se |
| 64053366 | 418 | | | | | 22.1% @ 10 nM | 3.5 |
| 64053340 | 419 | | | 33.0 | | 29.58% @ 10 nM | 4.2 |
| 64053236 | 420 | | | | | 28.0% @ 10 nM | 13.2 |
| 64053223 | 421 | | | | | 33.0% @ 10 nM | 5.8 |
| 64053210 | 423 | | | | | 41.7% @ 10 nM | 6.2 |
| 64053301 | 426 | | | 10.7 | | 45.83% @ 10 nM | 3.3 |
| 64053275 | 427 | | | 4.9 | | 48.69% @ 10 nM | 4.1 |
| 64053327 | 428 | | | 7.9 | | 51.9% @ 10 nM | 2.6 |
| 64159108 | 663 | | | 53.5 | | 13.3% @ 10 nM | 9.7 |
| 64151477 | 664 | | | 400.4 | | 14.4% @ 30 nM | 4.8 |
| 64053288 | 665 | | | | | 17.8% @ 10 nM | 4.1 |
| 64106666 | 666 | | | 36.3 | | 19.6% @ 10 nM | 5.4 |
| 64159134 | 667 | | | 131.7 | | 21.3% @ 30 nM | 3.2 |
| 64106575 | 668 | | | 18.1 | | 23.57% @ 10 nM | 6.5 |
| 64106627 | 669 | | | 32.4 | | 26.3% @ 10 nM | 3.0 |
| 64106640 | 670 | | | 19.3 | | 26.3% @ 10 nM | 4.6 |
| 64106653 | 671 | | | 20.4 | | 26.4% @ 10 nM | 6.6 |
| 64159121 | 672 | | | 44.2 | | 36.1% @ 30 nM | 11.2 |
| 64106757 | 673 | | | 14.4 | | 37.0% @ 10 nM | 2.2 |
| 64106744 | 674 | | | 11.1 | | 39.0% @ 10 nM | 3.4 |
| 64106705 | 675 | | | 8.8 | | 41.6% @ 10 nM | 4.3 |
| 64106718 | 676 | | | 11.4 | | 43.5% @ 10 nM | 5.7 |
| 64170171 | 677 | | | 6.2 | | 56.7% @ 10 nM | 6.9 |
| 64106731 | 678 | | | 3.7 | | 64.3% @ 10 nM | 4.9 |
| 64159082 | 679 | | | 3.6 | | 65.5% @ 10 nM | 8.0 |
| 64151503 | 680 | | | 3.6 | | 65.5% @ 10 nM | 8.0 |
| 64151438 | 681 | | | 2.5 | | 66.2% @ 10 nM | 7.1 |
| 64151464 | 682 | | | 5.6 | | 67.3% @ 10 nM | 8.8 |
| 64170145 | 683 | | | 2.2 | | 75.0% @ 10 nM | 4.4 |
| 64170132 | 684 | | | 1.2 | | 78.4% @ 10 nM | 3.7 |
| 64106601 | 685 | | | | | | |

Example 10. Generation of Variants of 63955918

Additional variants of 63955918 were designed in order to improve biodistribution of the resulting peptides.

W7 and W30 substitutions were also designed on a variety of family 3 inhibitory cysteine knot peptides to assess whether the improved selectivity and improved refolding properties conferred by those mutations extended beyond Protoxin-II to other highly homologous peptide sequences.

Family 3 spider toxins that inhibit Nav channels (NaSpTx) as defined by Klint et. al. (Toxicon 60:478-491, 2012), were chosen as scaffolds for incorporation of Q at position 7 and L at position 30 (numbering based on Seq ID 1), and include). These sequences include beta-theraphotoxin-Gr1c, beta-theraphotoxin-Gr1e, beta/kappa-theraphotoxin-Cg2a, kappa-theraphotoxin-Ps1a, kappa-theraphotoxin-Ps1b, kappa-theraphotoxin-Gr2b, kappa-theraphotoxin-Gr2c, kappa-theraphotoxin-Gr2d, kappa-theraphotoxin-Cg2a, kappa-theraphotoxin-Cg2b, kappa-theraphotoxin-Ec2c, beta-theraphotoxin-Gr1d, beta/kappa-theraphotoxin-Pm2a, kappa-theraphotoxin-Ec2a and kappa-theraphotoxin-Ec2b.

Figure 14:
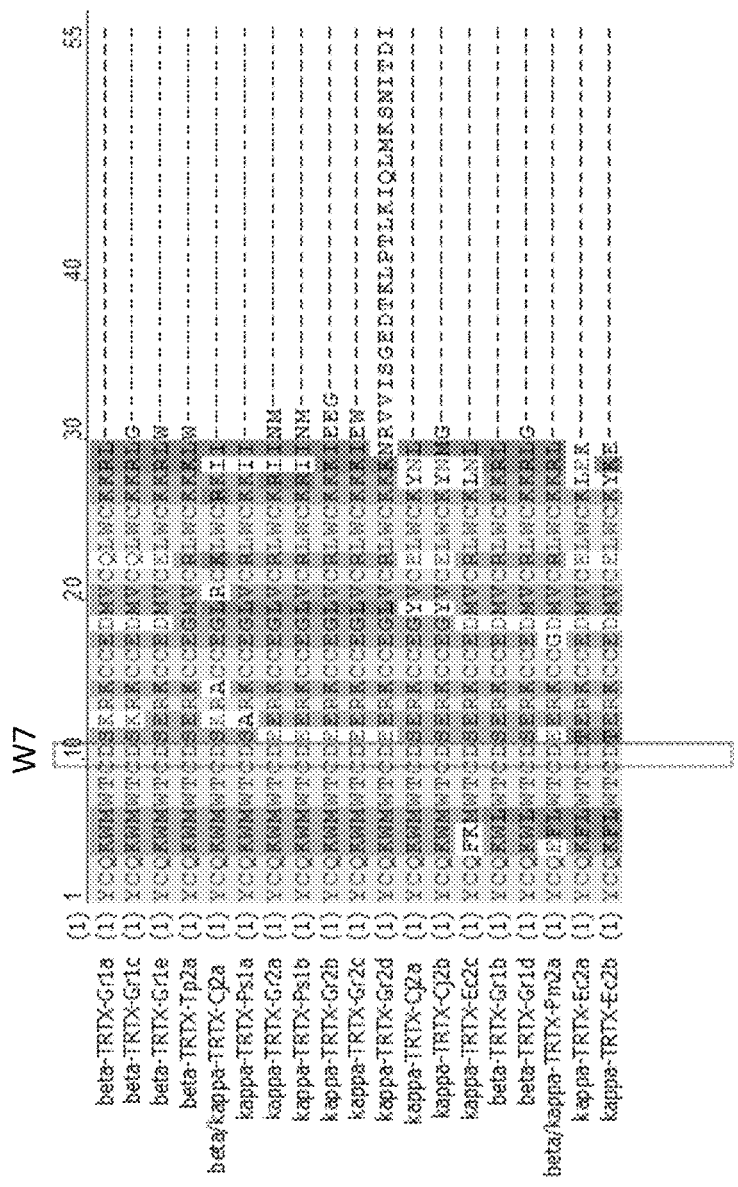
FIG. 14 shows the amino acid alignment of the Family 3 cysteine knot toxin peptides (SEQ ID NOS 738-740, 1 and 741-755, respectively, in order of appearance).

Additional family 3 NaSpTx scaffolds for mutation were identified in Arachnoserver (http://_www_arachnoserver_org/_mainMenu_html. Alignment of the family 3 toxins is shown in FIG. 14.

Table 22 shows the sequences of the designed variants.

TABLE 22

| Protein ID | Mutations | SEQ ID NO: | Protein sequence |
|---|---|---|---|
| (L-Lys(N-epsilon-(N-alpha-Palmitoyl-L-gamma-glutamyl))-PEG(2)-Protoxin-II-W7Q W30L | N-terminal addition of (L-Lys(N-epsilon-(N-alpha-Palmitoyl-L-gamma-glutamyl))-PEG(2) on Protoxin-II W7Q W30L | 686 | (L-Lys(N-epsilon-(N-alpha-Palmitoyl-L-gamma-glutamyl))-PEG(2)-YCQKWMQTCDSERKCCEGMVCRLWCKKKLL-COOH |
| (L-Lys(N-epsilon-(N-alpha-Palmitoyl-L-gamma-glutamyl))-GGGGS-Protoxin-II W7Q W30L | N-terminal addition of (L-Lys(N-epsilon-(N-alpha-Palmitoyl-L-gamma-glutamyl))GGGGS on Protoxin-II W7Q W30L | 687 | (L-Lys(N-epsilon-(N-alpha-Palmitoyl-L-gamma-glutamyl))-GGGGS-YCQKWMQTCDSERKCCEGMVCRLWCKKKLL-COOH |
| (L-Lys(N-epsilon-(N-alpha-Palmitoyl-L-gamma-glutamyl))-PEG(2)-Protoxin-II W7Q W30L K14F | N-terminal addition(L-Lys(N-epsilon-(N-alpha-Palmitoyl-L-gamma-glutamyl))-PEG(2) on Protoxin-IIW7Q W30L K14F | 688 | (L-Lys(N-epsilon-(N-alpha-Palmitoyl-L-gamma-glutamyl))-PEG(2)-YCQKWMQTCDSERFCCEGMVCRLWCKKKLL-COOH |
| (L-Lys(N-epsilon-(N-alpha-Palmitoyl-L-gamma-glutamyl))-GGGGS-Protoxin-II W7Q W30L K14F | N-terminal addition of (L-Lys(N-epsilon-(N-alpha-Palmitoyl-L-gamma-glutamyl))-GGGGS-on Protoxin-II W7Q W30L K14F | 689 | (L-Lys(N-epsilon-(N-alpha-Palmitoyl-L-gamma-glutamyl))-GGGGS-YCQKWMQTCDSERFCCEGMVCRLWCKKKLL-COOH |
| Protoxin-II W7Q W30L K14F D10asparagyl-4-aminobutane (-GP) | Protoxin-II W7Q W30L K14F D10asparagyl-4-aminobutane (-GP) | 690 | YCQKWMQTC-(Asparagyl-4-aminobutane)-SERFCCEGMVCRLWCKKKLL-COOH |
| Protoxin-II W7Q W30L G18P N methyl | Protoxin-II W7Q W30L G18P N-methyl | 691 | YCQKWMQTCDSERKCCEPMVCRLWCKKKLL-N-Me |
| Protoxin-II W7Q W30L Y1--> 4-bromo-Phe | Protoxin-II W7Q W30L Y1--> 4-bromo-Phe | 692 | (4-bromo-L-phenylalanine)-CQKWMQTCDSERKCCEGMVCRLWCKKKLL-COOH |
| Protoxin-II W7Q W30L W5--> 5-bromo-Trp | Protoxin-II W7Q W30L W5--> 5-bromo-Trp | 693 | YCQK-(5-bromo-L-tryptophan)-CQKWMQTCDSERKCCEGMVCRLWCKKKLL-COOH |
| Protoxin-II W7Q W30L W24--> 5-bromo-Trp | Protoxin-II W7Q W30L W24--> 5-bromo-Trp | 694 | YCQKWMQTCDSERKCCEGMVCRL-(5-bromo-L-tryptophan)-CKKKLL-COOH |

TABLE 22-continued

| Protein ID | Mutations | SEQ ID NO: | Protein sequence |
|---|---|---|---|
| Protoxin-II W7Q W30L Y1--> 4-chloro-Phe | Protoxin-II W7Q W30L Y1--> 4-chloro-Phe | 695 | (4-chloro-L-phenylalanine)-CQKWMQTCDSERKCCEGMVCRLWCKKKLL-COOH |
| Protoxin-II W7Q W30L Y1-->3-chloro-Tyr | Protoxin-II W7Q W30L Y1-->3-chloro-Tyr | 696 | (3-chloro-L-tyrosine)-CQKWMQTCDSERKCCEGMVCRLWCKKKLL-COOH |
| β/κ-theraphotoxin-Cg2a W7Q, R20E, I29W, addition of L30 | β/κ-theraphotoxin-Cg2a W7Q, R20E, I29W, addition of L30 | 697 | YCQKWMQTCDSKRACCEGLECKLWCRKIWL-NH2 |
| β-theraphotoxin-Gr1c W7Q G30L | β-theraphotoxin-Gr1c W7Q G30L | 698 | YCQKWMQTCDSKRKCCEDMVCQLWCKKRLL-COOH |
| β-theraphotoxin-Gr1e W7Q W30L | β-theraphotoxin-Gr1e W7Q W30L | 699 | YCQKWMQTCDSERKCCEDMVCELWCKKRLL-COOH |
| β/κ-theraphotoxin-Cg2a W7Q addition of L30 | β/κ-theraphotoxin-Cg2a W7Q addition of L30 | 700 | YCQKWMQTCDSKRACCEGLRCKLWCRKIIL-COOH |
| κ-theraphotoxin-Ps1a W7Q addition of L30 | κ-theraphotoxin-Ps1a W7Q addition of L30 | 701 | YCQKWMQTCDSARKCCEGLVCRLWCKKIIL-COOH |
| κ-theraphotoxin-Ps1b W7Q N30L | κ-theraphotoxin-Ps1b W7Q N30L | 702 | YCQKWMQTCDEERKCCEGLVCRLWCKRIILM-COOH |
| κ-theraphotoxin-Gr2b W7Q E30L | κ-theraphotoxin-Gr2b W7Q E30L | 703 | YCQKWMQTCDEERKCCEGLVCRLWCKKKILEG-COOH |
| κ-theraphotoxin-Gr2c W7Q E30L | κ-theraphotoxin-Gr2c W7Q E30L | 704 | YCQKWMQTCDEERKCCEGLVCRLWCKKKILW-COOH |
| κ-theraphotoxin-Gr2d W7Q R30L | κ-theraphotoxin-Gr2d W7Q R30L | 705 | YCQKWMQTCDEERKCCEGLVCRLWCKKKNLVVISGEDTKLPTLKIQLMKSNITDI-COOH |
| κ-theraphotoxin-Cg2a W7Q addition of L30 | κ-theraphotoxin-Cg2a W7Q addition of L30 | 706 | YCQKWMQTCDSERKCCEGYVCELWCKYNLL-COOH |
| κ-theraphotoxin-Cg2b W7Q G30L | κ-theraphotoxin-Cg2b W7Q G30L | 707 | YCQKWMQTCDSERKCCEGYVCELWCKYNML-COOH |
| (L-Lys(N-epsilon-(N-alpha-Palmitoyl-L-gamma-glutamyl))-Protoxin-II W7Q W30L | Addition of N-terminal (L-Lys(N-epsilon-(N-alpha-Palmitoyl-L-gamma-glutamyl)) on Protoxin-II W7Q W30L | 708 | (L-Lys(N-epsilon-(N-alpha-Palmitoyl-L-gamma-glutamyl))-YCQKWMQTCDSERKCCEGMVCRLWCKKKLL-COOH |
| Protoxin-II W7Q W30L S11--> beta-chloro-Ala | W7Q W30L S11--> beta-chloro-Ala | 709 | YCQKWMQTCD-(beta-chloro-L-alanine)-ERKCCEGMVCRLWCKKKLL-COOH |
| Protoxin-II W7Q W30L-PEG(2)-(L-Lys(N-epsilon-(N-alpha-Palmitoyl-L-gamma-glutamyl)) | Protoxin-II W7Q W30L with addition of C-terminal PEG(2)-(L-Lys(N-epsilon-(N-alpha-Palmitoyl-L-gamma-glutamyl)) | 710 | YCQKWMQTCDSERKCCEGMVCRLWCKKKLL-2xPEG-(L-Lys(N-epsilon-(N-alpha-Palmitoyl-L-gamma-glutamyl))-COOH |

TABLE 22-continued

| Protein ID | Mutations | SEQ ID NO: | Protein sequence |
|---|---|---|---|
| Protoxin-II W7Q W30L-GGGGS-(L-Lys(N-epsilon-(N-alpha-Palmitoyl-L-gamma-glutamyl)) | Protoxin-II W7Q W30L with C-terminal GGGGS-(L-Lys (N-epsilon-(N-alpha-Palmitoyl-L-gamma-glutamyl)) | 711 | YCQKWMQTCDSERKCCEGM VCRLWCKKKLL-GGGGS-(L-Lys(N-epsilon-(N-alpha-Palmitoyl-L-gamma-glutamyl))-COOH |
| Protoxin-II W7Q W30L (Y1--> 4-bromo-Phe), (S11--> beta-chloro-Ala) | Protoxin-II W7Q W30L (Y1--> 4-bromo-Phe), (S11--> beta-chloro-Ala) | 712 | (4-bromo-L-phenylalanine)-CQKWMQTCD-(beta-chloro-L-alanine)-ERKCCEGMVCRLWCKKKL L-COOH |
| Protoxin-II W7Q W30L (Y1-->4-bromo-Phe), (S11--> beta-chloro-Ala), (W24-->5-bromo-Trp) | Protoxin-II W7Q W30L (Y1-->4-bromo-Phe), (S11--> beta-chloro-Ala), (W24-->5-bromo-Trp) | 713 | (4-bromo-L-phenylalanine)-CQKWMQTCD-(beta-chloro-L-alanine)-ERKCCEGMVCRL-(5-bromo-L-CKKKLL-COOH |
| WW (S11--> beta-chloro-Ala), (W24-->5-bromo-Trp) | WW (S11--> beta-chloro-Ala), (W24-->5-bromo-Trp) | 714 | YCQKWMQTCD-(beta-chloro-L-alanine)-ERKCCEGMVCRL-(5-bromo-L-tryptophan)-CKKKLL-COOH |
| Protoxin-II W7Q W30L S11(L-Lys(N-epsilon-(N-alpha-Palmitoyl-L-gamma-glutamyl)) | Protoxin-II W7Q W30L S11(L-Lys(N-epsilon-(N-alpha-Palmitoyl-L-gamma-glutamyl)) | 715 | YCQKWMQTCD-(Lys(N-epsilon-(N-alpha-Palmitoyl-L-gamma-glutamyl))-ERKCCEGMVCRLWCKKKL L-COOH |
| Protoxin-II W7Q W30L E12(L-Lys(N-epsilon-(N-alpha-Palmitoyl-L-gamma-glutamyl)) | Protoxin-II W7Q W30L E12(L-Lys(N-epsilon-(N-alpha-Palmitoyl-L-gamma-glutamyl)) | 716 | YCQKWMQTCDS-(Lys(N-epsilon-(N-alpha-Palmitoyl-L-gamma-glutamyl))-RKCCEGMVCRLWCKKKLL-COOH |
| WW E17(L-Lys(N-epsilon-(N-alpha-Palmitoyl-L-gamma-glutamyl)) | WW E17(L-Lys(N-epsilon-(N-alpha-Palmitoyl-L-gamma-glutamyl)) | 717 | YCQKWMQTCDSERKCC-(Lys(N-epsilon-(N-alpha-Palmitoyl-L-gamma-glutamyl))-GMVCRLWCKKKLL-COOH |
| Protoxin-II W7Q W30L D10 L-asparagyl-4-aminobutane E12 L-glutamyl-4-aminobutane E17 L-glutamyl-4-aminobutane | Protoxin-II W7Q W30L D10-(L-asparagyl-4-aminobutane E12 L-glutamyl-4-aminobutane E17 L-glutamyl-4-aminobutane | 718 | YCQKWMQTC-(L-asparagyl-4-aminobutane)-S-(L-glutamyl-4-aminobutane)-RKCC-(L-glutamyl-4-aminobutane)-GMVCRLWCKKKLL-COOH |
| Protoxin-II W7Q W30L (Y1--> 4-bromo-Phe), (W5-->5-bromo-Trp) (W24--> 5-bromo-Trp) | Protoxin-II W7Q W30L (Y1--> 4-bromo-Phe), (W5-->5-bromo-Trp) (W24--> 5-bromo-Trp) | 719 | (4-bromo-L-phenylalanine)-CQK-(5-bromo-L-tryptophan)-MQTCDSERKCCEGMVCR L-(5-bromo-L-tryptophan)-CKKKLL-COOH |
| Protoxin-II W7Q W30L (Y1--> 4-bromo-Phe), (W24--> 5-bromo-Trp) | Protoxin-II W7Q W30L (Y1--> 4-bromo-Phe), (W24--> 5-bromo-Trp) | 720 | (4-bromo-L-phenylalanine)-CQKWMQTCDSERKCCEG MVCRL-(5-bromotryptophan)-CKKKLL-COOH |

TABLE 22-continued

| Protein ID | Mutations | SEQ ID NO: | Protein sequence |
|---|---|---|---|
| Protoxin-II W7Q W30L Y1-->3,4 di-chloro-Phe | Protoxin-II W7Q W30L Y1--3,4 di-chloro-Phe | 721 | (3,4-dichloro-L-phenylalanine)-CQKWMQTCDSERKCCEGMVCRLWCKKKLL-COOH |
| Protoxin-II W7Q W30L Y1-->3,5 di-bromo-Tyr | Protoxin-II W7Q W30L Y1-->3,5 di-bromo-Tyr | 722 | (3,5-dibromo-L-tyrosine)-CQKWMQTCDSERKCCEGMVCRLWCKKKLL-COOH |
| Protoxin-II W7Q W30L Y1--> 3,4,5 tri-fluoro-Phe | Protoxin-II W7Q W30L Y1--> 3,4,5 tri-fluoro-Phe | 723 | (3,4,5-trifluoro-L-phenylalanine)-CQKWMQTCDSERKCCEGMVCRLWCKKKLL-COOH |
| Protoxin-II W7Q W30L with additional N-terminal L-cyano-beta-alanine | Protoxin-II W7Q W30L with additional N-terminal L-cyano-beta-alanine | 724 | (L-cyano-beta-alanine)-YCQKWMQTCDSERKCCEGMVCRLWCKKKLL-COOH |
| Protoxin-II W7Q W30L with additional N-terminal L-propargylglycine | Protoxin-II W7Q W30L with additional N-terminal L-propargylglycine | 725 | (propargylglycine)-YCQKWMQTCDSERKCCEGMVCRLWCKKKLL-COOH |
| Protoxin-II W7Q W30L with additional N-terminal L-norvaline | Protoxin-II W7Q W30L with additional N-terminal L-norvaline | 726 | (L-norvaline)-YCQKWMQTCDSERKCCEGMVCRLWCKKKLL-COOH |
| κ-theraphotoxin-Ec2c W7Q addition of L30 | κ-theraphotoxin-Ec2c W7Q addition of L30 | 727 | YCQFKMQTCDSERKCCEDMVCRLWCKLNLL-COOH |
| β-theraphotoxin-Gr1d W7Q G30L | β-theraphotoxin-Gr1d W7Q G30L | 728 | YCQKWLQTCDSERKCCEDMVCRLWCKKRLL-COOH |
| β/κ-Theraphotoxin-Pm2a W7Q addition of L30 | β/κ-Theraphotoxin-Pm2a W7Q addition of L30 | 729 | YCQEFLQTCDEERKCCGDMVCRLWCKKRLL-COOH |
| κ-theraphotoxin-Ec2a W7Q addition of L30 | κ-theraphotoxin-Ec2a W7Q addition of L30 | 730 | YCQKFLQTCDTERKCCEDMVCELWCKLEKL-COOH |
| κ-theraphotoxin-Ec2b W7Q addition of L30 | κ-theraphotoxin-Ec2b W7Q addition of L30 | 731 | YCQKFLQTCDTERKCCEDMVCELWCKYKEL-COOH |
| Protoxin-II WQ W30L E12Y N-methyl | W7Q W30L E12Y N-methyl | 732 | YCQKWMQTCDSYRKCCEGMVCRLWCKKKLL-N-Me |
| Protoxin-II W7Q W30L Q3Y N-methyl | W7Q W30L Q3Y N-methyl | 733 | YCYKWMQTCDSERKCCEGMVCRLWCKKKLL-N-Me |
| Protoxin-II W7Q W30Y | W7Q W30Y | 734 | YCQKWMQTCDSERKCCEGMVCRLWCKKKLY-COOH |
| Protoxin-II W7Q W30F | W7Q W30F | 735 | YCQKWMQTCDSERKCCEGMVCRLWCKKKLF-COOH |
| Protoxin-II W7Q W30norvaline | W7Q W30norvaline | 736 | YCQKWMQTCDSERKCCEGMVCRLWCKKKL-(L-norvaline)--COOH |

The resulting variants incorporating non-natural amino acids are generated by standard solid-phase peptide synthesis and oxidative refolding methods.

The variants having peg group attached are generated via standard chemical conjugation methods.

The resulting variants are tested for their ability to inhibit Nav1.7 in veratridine-induced depolarization inhibition assay and QPatch assays as described in Example 3.

The generated variants are tested for their selectivity using methods described in Example 3.

We claim:

1. A method of treating Nav1.7-mediated pain in a subject, comprising administering to a subject in need thereof an effective amount of an isolated Protoxin-II variant or a fusion protein thereof to treat the pain, wherein the Protoxin-II variant has at least one amino acid substitution selected from the group consisting of W7Q and W30L; wherein residue numbering is according to SEQ ID NO: 1.

2. A method of treating Nav1.7-mediated pain in a subject, comprising administering to a subject in need thereof an effective amount of an isolated Protoxin-II variant or a fusion protein thereof, wherein the Protoxin-II variant inhibits human Nav1.7 activity with an $IC_{50}$ value of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, wherein the $IC_{50}$ value is measured using a veratridine-induced depolarization inhibition assay using fluorescence resonance energy transfer (FRET) in the presence of $25\times10^{-8}$ M 3-veratroylveracevine in HEK293 cells stably expressing human Nav1.7, wherein the Protoxin-II variant has a W7Q and/or a W30L substitution, wherein residue numbering is according to SEQ ID NO: 1.

3. The method of claim 1, wherein the isolated Protoxin-II variant comprises the sequence: $X_1X_2X_3CX_4X_5WX_6QX_7CX_8X_9X_{10}X_{11}X_{12}CCX_{13}X_{14}X_{15}X_{16}CX_{17}LWCX_{18}KKLX_{19}$ (SEQ ID NO: 432), wherein $X_1$ is G, P, A or deleted;
$X_2$ is P, A or deleted;
$X_3$ is S, Q, A, R or Y;
$X_4$ is Q, R, K, A, S, or Y;
$X_5$ is K, S, Q or R;
$X_6$ is M or F;
$X_7$ is T, S, R, K or Q;
$X_8$ is D, T or asparagyl-4-aminobutane;
$X_9$ is S, A R, I, or V;
$X_{10}$ is E, R, N, K, T, Q, Y or glutamyl-4-aminobutane;
$X_{11}$ is R or K;
$X_{12}$ is K, Q, S, A or F;
$X_{13}$ is E, Q, D, L, N or glutamyl-4-aminobutane;
$X_{14}$ is G, Q or P;
$X_{15}$ is M or F;
$X_{16}$ is V or S;
$X_{17}$ is R, T or N-omega methyl-L-arginine;
$X_{18}$ is K or R; and
$X_{19}$ is W or L,
optionally having an N-terminal extension or a C-terminal extension.

4. The method of claim 1, wherein the isolated Protoxin-II variant has a substitution at one or more residue positions $Y_1$, $W_7$, $S_{11}$, $E_{12}$, $K_{14}$, $E_{17}$, $G_{18}$, $R_{22}$ and $L_{29}$, when residue numbering is according to SEQ ID NO: 1.

5. The method of claim 1, wherein the isolated Protoxin-II variant is a derivative of the sequence YCQKWMQTCD-SERKCCEGMVCRLWCKKKLW-OH (SEQ ID NO: 424); wherein residue $Y_1$, $S_{11}$, $E_{12}$, $K_{14}$, $E_{17}$, $G_{18}$, $R_{22}$ and/or $L_{29}$ is substituted with
a) any other amino acid selected from the group consisting of alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine;
b) a non-natural amino acid; and
c) W30 is substituted by L.

6. The method of claim 1, wherein the isolated Protoxin-II variant is a derivative of the sequence YCQKWMQTCD-SERKCCEGMVCRLWCKKKLL-OH (SEQ ID NO: 425); wherein residue $Y_1$, $S_{11}$, $E_{12}$, $K_{14}$, $E_{17}$, $G_{18}$, $M_{19}$ and/or $L_{29}$ is substituted with
a) any other amino acid selected from the group consisting of alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine; or
b) a non-natural amino acid.

7. The method of claim 1, wherein the isolated Protoxin-II variant comprises an amino acid sequence that is at least 90% identical to the amino acid sequence of SEQ ID NO: 422 (GPYCQKWMQTCDSERKC-CEGMVCRLWCKKKLL-COOH); wherein the residue numbering is according to SEQ ID NO: 1.

8. The method of claim 1, wherein the isolated Protoxin-II variant comprises the sequence $X_1X_2X_3CQKWMQTCDX_4X_5RX_6CCX_7X_8X_9VCRL$ $WCKKKX_{10}X_{11}$ (SEQ ID NO: 737); wherein
$X_1$ is G, P, A or deleted;
$X_2$ is P, A or deleted;
$X_3$ is S, Q, A, R or Y;
$X_4$ is S, A, R, I or V;
$X_5$ is E, R, N, K, T, Q, Y or glutamyl-4-aminobutane;
$X_6$ is K, Q, S, A or F;
$X_7$ is E, Q, D, L, N or glutamyl-4-aminobutane;
$X_8$ is G, Q or P;
$X_9$ is M or F;
$X_{10}$ is L, V; and
$X_{11}$ is W or L.

9. The method of claim 1, wherein the isolated Protoxin-II variant further comprises an N-terminal extension and wherein the N-terminal extension comprises the amino acid sequence of SEQ ID NOs: 372, 373, 374, 375, 376, 377, 378, 379, 380, 381, 382, 383, 384 or 385.

10. The method of claim 1, wherein the isolated Protoxin-II variant further comprises a C-terminal extension and wherein the C-terminal extension comprises the amino acid sequence of SEQ ID NOs: 374, 386, 387, 388, 389, 390, 391, 392, 393, 394, 395, 396 or 397.

11. The method of claim 1, wherein the isolated Protoxin-II variant further comprises an N-terminal extension and/or a C-terminal extension and wherein the N-terminal and/or the C-terminal extension is conjugated to the Protoxin-II variant via a linker.

12. The method of claim 11, wherein the linker comprises the amino acid sequence of SEQ ID NOs: 383, 392, 398, 399, 400, 401 or 402.

13. The method of claim 1, wherein the isolated Protoxin-II variant inhibits human Nav1.7 activity with an $IC_{50}$ value of about $3\times10^{-8}$ M or less, when the $IC_{50}$ value is measured using a veratridine-induced depolarization inhibition assay using fluorescence resonance energy transfer (FRET) in the presence of $25\times10^{-8}$ M 3-veratroylveracevine in HEK293 cells stably expressing human Nav1.7.

14. The method of claim 13, wherein the isolated Protoxin-II variant inhibits human Nav1.7 activity with an $IC_{50}$ value of between about $3\times10^{-8}$ M to $1\times10^{-9}$ M.

15. The method of claim 1, wherein the isolated Protoxin-II variant inhibits Nav1.7 activity by at least 25%, when the Nav1.7 activity is measured using a patch clamp assay using an extracellular solution containing 137 mM NaCl, 5.4 mM KCl, 1 mM $MgCl_2$, 2 mM $CaCl_2$), 5 mM glucose, and 10 mM HEPES, pH=7.4, and osmolarity=315 mOsm, an intracellular solution containing 135 mM CsF, 10 mM CsCl, 5 mM EGTA, 5 mM NaCl and 10 mM HEPES, pH=7.3 and osmolarity=290 mOsm and a holding potential of −75 mV.

16. The method of claim 1, wherein the isolated Protoxin-II variant comprises the amino acid sequence $GPQCX_1X_2WX_3QX_4CX_5X_6X_7X_8X_9CCX_{10}X_{11}X_{12}$ $CX_{13}LWCX_{14}KKLL$ (SEQ ID NO: 433), wherein
$X_1$ is Q, R, K, A or S;
$X_2$ is K, S, Q or R;
$X_3$ is M or F;
$X_4$ is T, S, R, K or Q;
$X_5$ is D or T;
$X_6$ is S, A or R;
$X_7$ is E, R, N, K, T or Q;
$X_8$ is R or K;
$X_9$ is K, Q, S or A;
$X_{10}$ is E, Q or D;
$X_{11}$ is G or Q;
$X_{12}$ is V or S;
$X_{13}$ is R or T; and
$X_{14}$ is K or R.

17. The method of claim 1, wherein the isolated Protoxin-II variant comprises the amino acid sequence of SEQ ID NOs: 30, 40, 44, 52, 56, 59, 65, 78, 109, 110, 111, 114, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 162, 165, 166, 167, 168, 169, 170, 171, 172, 173, 174, 175, 177, 178, 179, 180, 182, 183, 184, 185, 186, 189, 190, 193, 195, 197, 199, 206, 207, 208, 209, 210, 211, 212, 213, 214, 215, 216, 217, 218, 224, 226, 227, 231, 232, 243, 244, 245, 247, 249, 252, 255, 258, 261, 263, 264, 265, 266, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 332, 334, 335, 336, 337, 339, 340, 341, 342, 346, 351, 358, 359, 364, 366, 367, 368, 369, 370, 371, 408, 409, 410, 411, 412, 413, 414, 415, 416, 417, 418, 419, 420, 421, 422, 423, 424, 425, 426, 427, 428, 429, 430, 431, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735 or 736.

18. The method of claim 1, wherein the isolated Protoxin-II variant comprises a free C-terminal carboxylic acid, amide, methylamide or butylamide group.

19. The method of claim 1, wherein the isolated fusion protein comprising the Protoxin-II variant is conjugated to a half-life extending moiety.

20. The method of claim 19, wherein the half-life extending moiety is human serum albumin (HSA), albumin binding domain (ABD), Fc or polyethylene glycol (PEG).

21. The method of claim 1, wherein the pain is chronic pain, acute pain, neuropathic pain, cancer pain, nociceptive pain, visceral pain, back pain, post-operative pain, thermal pain, phantom limb pain, or pain associated with inflammatory conditions, primary erythemalgia (PE), paroxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis.

22. The method of claim 21, wherein the Protoxin-II variant is administered peripherally.

23. The method of claim 22, wherein the Protoxin-II variant is administered locally to a joint, spinal cord, surgical wound, sites of injury or trauma, peripheral nerve fibers, urogenital organs, or inflamed tissues.

24. The method of claim 1, wherein the subject is a human.

* * * * *

SEQUENCE LISTING

<160> NUMBER OF SEQ ID NOS: 755

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Pro Ala Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Pro Gln Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 5

Gly Pro Arg Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Pro Ser Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Pro Tyr Cys Gln Lys Trp Phe Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Pro Tyr Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 10
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Pro Tyr Cys Gln Lys Trp Met Trp Thr Cys Asp Arg Glu Arg Lys
1               5                   10                  15

Cys Cys Glu Gly Met Val Cys Arg Leu Trp Cys Lys Lys Lys Leu Trp
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Pro Tyr Cys Gln Lys Trp Met Trp Thr Cys Asp Ser Lys Arg Lys
1               5                   10                  15

Cys Cys Glu Gly Met Val Cys Arg Leu Trp Cys Lys Lys Lys Leu Trp
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Pro Tyr Cys Gln Lys Trp Met Trp Thr Cys Asp Ser Asn Arg Lys
1               5                   10                  15

Cys Cys Glu Gly Met Val Cys Arg Leu Trp Cys Lys Lys Lys Leu Trp
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Pro Tyr Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Pro Tyr Cys Gln Lys Trp Met Trp Thr Cys Asp Ser Glu Arg Lys
1               5                   10                  15
```

Cys Cys Glu Gly Leu Val Cys Arg Leu Trp Cys Lys Lys Lys Leu Trp
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Pro Tyr Cys Gln Lys Trp Met Trp Thr Cys Asp Ser Glu Arg Lys
1               5                   10                  15

Cys Cys Glu Gly Met Val Cys Thr Leu Trp Cys Lys Lys Lys Leu Trp
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Arg Lys Lys Leu Trp
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Pro Ala Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Pro Ala Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Pro Ala Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Pro Gln Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Pro Gln Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Pro Gln Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Pro Arg Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 24

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Pro Arg Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Pro Arg Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Pro Ser Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Pro Ser Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Pro Ser Cys Gln Lys Trp Met Trp Thr Cys Asp Ser Glu Arg Lys
1               5                   10                  15
```

-continued

```
Cys Cys Glu Gly Phe Val Cys Arg Leu Trp Cys Lys Lys Lys Leu Trp
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Pro Tyr Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Pro Tyr Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Pro Ala Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Pro Ala Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 33

Gly Pro Ala Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Pro Ala Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Pro Gln Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Pro Gln Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Pro Gln Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

-continued

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Pro Arg Cys Gln Lys Trp Phe Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Pro Arg Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Pro Arg Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Pro Ser Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Pro Ser Cys Gln Lys Trp Phe Trp Thr Cys Asp Ala Glu Arg Lys

```
1               5                   10                  15
Cys Cys Glu Gly Met Val Cys Arg Leu Trp Cys Lys Lys Lys Leu Trp
            20                  25                  30
```

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gly Pro Ser Cys Gln Lys Trp Met Gln Thr Cys Asp Ala Glu Arg Lys
1               5                   10                  15
Cys Cys Glu Gly Met Val Cys Arg Leu Trp Cys Lys Lys Lys Leu Trp
            20                  25                  30
```

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gly Pro Ser Cys Gln Lys Trp Met Gln Thr Cys Asp Ser Glu Arg Lys
1               5                   10                  15
Cys Cys Glu Gly Phe Val Cys Arg Leu Trp Cys Lys Lys Lys Leu Trp
            20                  25                  30
```

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gly Pro Ser Cys Gln Lys Trp Met Trp Thr Cys Asp Ala Glu Arg Lys
1               5                   10                  15
Cys Cys Glu Gly Phe Val Cys Arg Leu Trp Cys Lys Lys Lys Leu Trp
            20                  25                  30
```

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gly Pro Tyr Cys Gln Lys Trp Phe Lys Thr Cys Asp Ala Glu Arg Lys
1               5                   10                  15
Cys Cys Glu Gly Met Val Cys Arg Leu Trp Cys Lys Lys Lys Leu Trp
            20                  25                  30
```

<210> SEQ ID NO 47
<211> LENGTH: 32
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 47

Gly Pro Tyr Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Gly Pro Tyr Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Gly Pro Ala Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Gly Pro Ala Cys Gln Lys Trp Phe Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

Gly Pro Ala Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Pro Ala Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Pro Ala Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Pro Gln Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Pro Gln Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Pro Gln Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Pro Arg Cys Gln Lys Trp Phe Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Pro Arg Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Pro Arg Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 61
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 61

Gly Pro Ser Cys Gln Lys Trp Phe Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Pro Ser Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Pro Ser Cys Gln Lys Trp Phe Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Pro Ser Cys Gln Lys Trp Phe Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Pro Ser Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30
```

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Pro Ser Cys Gln Lys Trp Phe Trp Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Pro Ser Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Pro Tyr Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Pro Tyr Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gly Pro Ala Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Pro Ala Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Pro Gln Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Pro Gln Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Pro Arg Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 75
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 75

Gly Pro Arg Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Pro Ser Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Pro Ser Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 79
<211> LENGTH: 1977
<212> TYPE: PRT
<213> ORGANISM: Homo Sapiens

<400> SEQUENCE: 79

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
```

```
              35                  40                  45
Pro Ser Ser Asp Leu Glu Ala Gly Lys Gln Leu Pro Phe Ile Tyr Gly
 50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Thr
                 85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Glu
    450                 455                 460
```

```
Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
            485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
            645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
            725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
            805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880
```

```
Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
                995                1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
```

-continued

|  | 1280 |  |  | 1285 |  |  | 1290 |  |  |
| --- | --- | --- | --- | --- | --- | --- | --- | --- | --- |

Glu Gly Met Arg Val Val Asn Ala Leu Ile Gly Ala Ile Pro
        1295              1300              1305

Ser Ile Met Asn Val Leu Leu Val Cys Leu Ile Phe Trp Leu Ile
        1310              1315              1320

Phe Ser Ile Met Gly Val Asn Leu Phe Ala Gly Lys Phe Tyr Glu
        1325              1330              1335

Cys Ile Asn Thr Thr Asp Gly Ser Arg Phe Pro Ala Ser Gln Val
        1340              1345              1350

Pro Asn Arg Ser Glu Cys Phe Ala Leu Met Asn Val Ser Gln Asn
        1355              1360              1365

Val Arg Trp Lys Asn Leu Lys Val Asn Phe Asp Asn Val Gly Leu
        1370              1375              1380

Gly Tyr Leu Ser Leu Leu Gln Val Ala Thr Phe Lys Gly Trp Thr
        1385              1390              1395

Ile Ile Met Tyr Ala Ala Val Asp Ser Val Asn Val Asp Lys Gln
        1400              1405              1410

Pro Lys Tyr Glu Tyr Ser Leu Tyr Met Tyr Ile Tyr Phe Val Val
        1415              1420              1425

Phe Ile Ile Phe Gly Ser Phe Phe Thr Leu Asn Leu Phe Ile Gly
        1430              1435              1440

Val Ile Ile Asp Asn Phe Asn Gln Gln Lys Lys Lys Leu Gly Gly
        1445              1450              1455

Gln Asp Ile Phe Met Thr Glu Glu Gln Lys Lys Tyr Tyr Asn Ala
        1460              1465              1470

Met Lys Lys Leu Gly Ser Lys Lys Pro Gln Lys Pro Ile Pro Arg
        1475              1480              1485

Pro Gly Asn Lys Ile Gln Gly Cys Ile Phe Asp Leu Val Thr Asn
        1490              1495              1500

Gln Ala Phe Asp Ile Ser Ile Met Val Leu Ile Cys Leu Asn Met
        1505              1510              1515

Val Thr Met Met Val Glu Lys Glu Gly Gln Ser Gln His Met Thr
        1520              1525              1530

Glu Val Leu Tyr Trp Ile Asn Val Val Phe Ile Ile Leu Phe Thr
        1535              1540              1545

Gly Glu Cys Val Leu Lys Leu Ile Ser Leu Arg His Tyr Tyr Phe
        1550              1555              1560

Thr Val Gly Trp Asn Ile Phe Asp Phe Val Val Val Ile Ile Ser
        1565              1570              1575

Ile Val Gly Met Phe Leu Ala Asp Leu Ile Glu Thr Tyr Phe Val
        1580              1585              1590

Ser Pro Thr Leu Phe Arg Val Ile Arg Leu Ala Arg Ile Gly Arg
        1595              1600              1605

Ile Leu Arg Leu Val Lys Gly Ala Lys Gly Ile Arg Thr Leu Leu
        1610              1615              1620

Phe Ala Leu Met Met Ser Leu Pro Ala Leu Phe Asn Ile Gly Leu
        1625              1630              1635

Leu Leu Phe Leu Val Met Phe Ile Tyr Ala Ile Phe Gly Met Ser
        1640              1645              1650

Asn Phe Ala Tyr Val Lys Lys Glu Asp Gly Ile Asn Asp Met Phe
        1655              1660              1665

Asn Phe Glu Thr Phe Gly Asn Ser Met Ile Cys Leu Phe Gln Ile
        1670              1675              1680

Thr Thr Ser Ala Gly Trp Asp Gly Leu Leu Ala Pro Ile Leu Asn
    1685                1690                1695

Ser Lys Pro Pro Asp Cys Asp Pro Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Gly Gly Ser Gly Gly Gly Ser Gly Gly Gly Ser Gly
1               5                   10                  15

Gly Gly Gly Ser
            20

```
<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser
                20                  25                  30

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Glu Val Leu Phe Gln Gly Pro
1               5

<210> SEQ ID NO 83
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
                20                  25                  30

Glu Val Ala His Arg Phe Lys Asp Leu Gly Glu Glu Asn Phe Lys Ala
            35                  40                  45

Leu Val Leu Ile Ala Phe Ala Gln Tyr Leu Gln Gln Cys Pro Phe Glu
        50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205
```

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
                260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
        290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
                340                 345                 350

Phe Leu Gly Met Phe Leu Tyr Glu Tyr Ala Arg Arg His Pro Asp Tyr
            355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
                420                 425                 430

Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
610                 615                 620

| | | | | | | | | | | | | |
|---|---|---|---|---|---|---|---|---|---|---|---|---|
| Gly | Gly | Gly | Gly | Ser | Gly | Gly | Gly | Ser | Leu | Glu | Val | Leu | Phe | Gln |
| 625 | | | | 630 | | | | 635 | | | | 640 |

| | | | | | | | | | | | | |
|---|---|---|---|---|---|---|---|---|---|---|---|---|
| Gly | Pro | Gln | Cys | Gln | Lys | Trp | Met | Gln | Thr | Cys | Asp | Ala | Glu | Arg | Lys |
| | | | 645 | | | | | 650 | | | | | 655 |

| | | | | | | | | | | | | |
|---|---|---|---|---|---|---|---|---|---|---|---|---|
| Cys | Cys | Glu | Gly | Phe | Val | Cys | Arg | Leu | Trp | Cys | Lys | Lys | Lys | Leu | Trp |
| | | | 660 | | | | | 665 | | | | | 670 |

<210> SEQ ID NO 84
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

| | | | | | |
|---|---|---|---|---|---|
| atggcttggg | tgtggacctt | gctattcctg | atggcggccg | cccaaagtat | acaggccggg | 60 |
| agccaccacc | accaccacca | cgacgcccac | aagagcgagg | tggcccaccg | gttcaaggac | 120 |
| ctgggcgagg | agaacttcaa | ggccctggtg | ctgatcgcct | tcgcccagta | cctgcagcag | 180 |
| tgccccttcg | aggaccacgt | gaagctggtg | aacgaggtga | ccgagttcgc | caagacctgc | 240 |
| gtggccgacg | agagcgccga | gaactgcgac | aagagcctgc | acaccctgtt | cggcgacaag | 300 |
| ctgtgcaccg | tggccaccct | gcgggagacc | tacggcgaga | tggccgactg | ctgcgccaag | 360 |
| caggagcccg | agcggaacga | gtgcttcctg | cagcacaagg | acgacaaccc | caacctgccc | 420 |
| cggctggtgc | ggcccgaggt | ggacgtgatg | tgcaccgcct | ccacgacaa | cgaggagacc | 480 |
| ttcctgaaga | agtacctgta | cgagatcgcc | cggcggcacc | cctacttcta | cgcccccgag | 540 |
| ctgctgttct | tcgccaagcg | gtacaaggcc | gccttcaccg | agtgctgcca | ggccgccgac | 600 |
| aaggccgcct | gctgctgcc | caagctggac | gagctgcggg | acgagggcaa | ggccagcagc | 660 |
| gccaagcagc | ggctgaagtg | cgccagcctg | cagaagttcg | gcgagcgggc | cttcaaggcc | 720 |
| tgggccgtgg | cccggctgag | ccagcggttc | ccaaggccg | agttcgccga | ggtgagcaag | 780 |
| ctggtgaccg | acctgaccaa | ggtgcacacc | gagtgctgcc | acggcgacct | gctggagtgc | 840 |
| gccgacgacc | gggccgacct | ggccaagtac | atctgcgaga | accaggacag | catcagcagc | 900 |
| aagctgaagg | agtgctgcga | gaagcccctg | ctggagaaga | gccactgcat | cgccgaggtg | 960 |
| gagaacgacg | agatgcccgc | cgacctgccc | agcctggccg | ccgacttcgt | ggagagcaag | 1020 |
| gacgtgtgca | agaactacgc | cgaggccaag | gacgtgttcc | tgggcatgtt | cctgtacgag | 1080 |
| tacgcccggc | ggcaccccga | ctacagcgtg | gtgctgctgc | tgcggctggc | caagacctac | 1140 |
| gagaccaccc | tggagaagtg | ctgcgccgcc | gccgaccccc | acgagtgcta | cgccaaggtg | 1200 |
| ttcgacgagt | tcaagcccct | ggtggaggag | ccccagaacc | tgatcaagca | gaactgcgag | 1260 |
| ctgttcgagc | agctgggcga | gtacaagttc | cagaacgccc | tgctggtgcg | gtacaccaag | 1320 |
| aaggtgcccc | aggtgagcac | ccccacccct | gtggaggtga | ccggaacct | gggcaaggtg | 1380 |
| ggcagcaagt | gctgcaagca | ccccgaggcc | aagcggatgc | cctgcgccga | ggactacctg | 1440 |
| agcgtggtgc | tgaaccagct | gtgcgtgctg | cacgagaaga | ccccgtgag | cgaccgggtg | 1500 |
| accaagtgct | gcaccgagag | cctggtgaac | cggcggccct | gcttcagcgc | cctggaggtg | 1560 |
| gacgagacct | acgtgcccaa | ggagttcaac | gccgagacct | tcaccttcca | cgccgacatc | 1620 |
| tgcaccctga | gcgagaagga | gcggcagatc | aagaagcaga | ccgccctggt | ggagctggtg | 1680 |
| aagcacaagc | ccaaggccac | caaggagcag | ctgaaggcct | gatgacga | cttcgccgcc | 1740 |
| ttcgtggaga | agtgctgcaa | ggccgacgac | aaggagacct | gcttcgccga | ggagggcaag | 1800 |

-continued

```
aagctggtgg ccgccagcca ggccgccctg ggcctgggca gcggcggcgg cggcagcggc    1860
ggcggcggat ctggtggagg tggcagtgga ggagggggat ccctcgaggt cctctttcag    1920
ggaccacagt gccagaagtg gatgcagaca tgcgacgccg agcgcaagtg ctgcgaaggc    1980
ttcgtgtgtc gcctgtggtg taaaaagaag ttgtggtga                           2019
```

<210> SEQ ID NO 85
<211> LENGTH: 672
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320
```

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
610                 615                 620

Gly Gly Gly Ser Gly Gly Gly Ser Leu Glu Val Leu Phe Gln
625                 630                 635                 640

Gly Pro Arg Cys Gln Lys Trp Met Gln Thr Cys Asp Ala Glu Arg Lys
                645                 650                 655

Cys Cys Glu Gly Phe Val Cys Arg Leu Trp Cys Lys Lys Leu Trp
            660                 665                 670

<210> SEQ ID NO 86
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atggcttggg tgtggacctt gctattcctg atggcggccg cccaaagtat acaggccggg     60

```
agccaccacc accaccacca cgacgcccac aagagcgagg tggcccaccg gttcaaggac      120
ctgggcgagg agaacttcaa ggccctggtg ctgatcgcct tcgcccagta cctgcagcag      180
tgccccttcg aggaccacgt gaagctggtg aacgaggtga ccgagttcgc caagacctgc      240
gtggccgacg agagcgccga gaactgcgac aagagcctgc acaccctgtt cggcgacaag      300
ctgtgcaccg tggccaccct gcgggagacc tacggcgaga tggccgactg ctgcgccaag      360
caggagcccg agcggaacga gtgcttcctg cagcacaagg acgacaaccc caacctgccc      420
cggctggtgc ggcccgaggt ggacgtgatg tgcaccgcct ccacgacaa cgaggagacc       480 ttcctgaaga agtacctgta cgagatcgcc cggcggcacc cctacttcta cgcccccgag      540
ctgctgttct tcgccaagcg gtacaaggcc gccttcaccg agtgctgcca ggccgccgac      600
aaggccgcct gcctgctgcc caagctggac gagctgcggg acgagggcaa ggccagcagc      660
gccaagcagc ggctgaagtg cgccagcctg cagaagttcg gcgagcgggc cttcaaggcc      720
tgggccgtgg cccggctgag ccagcggttc cccaaggcca gttcgccga ggtgagcaag       780 ctggtgaccg acctgaccaa ggtgcacacc gagtgctgcc acggcgacct gctggagtgc      840
gccgacgacc gggccgacct ggccaagtac atctgcgaga accaggacag catcagcagc      900
aagctgaagg agtgctgcga aagcccctg ctggagaaga gccactgcat cgccgaggtg       960
gagaacgacg agatgcccgc cgacctgccc agcctggccg ccgacttcgt ggagagcaag      1020
gacgtgtgca agaactacgc cgaggccaag gacgtgttcc tgggcatgtt cctgtacgag      1080
tacgcccggc ggcaccccga ctacagcgtg tgctgctgc tgcggctggc caagacctac       1140
gagaccaccc tggagaagtg ctgcgccgcc gccgaccccc acgagtgcta cgccaaggtg      1200
ttcgacgagt tcaagcccct ggtggaggag ccccagaacc tgatcaagca gaactgcgag      1260
ctgttcgagc agctgggcga gtacaagttc cagaacgccc tgctggtgcg gtacaccaag      1320
aaggtgcccc aggtgagcac ccccaccctg gtggaggtga ccggaacct gggcaaggtg       1380 ggcagcaagt gctgcaagca ccccgaggcc aagcggatgc cctgcgccga ggactacctg      1440
agcgtggtgc tgaaccagct gtgcgtgctg cacgagaaga cccccgtgag cgaccgggtg      1500
accaagtgct gcaccgagag cctggtgaac cggcggccct gcttcagcgc cctggaggtg      1560
gacgagacct acgtgcccaa ggagttcaac gccgagacct tcaccttcca cgccgacatc      1620
tgcaccctga gcgagaagga gcggcagatc aagaagcaga ccgccctggt ggagctggtg      1680
aagcacaagc ccaaggccac caaggagcag ctgaaggccg tgatggacga cttcgccgcc      1740
ttcgtggaga agtgctgcaa ggccgacgac aaggagacct gcttcgccga ggagggcaag      1800
aagctggtgg ccgccagcca ggccgccctg ggcctgggca gcggcggcgg cggcagcggc      1860
ggcggcggat ctggtggagg tggcagtgga ggaggggat ccctcgaggt cctctttcag       1920
ggaccacggt gccagaagtg gatgcagaca tgcgacgccg agcgcaagtg ctgcgaaggc      1980
ttcgtgtgtc gcctgtggtg taaaaagaag ttgtggtga                              2019
```

<210> SEQ ID NO 87
<211> LENGTH: 672
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Met Ala Trp Val Trp Thr Leu Leu Phe Leu Met Ala Ala Ala Gln Ser

-continued

```
1               5                   10                  15
Ile Gln Ala Gly Ser His His His His His Asp Ala His Lys Ser
                20                  25                  30
Glu Val Ala His Arg Phe Lys Asp Leu Gly Glu Glu Asn Phe Lys Ala
                35                  40                  45
Leu Val Leu Ile Ala Phe Ala Gln Tyr Leu Gln Gln Cys Pro Phe Glu
                50                  55                  60
Asp His Val Lys Leu Val Asn Glu Val Thr Glu Phe Ala Lys Thr Cys
65                  70                  75                  80
Val Ala Asp Glu Ser Ala Glu Asn Cys Asp Lys Ser Leu His Thr Leu
                85                  90                  95
Phe Gly Asp Lys Leu Cys Thr Val Ala Thr Leu Arg Glu Thr Tyr Gly
                100                 105                 110
Glu Met Ala Asp Cys Cys Ala Lys Gln Glu Pro Glu Arg Asn Glu Cys
                115                 120                 125
Phe Leu Gln His Lys Asp Asp Asn Pro Asn Leu Pro Arg Leu Val Arg
                130                 135                 140
Pro Glu Val Asp Val Met Cys Thr Ala Phe His Asp Asn Glu Glu Thr
145                 150                 155                 160
Phe Leu Lys Lys Tyr Leu Tyr Glu Ile Ala Arg Arg His Pro Tyr Phe
                165                 170                 175
Tyr Ala Pro Glu Leu Leu Phe Phe Ala Lys Arg Tyr Lys Ala Ala Phe
                180                 185                 190
Thr Glu Cys Cys Gln Ala Ala Asp Lys Ala Ala Cys Leu Leu Pro Lys
                195                 200                 205
Leu Asp Glu Leu Arg Asp Glu Gly Lys Ala Ser Ser Ala Lys Gln Arg
                210                 215                 220
Leu Lys Cys Ala Ser Leu Gln Lys Phe Gly Glu Arg Ala Phe Lys Ala
225                 230                 235                 240
Trp Ala Val Ala Arg Leu Ser Gln Arg Phe Pro Lys Ala Glu Phe Ala
                245                 250                 255
Glu Val Ser Lys Leu Val Thr Asp Leu Thr Lys Val His Thr Glu Cys
                260                 265                 270
Cys His Gly Asp Leu Leu Glu Cys Ala Asp Asp Arg Ala Asp Leu Ala
                275                 280                 285
Lys Tyr Ile Cys Glu Asn Gln Asp Ser Ile Ser Ser Lys Leu Lys Glu
                290                 295                 300
Cys Cys Glu Lys Pro Leu Leu Glu Lys Ser His Cys Ile Ala Glu Val
305                 310                 315                 320
Glu Asn Asp Glu Met Pro Ala Asp Leu Pro Ser Leu Ala Ala Asp Phe
                325                 330                 335
Val Glu Ser Lys Asp Val Cys Lys Asn Tyr Ala Glu Ala Lys Asp Val
                340                 345                 350
Phe Leu Gly Met Phe Leu Tyr Glu Tyr Ala Arg Arg His Pro Asp Tyr
                355                 360                 365
Ser Val Val Leu Leu Leu Arg Leu Ala Lys Thr Tyr Glu Thr Thr Leu
                370                 375                 380
Glu Lys Cys Cys Ala Ala Ala Asp Pro His Glu Cys Tyr Ala Lys Val
385                 390                 395                 400
Phe Asp Glu Phe Lys Pro Leu Val Glu Glu Pro Gln Asn Leu Ile Lys
                405                 410                 415
Gln Asn Cys Glu Leu Phe Glu Gln Leu Gly Glu Tyr Lys Phe Gln Asn
                420                 425                 430
```

```
Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
        450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Gly Ser Gly Gly Gly Gly Ser
    610                 615                 620

Gly Gly Gly Gly Ser Gly Gly Gly Ser Leu Glu Val Leu Phe Gln
625                 630                 635                 640

Gly Pro Ser Cys Gln Lys Trp Met Gln Thr Cys Asp Ala Glu Arg Lys
                645                 650                 655

Cys Cys Glu Gly Phe Val Cys Arg Leu Trp Cys Lys Lys Lys Leu Trp
            660                 665                 670

<210> SEQ ID NO 88
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgaca gagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct ccacgacaa cgaggagacc     480 ttcctgaaga agtacctgta cgagatcgcc cggcggcacc cctacttcta cgcccccgag     540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
```

```
gccaagcagc ggctgaagtg cgccagcctg cagaagttcg cgagcgggc cttcaaggcc      720
tgggccgtgg cccggctgag ccagcggttc cccaaggccg agttcgccga ggtgagcaag      780
ctggtgaccg acctgaccaa ggtgcacacc gagtgctgcc acggcgacct gctggagtgc      840
gccgacgacc gggccgacct ggccaagtac atctgcgaga accaggacag catcagcagc      900
aagctgaagg agtgctgcga aagcccctg ctggagaaga gccactgcat cgccgaggtg      960
gagaacgacg agatgcccgc cgacctgccc agcctggccg ccgacttcgt ggagagcaag     1020
gacgtgtgca agaactacgc cgaggccaag gacgtgttcc tgggcatgtt cctgtacgag     1080
tacgcccggc ggcaccccga ctacagcgtg gtgctgctgc tgcggctggc caagacctac     1140
gagaccaccc tggagaagtg ctgcgccgcc gccgaccccc acgagtgcta cgccaaggtg     1200
ttcgacgagt tcaagcccct ggtggaggag ccccagaacc tgatcaagca gaactgcgag     1260
ctgttcgagc agctgggcga gtacaagttc cagaacgccc tgctggtgcg gtacaccaag     1320
aaggtgcccc aggtgagcac cccaccctg gtggaggtga ccggaacct gggcaaggtg     1380
ggcagcaagt gctgcaagca ccccgaggcc aagcggatgc cctgcgccga ggactacctg     1440
agcgtggtgc tgaaccagct gtgcgtgctg cacgagaaga ccccgtgag cgaccgggtg     1500
accaagtgct gcaccgagag cctggtgaac cggcggcct gcttcagcgc cctggaggtg     1560
gacgagacct acgtgcccaa ggagttcaac gccgagacct tcaccttcca cgccgacatc     1620
tgcaccctga gcgagaagga gcggcagatc aagaagcaga ccgccctggt ggagctggtg     1680
aagcacaagc ccaaggccac caaggagcag ctgaaggccg tgatggacga cttcgccgcc     1740
ttcgtggaga gtgctgcaa ggccgacgac aaggagacct gcttcgccga ggagggcaag     1800
aagctggtgg ccgccagcca ggccgccctg ggcctgggca gcggcggcgg cggcagcggc     1860
ggcggcggat ctggtggagg tggcagtgga ggaggggat ccctcgaggt cctctttcag     1920
ggaccaagct gccagaagtg gatgcagaca tgcgacgccg agcgcaagtg ctgcgaaggc     1980
ttcgtgtgtc gcctgtggtg taaaaagaag ttgtggtga                            2019
```

<210> SEQ ID NO 89
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys

```
              115                 120                 125
Phe Leu Gln His Lys Asp Asp Asn Pro Asn Leu Pro Arg Leu Val Arg
    130                 135                 140
Pro Glu Val Asp Val Met Cys Thr Ala Phe His Asp Asn Glu Glu Thr
145                 150                 155                 160
Phe Leu Lys Lys Tyr Leu Tyr Glu Ile Ala Arg Arg His Pro Tyr Phe
                165                 170                 175
Tyr Ala Pro Glu Leu Leu Phe Phe Ala Lys Arg Tyr Lys Ala Ala Phe
                180                 185                 190
Thr Glu Cys Cys Gln Ala Ala Asp Lys Ala Ala Cys Leu Leu Pro Lys
                195                 200                 205
Leu Asp Glu Leu Arg Asp Glu Gly Lys Ala Ser Ser Ala Lys Gln Arg
    210                 215                 220
Leu Lys Cys Ala Ser Leu Gln Lys Phe Gly Glu Arg Ala Phe Lys Ala
225                 230                 235                 240
Trp Ala Val Ala Arg Leu Ser Gln Arg Phe Pro Lys Ala Glu Phe Ala
                245                 250                 255
Glu Val Ser Lys Leu Val Thr Asp Leu Thr Lys Val His Thr Glu Cys
                260                 265                 270
Cys His Gly Asp Leu Leu Glu Cys Ala Asp Asp Arg Ala Asp Leu Ala
                275                 280                 285
Lys Tyr Ile Cys Glu Asn Gln Asp Ser Ile Ser Ser Lys Leu Lys Glu
    290                 295                 300
Cys Cys Glu Lys Pro Leu Leu Glu Lys Ser His Cys Ile Ala Glu Val
305                 310                 315                 320
Glu Asn Asp Glu Met Pro Ala Asp Leu Pro Ser Leu Ala Ala Asp Phe
                325                 330                 335
Val Glu Ser Lys Asp Val Cys Lys Asn Tyr Ala Glu Ala Lys Asp Val
                340                 345                 350
Phe Leu Gly Met Phe Leu Tyr Glu Tyr Ala Arg Arg His Pro Asp Tyr
                355                 360                 365
Ser Val Val Leu Leu Leu Arg Leu Ala Lys Thr Tyr Glu Thr Thr Leu
    370                 375                 380
Glu Lys Cys Cys Ala Ala Ala Asp Pro His Glu Cys Tyr Ala Lys Val
385                 390                 395                 400
Phe Asp Glu Phe Lys Pro Leu Val Glu Glu Pro Gln Asn Leu Ile Lys
                405                 410                 415
Gln Asn Cys Glu Leu Phe Glu Gln Leu Gly Glu Tyr Lys Phe Gln Asn
                420                 425                 430
Ala Leu Leu Val Arg Tyr Thr Lys Lys Val Pro Gln Val Ser Thr Pro
                435                 440                 445
Thr Leu Val Glu Val Ser Arg Asn Leu Gly Lys Val Gly Ser Lys Cys
    450                 455                 460
Cys Lys His Pro Glu Ala Lys Arg Met Pro Cys Ala Glu Asp Tyr Leu
465                 470                 475                 480
Ser Val Val Leu Asn Gln Leu Cys Val Leu His Glu Lys Thr Pro Val
                485                 490                 495
Ser Asp Arg Val Thr Lys Cys Cys Thr Glu Ser Leu Val Asn Arg Arg
                500                 505                 510
Pro Cys Phe Ser Ala Leu Glu Val Asp Glu Thr Tyr Val Pro Lys Glu
                515                 520                 525
Phe Asn Ala Glu Thr Phe Thr Phe His Ala Asp Ile Cys Thr Leu Ser
                530                 535                 540
```

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Gly Ser
610                 615                 620

Gly Gly Gly Gly Ser Gly Gly Gly Ser Leu Glu Val Leu Phe Gln
625                 630                 635                 640

Gly Pro Ser Cys Gln Lys Trp Phe Trp Thr Cys Asp Ala Glu Arg Lys
                645                 650                 655

Cys Cys Glu Gly Phe Val Cys Arg Leu Trp Cys Lys Lys Lys Leu Trp
            660                 665                 670

<210> SEQ ID NO 90
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgaca gagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct ccacgacaa cgaggagacc     480 ttcctgaaga gtacctgta cgagatcgcc cggcggcacc cctacttcta cgcccccgag     540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggccg agttcgccga ggtgagcaag     780
ctggtgaccg acctgaccaa ggtgcacacc gagtgctgcc acggcgacct gctggagtgc     840
gccgacgacc gggccgacct ggccaagtac atctgcgaga accaggacag catcagcagc     900
aagctgaagg agtgctgcga aagcccctg ctggagaaga gccactgcat cgccgaggtg     960
gagaacgacg agatgcccgc cgacctgccc agcctggccg ccgacttcgt ggagagcaag    1020
gacgtgtgca agaactacgc cgaggccaag gacgtgttcc tgggcatgtt cctgtacgag    1080
tacgcccggc ggcacccga ctacagcgtg gtgctgctgc tgcggctggc caagacctac    1140
gagaccaccc tggagaagtg ctgcgccgcc gccgaccccc acgagtgcta cgccaaggtg    1200
ttcgacgagt tcaagcccct ggtggaggag ccccagaacc tgatcaagca gaactgcgag    1260
ctgttcgagc agctgggcga gtacaagttc cagaacgccc tgctggtgcg gtacaccaag    1320

```
aaggtgcccc aggtgagcac ccccaccctg gtggaggtga gccggaacct gggcaaggtg   1380
ggcagcaagt gctgcaagca ccccgaggcc aagcggatgc cctgcgccga ggactacctg   1440
agcgtggtgc tgaaccagct gtgcgtgctg cacgagaaga ccccgtgag cgaccgggtg    1500 accaagtgct gcaccgagag cctggtgaac cggcggccct gcttcagcgc cctggaggtg   1560
gacgagacct acgtgcccaa ggagttcaac gccgagacct tcaccttcca cgccgacatc   1620
tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga gtgctgcaa ggccgacgac aaggagacct gcttcgccga ggagggcaag    1800
aagctggtgg ccgccagcca ggccgccctg ggcctgggca gcggcggcgg cggcagcggc   1860
ggcggcggat ctggtggagg tggcagtgga ggaggggat ccctcgaggt cctctttcag    1920
ggaccaagct gccagaagtg gttctggaca tgcgacgccg agcgcaagtg ctgcgaaggc   1980
ttcgtgtgtc gcctgtggtg taaaaagaag ttgtggtga                          2019
```

<210> SEQ ID NO 91
<211> LENGTH: 672
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
```

-continued

```
             225                 230                 235                 240
Trp Ala Val Ala Arg Leu Ser Gln Arg Phe Pro Lys Ala Glu Phe Ala
                 245                 250                 255
Glu Val Ser Lys Leu Val Thr Asp Leu Thr Lys Val His Thr Glu Cys
                 260                 265                 270
Cys His Gly Asp Leu Leu Glu Cys Ala Asp Asp Arg Ala Asp Leu Ala
                 275                 280                 285
Lys Tyr Ile Cys Glu Asn Gln Asp Ser Ile Ser Ser Lys Leu Lys Glu
                 290                 295                 300
Cys Cys Glu Lys Pro Leu Leu Glu Lys Ser His Cys Ile Ala Glu Val
305                  310                 315                 320
Glu Asn Asp Glu Met Pro Ala Asp Leu Pro Ser Leu Ala Ala Asp Phe
                     325                 330                 335
Val Glu Ser Lys Asp Val Cys Lys Asn Tyr Ala Glu Ala Lys Asp Val
                 340                 345                 350
Phe Leu Gly Met Phe Leu Tyr Glu Tyr Ala Arg Arg His Pro Asp Tyr
                 355                 360                 365
Ser Val Val Leu Leu Leu Arg Leu Ala Lys Thr Tyr Glu Thr Thr Leu
                 370                 375                 380
Glu Lys Cys Cys Ala Ala Ala Asp Pro His Glu Cys Tyr Ala Lys Val
385                  390                 395                 400
Phe Asp Glu Phe Lys Pro Leu Val Glu Glu Pro Gln Asn Leu Ile Lys
                 405                 410                 415
Gln Asn Cys Glu Leu Phe Glu Gln Leu Gly Glu Tyr Lys Phe Gln Asn
                 420                 425                 430
Ala Leu Leu Val Arg Tyr Thr Lys Lys Val Pro Gln Val Ser Thr Pro
                 435                 440                 445
Thr Leu Val Glu Val Ser Arg Asn Leu Gly Lys Val Gly Ser Lys Cys
                 450                 455                 460
Cys Lys His Pro Glu Ala Lys Arg Met Pro Cys Ala Glu Asp Tyr Leu
465                  470                 475                 480
Ser Val Val Leu Asn Gln Leu Cys Val Leu His Glu Lys Thr Pro Val
                 485                 490                 495
Ser Asp Arg Val Thr Lys Cys Cys Thr Glu Ser Leu Val Asn Arg Arg
                 500                 505                 510
Pro Cys Phe Ser Ala Leu Glu Val Asp Glu Thr Tyr Val Pro Lys Glu
                 515                 520                 525
Phe Asn Ala Glu Thr Phe Thr Phe His Ala Asp Ile Cys Thr Leu Ser
                 530                 535                 540
Glu Lys Glu Arg Gln Ile Lys Lys Gln Thr Ala Leu Val Glu Leu Val
545                  550                 555                 560
Lys His Lys Pro Lys Ala Thr Lys Glu Gln Leu Lys Ala Val Met Asp
                 565                 570                 575
Asp Phe Ala Ala Phe Val Glu Lys Cys Cys Lys Ala Asp Asp Lys Glu
                 580                 585                 590
Thr Cys Phe Ala Glu Glu Gly Lys Lys Leu Val Ala Ala Ser Gln Ala
                 595                 600                 605
Ala Leu Gly Leu Gly Ser Gly Gly Gly Ser Gly Gly Gly Ser
                 610                 615                 620
Gly Gly Gly Gly Ser Gly Gly Gly Ser Leu Glu Val Leu Phe Gln
625                  630                 635                 640
Gly Pro Ser Cys Gln Lys Trp Phe Trp Thr Cys Asp Ala Glu Arg Lys
                 645                 650                 655
```

Cys Cys Glu Gly Leu Val Cys Arg Leu Trp Cys Lys Lys Lys Leu Trp
            660                 665                 670

<210> SEQ ID NO 92
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| | |
|---|---|
| atggcttggg tgtggacctt gctattcctg atggcggccg cccaaagtat acaggccggg | 60 |
| agccaccacc accaccacca cgacgcccac aagagcgagg tggcccaccg gttcaaggac | 120 |
| ctgggcgagg agaacttcaa ggccctggtg ctgatcgcct tcgcccagta cctgcagcag | 180 |
| tgccccttcg aggaccacgt gaagctggtg aacgaggtga ccgagttcgc caagacctgc | 240 |
| gtggccgacg agagcgccga gaactgcgac aagagcctgc acaccctgtt cggcgacaag | 300 |
| ctgtgcaccg tggccaccct gcgggagacc tacgcgaga tggccgactg ctgcgccaag | 360 |
| caggagcccg agcggaacga gtgcttcctg cagcacaagg acgacaaccc caacctgccc | 420 |
| cggctggtgc ggcccgaggt ggacgtgatg tgcaccgcct ccacgacaa cgaggagacc | 480 |
| ttcctgaaga gtacctgta cgagatcgcc cggcggcacc cctacttcta cgcccccgag | 540 |
| ctgctgttct tcgccaagcg gtacaaggcc gccttcaccg agtgctgcca ggccgccgac | 600 |
| aaggccgcct gcctgctgcc caagctggac gagctgcggg acgagggcaa ggccagcagc | 660 |
| gccaagcagc ggctgaagtg cgccagcctg cagaagttcg gcgagcgggc cttcaaggcc | 720 |
| tgggccgtgg cccggctgag ccagcggttc cccaaggccg agttcgccga ggtgagcaag | 780 |
| ctggtgaccg acctgaccaa ggtgcacacc gagtgctgcc acggcgacct gctggagtgc | 840 |
| gccgacgacc gggccgacct ggccaagtac atctgcgaga accaggacag catcagcagc | 900 |
| aagctgaagg agtgctgcga aagcccctg ctggagaaga gccactgcat cgccgaggtg | 960 |
| gagaacgacg agatgcccgc cgacctgccc agcctggccg ccgacttcgt ggagagcaag | 1020 |
| gacgtgtgca gaactacgc cgaggccaag gacgtgttcc tgggcatgtt cctgtacgag | 1080 |
| tacgcccggc ggcaccccga ctacagcgtg gtgctgctgc tgcggctggc caagacctac | 1140 |
| gagaccaccc tggagaagtg ctgcgccgcc gccgaccccc acgagtgcta cgccaaggtg | 1200 |
| ttcgacgagt tcaagcccct ggtggaggag ccccagaacc tgatcaagca gaactgcgag | 1260 |
| ctgttcgagc agctgggcga gtacaagttc cagaacgccc tgctggtgcg gtacaccaag | 1320 |
| aaggtgcccc aggtgagcac ccccacccctg gtggaggtga ccggaacct gggcaaggtg | 1380 |
| ggcagcaagt gctgcaagca cccgaggcc aagcggatgc cctgcgccga ggactacctg | 1440 |
| agcgtggtgc tgaaccagct gtgcgtgctg cacgagaaga cccccgtgag cgaccgggtg | 1500 |
| accaagtgct gcaccgagag cctggtgaac cggcggccct gcttcagcgc cctggaggtg | 1560 |
| gacgagacct acgtgcccaa ggagttcaac gccgagacct tcaccttcca cgccgacatc | 1620 |
| tgcaccctga cgagaagga gcggcagatc aagaagcaga ccgccctggt ggagctggtg | 1680 |
| aagcacaagc ccaaggccac caaggagcag ctgaaggccg tgatggacga cttcgccgcc | 1740 |
| ttcgtggaga gtgctgcaa ggccgacgac aaggagacct gcttcgccga ggagggcaag | 1800 |
| aagctggtgg ccgccagcca ggcgccctg gcctgggca cggcggcgg cggcagcggc | 1860 |
| ggcggcggat ctggtggagg tggcagtgga ggagggggat ccctcgaggt cctctttcag | 1920 |

```
ggaccaagct gccagaagtg gttctggacc tgcgacgccg agcggaagtg ctgcgagggc   1980
ctggtgtgcc ggctgtggtg caagaagaag ctgtggtga                          2019
```

<210> SEQ ID NO 93
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
```

Phe Leu Gly Met Phe Leu Tyr Glu Tyr Ala Arg Arg His Pro Asp Tyr
               340                 345                 350
        355                 360                 365

Ser Val Val Leu Leu Leu Arg Leu Ala Lys Thr Tyr Glu Thr Thr Leu
    370                 375                 380

Glu Lys Cys Cys Ala Ala Asp Pro His Glu Cys Tyr Ala Lys Val
385                 390                 395                 400

Phe Asp Glu Phe Lys Pro Leu Val Glu Pro Gln Asn Leu Ile Lys
                405                 410                 415

Gln Asn Cys Glu Leu Phe Glu Gln Leu Gly Glu Tyr Lys Phe Gln Asn
                420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Gly Ser Gly Gly Gly Ser
    610                 615                 620

Gly Gly Gly Gly Ser Gly Gly Gly Ser Leu Glu Val Leu Phe Gln
625                 630                 635                 640

Gly Pro Arg Cys Gln Lys Trp Phe Gln Thr Cys Asp Ala Glu Arg Lys
                645                 650                 655

Cys Cys Glu Gly Phe Val Cys Arg Leu Trp Cys Lys Lys Lys Leu Trp
                660                 665                 670

<210> SEQ ID NO 94
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
atggcttggg tgtggaccttg ctattcctg atggcggccg cccaaagtat acaggccggg    60
agccaccacc accaccacca cgacgcccac aagagcgagg tggccaccg gttcaaggac   120 ctgggcgagg agaacttcaa ggccctggtg ctgatcgcct tcgcccagta cctgcagcag   180

```
tgccccttcg aggaccacgt gaagctggtg aacgaggtga ccgagttcgc caagacctgc    240
gtggccgacg agagcgccga gaactgcgac aagagcctgc acaccctgtt cggcgacaag    300
ctgtgcaccg tggccaccct gcgggagacc tacggcgaga tggccgactg ctgcgccaag    360
caggagcccg agcggaacga gtgcttcctg cagcacaagg acgacaaccc caacctgccc    420
cggctggtgc ggcccgaggt ggacgtgatg tgcaccgcct ccacgacaa cgaggagacc    480 ttcctgaaga gtacctgta cgagatcgcc cggcggcacc cctacttcta cgcccccgag    540
ctgctgttct cgccaagcg gtacaaggcc gccttcaccg agtgctgcca ggccgccgac    600
aaggccgcct gcctgctgcc caagctggac gagctgcggg acgagggcaa ggccagcagc    660
gccaagcagc ggctgaagtg cgccagcctg cagaagttcg gcgagcgggc cttcaaggcc    720
tgggccgtgg cccggctgag ccagcggttc cccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga aagcccctg ctggagaaga gccactgcat cgccgaggtg    960
gagaacgacg agatgcccgc cgacctgccc agcctggccg ccgacttcgt ggagagcaag   1020
gacgtgtgca agaactacgc cgaggccaag gacgtgttcc tgggcatgtt cctgtacgag   1080
tacgcccggc ggcacccga ctacagcgtg gtgctgctgc tgcggctggc caagacctac   1140
gagaccaccc tggagaagtg ctgcgccgcc gccgacccc acgagtgcta cgccaaggtg   1200
ttcgacgagt tcaagcccct ggtggaggag ccccagaacc tgatcaagca gaactgcgag   1260
ctgttcgagc agctgggcga gtacaagttc cagaacgccc tgctggtgcg gtacaccaag   1320
aaggtgcccc aggtgagcac ccccaccctg gtggaggtga gccggaacct gggcaaggtg   1380
ggcagcaagt gctgcaagca ccccgaggcc aagcggatgc cctgcgccga ggactacctg   1440
agcgtggtgc tgaaccagct gtgcgtgctg cacgagaaga ccccgtgag cgaccgggtg   1500 accaagtgct gcaccgagag cctggtgaac cggcggccct gcttcagcgc cctggaggtg   1560
gacgagacct acgtgcccaa ggagttcaac gccgagacct tcaccttcca cgccgacatc   1620
tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga gtgctgcaa ggccgacgac aaggagacct gcttcgccga ggagggcaag   1800
aagctggtgg ccgccagcca ggccgccctg ggcctgggca gcggcggcgg cggcagcggc   1860
ggcggcggat ctggtggagg tggcagtgga ggaggggat ccctcgaggt cctctttcag   1920
ggaccacggt gccagaagtg gttccagaca tgcgacgccg agcgcaagtg ctgcgaaggc   1980
ttcgtgtgtc gcctgtggtg taaaaagaag ttgtggtga                          2019
```

<210> SEQ ID NO 95
<211> LENGTH: 672
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

-continued

Glu Val Ala His Arg Phe Lys Asp Leu Gly Glu Asn Phe Lys Ala
      35                  40                  45

Leu Val Leu Ile Ala Phe Ala Gln Tyr Leu Gln Gln Cys Pro Phe Glu
 50                  55                  60

Asp His Val Lys Leu Val Asn Glu Val Thr Glu Phe Ala Lys Thr Cys
 65                  70                  75                  80

Val Ala Asp Glu Ser Ala Glu Asn Cys Asp Lys Ser Leu His Thr Leu
                 85                  90                  95

Phe Gly Asp Lys Leu Cys Thr Val Ala Thr Leu Arg Glu Thr Tyr Gly
             100                 105                 110

Glu Met Ala Asp Cys Cys Ala Lys Gln Glu Pro Glu Arg Asn Glu Cys
             115                 120                 125

Phe Leu Gln His Lys Asp Asp Asn Pro Asn Leu Pro Arg Leu Val Arg
130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
            195                 200                 205

Leu Asp Glu Leu Arg Asp Glu Gly Lys Ala Ser Ser Ala Lys Gln Arg
210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
            275                 280                 285

Lys Tyr Ile Cys Glu Asn Gln Asp Ser Ile Ser Ser Lys Leu Lys Glu
290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
            355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
435                 440                 445

Thr Leu Val Glu Val Ser Arg Asn Leu Gly Lys Val Gly Ser Lys Cys

```
                450             455             460
Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
            515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
        610                 615                 620

Gly Gly Gly Gly Ser Gly Gly Gly Ser Leu Glu Val Leu Phe Gln
625                 630                 635                 640

Gly Pro Gln Cys Gln Lys Trp Phe Gln Thr Cys Asp Ser Glu Arg Lys
                645                 650                 655

Cys Cys Glu Gly Met Val Cys Arg Leu Trp Cys Lys Lys Lys Leu Trp
                660                 665                 670

<210> SEQ ID NO 96
<211> LENGTH: 1959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gggagccacc accaccacca ccacgacgcc cacaagagcg aggtggccca ccggttcaag      60
gacctgggcg aggagaactt caaggccctg gtgctgatcg ccttcgccca gtacctgcag     120
cagtgcccct tcgaggacca cgtgaagctg gtgaacgagg tgaccgagtt cgccaagacc     180
tgcgtggccg acgagagcgc cgagaactgc gacaagagcc tgcacaccct gttcggcgac     240
aagctgtgca ccgtgccacc ctgcgggag acctacggcg agatggccga ctgctgcgcc     300
aagcaggagc ccgagcggaa cgagtgcttc ctgcagcaca ggacgacaa ccccaacctg     360 ccccggctgg tgcggcccga ggtggacgtg atgtgcaccg ccttccacga caacgaggag     420
accttcctga gaagtaccct gtacgagatc gcccggcggc accctactt ctacgccccc     480 gagctgctgt tcttcgccaa gcggtacaag gccgccttca ccgagtgctg ccaggccgcc     540
gacaaggccg cctgcctgct gcccaagctg gacgagctgc gggacgaggg caaggccagc     600
agcgccaagc agcggctgaa gtgcgccagc ctgcagaagt tcggcgagcg ggccttcaag     660
gcctgggccg tggccggct gagccagcgg ttccccaagg ccgagttcgc cgaggtgagc     720
aagctggtga ccgacctgac caaggtgcac accgagtgct gccacggcga cctgctggag     780
tgcgccgacg accgggccga cctggccaag tacatctgcg agaaccagga cagcatcagc     840
```

```
agcaagctga aggagtgctg cgagaagccc ctgctggaga agagccactg catcgccgag   900
gtggagaacg acgagatgcc cgccgacctg cccagcctgg ccgccgactt cgtggagagc   960
aaggacgtgt gcaagaacta cgccgaggcc aaggacgtgt cctgggcat gttcctgtac   1020
gagtacgccc ggcggcaccc cgactacagc gtggtgctgc tgctgcggct ggccaagacc   1080
tacgagacca ccctggagaa gtgctgcgcc gccgccgacc ccacgagtg ctacgccaag   1140
gtgttcgaca gttcaagcc cctggtggag gagccccaga acctgatcaa gcagaactgc   1200
gagctgttcg agcagctggg cgagtacaag ttccagaacg ccctgctggt gcggtacacc   1260
aagaaggtgc cccaggtgag caccccacc ctggtggagg tgagccggaa cctgggcaag   1320
gtgggcagca agtgctgcaa gcaccccgag gccaagcgga tgccctgcgc cgaggactac   1380
ctgagcgtgt gctgaaccca gctgtgcgtg ctgcacgaga agaccccgt gagcgaccgg   1440
gtgaccaagt gctgcaccga gagcctggtg aaccggcggc cctgcttcag cgccctggag   1500
gtggacgaga cctacgtgcc caaggagttc aacgccgaga ccttcacctt ccacgccgac   1560
atctgcaccc tgagcgagaa ggagcggcag atcaagaagc agaccgccct ggtggagctg   1620
gtgaagcaca agcccaaggc caccaaggag cagctgaagg ccgtgatgga cgacttcgcc   1680
gccttcgtgg agaagtgctg caaggccgac gacaaggaga cctgcttcgc cgaggagggc   1740
aagaagctgg tggccgccag ccaggccgcc ctgggcctgg cagcggcgg cggcggcagc   1800
ggcggcggcg gatctggtgg aggtggcagt ggaggagggg gatccctcga ggtcctcttt   1860
cagggaccac agtgccagaa gtggttccag acatgcgaca gcgagcgcaa gtgctgcgaa   1920
ggcatggtgt gtcgcctgtg gtgtaaaaag aagttgtgg                          1959
```

<210> SEQ ID NO 97
<211> LENGTH: 672
<212> TYPE: PRT
<213> ORGANISM: Artificial Sequence
<220> FEATURE:
<223> OTHER INFORMATION: Description of Artificial Sequence: Synthetic
      G

<400> SEQUENCE: 97

```
Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160
```

```
Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575
```

| | | | | | | | | | | |
|---|---|---|---|---|---|---|---|---|---|---|
|Asp|Phe|Ala|Ala|Phe|Val|Glu|Lys|Cys|Cys|Lys|Ala|Asp|Asp|Lys|Glu|
| | |580| | | | |585| | | | |590| | | |
|Thr|Cys|Phe|Ala|Glu|Glu|Gly|Lys|Lys|Leu|Val|Ala|Ala|Ser|Gln|Ala|
| | | |595| | | | |600| | | | |605| | |
|Ala|Leu|Gly|Leu|Gly|Ser|Gly|Gly|Gly|Ser|Gly|Gly|Gly|Gly|Ser|
| | |610| | | | |615| | | | |620| | | |
|Gly|Gly|Gly|Gly|Ser|Gly|Gly|Gly|Ser|Leu|Glu|Val|Leu|Phe|Gln|
|625| | | | |630| | | | |635| | | | |640|
|Gly|Pro|Ala|Cys|Gln|Lys|Trp|Phe|Gln|Thr|Cys|Asp|Ser|Glu|Arg|Lys|
| | | | |645| | | | |650| | | | |655| | |
|Cys|Cys|Glu|Gly|Leu|Val|Cys|Arg|Leu|Trp|Cys|Lys|Lys|Lys|Leu|Trp|
| | | |660| | | | |665| | | | |670| | |

<210> SEQ ID NO 98
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagaccctgc   240
gtggccgacg agagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct tccacgacaa cgaggagacc     480
ttcctgaaga agtacctgta cgagatcgcc cggcggcacc cctacttcta cgcccccgag     540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggcca gttcgccga ggtgagcaag      780
ctggtgaccg acctgaccaa ggtgcacacc gagtgctgcc acggcgacct gctggagtgc     840
gccgacgacc gggccgacct ggccaagtac atctgcgaga accaggacag catcagcagc     900
aagctgaagg agtgctgcga aagcccctg ctggagaaga gccactgcat cgccgaggtg      960
gagaacgacg agatgcccgc cgacctgccc agcctggccg ccgacttcgt ggagagcaag    1020
gacgtgtgca gaactacgc cgaggccaag gacgtgttcc tgggcatgtt cctgtacgag     1080
tacgcccggc ggcaccccga ctacagcgtg gtgctgctgc tgcggctggc caagacctac    1140
gagaccaccc tggagaagtg ctgcgccgcc gccgaccccc acgagtgcta cgccaaggtg    1200
ttcgacgagt tcaagcccct ggtggaggag ccccagaacc tgatcaagca gaactgcgag    1260
ctgttcgagc agctgggcga gtacaagttc cagaacgccc tgctggtgcg gtacaccaag    1320
aaggtgcccc aggtgagcac ccccacccctg gtggaggtga ccggaacct gggcaaggtg    1380
ggcagcaagt gctgcaagca ccccgaggcc aagcggatgc cctgcgccga ggactacctg    1440
agcgtggtgc tgaaccagct gtgcgtgctg cacgagaaga cccccgtgag cgaccgggtg    1500
```

```
accaagtgct gcaccgagag cctggtgaac cggcggccct gcttcagcgc cctggaggtg    1560
gacgagacct acgtgcccaa ggagttcaac gccgagacct tcaccttcca cgccgacatc    1620
tgcaccctga gcgagaagga gcggcagatc aagaagcaga ccgccctggt ggagctggtg    1680
aagcacaagc ccaaggccac caaggagcag ctgaaggccg tgatggacga cttcgccgcc    1740
ttcgtggaga agtgctgcaa ggccgacgac aaggagacct gcttcgccga ggagggcaag    1800
aagctggtgg ccgccagcca ggccgccctg gcctgggca cgcggcggcg cggcagcggc    1860
ggcggcggat ctggtggagg tggcagtgga ggagggggat ccctcgaggt cctctttcag    1920
ggaccagcct gccagaagtg gttccagacc tgcgacagcg agcggaagtg ctgcgagggc    1980
ctggtgtgcc ggctgtggtg caagaagaag ctgtggtga                          2019
```

<210> SEQ ID NO 99
<211> LENGTH: 672
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 99

```
Met Ala Trp Val Trp Thr Leu Leu Phe Leu Met Ala Ala Gln Ser
 1               5                  10                  15

Ile Gln Ala Gly Ser His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270
```

```
Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
    610                 615                 620

Gly Gly Gly Ser Gly Gly Gly Ser Leu Glu Val Leu Phe Gln
625                 630                 635                 640

Gly Pro Gln Cys Gln Lys Trp Phe Gln Thr Cys Asp Ser Glu Arg Lys
                645                 650                 655

Cys Cys Glu Gly Leu Val Cys Arg Leu Trp Cys Lys Lys Leu Trp
            660                 665                 670
```

<210> SEQ ID NO 100
<211> LENGTH: 2019

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

| | | | | | |
|---|---|---|---|---|---|
| atggcttggg | tgtggacctt | gctattcctg | atggcggccg | cccaaagtat | acaggccggg | 60 |
| agccaccacc | accaccacca | cgacgcccac | aagagcgagg | tggcccaccg | gttcaaggac | 120 |
| ctgggcgagg | agaacttcaa | ggccctggtg | ctgatcgcct | tcgcccagta | cctgcagcag | 180 |
| tgccccttcg | aggaccacgt | gaagctggtg | aacgaggtga | ccgagttcgc | caagacctgc | 240 |
| gtggccgacg | agagcgccga | gaactgcgac | aagagcctgc | acaccctgtt | cggcgacaag | 300 |
| ctgtgcaccg | tggccaccct | gcgggagacc | tacggcgaga | tggccgactg | ctgcgccaag | 360 |
| caggagcccg | agcggaacga | gtgcttcctg | cagcacaagg | acgacaaccc | caacctgccc | 420 |
| cggctggtgc | ggcccgaggt | ggacgtgatg | tgcaccgcct | tccacgacaa | cgaggagacc | 480 |
| ttcctgaaga | agtacctgta | cgagatcgcc | cggcggcacc | cctacttcta | cgcccccgag | 540 |
| ctgctgttct | tcgccaagcg | gtacaaggcc | gccttcaccg | agtgctgcca | ggccgccgac | 600 |
| aaggccgcct | gcctgctgcc | caagctggac | gagctgcggg | acgagggcaa | ggccagcagc | 660 |
| gccaagcagc | ggctgaagtg | cgccagcctg | cagaagttcg | gcgagcgggc | cttcaaggcc | 720 |
| tgggccgtgg | cccggctgag | ccagcggttc | cccaaggccg | agttcgccga | ggtgagcaag | 780 |
| ctggtgaccg | acctgaccaa | ggtgcacacc | gagtgctgcc | acggcgacct | gctggagtgc | 840 |
| gccgacgacc | gggccgacct | ggccaagtac | atctgcgaga | accaggacag | catcagcagc | 900 |
| aagctgaagg | agtgctgcga | gaagcccctg | ctggagaaga | gccactgcat | cgccgaggtg | 960 |
| gagaacgacg | agatgcccgc | cgacctgccc | agcctggccg | ccgacttcgt | ggagagcaag | 1020 |
| gacgtgtgca | agaactacgc | cgaggccaag | gacgtgttcc | tgggcatgtt | cctgtacgag | 1080 |
| tacgcccggc | ggcaccccga | ctacagcgtg | gtgctgctgc | tgcggctggc | caagacctac | 1140 |
| gagaccaccc | tggagaagtg | cctgcgccgc | cgacccccc | acgagtgcta | cgccaaggtg | 1200 |
| ttcgacgagt | tcaagcccct | ggtggaggag | ccccagaacc | tgatcaagca | gaactgcgag | 1260 |
| ctgttcgagc | agctgggcga | gtacaagttc | cagaacgccc | tgctggtgcg | gtacaccaag | 1320 |
| aaggtgcccc | aggtgagcac | ccccaccctg | gtggaggtga | ccggaacct | gggcaaggtg | 1380 |
| ggcagcaagt | gctgcaagca | ccccgaggcc | aagcggatgc | cctgcgccga | ggactacctg | 1440 |
| agcgtggtgc | tgaaccagct | gtgcgtgctg | cacgagaaga | cccccgtgag | cgaccgggtg | 1500 |
| accaagtgct | gcaccgagag | cctggtgaac | cggcggccct | gcttcagcgc | cctggaggtg | 1560 |
| gacgagacct | acgtgcccaa | ggagttcaac | gccgagacct | tcaccttcca | cgccgacatc | 1620 |
| tgcaccctga | gcgagaagga | gcggcagatc | aagaagcaga | ccgccctggt | ggagctggtg | 1680 |
| aagcacaagc | ccaaggccac | caaggagcag | ctgaaggccg | tgatggacga | cttcgccgcc | 1740 |
| ttcgtggaga | agtgctgcaa | ggccgacgac | aaggagacct | gcttcgccga | ggagggcaag | 1800 |
| aagctggtgg | ccgccagcca | ggccgccctg | ggcctgggca | gcggcggcgg | cggcagcggc | 1860 |
| ggcggcggat | ctggtggagg | tggcagtgga | ggaggggat | ccctcgaggt | cctctttcag | 1920 |
| ggaccacagt | gccagaagtg | gttccagacc | tgcgacagcg | agcggaagtg | ctgcgagggc | 1980 |
| ctggtgtgcc | ggctgtggtg | caagaagaag | ctgtggtga | | | 2019 |

<210> SEQ ID NO 101
<211> LENGTH: 672

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Ala Trp Val Trp Thr Leu Leu Phe Leu Met Ala Ala Ala Gln Ser
1               5                   10                  15

Ile Gln Ala Gly Ser His His His His His Asp Ala His Lys Ser
            20                  25                  30

Glu Val Ala His Arg Phe Lys Asp Leu Gly Glu Glu Asn Phe Lys Ala
            35                  40                  45

Leu Val Leu Ile Ala Phe Ala Gln Tyr Leu Gln Gln Cys Pro Phe Glu
        50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380
```

```
Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Tyr Lys Phe Gln Asn
            420                 425                 430

Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
            515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
    595                 600                 605

Ala Leu Gly Leu Gly Ser Gly Gly Gly Ser Gly Gly Gly Gly Ser
            610                 615                 620

Gly Gly Gly Gly Ser Gly Gly Gly Gly Ser Leu Glu Val Leu Phe Gln
625                 630                 635                 640

Gly Pro Ser Cys Gln Lys Trp Phe Gln Thr Cys Asp Ser Glu Arg Lys
                645                 650                 655

Cys Cys Glu Gly Leu Val Cys Arg Leu Trp Cys Lys Lys Lys Leu Trp
            660                 665                 670

<210> SEQ ID NO 102
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgacg agagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
```

```
cggctggtgc ggcccgaggt ggacgtgatg tgcaccgcct tccacgacaa cgaggagacc    480
ttcctgaaga agtacctgta cgagatcgcc cggcggcacc cctacttcta cgcccccgag    540
ctgctgttct tcgccaagcg gtacaaggcc gccttcaccg agtgctgcca ggccgccgac    600
aaggccgcct gctgctgcc caagctggac gagctgcggg acgagggcaa ggccagcagc    660
gccaagcagc ggctgaagtg cgccagcctg cagaagttcg gcgagcgggc cttcaaggcc    720
tgggccgtgg cccggctgag ccagcggttc cccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga aagcccctg ctggagaaga gccactgcat cgccgaggtg    960
gagaacgacg agatgcccgc cgacctgccc agcctggccg ccgacttcgt ggagagcaag    1020
gacgtgtgca agaactacgc cgaggccaag gacgtgttcc tgggcatgtt cctgtacgag    1080
tacgcccggc ggcaccccga ctacagcgtg gtgctgctgc tgcggctggc caagacctac    1140
gagaccaccc tggagaagtg ctgcgccgcc gccgaccccc acgagtgcta cgccaaggtg    1200
ttcgacgagt tcaagcccct ggtggaggag ccccagaacc tgatcaagca gaactgcgag    1260
ctgttcgagc agctgggcga gtacaagttc cagaacgccc tgctggtgcg gtacaccaag    1320
aaggtgcccc aggtgagcac ccccacccctg gtggaggtga ccggaaccct gggcaaggtg    1380
ggcagcaagt gctgcaagca ccccgaggcc aagcggatgc cctgcgccga ggactacctg    1440
agcgtggtgc tgaaccagct gtgcgtgctg cacgagaaga ccccgtgag cgaccgggtg    1500 accaagtgct gcaccgagag cctggtgaac cggcggccct gcttcagcgc cctggaggtg    1560
gacgagacct acgtgcccaa ggagttcaac gccgagacct tcaccttcca cgccgacatc    1620
tgcaccctga gcgagaagga cggcagatc aagaagcaga ccgccctggt ggagctggtg    1680
aagcacaagc ccaaggccac caaggagcag ctgaaggccg tgatggacga cttcgccgcc    1740
ttcgtggaga agtgctgcaa ggccgacgac aaggagacct gcttcgccga gggggcaag    1800 aagctggtgg ccgccagcca ggccgccctg ggcctgggca gcggcggcgg cggcagcggc    1860
ggcggcggat ctggtggagg tggcagtgga ggaggggat ccctcgaggt cctctttcag    1920
ggaccaagct gccagaagtg gttccagaca tgcgacagcg agcgcaagtg ctgcgaaggc    1980
ttagtgtgtc gcctgtggtg taaaaagaag ttgtggtga                          2019
```

<210> SEQ ID NO 103
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys

-continued

```
               65                  70                  75                  80
Val Ala Asp Glu Ser Ala Glu Asn Cys Asp Lys Ser Leu His Thr Leu
                    85                  90                  95

Phe Gly Asp Lys Leu Cys Thr Val Ala Thr Leu Arg Glu Thr Tyr Gly
                100                 105                 110

Glu Met Ala Asp Cys Cys Ala Lys Gln Glu Pro Glu Arg Asn Glu Cys
                115                 120                 125

Phe Leu Gln His Lys Asp Asp Asn Pro Asn Leu Pro Arg Leu Val Arg
            130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
                180                 185                 190

Thr Glu Cys Cys Gln Ala Ala Asp Lys Ala Ala Cys Leu Leu Pro Lys
            195                 200                 205

Leu Asp Glu Leu Arg Asp Glu Gly Lys Ala Ser Ser Ala Lys Gln Arg
210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
                260                 265                 270

Cys His Gly Asp Leu Leu Glu Cys Ala Asp Asp Arg Ala Asp Leu Ala
            275                 280                 285

Lys Tyr Ile Cys Glu Asn Gln Asp Ser Ile Ser Ser Lys Leu Lys Glu
            290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
                340                 345                 350

Phe Leu Gly Met Phe Leu Tyr Glu Tyr Ala Arg Arg His Pro Asp Tyr
            355                 360                 365

Ser Val Val Leu Leu Leu Arg Leu Ala Lys Thr Tyr Glu Thr Thr Leu
            370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
                420                 425                 430

Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495
```

| | | | | | | | | | | | |
|---|---|---|---|---|---|---|---|---|---|---|---|
|Ser|Asp|Arg|Val|Thr|Lys|Cys|Cys|Thr|Glu|Ser|Leu|Val|Asn|Arg|Arg|
| | | |500| | |505| | | |510| |

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Gly Ser
        610                 615                 620

Gly Gly Gly Ser Gly Gly Gly Ser Leu Glu Val Leu Phe Gln
625                 630                 635                 640

Gly Pro Gln Cys Gln Lys Trp Met Gln Thr Cys Asp Arg Glu Arg Lys
                645                 650                 655

Cys Cys Glu Gly Phe Val Cys Thr Leu Trp Cys Arg Lys Lys Leu Trp
                660                 665                 670

<210> SEQ ID NO 104
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgaca gagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct ccacgacaa cgaggagacc     480
ttcctgaaga gtacctgta cgagatcgcc cggcggcacc cctacttcta cgcccccgag     540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggccg agttcgccga ggtgagcaag     780
ctggtgaccg acctgaccaa ggtgcacacc gagtgctgcc acggcgacct gctggagtgc     840
gccgacgacc gggccgacct ggccaagtac atctgcgaga accaggacag catcagcagc     900
aagctgaagg agtgctgcga aagcccctg ctggagaaga gccactgcat cgccgaggtg     960
gagaacgacg agatgcccgc cgacctgccc agcctggccg ccgacttcgt ggagagcaag    1020
```

-continued

```
gacgtgtgca agaactacgc cgaggccaag gacgtgttcc tgggcatgtt cctgtacgag   1080
tacgcccggc ggcaccccga ctacagcgtg gtgctgctgc tgcggctggc caagacctac   1140
gagaccaccc tggagaagtg ctgcgccgcc gccgaccccc acgagtgcta cgccaaggtg   1200
ttcgacgagt tcaagcccct ggtggaggag ccccagaacc tgatcaagca gaactgcgag   1260
ctgttcgagc agctgggcga gtacaagttc agaacgccc tgctggtgcg gtacaccaag    1320
aaggtgcccc aggtgagcac ccccaccctg gtggaggtga ccggaacct gggcaaggtg    1380 ggcagcaagt gctgcaagca ccccgaggcc aagcggatgc cctgcgccga ggactacctg   1440
agcgtggtgc tgaaccagct gtgcgtgctg cacgagaaga ccccgtgag cgaccgggtg    1500 accaagtgct gcaccgagag cctggtgaac cggcggccct gcttcagcgc cctggaggtg   1560
gacgagacct acgtgcccaa ggagttcaac gccgagacct tcaccttcca cgccgacatc   1620
tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga agtgctgcaa ggccgacgac aaggagacct gcttcgccga ggagggcaag   1800
aagctggtgg ccgccagcca ggccgccctg ggcctgggca gcggcggcgg cggcagcggc   1860
ggcggcggat ctggtggagg tggcagtgga ggaggggat ccctcgaggt cctctttcag    1920
ggaccacagt gccagaagtg gatgcagacc tgcgaccggg agcggaagtg ctgcgagggc   1980
ttcgtgtgca ccctgtggtg ccggaagaag ctgtggtga                           2019
```

<210> SEQ ID NO 105
<211> LENGTH: 2016
<212> TYPE: PRT
<213> ORGANISM: Homo sapiens

<400> SEQUENCE: 105

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
```

```
            195                 200                 205
Phe Val Asp Leu Gly Asn Val Ser Ala Leu Arg Thr Phe Arg Val Leu
210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                    245                 250                 255

Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                    325                 330                 335

Glu Gly Tyr Arg Cys Leu Lys Ala Gly Glu Asn Pro Asp His Gly Tyr
                340                 345                 350

Thr Ser Phe Asp Ser Phe Ala Trp Ala Phe Leu Ala Leu Phe Arg Leu
            355                 360                 365

Met Thr Gln Asp Cys Trp Glu Arg Leu Tyr Gln Gln Thr Leu Arg Ser
370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                    405                 410                 415

Glu Glu Gln Asn Gln Ala Thr Ile Ala Glu Thr Glu Glu Lys Glu Lys
                420                 425                 430

Arg Phe Gln Glu Ala Met Glu Met Leu Lys Lys Glu His Glu Ala Leu
            435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                    485                 490                 495

Ser Asp Ser Glu Asp Gly Pro Arg Ala Met Asn His Leu Ser Leu Thr
                500                 505                 510

Arg Gly Leu Ser Arg Thr Ser Met Lys Pro Arg Ser Ser Arg Gly Ser
            515                 520                 525

Ile Phe Thr Phe Arg Arg Arg Asp Leu Gly Ser Glu Ala Asp Phe Ala
530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                    565                 570                 575

Ser Pro Gly Thr Ser Ala Pro Gly His Ala Leu His Gly Lys Lys Asn
                580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
610                 615                 620
```

```
Glu His Pro Pro Asp Thr Thr Thr Pro Ser Glu Pro Gly Gly Pro
625                 630                 635                 640

Gln Met Leu Thr Ser Gln Ala Pro Cys Val Asp Gly Phe Glu Glu Pro
            645                 650                 655

Gly Ala Arg Gln Arg Ala Leu Ser Ala Val Ser Val Leu Thr Ser Ala
                660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
            725                 730                 735

Glu His Tyr Asn Met Thr Ser Glu Phe Glu Glu Met Leu Gln Val Gly
                740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
            805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
                900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
            995                 1000                1005

Tyr Ser Pro Pro Pro Pro Glu Thr Glu Lys Val Pro Pro Thr Arg
    1010                1015                1020

Lys Glu Thr Arg Phe Glu Glu Gly Glu Gln Pro Gly Gln Gly Thr
    1025                1030                1035
```

-continued

```
Pro Gly Asp Pro Glu Pro Val Cys Val Pro Ile Ala  Val Ala Glu
    1040                1045                1050

Ser Asp Thr Asp Asp Gln Glu Asp Glu Glu Asn  Ser Leu Gly
    1055                1060                1065

Thr Glu Glu Glu Ser Ser Lys Gln Gln Glu Ser  Gln Pro Val Ser
    1070                1075                1080

Gly Gly Pro Glu Ala Pro Pro Asp Ser Arg Thr  Trp Ser Gln Val
    1085                1090                1095

Ser Ala Thr Ala Ser Ser Glu Ala Glu Ala Ser  Ala Ser Gln Ala
    1100                1105                1110

Asp Trp Arg Gln Gln Trp Lys Ala Glu Pro Gln  Ala Pro Gly Cys
    1115                1120                1125

Gly Glu Thr Pro Glu Asp Ser Cys Ser Glu Gly  Ser Thr Ala Asp
    1130                1135                1140

Met Thr Asn Thr Ala Glu Leu Leu Glu Gln Ile  Pro Asp Leu Gly
    1145                1150                1155

Gln Asp Val Lys Asp Pro Glu Asp Cys Phe Thr  Glu Gly Cys Val
    1160                1165                1170

Arg Arg Cys Pro Cys Cys Ala Val Asp Thr Thr  Gln Ala Pro Gly
    1175                1180                1185

Lys Val Trp Trp Arg Leu Arg Lys Thr Cys Tyr  His Ile Val Glu
    1190                1195                1200

His Ser Trp Phe Glu Thr Phe Ile Ile Phe Met  Ile Leu Leu Ser
    1205                1210                1215

Ser Gly Ala Leu Ala Phe Glu Asp Ile Tyr Leu  Glu Glu Arg Lys
    1220                1225                1230

Thr Ile Lys Val Leu Leu Glu Tyr Ala Asp Lys  Met Phe Thr Tyr
    1235                1240                1245

Val Phe Val Leu Glu Met Leu Leu Lys Trp Val  Ala Tyr Gly Phe
    1250                1255                1260

Lys Lys Tyr Phe Thr Asn Ala Trp Cys Trp Leu  Asp Phe Leu Ile
    1265                1270                1275

Val Asp Val Ser Leu Val Ser Leu Val Ala Asn  Thr Leu Gly Phe
    1280                1285                1290

Ala Glu Met Gly Pro Ile Lys Ser Leu Arg Thr  Leu Arg Ala Leu
    1295                1300                1305

Arg Pro Leu Arg Ala Leu Ser Arg Phe Glu Gly  Met Arg Val Val
    1310                1315                1320

Val Asn Ala Leu Val Gly Ala Ile Pro Ser Ile  Met Asn Val Leu
    1325                1330                1335

Leu Val Cys Leu Ile Phe Trp Leu Ile Phe Ser  Ile Met Gly Val
    1340                1345                1350

Asn Leu Phe Ala Gly Lys Phe Gly Arg Cys Ile  Asn Gln Thr Glu
    1355                1360                1365

Gly Asp Leu Pro Leu Asn Tyr Thr Ile Val Asn  Asn Lys Ser Gln
    1370                1375                1380

Cys Glu Ser Leu Asn Leu Thr Gly Glu Leu Tyr  Trp Thr Lys Val
    1385                1390                1395

Lys Val Asn Phe Asp Asn Val Gly Ala Gly Tyr  Leu Ala Leu Leu
    1400                1405                1410

Gln Val Ala Thr Phe Lys Gly Trp Met Asp Ile  Met Tyr Ala Ala
    1415                1420                1425

Val Asp Ser Arg Gly Tyr Glu Glu Gln Pro Gln  Trp Glu Tyr Asn
```

-continued

```
            1430                1435                1440
Leu Tyr Met Tyr Ile Tyr Phe Val Ile Phe Ile Ile Phe Gly Ser
    1445                1450                1455
Phe Phe Thr Leu Asn Leu Phe Ile Gly Val Ile Ile Asp Asn Phe
    1460                1465                1470
Asn Gln Gln Lys Lys Lys Leu Gly Gly Gln Asp Ile Phe Met Thr
    1475                1480                1485
Glu Glu Gln Lys Lys Tyr Tyr Asn Ala Met Lys Lys Leu Gly Ser
    1490                1495                1500
Lys Lys Pro Gln Lys Pro Ile Pro Arg Pro Leu Asn Lys Tyr Gln
    1505                1510                1515
Gly Phe Ile Phe Asp Ile Val Thr Lys Gln Ala Phe Asp Val Thr
    1520                1525                1530
Ile Met Phe Leu Ile Cys Leu Asn Met Val Thr Met Met Val Glu
    1535                1540                1545
Thr Asp Asp Gln Ser Pro Glu Lys Ile Asn Ile Leu Ala Lys Ile
    1550                1555                1560
Asn Leu Leu Phe Val Ala Ile Phe Thr Gly Glu Cys Ile Val Lys
    1565                1570                1575
Leu Ala Ala Leu Arg His Tyr Tyr Phe Thr Asn Ser Trp Asn Ile
    1580                1585                1590
Phe Asp Phe Val Val Val Ile Leu Ser Ile Val Gly Thr Val Leu
    1595                1600                1605
Ser Asp Ile Ile Gln Lys Tyr Phe Phe Ser Pro Thr Leu Phe Arg
    1610                1615                1620
Val Ile Arg Leu Ala Arg Ile Gly Arg Ile Leu Arg Leu Ile Arg
    1625                1630                1635
Gly Ala Lys Gly Ile Arg Thr Leu Leu Phe Ala Leu Met Met Ser
    1640                1645                1650
Leu Pro Ala Leu Phe Asn Ile Gly Leu Leu Leu Phe Leu Val Met
    1655                1660                1665
Phe Ile Tyr Ser Ile Phe Gly Met Ala Asn Phe Ala Tyr Val Lys
    1670                1675                1680
Trp Glu Ala Gly Ile Asp Asp Met Phe Asn Phe Gln Thr Phe Ala
    1685                1690                1695
Asn Ser Met Leu Cys Leu Phe Gln Ile Thr Thr Ser Ala Gly Trp
    1700                1705                1710
Asp Gly Leu Leu Ser Pro Ile Leu Asn Thr Gly Pro Pro Tyr Cys
    1715                1720                1725
Asp Pro Thr Leu Pro Asn Ser Asn Gly Ser Arg Gly Asp Cys Gly
    1730                1735                1740
Ser Pro Ala Val Gly Ile Leu Phe Phe Thr Thr Tyr Ile Ile Ile
    1745                1750                1755
Ser Phe Leu Ile Val Val Asn Met Tyr Ile Ala Ile Ile Leu Glu
    1760                1765                1770
Asn Phe Ser Val Ala Thr Glu Glu Ser Thr Glu Pro Leu Ser Glu
    1775                1780                1785
Asp Asp Phe Asp Met Phe Tyr Glu Ile Trp Glu Lys Phe Asp Pro
    1790                1795                1800
Glu Ala Thr Gln Phe Ile Glu Tyr Ser Val Leu Ser Asp Phe Ala
    1805                1810                1815
Asp Ala Leu Ser Glu Pro Leu Arg Ile Ala Lys Pro Asn Gln Ile
    1820                1825                1830
```

Ser Leu Ile Asn Met Asp Leu Pro Met Val Ser Gly Asp Arg Ile
    1835                1840                1845

His Cys Met Asp Ile Leu Phe Ala Phe Thr Lys Arg Val Leu Gly
    1850                1855                1860

Glu Ser Gly Glu Met Asp Ala Leu Lys Ile Gln Met Glu Glu Lys
    1865                1870                1875

Phe Met Ala Ala Asn Pro Ser Lys Ile Ser Tyr Glu Pro Ile Thr
    1880                1885                1890

Thr Thr Leu Arg Arg Lys His Glu Val Ser Ala Met Val Ile
    1895                1900                1905

Gln Arg Ala Phe Arg Arg His Leu Leu Gln Arg Ser Leu Lys His
    1910                1915                1920

Ala Ser Phe Leu Phe Arg Gln Gln Ala Gly Ser Gly Leu Ser Glu
    1925                1930                1935

Glu Asp Ala Pro Glu Arg Glu Gly Leu Ile Ala Tyr Val Met Ser
    1940                1945                1950

Glu Asn Phe Ser Arg Pro Leu Gly Pro Pro Ser Ser Ser Ser Ile
    1955                1960                1965

Ser Ser Thr Ser Phe Pro Pro Ser Tyr Asp Ser Val Thr Arg Ala
    1970                1975                1980

Thr Ser Asp Asn Leu Gln Val Arg Gly Ser Asp Tyr Ser His Ser
    1985                1990                1995

Glu Asp Leu Ala Asp Phe Pro Pro Ser Pro Asp Arg Asp Arg Glu
    2000                2005                2010

Ser Ile Val
    2015

<210> SEQ ID NO 106
<211> LENGTH: 612
<212> TYPE: PRT
<213> ORGANISM: Homo sapiens

<400> SEQUENCE: 106

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe

-continued

```
                165                 170                 175
Tyr Ala Pro Glu Leu Leu Phe Phe Ala Lys Arg Tyr Lys Ala Ala Phe
            180                 185                 190
Thr Glu Cys Cys Gln Ala Ala Asp Lys Ala Ala Cys Leu Leu Pro Lys
        195                 200                 205
Leu Asp Glu Leu Arg Asp Glu Gly Lys Ala Ser Ser Ala Lys Gln Arg
    210                 215                 220
Leu Lys Cys Ala Ser Leu Gln Lys Phe Gly Glu Arg Ala Phe Lys Ala
225                 230                 235                 240
Trp Ala Val Ala Arg Leu Ser Gln Arg Phe Pro Lys Ala Glu Phe Ala
                245                 250                 255
Glu Val Ser Lys Leu Val Thr Asp Leu Thr Lys Val His Thr Glu Cys
            260                 265                 270
Cys His Gly Asp Leu Leu Glu Cys Ala Asp Asp Arg Ala Asp Leu Ala
        275                 280                 285
Lys Tyr Ile Cys Glu Asn Gln Asp Ser Ile Ser Ser Lys Leu Lys Glu
    290                 295                 300
Cys Cys Glu Lys Pro Leu Leu Glu Lys Ser His Cys Ile Ala Glu Val
305                 310                 315                 320
Glu Asn Asp Glu Met Pro Ala Asp Leu Pro Ser Leu Ala Ala Asp Phe
                325                 330                 335
Val Glu Ser Lys Asp Val Cys Lys Asn Tyr Ala Glu Ala Lys Asp Val
            340                 345                 350
Phe Leu Gly Met Phe Leu Tyr Glu Tyr Ala Arg Arg His Pro Asp Tyr
        355                 360                 365
Ser Val Val Leu Leu Leu Arg Leu Ala Lys Thr Tyr Glu Thr Thr Leu
    370                 375                 380
Glu Lys Cys Cys Ala Ala Ala Asp Pro His Glu Cys Tyr Ala Lys Val
385                 390                 395                 400
Phe Asp Glu Phe Lys Pro Leu Val Glu Glu Pro Gln Asn Leu Ile Lys
                405                 410                 415
Gln Asn Cys Glu Leu Phe Glu Gln Leu Gly Glu Tyr Lys Phe Gln Asn
            420                 425                 430
Ala Leu Leu Val Arg Tyr Thr Lys Lys Val Pro Gln Val Ser Thr Pro
        435                 440                 445
Thr Leu Val Glu Val Ser Arg Asn Leu Gly Lys Val Gly Ser Lys Cys
    450                 455                 460
Cys Lys His Pro Glu Ala Lys Arg Met Pro Cys Ala Glu Asp Tyr Leu
465                 470                 475                 480
Ser Val Val Leu Asn Gln Leu Cys Val Leu His Glu Lys Thr Pro Val
                485                 490                 495
Ser Asp Arg Val Thr Lys Cys Cys Thr Glu Ser Leu Val Asn Arg Arg
            500                 505                 510
Pro Cys Phe Ser Ala Leu Glu Val Asp Glu Thr Tyr Val Pro Lys Glu
        515                 520                 525
Phe Asn Ala Glu Thr Phe Thr Phe His Ala Asp Ile Cys Thr Leu Ser
    530                 535                 540
Glu Lys Glu Arg Gln Ile Lys Lys Gln Thr Ala Leu Val Glu Leu Val
545                 550                 555                 560
Lys His Lys Pro Lys Ala Thr Lys Glu Gln Leu Lys Ala Val Met Asp
                565                 570                 575
Asp Phe Ala Ala Phe Val Glu Lys Cys Cys Lys Ala Asp Asp Lys Glu
            580                 585                 590
```

```
Thr Cys Phe Ala Glu Glu Gly Lys Lys Leu Val Ala Ala Ser Gln Ala
        595                 600                 605

Ala Leu Gly Leu
    610
```

<210> SEQ ID NO 107
<211> LENGTH: 93
<212> TYPE: DNA
<213> ORGANISM: Tixopelma pruriens

<400> SEQUENCE: 107

```
tactgccaga agtggatgtg gacatgcgac agcgagcgca agtgctgcga aggcatggtg    60
tgtcgcctgt ggtgtaaaaa gaagttgtgg tga                                 93
```

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 108

```
His His His His His His
1               5
```

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Ser Cys Gln Lys Trp Met Gln Thr Cys Asp Ala Glu Arg Lys Cys Cys
1               5                   10                  15

Glu Gly Phe Val Cys Arg Leu Trp Cys Lys Lys Lys Leu Trp
            20                  25                  30
```

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Ser Cys Gln Lys Trp Met Gln Thr Cys Asp Ala Glu Arg Lys Cys Cys
1               5                   10                  15

Glu Gly Phe Val Cys Arg Leu Trp Cys Lys Lys Lys Leu Trp
            20                  25                  30
```

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Gly Pro Gln Cys Gln Lys Trp Met Gln Thr Cys Asp Ala Glu Arg Lys
```

```
                1               5                   10                  15
Cys Cys Glu Gly Phe Val Cys Arg Leu Trp Cys Lys Lys Lys Leu Trp
                20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gly Pro Ser Cys Gln Lys Trp Phe Trp Thr Cys Asp Ala Glu Arg Lys
1               5                   10                  15
Cys Cys Glu Gly Leu Val Cys Arg Leu Trp Cys Lys Lys Lys Leu Trp
                20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Pro Gln Cys Gln Lys Trp Met Gln Thr Cys Asp Ala Glu Arg Lys
1               5                   10                  15
Cys Cys Glu Gly Phe Ser Cys Thr Leu Trp Cys Lys Lys Lys Leu Trp
                20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Cys Gln Lys Trp Met Gln Thr Cys Asp Ala Glu Arg Lys Cys Cys
1               5                   10                  15
Glu Gly Phe Ser Cys Thr Leu Trp Cys Lys Lys Lys Leu Trp
                20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ala Cys Gln Cys Gln Lys Trp Met Gln Thr Cys Asp Ala Glu Arg Lys
1               5                   10                  15
Cys Cys Glu Gly Phe Ser Cys Thr Leu Trp Cys Lys Lys Lys Leu Trp
                20                  25                  30

<210> SEQ ID NO 116
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 116

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Cys Gln Lys Trp Met Gln Thr Cys Asp Arg Glu Arg Lys Cys Cys
1               5                   10                  15

Glu Gly Phe Val Cys Thr Leu Trp Cys Arg Lys Lys Leu Trp
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Cys Gln Lys Trp Met Gln Thr Cys Asp Arg Glu Arg Lys Cys Cys
1               5                   10                  15

Glu Gly Phe Val Cys Thr Leu Trp Cys Arg Lys Lys Leu Trp
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Pro Gln Cys Gln Lys Trp Met Gln Thr Cys Asp Arg Thr Arg Lys
1               5                   10                  15

Cys Cys Glu Gly Phe Val Cys Thr Leu Trp Cys Arg Lys Lys Leu Trp
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Pro Gln Cys Gln Lys Trp Met Gln Thr Cys Asp Arg Thr Arg Lys
1               5                   10                  15

Cys Cys Glu Gly Phe Val Cys Thr Leu Trp Cys Arg Lys Lys Leu Trp
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Pro Ser Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gly Pro Ser Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30
```

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Gly Pro Ser Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30
```

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Gly Pro Gln Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30
```

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Gly Pro Gln Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30
```

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Gly Pro Gln Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30
```

<210> SEQ ID NO 130
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 130

Gly Pro Gln Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Pro Gln Cys Gln Lys Trp Met Gln Thr Cys Asp Arg Glu Arg Lys
1               5                   10                  15

Cys Cys Glu Gly Phe Val Cys Arg Leu Trp Cys Lys Lys Lys Leu Trp
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Pro Gln Cys Gln Lys Trp Met Gln Thr Cys Asp Ala Asn Arg Lys
1               5                   10                  15

Cys Cys Glu Gly Phe Val Cys Arg Leu Trp Cys Lys Lys Lys Leu Trp
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Pro Gln Cys Gln Lys Trp Met Gln Thr Cys Asp Ala Arg Arg Lys
1               5                   10                  15

Cys Cys Glu Gly Phe Val Cys Arg Leu Trp Cys Lys Lys Lys Leu Trp
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Arg Lys Lys Leu Trp
            20                  25                  30
```

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gly Pro Gln Cys Gln Lys Trp Met Gln Thr Cys Asp Arg Asn Arg Lys
1               5                   10                  15

Cys Cys Glu Gly Phe Val Cys Arg Leu Trp Cys Lys Lys Lys Leu Trp
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gly Pro Gln Cys Gln Lys Trp Met Gln Thr Cys Asp Arg Arg Arg Lys
1               5                   10                  15

Cys Cys Glu Gly Phe Val Cys Arg Leu Trp Cys Lys Lys Lys Leu Trp
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Lys Lys Lys Leu Trp
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gly Pro Gln Cys Gln Lys Trp Met Gln Thr Cys Asp Arg Glu Arg Lys
1               5                   10                  15

Cys Cys Glu Gly Phe Val Cys Arg Leu Trp Cys Arg Lys Lys Leu Trp
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gly Pro Gln Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gly Pro Gln Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gly Pro Gln Cys Gln Lys Trp Met Gln Thr Cys Asp Ala Asn Arg Lys
1               5                   10                  15

Cys Cys Glu Gly Phe Val Cys Arg Leu Trp Cys Arg Lys Lys Leu Trp
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gly Pro Gln Cys Gln Lys Trp Met Gln Thr Cys Asp Ala Arg Arg Lys
1               5                   10                  15

Cys Cys Glu Gly Phe Val Cys Arg Leu Trp Cys Arg Lys Lys Leu Trp
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Pro Gln Cys Gln Lys Trp Met Gln Thr Cys Asp Ala Glu Arg Lys
1               5                   10                  15

Cys Cys Glu Gly Phe Val Cys Thr Leu Trp Cys Arg Lys Lys Leu Trp
            20                  25                  30

<210> SEQ ID NO 144
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 144

Gly Pro Gln Cys Gln Lys Trp Met Gln Thr Cys Asp Arg Asn Arg Lys
1               5                   10                  15

Cys Cys Glu Gly Phe Val Cys Thr Leu Trp Cys Lys Lys Lys Leu Trp
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gly Pro Gln Cys Gln Lys Trp Met Gln Thr Cys Asp Arg Arg Arg Lys
1               5                   10                  15

Cys Cys Glu Gly Phe Val Cys Thr Leu Trp Cys Lys Lys Lys Leu Trp
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gly Pro Gln Cys Gln Lys Trp Met Gln Thr Cys Asp Arg Asn Arg Lys
1               5                   10                  15

Cys Cys Glu Gly Phe Val Cys Arg Leu Trp Cys Arg Lys Lys Leu Trp
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gly Pro Gln Cys Gln Lys Trp Met Gln Thr Cys Asp Arg Arg Arg Lys
1               5                   10                  15

Cys Cys Glu Gly Phe Val Cys Arg Leu Trp Cys Arg Lys Lys Leu Trp
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gly Pro Gln Cys Gln Lys Trp Met Gln Thr Cys Asp Ala Asn Arg Lys
1               5                   10                  15

Cys Cys Glu Gly Phe Val Cys Thr Leu Trp Cys Arg Lys Lys Leu Trp
```

20                  25                  30

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gly Pro Gln Cys Gln Lys Trp Met Gln Thr Cys Asp Ala Arg Arg Lys
1               5                  10                  15

Cys Cys Glu Gly Phe Val Cys Thr Leu Trp Cys Arg Lys Lys Leu Trp
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gly Pro Gln Cys Gln Lys Trp Met Gln Thr Cys Asp Arg Asn Arg Lys
1               5                  10                  15

Cys Cys Glu Gly Phe Val Cys Thr Leu Trp Cys Arg Lys Lys Leu Trp
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gly Pro Gln Cys Gln Lys Trp Met Gln Thr Cys Asp Arg Arg Arg Lys
1               5                  10                  15

Cys Cys Glu Gly Phe Val Cys Thr Leu Trp Cys Arg Lys Lys Leu Trp
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gly Pro Gln Cys Gln Lys Trp Met Gln Thr Cys Asp Ala Lys Arg Lys
1               5                  10                  15

Cys Cys Glu Gly Phe Val Cys Arg Leu Trp Cys Lys Lys Lys Leu Trp
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Pro Gln Cys Gln Lys Trp Met Gln Thr Cys Asp Arg Lys Arg Lys
1               5                   10                  15

Cys Cys Glu Gly Phe Val Cys Arg Leu Trp Cys Lys Lys Lys Leu Trp
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Pro Gln Cys Gln Lys Trp Met Gln Thr Cys Asp Ala Lys Arg Lys
1               5                   10                  15

Cys Cys Glu Gly Phe Val Cys Thr Leu Trp Cys Lys Lys Lys Leu Trp
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Pro Gln Cys Gln Lys Trp Met Gln Thr Cys Asp Ala Lys Arg Lys
1               5                   10                  15

Cys Cys Glu Gly Phe Val Cys Arg Leu Trp Cys Arg Lys Lys Leu Trp
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gly Pro Gln Cys Gln Lys Trp Met Gln Thr Cys Asp Arg Lys Arg Lys
1               5                   10                  15

Cys Cys Glu Gly Phe Val Cys Thr Leu Trp Cys Lys Lys Lys Leu Trp
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gly Pro Gln Cys Gln Lys Trp Met Gln Thr Cys Asp Arg Lys Arg Lys
1               5                   10                  15

Cys Cys Glu Gly Phe Val Cys Arg Leu Trp Cys Arg Lys Lys Leu Trp
            20                  25                  30

<210> SEQ ID NO 158
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gly Pro Gln Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gly Pro Gln Cys Gln Lys Trp Met Gln Thr Cys Asp Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gly Pro Gln Cys Gln Lys Trp Met Trp Thr Cys Asp Ala Arg Arg Lys
1               5                   10                  15

Cys Cys Glu Gly Phe Val Cys Thr Leu Trp Cys Arg Lys Lys Leu Trp
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gly Pro Gln Cys Gln Lys Trp Met Trp Thr Cys Asp Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gly Pro Ala Ala Ala Ala Ala Gln Cys Gln Lys Trp Met Gln Thr Cys
1               5                   10                  15
```

Asp Ala Glu Arg Lys Cys Cys Glu Gly Phe Val Cys Arg Leu Trp Cys
            20                  25                  30

Lys Lys Lys Leu Trp
        35

<210> SEQ ID NO 163
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gly Pro Ala Pro Ala Pro Ala Gln Cys Gln Lys Trp Met Gln Thr Cys
1               5                   10                  15

Asp Ala Glu Arg Lys Cys Cys Glu Gly Phe Val Cys Arg Leu Trp Cys
            20                  25                  30

Lys Lys Lys Leu Trp
        35

<210> SEQ ID NO 164
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Ala Pro Ala Pro Ala
        35

<210> SEQ ID NO 165
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Gly Gly Gly Gly
        35

<210> SEQ ID NO 166
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro
            20              25              30

Gly Ser Gln Cys Gln Lys Trp Met Gln Thr Cys Asp Ala Glu Arg Lys
        35              40              45

Cys Cys Glu Gly Phe Val Cys Arg Leu Trp Cys Lys Lys Lys Leu Trp
50              55              60

<210> SEQ ID NO 167
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Ser Ala Pro Ala Pro Ala Pro Ala Pro Gly Ser Cys Cys
        35                  40                  45

Asn Cys Ser Ser Lys Trp Cys Arg Asp His Ser Arg Cys Cys
50                  55                  60

<210> SEQ ID NO 168
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Ser Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
50                  55                  60

Cys Arg Asp His Ser Arg Cys Cys Gly Arg
65                  70

<210> SEQ ID NO 169
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro
            20                  25                  30

Ala Pro Ala Pro Ala Pro Ala Pro Gly Ser Gln Cys Gln Lys
        35                  40                  45

Trp Met Gln Thr Cys Asp Ala Glu Arg Lys Cys Cys Glu Gly Phe Val
    50                  55                  60

Cys Arg Leu Trp Cys Lys Lys Lys Leu Trp
65                  70

<210> SEQ ID NO 170
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Ser Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
    50                  55                  60

Cys Arg Asp His Ser Arg Cys Cys
65                  70

<210> SEQ ID NO 171
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gly Pro Cys Cys Asn Cys Ser Ser Lys Trp Cys Arg Asp His Ser Arg
1               5                   10                  15

Cys Cys Gly Ser Ala Pro Ala Pro Ala Pro Ala Pro Ala Pro Ala Pro
            20                  25                  30

Ala Pro Ala Pro Ala Pro Ala Pro Gly Ser Gln Cys Gln Lys Trp Met
        35                  40                  45

Gln Thr Cys Asp Ala Glu Arg Lys Cys Cys Glu Gly Phe Val Cys Arg
    50                  55                  60

Leu Trp Cys Lys Lys Lys Leu Trp
65                  70

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gly Pro Gln Cys Arg Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 173
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 173

Gly Pro Gln Cys Lys Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Pro Gln Cys Thr Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gly Pro Gln Cys Ala Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Pro Gln Cys Glu Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Pro Gln Cys Ser Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
```

<210> SEQ ID NO 178
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Pro Gln Cys Gln Arg Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Pro Gln Cys Gln Thr Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Pro Gln Cys Gln Ala Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Pro Gln Cys Gln Asp Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Pro Gln Cys Gln Glu Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gly Pro Gln Cys Gln Gln Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Pro Gln Cys Gln Ser Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Pro Gln Cys Gln Lys Trp Met Gln Arg Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gly Pro Gln Cys Gln Lys Trp Met Gln Lys Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 187
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gly Pro Gln Cys Gln Lys Trp Met Gln Asp Cys Asp Arg Glu Arg Lys
1               5                  10                  15

Cys Cys Glu Gly Phe Val Cys Thr Leu Trp Cys Arg Lys Lys Leu Trp
            20                  25                  30

<210> SEQ ID NO 188
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Pro Gln Cys Gln Lys Trp Met Gln Glu Cys Asp Arg Glu Arg Lys
1               5                  10                  15

Cys Cys Glu Gly Phe Val Cys Thr Leu Trp Cys Arg Lys Lys Leu Trp
            20                  25                  30

<210> SEQ ID NO 189
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Pro Gln Cys Gln Lys Trp Met Gln Gln Cys Asp Arg Glu Arg Lys
1               5                  10                  15

Cys Cys Glu Gly Phe Val Cys Thr Leu Trp Cys Arg Lys Lys Leu Trp
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Pro Gln Cys Gln Lys Trp Met Gln Ser Cys Asp Arg Glu Arg Lys
1               5                  10                  15

Cys Cys Glu Gly Phe Val Cys Thr Leu Trp Cys Arg Lys Lys Leu Trp
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Pro Gln Cys Gln Lys Trp Met Gln Thr Cys Arg Arg Glu Arg Lys
1               5                  10                  15
```

Cys Cys Glu Gly Phe Val Cys Thr Leu Trp Cys Arg Lys Lys Leu Trp
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gly Pro Gln Cys Gln Lys Trp Met Gln Thr Cys Lys Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Pro Gln Cys Gln Lys Trp Met Gln Thr Cys Thr Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Pro Gln Cys Gln Lys Trp Met Gln Thr Cys Ala Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gly Pro Gln Cys Gln Lys Trp Met Gln Thr Cys Gln Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Pro Gln Cys Gln Lys Trp Met Gln Thr Cys Ser Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gly Pro Gln Cys Gln Lys Trp Met Gln Thr Cys Asp Arg Gln Arg Lys
1               5                   10                  15

Cys Cys Glu Gly Phe Val Cys Thr Leu Trp Cys Arg Lys Lys Leu Trp
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Pro Gln Cys Gln Lys Trp Met Gln Thr Cys Asp Arg Thr Arg Lys
1               5                   10                  15

Cys Cys Glu Gly Phe Val Cys Thr Leu Trp Cys Arg Lys Lys Leu Trp
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gly Pro Gln Cys Gln Lys Trp Met Gln Thr Cys Asp Arg Glu Lys Lys
1               5                   10                  15

Cys Cys Glu Gly Phe Val Cys Thr Leu Trp Cys Arg Lys Lys Leu Trp
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Pro Gln Cys Gln Lys Trp Met Gln Thr Cys Asp Arg Glu Thr Lys
1               5                   10                  15

Cys Cys Glu Gly Phe Val Cys Thr Leu Trp Cys Arg Lys Lys Leu Trp
            20                  25                  30

<210> SEQ ID NO 201

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Pro Gln Cys Gln Lys Trp Met Gln Thr Cys Asp Arg Glu Ala Lys
1               5                   10                  15

Cys Cys Glu Gly Phe Val Cys Thr Leu Trp Cys Arg Lys Lys Leu Trp
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Pro Gln Cys Gln Lys Trp Met Gln Thr Cys Asp Arg Glu Asp Lys
1               5                   10                  15

Cys Cys Glu Gly Phe Val Cys Thr Leu Trp Cys Arg Lys Lys Leu Trp
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Pro Gln Cys Gln Lys Trp Met Gln Thr Cys Asp Arg Glu Gln Lys
1               5                   10                  15

Cys Cys Glu Gly Phe Val Cys Thr Leu Trp Cys Arg Lys Lys Leu Trp
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Pro Gln Cys Gln Lys Trp Met Gln Thr Cys Asp Arg Glu Ser Lys
1               5                   10                  15

Cys Cys Glu Gly Phe Val Cys Thr Leu Trp Cys Arg Lys Lys Leu Trp
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Pro Gln Cys Gln Lys Trp Met Gln Thr Cys Asp Arg Glu Arg Arg
1               5                   10                  15
```

Cys Cys Glu Gly Phe Val Cys Thr Leu Trp Cys Arg Lys Lys Leu Trp
            20                  25                  30

<210> SEQ ID NO 206
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Pro Gln Cys Gln Lys Trp Met Gln Thr Cys Asp Arg Glu Arg Thr
1               5                   10                  15

Cys Cys Glu Gly Phe Val Cys Thr Leu Trp Cys Arg Lys Lys Leu Trp
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gly Pro Gln Cys Gln Lys Trp Met Gln Thr Cys Asp Arg Glu Arg Ala
1               5                   10                  15

Cys Cys Glu Gly Phe Val Cys Thr Leu Trp Cys Arg Lys Lys Leu Trp
            20                  25                  30

<210> SEQ ID NO 208
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Pro Gln Cys Gln Asp Trp Met Gln Thr Cys Asp Arg Glu Arg Asp
1               5                   10                  15

Cys Cys Glu Gly Phe Val Cys Thr Leu Trp Cys Arg Lys Lys Leu Trp
            20                  25                  30

<210> SEQ ID NO 209
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gly Pro Gln Cys Gln Glu Trp Met Gln Thr Cys Asp Arg Glu Arg Glu
1               5                   10                  15

Cys Cys Glu Gly Phe Val Cys Thr Leu Trp Cys Arg Lys Lys Leu Trp
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Gly Pro Gln Cys Gln Lys Trp Met Gln Thr Cys Asp Arg Glu Arg Gln
1               5                   10                  15

Cys Cys Glu Gly Phe Val Cys Thr Leu Trp Cys Arg Lys Lys Leu Trp
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gly Pro Gln Cys Gln Lys Trp Met Gln Thr Cys Asp Arg Glu Arg Ser
1               5                   10                  15

Cys Cys Glu Gly Phe Val Cys Thr Leu Trp Cys Arg Lys Lys Leu Trp
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gly Pro Gln Cys Gln Lys Trp Met Gln Thr Cys Asp Arg Glu Arg Lys
1               5                   10                  15

Cys Cys Arg Gly Phe Val Cys Thr Leu Trp Cys Arg Lys Lys Leu Trp
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Pro Gln Cys Gln Lys Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Pro Gln Cys Gln Lys Trp Met Gln Thr Cys Asp Arg Glu Arg Lys
1               5                   10                  15

Cys Cys Thr Gly Phe Val Cys Thr Leu Trp Cys Arg Lys Lys Leu Trp
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

Gly Pro Gln Cys Gln Lys Trp Met Gln Thr Cys Asp Arg Glu Arg Lys
1               5                   10                  15

Cys Cys Ala Gly Phe Val Cys Thr Leu Trp Cys Arg Lys Lys Leu Trp
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Gly Pro Gln Cys Gln Lys Trp Met Gln Thr Cys Asp Arg Glu Arg Lys
1               5                   10                  15

Cys Cys Asp Gly Phe Val Cys Thr Leu Trp Cys Arg Lys Lys Leu Trp
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

Gly Pro Gln Cys Gln Lys Trp Met Gln Thr Cys Asp Arg Glu Arg Lys
1               5                   10                  15

Cys Cys Gln Gly Phe Val Cys Thr Leu Trp Cys Arg Lys Lys Leu Trp
            20                  25                  30

<210> SEQ ID NO 218
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

Gly Pro Gln Cys Gln Lys Trp Met Gln Thr Cys Asp Arg Glu Arg Lys
1               5                   10                  15

Cys Cys Ser Gly Phe Val Cys Thr Leu Trp Cys Arg Lys Lys Leu Trp
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

Gly Pro Gln Cys Gln Lys Trp Met Gln Thr Cys Asp Arg Glu Arg Lys

```
1               5                   10                  15
Cys Cys Glu Arg Phe Val Cys Thr Leu Trp Cys Arg Lys Lys Leu Trp
                20                  25                  30

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gly Pro Gln Cys Gln Lys Trp Met Gln Thr Cys Asp Arg Glu Arg Lys
1               5                   10                  15

Cys Cys Glu Lys Phe Val Cys Thr Leu Trp Cys Arg Lys Lys Leu Trp
                20                  25                  30

<210> SEQ ID NO 221
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gly Pro Gln Cys Gln Lys Trp Met Gln Thr Cys Asp Arg Glu Arg Lys
1               5                   10                  15

Cys Cys Glu Thr Phe Val Cys Thr Leu Trp Cys Arg Lys Lys Leu Trp
                20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gly Pro Gln Cys Gln Lys Trp Met Gln Thr Cys Asp Arg Glu Arg Lys
1               5                   10                  15

Cys Cys Glu Ala Phe Val Cys Thr Leu Trp Cys Arg Lys Lys Leu Trp
                20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Pro Gln Cys Gln Lys Trp Met Gln Thr Cys Asp Arg Glu Arg Lys
1               5                   10                  15

Cys Cys Glu Asp Phe Val Cys Thr Leu Trp Cys Arg Lys Lys Leu Trp
                20                  25                  30

<210> SEQ ID NO 224
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 224

Gly Pro Gln Cys Gln Lys Trp Met Gln Thr Cys Asp Arg Glu Arg Lys
1               5                   10                  15

Cys Cys Glu Gln Phe Val Cys Thr Leu Trp Cys Arg Lys Lys Leu Trp
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gly Pro Gln Cys Gln Lys Trp Met Gln Thr Cys Asp Arg Glu Arg Lys
1               5                   10                  15

Cys Cys Glu Ser Phe Val Cys Thr Leu Trp Cys Arg Lys Lys Leu Trp
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gly Pro Gln Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gly Pro Gln Cys Gln Lys Trp Met Gln Thr Cys Asp Arg Glu Arg Lys
1               5                   10                  15

Cys Cys Glu Gly Phe Thr Cys Thr Leu Trp Cys Arg Lys Lys Leu Trp
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gly Pro Gln Cys Gln Lys Trp Met Gln Thr Cys Asp Arg Glu Arg Lys
1               5                   10                  15

Cys Cys Glu Gly Phe Gln Cys Thr Leu Trp Cys Arg Lys Lys Leu Trp
            20                  25                  30
```

<210> SEQ ID NO 229
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Arg Lys Leu Trp
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Ala Lys Leu Trp
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Arg Leu Trp
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Thr Leu Trp
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Ala Leu Trp
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Gln Leu Trp
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Ser Leu Trp
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Asp
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gly Pro Gln Cys Gln Lys Trp Met Gln Thr Cys Arg Arg Arg Arg Lys
1               5                   10                  15

Cys Cys Glu Gly Phe Val Cys Thr Leu Trp Cys Arg Lys Lys Leu Trp
            20                  25                  30

<210> SEQ ID NO 238
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 238

Gly Pro Gln Cys Gln Lys Trp Met Gln Thr Cys Lys Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gly Pro Gln Cys Gln Lys Trp Met Gln Thr Cys Arg Arg Arg Asp Lys
1               5                   10                  15

Cys Cys Glu Gly Phe Val Cys Thr Leu Trp Cys Arg Lys Lys Leu Trp
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gly Pro Gln Cys Gln Lys Trp Met Gln Thr Cys Lys Arg Lys Asp Lys
1               5                   10                  15

Cys Cys Glu Gly Phe Val Cys Thr Leu Trp Cys Arg Lys Lys Leu Trp
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gly Pro Gln Cys Gln Lys Trp Met Gln Thr Cys Arg Arg Arg Glu Lys
1               5                   10                  15

Cys Cys Glu Gly Phe Val Cys Thr Leu Trp Cys Arg Lys Lys Leu Trp
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gly Pro Gln Cys Gln Lys Trp Met Gln Thr Cys Lys Arg Lys Glu Lys
1               5                   10                  15

Cys Cys Glu Gly Phe Val Cys Thr Leu Trp Cys Arg Lys Lys Leu Trp
            20                  25                  30
```

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gly Pro Gln Cys Gln Asp Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gly Pro Gln Cys Gln Glu Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gly Pro Gln Cys Gln Glu Trp Met Gln Thr Cys Asp Arg Glu Arg Lys
1               5                   10                  15

Cys Cys Arg Gly Phe Val Cys Thr Leu Trp Cys Arg Lys Lys Leu Trp
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Gly
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Pro Gln Cys Gln Lys Phe Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gly Pro Gln Cys Gln Lys Trp Met Gln Thr Cys Asp Glu Glu Arg Lys
1               5                   10                  15

Cys Cys Glu Gly Phe Val Cys Thr Leu Trp Cys Arg Lys Lys Leu Trp
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gly Pro Gln Cys Gln Lys Trp Met Gln Thr Cys Asp Arg Glu Arg Lys
1               5                   10                  15

Cys Cys Gly Gly Phe Val Cys Thr Leu Trp Cys Arg Lys Lys Leu Trp
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gly Pro Gln Cys Gln Lys Trp Met Gln Thr Cys Asp Arg Glu Arg Lys
1               5                   10                  15

Cys Cys Glu Gly Leu Val Cys Thr Leu Trp Cys Arg Lys Lys Leu Trp
            20                  25                  30

<210> SEQ ID NO 251
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Ser Pro Gly Ala Arg Ala Phe
            35                  40

-continued

```
<210> SEQ ID NO 252
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ser Pro Gly Ala Arg Ala Phe
        35

<210> SEQ ID NO 253
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Asp Gly Pro Trp Arg Lys
        35                  40                  45

Met

<210> SEQ ID NO 254
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Asp Gly Pro Trp Arg Lys Met
        35                  40

<210> SEQ ID NO 255
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Asp Gly Pro Trp Arg Lys Met
```

<210> SEQ ID NO 256
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Phe Gly Gln Lys Ala Ser
        35                  40                  45

Ser

<210> SEQ ID NO 257
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Phe Gly Gln Lys Ala Ser Ser
        35                  40

<210> SEQ ID NO 258
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Phe Gly Gln Lys Ala Ser Ser
        35

<210> SEQ ID NO 259
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp

```
                 20                  25                  30

Ala Pro Ala Pro Ala Pro Ala Pro Ala Pro Gln Arg Phe Val Thr Gly
             35                  40                  45

His Phe Gly Gly Leu Tyr Pro Ala Asn Gly
             50                  55

<210> SEQ ID NO 260
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Gln Arg Phe Val Thr Gly His Phe Gly Gly Leu
        35                  40                  45

Tyr Pro Ala Asn Gly
    50

<210> SEQ ID NO 261
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gln Arg Phe Val Thr Gly His Phe Gly Gly Leu Tyr Pro Ala Asn Gly
        35                  40                  45

<210> SEQ ID NO 262
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Arg Arg Arg Arg Arg
        35                  40                  45

Arg Arg Arg Arg
    50

<210> SEQ ID NO 263
<211> LENGTH: 43
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 263

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Arg Arg Arg Arg Arg Arg Arg Arg Arg Arg
        35                  40

<210> SEQ ID NO 264
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Tyr Gly Arg Lys Lys Arg
        35                  40                  45

Arg Gln Arg Arg Arg
    50

<210> SEQ ID NO 265
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Tyr Gly Arg Lys Lys Arg Arg Gln Arg Arg Arg
        35                  40                  45

<210> SEQ ID NO 266
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Tyr Gly Arg Lys Lys Arg Arg Gln Arg Arg Arg
        35                  40
```

```
<210> SEQ ID NO 267
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro
        35                  40

<210> SEQ ID NO 268
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala
        35

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gly Pro Arg Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gly Pro Ser Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 271
<211> LENGTH: 32
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 271

Gly Pro Tyr Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 272
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 272

Gly Pro Ala Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 273
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 273

Gly Pro Gln Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 274
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 274

Gly Pro Arg Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 275
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 275

Gly Pro Ser Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 276
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Gly Pro Tyr Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 277
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Gly Pro Ala Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 278
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Gly Pro Arg Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 279
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Gly Pro Ser Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 280
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gly Pro Tyr Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 281
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gly Pro Ala Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 282
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gly Pro Gln Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gly Pro Arg Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 284
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gly Pro Ser Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 285
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 285

Gly Pro Tyr Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 286
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gly Pro Ala Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 287
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gly Pro Arg Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 288
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gly Pro Ser Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 289
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gly Pro Tyr Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30
```

```
<210> SEQ ID NO 290
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Gly Pro Ala Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30

<210> SEQ ID NO 291
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gly Pro Arg Cys Gln Lys Trp Met Gln Thr Cys Asp Arg Glu Arg Lys
1               5                   10                  15
Cys Cys Glu Gly Phe Ser Cys Thr Leu Trp Cys Arg Lys Lys Leu Trp
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gly Pro Ser Cys Gln Lys Trp Met Gln Thr Cys Asp Arg Glu Arg Lys
1               5                   10                  15
Cys Cys Glu Gly Phe Ser Cys Thr Leu Trp Cys Arg Lys Lys Leu Trp
            20                  25                  30

<210> SEQ ID NO 293
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gly Pro Tyr Cys Gln Lys Trp Met Gln Thr Cys Asp Arg Glu Arg Lys
1               5                   10                  15
Cys Cys Glu Gly Phe Ser Cys Thr Leu Trp Cys Arg Lys Lys Leu Trp
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294
```

Gly Pro Ala Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gly Pro Arg Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 296
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gly Pro Tyr Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 297
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gly Pro Arg Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 298
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gly Pro Ser Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 299
<211> LENGTH: 32
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 299

Gly Pro Tyr Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 300
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gly Pro Ala Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gly Pro Arg Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gly Pro Ser Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gly Pro Tyr Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp

```
                        20                  25                  30

<210> SEQ ID NO 304
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Gly Pro Ala Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Gly Pro Arg Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Gly Pro Ala Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Gly Pro Arg Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 308

Gly Pro Ser Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gly Pro Tyr Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 310
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Gly Pro Ala Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gly Pro Arg Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Gly Pro Ser Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 313
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Gly Pro Tyr Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gly Pro Ala Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 315
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gly Pro Arg Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Gly Pro Tyr Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Gly Pro Ala Cys Gln Lys Trp Met Gln Thr Cys Asp Ala Glu Arg Lys
1               5                   10                  15
```

```
Cys Cys Glu Gly Phe Ser Cys Arg Leu Trp Cys Lys Lys Lys Leu Trp
         20                  25                  30
```

<210> SEQ ID NO 318
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

```
Gly Pro Arg Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
         20                  25                  30
```

<210> SEQ ID NO 319
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

```
Gly Pro Ser Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
         20                  25                  30
```

<210> SEQ ID NO 320
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

```
Gly Pro Tyr Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
         20                  25                  30
```

<210> SEQ ID NO 321
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

```
Gly Pro Ala Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
         20                  25                  30
```

<210> SEQ ID NO 322
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Gly Pro Arg Cys Gln Lys Trp Met Gln Thr Cys Asp Ala Asn Arg Lys
1               5                   10                  15
Cys Cys Glu Gly Phe Ser Cys Arg Leu Trp Cys Lys Lys Lys Leu Trp
            20                  25                  30

<210> SEQ ID NO 323
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gly Pro Ser Cys Gln Lys Trp Met Gln Thr Cys Asp Ala Asn Arg Lys
1               5                   10                  15
Cys Cys Glu Gly Phe Ser Cys Arg Leu Trp Cys Lys Lys Lys Leu Trp
            20                  25                  30

<210> SEQ ID NO 324
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Gly Pro Tyr Cys Gln Lys Trp Met Gln Thr Cys Asp Ala Asn Arg Lys
1               5                   10                  15
Cys Cys Glu Gly Phe Ser Cys Arg Leu Trp Cys Lys Lys Lys Leu Trp
            20                  25                  30

<210> SEQ ID NO 325
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gly Pro Tyr Cys Gln Lys Trp Met Gln Thr Cys Asp Ala Asn Arg Lys
1               5                   10                  15
Cys Cys Glu Gly Phe Ser Cys Arg Leu Trp Cys Lys Lys Lys Leu Trp
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gly Pro Ala Cys Gln Lys Trp Met Gln Thr Cys Asp Ala Asn Arg Lys
1               5                   10                  15
Cys Cys Glu Gly Phe Ser Cys Arg Leu Trp Cys Lys Lys Lys Leu Trp
            20                  25                  30

<210> SEQ ID NO 327

```
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ser His Ser Asn Thr Gln Thr Leu Ala Lys Ala Pro Glu His Thr Gly
        35                  40                  45

<210> SEQ ID NO 328
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Gly Pro Ser His Ser Asn Thr Gln Thr Leu Ala Lys Ala Pro Glu His
1               5                   10                  15

Thr Gly Ala Pro Ala Pro Ala Pro Ala Pro Ala Pro Ala Pro Ala Pro
            20                  25                  30

Ala Pro Ala Pro Ala Pro Gln Cys Gln Lys Trp Met Gln Thr Cys Asp
        35                  40                  45

Arg Glu Arg Lys Cys Cys Glu Gly Phe Val Cys Thr Leu Trp Cys Arg
    50                  55                  60

Lys Lys Leu Trp
65

<210> SEQ ID NO 329
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gly Pro Ser His Ser Asn Thr Gln Thr Leu Ala Lys Ala Pro Glu His
1               5                   10                  15

Thr Gly Ala Pro Ala Pro Ala Pro Ala Pro Ala Pro Gln Cys Gln Lys
            20                  25                  30

Trp Met Gln Thr Cys Asp Arg Glu Arg Lys Cys Cys Glu Gly Phe Val
        35                  40                  45

Cys Thr Leu Trp Cys Arg Lys Lys Leu Trp
    50                  55

<210> SEQ ID NO 330
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gly Pro Ser His Ser Asn Thr Gln Thr Leu Ala Lys Ala Pro Glu His
```

```
                1               5                  10                  15
Thr Gly Gln Cys Gln Lys Trp Met Gln Thr Cys Asp Arg Glu Arg Lys
                20                  25                  30
Cys Cys Glu Gly Phe Val Cys Thr Leu Trp Cys Arg Lys Lys Leu Trp
        35                  40                  45

<210> SEQ ID NO 331
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Ala Trp
                20                  25                  30

<210> SEQ ID NO 332
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Gly Pro Ala Ala Ala Ala Ala Gln Cys Gln Lys Trp Met Gln Thr Cys
1               5                   10                  15
Asp Arg Glu Arg Lys Cys Cys Glu Gly Phe Val Cys Thr Leu Trp Cys
                20                  25                  30
Arg Lys Lys Leu Trp
        35

<210> SEQ ID NO 333
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gly Pro Ala Pro Ala Pro Ala Gln Cys Gln Lys Trp Met Gln Thr Cys
1               5                   10                  15
Asp Arg Glu Arg Lys Cys Cys Glu Gly Phe Val Cys Thr Leu Trp Cys
                20                  25                  30
Arg Lys Lys Leu Trp
        35

<210> SEQ ID NO 334
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gly Pro Gln Cys Gln Lys Trp Met Gln Thr Cys Asp Arg Glu Arg Lys
1               5                   10                  15
```

```
Cys Cys Glu Gly Phe Val Cys Thr Leu Trp Cys Arg Lys Lys Leu Trp
            20                  25                  30

Ala Ala Ala Ala Ala
        35

<210> SEQ ID NO 335
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Gly Gly Gly Gly
        35

<210> SEQ ID NO 336
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro Ala Pro
            20                  25                  30

Ala Pro Ala Pro Ala Pro Ala Pro Ala Pro Gly Ser Gln Cys Gln Lys
        35                  40                  45

Trp Met Gln Thr Cys Asp Arg Glu Arg Lys Cys Cys Glu Gly Phe Val
    50                  55                  60

Cys Thr Leu Trp Cys Arg Lys Lys Leu Trp
65                  70

<210> SEQ ID NO 337
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gly Pro Cys Cys Asn Cys Ser Ser Lys Trp Cys Arg Asp His Ser Arg
1               5                   10                  15

Cys Cys Gly Ser Ala Pro Ala Pro Ala Pro Ala Pro Ala Pro Ala Pro
            20                  25                  30

Ala Pro Ala Pro Ala Pro Gly Ser Gln Cys Gln Lys Trp Met
        35                  40                  45

Gln Thr Cys Asp Arg Glu Arg Lys Cys Cys Glu Gly Phe Val Cys Thr
    50                  55                  60

Leu Trp Cys Arg Lys Lys Leu Trp
65                  70
```

```
<210> SEQ ID NO 338
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gly Pro Cys Cys Asn Cys Ser Ser Lys Trp Cys Arg Asp His Ser Arg
1               5                   10                  15

Cys Cys Gly Ser Ala Pro Ala Pro Ala Pro Ala Pro Ala Pro Gly Ser
            20                  25                  30

Gln Cys Gln Lys Trp Met Gln Thr Cys Asp Arg Glu Arg Lys Cys Cys
        35                  40                  45

Glu Gly Phe Val Cys Thr Leu Trp Cys Arg Lys Lys Leu Trp
    50                  55                  60

<210> SEQ ID NO 339
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
    50                  55                  60

Cys Arg Asp His Ser Arg Cys Cys
65                  70

<210> SEQ ID NO 340
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
    50                  55                  60

Cys Arg Asp His Ser Arg Cys Cys Gly Arg
65                  70

<210> SEQ ID NO 341
<211> LENGTH: 62
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 341

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Gly Ser Cys Cys
        35                  40                  45

Asn Cys Ser Ser Lys Trp Cys Arg Asp His Ser Arg Cys Cys
    50                  55                  60

<210> SEQ ID NO 342
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Gly Ser Cys Cys
        35                  40                  45

Asn Cys Ser Ser Lys Trp Cys Arg Asp His Ser Arg Cys Cys Gly Arg
    50                  55                  60

<210> SEQ ID NO 343
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Gly Pro Ser Pro Gly Ala Arg Ala Phe Ala Pro Ala Pro Ala Pro Ala
1               5                   10                  15

Pro Ala Pro Gln Cys Gln Lys Trp Met Gln Thr Cys Asp Arg Glu Arg
            20                  25                  30

Lys Cys Cys Glu Gly Phe Val Cys Thr Leu Trp Cys Arg Lys Lys Leu
        35                  40                  45

Trp

<210> SEQ ID NO 344
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Gly Pro Ser Pro Gly Ala Arg Ala Phe Ala Pro Ala Pro Ala Gln Cys
1               5                   10                  15

Gln Lys Trp Met Gln Thr Cys Asp Arg Glu Arg Lys Cys Cys Glu Gly
            20                  25                  30
```

```
Phe Val Cys Thr Leu Trp Cys Arg Lys Lys Leu Trp
        35                  40
```

<210> SEQ ID NO 345
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

```
Gly Pro Ser Pro Gly Ala Arg Ala Phe Gln Cys Gln Lys Trp Met Gln
1               5                   10                  15

Thr Cys Asp Arg Glu Arg Lys Cys Cys Glu Gly Phe Val Cys Thr Leu
            20                  25                  30

Trp Cys Arg Lys Lys Leu Trp
        35
```

<210> SEQ ID NO 346
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

```
Gly Pro Asp Gly Pro Trp Arg Lys Met Ala Pro Ala Pro Ala Pro Ala
1               5                   10                  15

Pro Ala Pro Gln Cys Gln Lys Trp Met Gln Thr Cys Asp Arg Glu Arg
            20                  25                  30

Lys Cys Cys Glu Gly Phe Val Cys Thr Leu Trp Cys Arg Lys Lys Leu
        35                  40                  45

Trp
```

<210> SEQ ID NO 347
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

```
Gly Pro Asp Gly Pro Trp Arg Lys Met Ala Pro Ala Pro Ala Gln Cys
1               5                   10                  15

Gln Lys Trp Met Gln Thr Cys Asp Arg Glu Arg Lys Cys Cys Glu Gly
            20                  25                  30

Phe Val Cys Thr Leu Trp Cys Arg Lys Lys Leu Trp
        35                  40
```

<210> SEQ ID NO 348
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

```
Gly Pro Asp Gly Pro Trp Arg Lys Met Gln Cys Gln Lys Trp Met Gln
1               5                   10                  15
```

```
Thr Cys Asp Arg Glu Arg Lys Cys Cys Glu Gly Phe Val Cys Thr Leu
            20                  25                  30

Trp Cys Arg Lys Lys Leu Trp
        35
```

<210> SEQ ID NO 349
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

```
Gly Pro Phe Gly Gln Lys Ala Ser Ser Ala Pro Ala Pro Ala Gln Cys
1               5                   10                  15

Gln Lys Trp Met Gln Thr Cys Asp Arg Glu Arg Lys Cys Cys Glu Gly
            20                  25                  30

Phe Val Cys Thr Leu Trp Cys Arg Lys Lys Leu Trp
        35                  40
```

<210> SEQ ID NO 350
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

```
Gly Pro Phe Gly Gln Lys Ala Ser Ser Gln Cys Gln Lys Trp Met Gln
1               5                   10                  15

Thr Cys Asp Arg Glu Arg Lys Cys Cys Glu Gly Phe Val Cys Thr Leu
            20                  25                  30

Trp Cys Arg Lys Lys Leu Trp
        35
```

<210> SEQ ID NO 351
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

```
Gly Pro Gln Arg Phe Val Thr Gly His Phe Gly Gly Leu Tyr Pro Ala
1               5                   10                  15

Asn Gly Ala Pro Ala Pro Ala Pro Ala Pro Gln Cys Gln Lys
            20                  25                  30

Trp Met Gln Thr Cys Asp Arg Glu Arg Lys Cys Cys Glu Gly Phe Val
        35                  40                  45

Cys Thr Leu Trp Cys Arg Lys Lys Leu Trp
    50                  55
```

<210> SEQ ID NO 352
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Gly Pro Gln Arg Phe Val Thr Gly His Phe Gly Gly Leu Tyr Pro Ala
1               5                   10                  15

Asn Gly Ala Pro Ala Pro Ala Gln Cys Gln Lys Trp Met Gln Thr Cys
            20                  25                  30

Asp Arg Glu Arg Lys Cys Cys Glu Gly Phe Val Cys Thr Leu Trp Cys
        35                  40                  45

Arg Lys Lys Leu Trp
    50

<210> SEQ ID NO 353
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Gly Pro Gln Arg Phe Val Thr Gly His Phe Gly Gly Leu Tyr Pro Ala
1               5                   10                  15

Asn Gly Gln Cys Gln Lys Trp Met Gln Thr Cys Asp Arg Glu Arg Lys
            20                  25                  30

Cys Cys Glu Gly Phe Val Cys Thr Leu Trp Cys Arg Lys Lys Leu Trp
        35                  40                  45

<210> SEQ ID NO 354
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gly Pro Arg Arg Arg Arg Arg Arg Arg Arg Arg Arg Arg Ala Pro Ala
1               5                   10                  15

Pro Ala Pro Ala Pro Ala Pro Gln Cys Gln Lys Trp Met Gln Thr Cys
            20                  25                  30

Asp Arg Glu Arg Lys Cys Cys Glu Gly Phe Val Cys Thr Leu Trp Cys
        35                  40                  45

Arg Lys Lys Leu Trp
    50

<210> SEQ ID NO 355
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Gly Pro Arg Arg Arg Arg Arg Arg Arg Arg Arg Arg Arg Ala Pro Ala
1               5                   10                  15

Pro Ala Gln Cys Gln Lys Trp Met Gln Thr Cys Asp Arg Glu Arg Lys
            20                  25                  30

Cys Cys Glu Gly Phe Val Cys Thr Leu Trp Cys Arg Lys Lys Leu Trp
        35                  40                  45

<210> SEQ ID NO 356

<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gly Pro Arg Arg Arg Arg Arg Arg Arg Arg Arg Arg Gln Cys Gln
1               5                   10                  15

Lys Trp Met Gln Thr Cys Asp Arg Glu Arg Lys Cys Cys Glu Gly Phe
                20                  25                  30

Val Cys Thr Leu Trp Cys Arg Lys Lys Leu Trp
            35                  40

<210> SEQ ID NO 357
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Gly Pro Tyr Gly Arg Lys Lys Arg Arg Gln Arg Arg Arg Gln Cys Gln
1               5                   10                  15

Lys Trp Met Gln Thr Cys Asp Arg Glu Arg Lys Cys Cys Glu Gly Phe
                20                  25                  30

Val Cys Thr Leu Trp Cys Arg Lys Lys Leu Trp
            35                  40

<210> SEQ ID NO 358
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Gly Pro Ala Pro Ala Pro Ala Pro Ala Pro Ala Pro Gln Cys Gln Lys
1               5                   10                  15

Trp Met Gln Thr Cys Asp Arg Glu Arg Lys Cys Cys Glu Gly Phe Val
                20                  25                  30

Cys Thr Leu Trp Cys Arg Lys Lys Leu Trp
            35                  40

<210> SEQ ID NO 359
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ser Tyr Thr Lys Thr Cys Lys
                20                  25                  30

Asp Lys Ser Ser Ala Gly Gly Gly Ser Ala Pro Ala Pro Ala Pro
            35                  40                  45

Ala Pro Ala Pro Ala Pro Ala Pro Ala Pro Ala Pro Ala Pro Ala Pro

```
                50                  55                  60
Ala Pro Ala Pro Ala Pro Ala Pro Gly Gly Gly Ser Gln Cys Gln
 65                  70                  75                  80

Lys Trp Met Gln Thr Cys Asp Arg Glu Arg Lys Cys Cys Glu Gly Phe
                 85                  90                  95

Val Cys Thr Leu Trp Cys Arg Lys Lys Leu Trp
                100                 105

<210> SEQ ID NO 360
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Gly Pro Gln Cys Gln Lys Trp Met Gln Thr Cys Asp Arg Glu Arg Lys
 1               5                  10                  15

Cys Cys Glu Gly Phe Val Cys Thr Leu Trp Cys Arg Lys Lys Leu Trp
                20                  25                  30

Gly Gly Gly Gly Ser Ala Pro Ala Pro Ala Pro Ala Pro Ala Pro Ala
                35                  40                  45

Pro Ala Pro Ala Pro Ala Pro Ala Pro Ala Pro Ala Pro Ala Pro Ala
 50                  55                  60

Pro Ala Pro Gly Gly Gly Ser Gly Trp Cys Gly Asp Pro Gly Ala
 65                  70                  75                  80

Thr Cys Gly Lys Leu Arg Leu Tyr Cys Cys Ser Gly Phe Cys Asp Ser
                 85                  90                  95

Tyr Thr Lys Thr Cys Lys Asp Lys Ser Ser Ala
                100                 105

<210> SEQ ID NO 361
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Gly Pro Gly Trp Cys Gly Asp Pro Gly Ala Thr Cys Gly Lys Leu Arg
 1               5                  10                  15

Leu Tyr Cys Cys Ser Gly Phe Cys Asp Ala Tyr Thr Lys Thr Cys Lys
                20                  25                  30

Asp Lys Ser Ser Ala Gly Gly Gly Ser Ala Pro Ala Pro Ala Pro
                35                  40                  45

Ala Pro Ala Pro Ala Pro Ala Pro Ala Pro Ala Pro Ala Pro Ala Pro
 50                  55                  60

Ala Pro Ala Pro Ala Pro Gly Gly Gly Ser Gln Cys Gln
 65                  70                  75                  80

Lys Trp Met Gln Thr Cys Asp Arg Glu Arg Lys Cys Cys Glu Gly Phe
                 85                  90                  95

Val Cys Thr Leu Trp Cys Arg Lys Lys Leu Trp
                100                 105

<210> SEQ ID NO 362
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 362

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Gly Gly Gly Ser Ala Pro Ala Pro Ala Pro Ala Pro Ala
        35                  40                  45

Pro Ala Pro Ala Pro Ala Pro Ala Pro Ala Pro Ala Pro Ala Pro Ala
    50                  55                  60

Pro Ala Pro Gly Gly Gly Ser Gly Trp Cys Gly Asp Pro Gly Ala
65                  70                  75                  80

Thr Cys Gly Lys Leu Arg Leu Tyr Cys Cys Ser Gly Phe Cys Asp Ala
                85                  90                  95

Tyr Thr Lys Thr Cys Lys Asp Lys Ser Ser Ala
                100                 105

<210> SEQ ID NO 363
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Gly Pro Gly Trp Cys Gly Asp Pro Gly Ala Thr Cys Gly Lys Leu Arg
1               5                   10                  15

Leu Tyr Cys Cys Ser Gly Phe Cys Asp Cys Tyr Thr Lys Thr Cys Lys
            20                  25                  30

Asp Lys Ser Ser Ala Gly Gly Gly Ser Ala Pro Ala Pro Ala Pro
        35                  40                  45

Ala Pro Ala Pro Ala Pro Ala Pro Ala Pro Ala Pro Ala Pro Ala Pro
    50                  55                  60

Ala Pro Ala Pro Ala Pro Ala Pro Gly Gly Gly Ser Gln Cys Gln
65                  70                  75                  80

Lys Trp Met Gln Thr Cys Asp Arg Glu Arg Lys Cys Cys Glu Gly Phe
                85                  90                  95

Val Cys Thr Leu Trp Cys Arg Lys Lys Leu Trp
            100                 105

<210> SEQ ID NO 364
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Gly Gly Gly Ser Ala Pro Ala Pro Ala Pro Ala Pro Ala
        35                  40                  45

-continued

Pro Ala Pro Ala Pro Ala Pro Ala Pro Gly Gly Gly Ser
    50                  55                  60

Gly Ser Cys Cys Asn Cys Ser Ser Lys Trp Cys Arg Asp His Ser Arg
65                  70                  75                  80

Cys Cys Gly Arg

<210> SEQ ID NO 365
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Gly Gly Gly Ser Ala Pro Ala Pro Ala Pro Ala Pro Ala
        35                  40                  45

Pro Ala Pro Ala Pro Ala Pro Ala Pro Gly Gly Gly Ser
    50                  55                  60

Gly Ser Cys Cys Asn Cys Ser Ser Lys Trp Cys Arg Asp His Ser Arg
65                  70                  75                  80

Cys Cys

<210> SEQ ID NO 366
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Gly Pro Cys Cys Asn Cys Ser Ser Lys Trp Cys Arg Asp His Ser Arg
1               5                   10                  15

Cys Cys Gly Arg Gly Ser Gly Gly Gly Ser Ala Pro Ala Pro Ala
            20                  25                  30

Pro Ala Pro Ala Pro Ala Pro Ala Pro Ala Pro Ala Pro Gly
        35                  40                  45

Gly Gly Ser Gly Ser Gln Cys Gln Lys Trp Met Gln Thr Cys Asp
    50                  55                  60

Arg Glu Arg Lys Cys Cys Glu Gly Phe Val Cys Thr Leu Trp Cys Arg
65                  70                  75                  80

Lys Lys Leu Trp

<210> SEQ ID NO 367
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Gly Pro Cys Arg Thr Ile Gly Pro Ser Val Cys Ala Pro Ala Pro Ala
1               5                   10                  15

Pro Ala Pro Ala Pro Ala Pro Ala Pro Ala Pro Gln
         20                  25                  30

Cys Gln Lys Trp Met Gln Thr Cys Asp Arg Glu Arg Lys Cys Cys Glu
         35                  40                  45

Gly Phe Val Cys Thr Leu Trp Cys Arg Lys Lys Leu Trp
         50                  55                  60

<210> SEQ ID NO 368
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Gly Pro Cys Arg Thr Ile Gly Pro Ser Val Cys Ala Pro Ala Pro Ala
1               5                   10                  15

Pro Ala Pro Ala Pro Gln Cys Gln Lys Trp Met Gln Thr Cys Asp Arg
         20                  25                  30

Glu Arg Lys Cys Cys Glu Gly Phe Val Cys Thr Leu Trp Cys Arg Lys
         35                  40                  45

Lys Leu Trp
         50

<210> SEQ ID NO 369
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Gly Pro Cys Arg Thr Ile Gly Pro Ser Val Cys Ala Pro Ala Pro Ala
1               5                   10                  15

Gln Cys Gln Lys Trp Met Gln Thr Cys Asp Arg Glu Arg Lys Cys Cys
         20                  25                  30

Glu Gly Phe Val Cys Thr Leu Trp Cys Arg Lys Lys Leu Trp
         35                  40                  45

<210> SEQ ID NO 370
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Gly Pro Cys Arg Thr Ile Gly Pro Ser Val Cys Gln Cys Gln Lys Trp
1               5                   10                  15

Met Gln Thr Cys Asp Arg Glu Arg Lys Cys Cys Glu Gly Phe Val Cys
         20                  25                  30

Thr Leu Trp Cys Arg Lys Lys Leu Trp
         35                  40

<210> SEQ ID NO 371
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 371

```
Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30
Ala Pro Ala Pro Ala Cys Arg Thr Ile Gly Pro Ser Val Cys
        35                  40                  45
```

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

```
Gly Pro Ala Ala Ala Ala Ala
1               5
```

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

```
Gly Pro Ala Pro Ala Pro Ala
1               5
```

<210> SEQ ID NO 374
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

```
Gly Gly Gly Gly Gly
1               5
```

<210> SEQ ID NO 375
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

```
Gly Pro Cys Cys Asn Cys Ser Ser Lys Trp Cys Arg Asp His Ser Arg
1               5                   10                  15
Cys Cys
```

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 376

Gly Pro Ser Pro Gly Ala Arg Ala Phe
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Pro Asp Gly Pro Trp Arg Lys Met
1               5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gly Pro Phe Gly Gln Lys Ala Ser Ser
1               5

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Pro Cys Arg Thr Ile Gly Pro Ser Val Cys
1               5                   10

<210> SEQ ID NO 380
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Pro Ser His Ser Asn Thr Gln Thr Leu Ala Lys Ala Pro Glu His
1               5                   10                  15

Thr Gly

<210> SEQ ID NO 381
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gly Pro Gln Arg Phe Val Thr Gly His Phe Gly Gly Leu Tyr Pro Ala
1               5                   10                  15

Asn Gly
```

<210> SEQ ID NO 382
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ser Tyr Thr Lys Thr Cys Lys
            20                  25                  30

Asp Lys Ser Ser Ala
        35

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Pro Ala Pro Ala Pro Ala Pro Ala Pro
1               5                   10

<210> SEQ ID NO 384
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gly Pro Tyr Gly Arg Lys Lys Arg Arg Gln Arg Arg Arg
1               5                   10

<210> SEQ ID NO 385
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gly Pro Arg Arg Arg Arg Arg Arg Arg Arg Arg Arg Arg
1               5                   10

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Cys Arg Thr Ile Gly Pro Ser Val Cys
1               5

<210> SEQ ID NO 387

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Tyr Gly Arg Lys Lys Arg Arg Gln Arg Arg Arg
1               5                   10

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Asp Gly Pro Trp Arg Lys Met
1               5

<210> SEQ ID NO 389
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Cys Cys Asn Cys Ser Ser Lys Trp Cys Arg Asp His Ser Arg Cys Cys
1               5                   10                  15

<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Arg Arg Arg Arg Arg Arg Arg Arg Arg Arg
1               5                   10

<210> SEQ ID NO 391
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ser His Ser Asn Thr Gln Thr Leu Ala Lys Ala Pro Glu His Thr Gly
1               5                   10                  15

<210> SEQ ID NO 392
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392
```

```
Ala Pro Ala Pro Ala
1               5

<210> SEQ ID NO 393
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Ala Ala Ala Ala
1               5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Phe Gly Gln Lys Ala Ser Ser
1               5

<210> SEQ ID NO 395
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gln Arg Phe Val Thr Gly His Phe Gly Gly Leu Tyr Pro Ala Asn Gly
1               5                   10                  15

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ser Pro Gly Ala Arg Ala Phe
1               5

<210> SEQ ID NO 397
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ala Tyr Thr Lys Thr Cys Lys
                20                  25                  30

Asp Lys Ser Ser Ala
        35
```

<210> SEQ ID NO 398
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Ser Ala Pro Ala Pro Ala Pro Ala Pro Ala Pro Gly Ser
1               5                   10

<210> SEQ ID NO 399
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Ser Ala Pro Ala Pro Ala Pro Ala Pro Ala Pro Ala Pro Ala Pro
1               5                   10                  15

Ala Pro Ala Pro Ala Pro Gly Ser
            20

<210> SEQ ID NO 400
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gly Gly Gly Gly Ser Ala Pro Ala Pro Ala Pro Ala Pro Ala Pro Ala
1               5                   10                  15

Pro Ala Pro Ala Pro Ala Pro Ala Pro Ala Pro Ala Pro Ala Pro Ala
            20                  25                  30

Pro Ala Pro Gly Gly Gly Gly Ser
        35                  40

<210> SEQ ID NO 401
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gly Ser Gly Gly Gly Gly Ser Ala Pro Ala Pro Ala Pro Ala Pro Ala
1               5                   10                  15

Pro Ala Pro Ala Pro Ala Pro Ala Pro Ala Pro Gly Gly Gly Gly Ser
            20                  25                  30

Gly Ser

<210> SEQ ID NO 402
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 402

Ala Pro Ala Pro Ala Pro Ala Pro Ala Pro Ala Pro Ala Pro Ala Pro
1               5                   10                  15

Ala Pro Ala Pro
            20

<210> SEQ ID NO 403
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Pro, Ala or absent
<220> FEATURE:
<221> NAME/KEY: MOD_RES
<222> LOCATION: (2)..(2)
<223> OTHER INFORMATION: Pro, Ala or absent
<220> FEATURE:
<221> NAME/KEY: MOD_RES
<222> LOCATION: (3)..(3)
<223> OTHER INFORMATION: Ser, Gln, Ala, Arg or Tyr
<220> FEATURE:
<221> NAME/KEY: MOD_RES
<222> LOCATION: (5)..(5)
<223> OTHER INFORMATION: Gln, Arg, Lys, Ala or Ser
<220> FEATURE:
<221> NAME/KEY: MOD_RES
<222> LOCATION: (6)..(6)
<223> OTHER INFORMATION: Lys, Ser, Gln or Arg
<220> FEATURE:
<221> NAME/KEY: MOD_RES
<222> LOCATION: (8)..(8)
<223> OTHER INFORMATION: Met or Phe
<220> FEATURE:
<221> NAME/KEY: MOD_RES
<222> LOCATION: (10)..(10)
<223> OTHER INFORMATION: Thr, Ser, Arg, Lys or Gln
<220> FEATURE:
<221> NAME/KEY: MOD_RES
<222> LOCATION: (12)..(12)
<223> OTHER INFORMATION: Asp or Thr
<220> FEATURE:
<221> NAME/KEY: MOD_RES
<222> LOCATION: (13)..(13)
<223> OTHER INFORMATION: Ser, Ala or Arg
<220> FEATURE:
<221> NAME/KEY: MOD_RES
<222> LOCATION: (14)..(14)
<223> OTHER INFORMATION: Glu, Arg, Asn, Lys, Thr or Gln
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (16)..(16)
<223> OTHER INFORMATION: Lys, Gln, Ser or Ala
<220> FEATURE:
<221> NAME/KEY: MOD_RES
<222> LOCATION: (19)..(19)
<223> OTHER INFORMATION: Glu, Gln or Asp
<220> FEATURE:
<221> NAME/KEY: MOD_RES
<222> LOCATION: (20)..(20)
<223> OTHER INFORMATION: Gly or Gln
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
```

<223> OTHER INFORMATION: Arg or Thr
<220> FEATURE:
<221> NAME/KEY: MOD_RES
<222> LOCATION: (28)..(28)
<223> OTHER INFORMATION: Lys or Arg

<400> SEQUENCE: 403

Xaa Xaa Xaa Cys Xaa Xaa Trp Xaa Gln Xaa Cys Xaa Xaa Xaa Xaa
1               5                   10                  15

Cys Cys Xaa Xaa Phe Xaa Cys Xaa Leu Trp Cys Xaa Lys Lys Leu Trp
            20                  25                  30

<210> SEQ ID NO 404
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Gln, Arg, Lys, Ala or Ser
<220> FEATURE:
<221> NAME/KEY: MOD_RES
<222> LOCATION: (6)..(6)
<223> OTHER INFORMATION: Lys, Ser, Gln or Arg
<220> FEATURE:
<221> NAME/KEY: MOD_RES
<222> LOCATION: (8)..(8)
<223> OTHER INFORMATION: Met or Phe
<220> FEATURE:
<221> NAME/KEY: MOD_RES
<222> LOCATION: (10)..(10)
<223> OTHER INFORMATION: Thr, Ser, Arg, Lys or Gln
<220> FEATURE:
<221> NAME/KEY: MOD_RES
<222> LOCATION: (12)..(12)
<223> OTHER INFORMATION: Asp or Thr
<220> FEATURE:
<221> NAME/KEY: MOD_RES
<222> LOCATION: (13)..(13)
<223> OTHER INFORMATION: Ser, Ala or Arg
<220> FEATURE:
<221> NAME/KEY: MOD_RES
<222> LOCATION: (14)..(14)
<223> OTHER INFORMATION: Glu, Arg, Asn, Lys, Thr or Gln
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (16)..(16)
<223> OTHER INFORMATION: Lys, Gln, Ser or Ala
<220> FEATURE:
<221> NAME/KEY: MOD_RES
<222> LOCATION: (19)..(19)
<223> OTHER INFORMATION: Glu, Gln or Asp
<220> FEATURE:
<221> NAME/KEY: MOD_RES
<222> LOCATION: (20)..(20)
<223> OTHER INFORMATION: Gly or Gln
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
<223> OTHER INFORMATION: Arg or Thr
<220> FEATURE:
<221> NAME/KEY: MOD_RES
<222> LOCATION: (28)..(28)
<223> OTHER INFORMATION: Lys or Arg -continued

<400> SEQUENCE: 404

Gly Pro Gln Cys Xaa Xaa Trp Xaa Gln Xaa Cys Xaa Xaa Xaa Xaa
1               5                   10                  15

Cys Cys Xaa Xaa Phe Xaa Cys Xaa Leu Trp Cys Xaa Lys Lys Leu Trp
                20                  25                  30

<210> SEQ ID NO 405
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Tyr, Gln, Ala, Ser or Arg
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (13)..(13)
<223> OTHER INFORMATION: Ser, Arg or Ala
<220> FEATURE:
<221> NAME/KEY: MOD_RES
<222> LOCATION: (14)..(14)
<223> OTHER INFORMATION: Glu, Thr or Asn
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
<223> OTHER INFORMATION: Arg or Thr
<220> FEATURE:
<221> NAME/KEY: MOD_RES
<222> LOCATION: (28)..(28)
<223> OTHER INFORMATION: Lys or Arg

<400> SEQUENCE: 405

Gly Pro Xaa Cys Gln Lys Trp Met Gln Xaa Cys Asp Xaa Xaa Arg Lys
1               5                   10                  15

Cys Cys Xaa Gly Phe Xaa Cys Xaa Leu Trp Cys Xaa Lys Lys Leu Trp
                20                  25                  30

<210> SEQ ID NO 406
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (13)..(13)
<223> OTHER INFORMATION: Ser, Arg or Ala
<220> FEATURE:
<221> NAME/KEY: MOD_RES
<222> LOCATION: (14)..(14)
<223> OTHER INFORMATION: Glu, Thr or Asn
<220> FEATURE:
<221> NAME/KEY: MOD_RES

```
<222> LOCATION: (19)..(19)
<223> OTHER INFORMATION: Glu or Gln
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
<223> OTHER INFORMATION: Arg or Thr
<220> FEATURE:
<221> NAME/KEY: MOD_RES
<222> LOCATION: (28)..(28)
<223> OTHER INFORMATION: Lys or Arg

<400> SEQUENCE: 406

Gly Pro Gln Cys Gln Lys Trp Met Gln Xaa Cys Asp Xaa Xaa Arg Lys
1               5                   10                  15

Cys Cys Xaa Gly Phe Xaa Cys Xaa Leu Trp Cys Xaa Lys Lys Leu Trp
            20                  25                  30

<210> SEQ ID NO 407
<211> LENGTH: 1980
<212> TYPE: PRT
<213> ORGANISM: Homo sapiens

<400> SEQUENCE: 407

Met Ala Ala Arg Leu Leu Ala Pro Pro Gly Pro Asp Ser Phe Lys Pro
1               5                   10                  15

Phe Thr Pro Glu Ser Leu Ala Asn Ile Glu Arg Arg Ile Ala Glu Ser
            20                  25                  30

Lys Leu Lys Lys Pro Pro Lys Ala Asp Gly Ser His Arg Glu Asp Asp
        35                  40                  45

Glu Asp Ser Lys Pro Lys Pro Asn Ser Asp Leu Glu Ala Gly Lys Ser
    50                  55                  60

Leu Pro Phe Ile Tyr Gly Asp Ile Pro Gln Gly Leu Val Ala Val Pro
65                  70                  75                  80

Leu Glu Asp Phe Asp Pro Tyr Tyr Leu Thr Gln Lys Thr Phe Val Val
                85                  90                  95

Leu Asn Arg Gly Lys Thr Leu Phe Arg Phe Ser Ala Thr Pro Ala Leu
            100                 105                 110

Tyr Ile Leu Ser Pro Phe Asn Leu Ile Arg Arg Ile Ala Ile Lys Ile
        115                 120                 125

Leu Ile His Ser Val Phe Ser Met Ile Ile Met Cys Thr Ile Leu Thr
    130                 135                 140

Asn Cys Val Phe Met Thr Phe Ser Asn Pro Pro Asp Trp Ser Lys Asn
145                 150                 155                 160

Val Glu Tyr Thr Phe Thr Gly Ile Tyr Thr Phe Glu Ser Leu Val Lys
                165                 170                 175

Ile Ile Ala Arg Gly Phe Cys Ile Asp Gly Phe Thr Phe Leu Arg Asp
            180                 185                 190

Pro Trp Asn Trp Leu Asp Phe Ser Val Ile Met Met Ala Tyr Ile Thr
        195                 200                 205

Glu Phe Val Asn Leu Gly Asn Val Ser Ala Leu Arg Thr Phe Arg Val
    210                 215                 220

Leu Arg Ala Leu Lys Thr Ile Ser Val Ile Pro Gly Leu Lys Thr Ile
225                 230                 235                 240

Val Gly Ala Leu Ile Gln Ser Val Lys Lys Leu Ser Asp Val Met Ile
                245                 250                 255
```

-continued

```
Leu Thr Val Phe Cys Leu Ser Val Phe Ala Leu Ile Gly Leu Gln Leu
            260                 265                 270

Phe Met Gly Asn Leu Arg Asn Lys Cys Val Val Trp Pro Ile Asn Phe
        275                 280                 285

Asn Glu Ser Tyr Leu Glu Asn Gly Thr Lys Gly Phe Asp Trp Glu Glu
    290                 295                 300

Tyr Ile Asn Asn Lys Thr Asn Phe Tyr Thr Val Pro Gly Met Leu Glu
305                 310                 315                 320

Pro Leu Leu Cys Gly Asn Ser Ser Asp Ala Gly Gln Cys Pro Glu Gly
                325                 330                 335

Tyr Gln Cys Met Lys Ala Gly Arg Asn Pro Asn Tyr Gly Tyr Thr Ser
            340                 345                 350

Phe Asp Thr Phe Ser Trp Ala Phe Leu Ala Leu Phe Arg Leu Met Thr
        355                 360                 365

Gln Asp Tyr Trp Glu Asn Leu Tyr Gln Leu Thr Leu Arg Ala Ala Gly
    370                 375                 380

Lys Thr Tyr Met Ile Phe Phe Val Leu Val Ile Phe Val Gly Ser Phe
385                 390                 395                 400

Tyr Leu Val Asn Leu Ile Leu Ala Val Val Ala Met Ala Tyr Glu Glu
                405                 410                 415

Gln Asn Gln Ala Thr Leu Glu Glu Ala Glu Gln Lys Glu Ala Glu Phe
            420                 425                 430

Lys Ala Met Leu Glu Gln Leu Lys Lys Gln Gln Glu Ala Gln Ala
        435                 440                 445

Ala Ala Met Ala Thr Ser Ala Gly Thr Val Ser Glu Asp Ala Ile Glu
450                 455                 460

Glu Glu Gly Glu Glu Gly Gly Gly Ser Pro Arg Ser Ser Glu Ile
465                 470                 475                 480

Ser Lys Leu Ser Ser Lys Ser Ala Lys Glu Arg Arg Asn Arg Arg Lys
                485                 490                 495

Lys Arg Lys Gln Lys Glu Leu Ser Glu Gly Glu Glu Lys Gly Asp Pro
            500                 505                 510

Glu Lys Val Phe Lys Ser Glu Ser Glu Asp Gly Met Arg Arg Lys Ala
        515                 520                 525

Phe Arg Leu Pro Asp Asn Arg Ile Gly Arg Lys Phe Ser Ile Met Asn
530                 535                 540

Gln Ser Leu Leu Ser Ile Pro Gly Ser Pro Phe Leu Ser Arg His Asn
545                 550                 555                 560

Ser Lys Ser Ser Ile Phe Ser Phe Arg Gly Pro Gly Arg Phe Arg Asp
                565                 570                 575

Pro Gly Ser Glu Asn Glu Phe Ala Asp Asp Glu His Ser Thr Val Glu
            580                 585                 590

Glu Ser Glu Gly Arg Arg Asp Ser Leu Phe Ile Pro Ile Arg Ala Arg
        595                 600                 605

Glu Arg Arg Ser Ser Tyr Ser Gly Tyr Ser Gly Tyr Ser Gln Gly Ser
610                 615                 620

Arg Ser Ser Arg Ile Phe Pro Ser Leu Arg Arg Ser Val Lys Arg Asn
625                 630                 635                 640

Ser Thr Val Asp Cys Asn Gly Val Val Ser Leu Ile Gly Gly Pro Gly
                645                 650                 655

Ser His Ile Gly Gly Arg Leu Leu Pro Glu Ala Thr Thr Glu Val Glu
            660                 665                 670

Ile Lys Lys Lys Gly Pro Gly Ser Leu Leu Val Ser Met Asp Gln Leu
```

```
            675                 680                 685
Ala Ser Tyr Gly Arg Lys Asp Arg Ile Asn Ser Ile Met Ser Val Val
690                 695                 700
Thr Asn Thr Leu Val Glu Glu Leu Glu Glu Ser Gln Arg Lys Cys Pro
705                 710                 715                 720
Pro Cys Trp Tyr Lys Phe Ala Asn Thr Phe Leu Ile Trp Glu Cys His
                725                 730                 735
Pro Tyr Trp Ile Lys Leu Lys Glu Ile Val Asn Leu Ile Val Met Asp
                740                 745                 750
Pro Phe Val Asp Leu Ala Ile Thr Ile Cys Ile Val Leu Asn Thr Leu
                755                 760                 765
Phe Met Ala Met Glu His His Pro Met Thr Pro Gln Phe Glu His Val
770                 775                 780
Leu Ala Val Gly Asn Leu Val Phe Thr Gly Ile Phe Thr Ala Glu Met
785                 790                 795                 800
Phe Leu Lys Leu Ile Ala Met Asp Pro Tyr Tyr Tyr Phe Gln Glu Gly
                805                 810                 815
Trp Asn Ile Phe Asp Gly Phe Ile Val Ser Leu Ser Leu Met Glu Leu
                820                 825                 830
Ser Leu Ala Asp Val Glu Gly Leu Ser Val Leu Arg Ser Phe Arg Leu
                835                 840                 845
Leu Arg Val Phe Lys Leu Ala Lys Ser Trp Pro Thr Leu Asn Met Leu
850                 855                 860
Ile Lys Ile Ile Gly Asn Ser Val Gly Ala Leu Gly Asn Leu Thr Leu
865                 870                 875                 880
Val Leu Ala Ile Ile Val Phe Ile Phe Ala Val Val Gly Met Gln Leu
                885                 890                 895
Phe Gly Lys Ser Tyr Lys Glu Cys Val Cys Lys Ile Asn Gln Asp Cys
                900                 905                 910
Glu Leu Pro Arg Trp His Met His Asp Phe Phe His Ser Phe Leu Ile
                915                 920                 925
Val Phe Arg Val Leu Cys Gly Glu Trp Ile Glu Thr Met Trp Asp Cys
930                 935                 940
Met Glu Val Ala Gly Gln Ala Met Cys Leu Ile Val Phe Met Met Val
945                 950                 955                 960
Met Val Ile Gly Asn Leu Val Val Leu Asn Leu Phe Leu Ala Leu Leu
                965                 970                 975
Leu Ser Ser Phe Ser Ala Asp Asn Leu Ala Ala Thr Asp Asp Asp Gly
                980                 985                 990
Glu Met Asn Asn Leu Gln Ile Ser Val Ile Arg Ile Lys Lys Gly Val
                995                 1000                1005
Ala Trp Thr Lys Leu Lys Val His Ala Phe Met Gln Ala His Phe
        1010                1015                1020
Lys Gln Arg Glu Ala Asp Glu Val Lys Pro Leu Asp Glu Leu Tyr
        1025                1030                1035
Glu Lys Lys Ala Asn Cys Ile Ala Asn His Thr Gly Ala Asp Ile
        1040                1045                1050
His Arg Asn Gly Asp Phe Gln Lys Asn Gly Asn Gly Thr Thr Ser
        1055                1060                1065
Gly Ile Gly Ser Ser Val Glu Lys Tyr Ile Ile Asp Glu Asp His
        1070                1075                1080
Met Ser Phe Ile Asn Asn Pro Asn Leu Thr Val Arg Val Pro Ile
        1085                1090                1095
```

-continued

```
Ala Val Gly Glu Ser Asp Phe Glu Asn Leu Asn Thr Glu Asp Val
    1100            1105                1110
Ser Ser Glu Ser Asp Pro Glu Gly Ser Lys Asp Lys Leu Asp Asp
    1115            1120                1125
Thr Ser Ser Ser Glu Gly Ser Thr Ile Asp Ile Lys Pro Glu Val
    1130            1135                1140
Glu Glu Val Pro Val Glu Gln Pro Glu Glu Tyr Leu Asp Pro Asp
    1145            1150                1155
Ala Cys Phe Thr Glu Gly Cys Val Gln Arg Phe Lys Cys Cys Gln
    1160            1165                1170
Val Asn Ile Glu Glu Gly Leu Gly Lys Ser Trp Trp Ile Leu Arg
    1175            1180                1185
Lys Thr Cys Phe Leu Ile Val Glu His Asn Trp Phe Glu Thr Phe
    1190            1195                1200
Ile Ile Phe Met Ile Leu Leu Ser Ser Gly Ala Leu Ala Phe Glu
    1205            1210                1215
Asp Ile Tyr Ile Glu Gln Arg Lys Thr Ile Arg Thr Ile Leu Glu
    1220            1225                1230
Tyr Ala Asp Lys Val Phe Thr Tyr Ile Phe Ile Leu Glu Met Leu
    1235            1240                1245
Leu Lys Trp Thr Ala Tyr Gly Phe Val Lys Phe Thr Asn Ala
    1250            1255                1260
Trp Cys Trp Leu Asp Phe Leu Ile Val Ala Val Ser Leu Val Ser
    1265            1270                1275
Leu Ile Ala Asn Ala Leu Gly Tyr Ser Glu Leu Gly Ala Ile Lys
    1280            1285                1290
Ser Leu Arg Thr Leu Arg Ala Leu Arg Pro Leu Arg Ala Leu Ser
    1295            1300                1305
Arg Phe Glu Gly Met Arg Val Val Val Asn Ala Leu Val Gly Ala
    1310            1315                1320
Ile Pro Ser Ile Met Asn Val Leu Leu Val Cys Leu Ile Phe Trp
    1325            1330                1335
Leu Ile Phe Ser Ile Met Gly Val Asn Leu Phe Ala Gly Lys Tyr
    1340            1345                1350
His Tyr Cys Phe Asn Glu Thr Ser Glu Ile Arg Phe Glu Ile Glu
    1355            1360                1365
Asp Val Asn Asn Lys Thr Glu Cys Glu Lys Leu Met Glu Gly Asn
    1370            1375                1380
Asn Thr Glu Ile Arg Trp Lys Asn Val Lys Ile Asn Phe Asp Asn
    1385            1390                1395
Val Gly Ala Gly Tyr Leu Ala Leu Leu Gln Val Ala Thr Phe Lys
    1400            1405                1410
Gly Trp Met Asp Ile Met Tyr Ala Ala Val Asp Ser Arg Lys Pro
    1415            1420                1425
Asp Glu Gln Pro Lys Tyr Glu Asp Asn Ile Tyr Met Tyr Ile Tyr
    1430            1435                1440
Phe Val Ile Phe Ile Ile Phe Gly Ser Phe Phe Thr Leu Asn Leu
    1445            1450                1455
Phe Ile Gly Val Ile Ile Asp Asn Phe Asn Gln Gln Lys Lys Lys
    1460            1465                1470
Phe Gly Gly Gln Asp Ile Phe Met Thr Glu Glu Gln Lys Lys Tyr
    1475            1480                1485
```

```
Tyr Asn Ala Met Lys Lys Leu Gly Ser Lys Lys Pro  Gln Lys Pro
    1490            1495                1500

Ile Pro Arg Pro Leu Asn Lys Ile Gln Gly Ile Val  Phe Asp Phe
    1505            1510                1515

Val Thr Gln Gln Ala Phe Asp Ile Val Ile Met Met  Leu Ile Cys
    1520            1525                1530

Leu Asn Met Val Thr Met Met Val Glu Thr Asp Thr  Gln Ser Lys
    1535            1540                1545

Gln Met Glu Asn Ile Leu Tyr Trp Ile Asn Leu Val  Phe Val Ile
    1550            1555                1560

Phe Phe Thr Cys Glu Cys Val Leu Lys Met Phe Ala  Leu Arg His
    1565            1570                1575

Tyr Tyr Phe Thr Ile Gly Trp Asn Ile Phe Asp Phe  Val Val Val
    1580            1585                1590

Ile Leu Ser Ile Val Gly Met Phe Leu Ala Asp Ile  Ile Glu Lys
    1595            1600                1605

Tyr Phe Val Ser Pro Thr Leu Phe Arg Val Ile Arg  Leu Ala Arg
    1610            1615                1620

Ile Gly Arg Ile Leu Arg Leu Ile Lys Gly Ala Lys  Gly Ile Arg
    1625            1630                1635

Thr Leu Leu Phe Ala Leu Met Met Ser Leu Pro Ala  Leu Phe Asn
    1640            1645                1650

Ile Gly Leu Leu Leu Phe Leu Val Met Phe Ile Phe  Ser Ile Phe
    1655            1660                1665

Gly Met Ser Asn Phe Ala Tyr Val Lys His Glu Ala  Gly Ile Asp
    1670            1675                1680

Asp Met Phe Asn Phe Glu Thr Phe Gly Asn Ser Met  Ile Cys Leu
    1685            1690                1695

Phe Gln Ile Thr Thr Ser Ala Gly Trp Asp Gly Leu  Leu Leu Pro
    1700            1705                1710

Ile Leu Asn Arg Pro Pro Asp Cys Ser Leu Asp Lys  Glu His Pro
    1715            1720                1725

Gly Ser Gly Phe Lys Gly Asp Cys Gly Asn Pro Ser  Val Gly Ile
    1730            1735                1740

Phe Phe Phe Val Ser Tyr Ile Ile Ile Ser Phe Leu  Ile Val Val
    1745            1750                1755

Asn Met Tyr Ile Ala Ile Ile Leu Glu Asn Phe Ser  Val Ala Thr
    1760            1765                1770

Glu Glu Ser Ala Asp Pro Leu Ser Glu Asp Asp Phe  Glu Thr Phe
    1775            1780                1785

Tyr Glu Ile Trp Glu Lys Phe Asp Pro Asp Ala Thr  Gln Phe Ile
    1790            1795                1800

Glu Tyr Cys Lys Leu Ala Asp Phe Ala Asp Ala Leu  Glu His Pro
    1805            1810                1815

Leu Arg Val Pro Lys Pro Asn Thr Ile Glu Leu Ile  Ala Met Asp
    1820            1825                1830

Leu Pro Met Val Ser Gly Asp Arg Ile His Cys Leu  Asp Ile Leu
    1835            1840                1845

Phe Ala Phe Thr Lys Arg Val Leu Gly Asp Ser Gly  Glu Leu Asp
    1850            1855                1860

Ile Leu Arg Gln Gln Met Glu Glu Arg Phe Val Ala  Ser Asn Pro
    1865            1870                1875

Ser Lys Val Ser Tyr Glu Pro Ile Thr Thr Thr Leu  Arg Arg Lys
```

```
                1880                1885                1890

Gln Glu Glu Val Ser Ala Val Val Leu Gln Arg Ala Tyr Arg Gly
        1895                1900                1905

His Leu Ala Arg Arg Gly Phe Ile Cys Lys Lys Thr Thr Ser Asn
        1910                1915                1920

Lys Leu Glu Asn Gly Gly Thr His Arg Glu Lys Lys Glu Ser Thr
        1925                1930                1935

Pro Ser Thr Ala Ser Leu Pro Ser Tyr Asp Ser Val Thr Lys Pro
        1940                1945                1950

Glu Lys Glu Lys Gln Gln Arg Ala Glu Glu Gly Arg Arg Glu Arg
        1955                1960                1965

Ala Lys Arg Gln Lys Glu Val Arg Glu Ser Lys Cys
        1970                1975                1980

<210> SEQ ID NO 408
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Leu
            20                  25                  30

<210> SEQ ID NO 409
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Phe
            20                  25                  30

<210> SEQ ID NO 410
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Tyr
            20                  25                  30

<210> SEQ ID NO 411
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 411

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Gly
            20                  25                  30

<210> SEQ ID NO 412
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Ile
            20                  25                  30

<210> SEQ ID NO 413
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Val
            20                  25                  30

<210> SEQ ID NO 414
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Gly Pro Tyr Cys Gln Lys Trp Met Tyr Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 415
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Gly Pro Tyr Cys Gln Lys Trp Met Glu Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 416

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 417
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: N-Me-Arg

<400> SEQUENCE: 417

Tyr Cys Gln Lys Trp Met Gln Thr Cys Asp Ala Glu Arg Lys Cys Cys
1               5                   10                  15

Glu Gly Phe Ser Cys Arg Leu Trp Cys Lys Lys Lys Leu Leu
            20                  25                  30

<210> SEQ ID NO 418
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Tyr Cys Gln Lys Trp Met Gln Thr Cys Asp Asp Glu Arg Lys Cys Cys
1               5                   10                  15

Glu Gly Met Val Cys Arg Leu Trp Cys Lys Lys Lys Leu Leu
            20                  25                  30

<210> SEQ ID NO 419
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Tyr Cys Gln Lys Trp Met Gln Thr Cys Asp Ser Glu Arg Phe Cys Cys
1               5                   10                  15

Glu Gly Met Val Cys Arg Leu Trp Cys Lys Lys Lys Leu Leu
            20                  25                  30

<210> SEQ ID NO 420
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 420

Gly Pro Tyr Cys Gln Lys Trp Met Gln Thr Cys Asp Ser Glu Arg Phe
1               5                   10                  15

Cys Cys Glu Gly Met Val Cys Arg Leu Trp Cys Lys Lys Lys Leu Leu
            20                  25                  30

<210> SEQ ID NO 421
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Gly Pro Tyr Cys Gln Lys Trp Met Gln Thr Cys Asp Ile Glu Arg Lys
1               5                   10                  15

Cys Cys Glu Gly Met Val Cys Arg Leu Trp Cys Lys Lys Lys Leu Leu
            20                  25                  30

<210> SEQ ID NO 422
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Leu
            20                  25                  30

<210> SEQ ID NO 423
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Gly Pro Tyr Cys Gln Lys Trp Met Gln Thr Cys Asp Ser Glu Arg Lys
1               5                   10                  15

Cys Cys Asn Gly Met Val Cys Arg Leu Trp Cys Lys Lys Lys Leu Leu
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 425
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 426
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Gly Pro Tyr Cys Gln Lys Trp Met Gln Thr Cys Asp Val Glu Arg Lys
1               5                   10                  15

Cys Cys Glu Gly Met Val Cys Arg Leu Trp Cys Lys Lys Lys Leu Leu
            20                  25                  30

<210> SEQ ID NO 427
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Gly Pro Tyr Cys Gln Lys Trp Met Gln Thr Cys Asp Ser Glu Arg Lys
1               5                   10                  15

Cys Cys Leu Gly Met Val Cys Arg Leu Trp Cys Lys Lys Lys Leu Leu
            20                  25                  30

<210> SEQ ID NO 428
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Tyr Cys Gln Lys Trp Met Gln Thr Cys Asp Ser Glu Arg Lys Cys Cys
1               5                   10                  15

Asn Gly Met Val Cys Arg Leu Trp Cys Lys Lys Lys Leu Leu
            20                  25                  30

<210> SEQ ID NO 429
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Gly Pro Tyr Cys Gln Lys Trp Met Trp Thr Cys Asp Ser Glu Arg Lys
1               5                   10                  15
```

```
Cys Cys Tyr Gly Met Val Cys Arg Leu Trp Cys Lys Lys Lys Leu Trp
            20                  25                  30
```

<210> SEQ ID NO 430
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

```
Gly Pro Tyr Cys Gln Lys Trp Met Trp Thr Cys Asp Ser Glu Arg Lys
1               5                   10                  15

Cys Cys Ile Gly Met Val Cys Arg Leu Trp Cys Lys Lys Lys Leu Trp
            20                  25                  30
```

<210> SEQ ID NO 431
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

```
Gly Pro Tyr Cys Gln Lys Trp Met Trp Thr Cys Asp Ser Glu Arg Lys
1               5                   10                  15

Cys Cys Leu Gly Met Val Cys Arg Leu Trp Cys Lys Lys Lys Leu Trp
            20                  25                  30
```

<210> SEQ ID NO 432
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Pro, Ala or absent
<220> FEATURE:
<221> NAME/KEY: MOD_RES
<222> LOCATION: (2)..(2)
<223> OTHER INFORMATION: Pro, Ala or absent
<220> FEATURE:
<221> NAME/KEY: MOD_RES
<222> LOCATION: (3)..(3)
<223> OTHER INFORMATION: Ser, Gln, Ala, Arg or Tyr
<220> FEATURE:
<221> NAME/KEY: MOD_RES
<222> LOCATION: (5)..(5)
<223> OTHER INFORMATION: Gln, Arg, Lys, Ala, Ser or Tyr
<220> FEATURE:
<221> NAME/KEY: MOD_RES
<222> LOCATION: (6)..(6)
<223> OTHER INFORMATION: Lys, Ser, Gln or Arg
<220> FEATURE:
<221> NAME/KEY: MOD_RES
<222> LOCATION: (8)..(8)
<223> OTHER INFORMATION: Met or Phe
<220> FEATURE:
<221> NAME/KEY: MOD_RES
<222> LOCATION: (10)..(10)
<223> OTHER INFORMATION: Thr, Ser, Arg, Lys or Gln
<220> FEATURE:
<221> NAME/KEY: MOD_RES
<222> LOCATION: (12)..(12)
<223> OTHER INFORMATION: Asp, Thr or asparagyl-4-aminobutane
<220> FEATURE:
<221> NAME/KEY: MOD_RES

```
<222> LOCATION: (13)..(13)
<223> OTHER INFORMATION: Ser, Ala, Arg, Ile or Val
<220> FEATURE:
<221> NAME/KEY: MOD_RES
<222> LOCATION: (14)..(14)
<223> OTHER INFORMATION: Glu, Arg, Asn, Lys, Thr, Gln, Tyr or glutamyl-
      4-aminobutane
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (16)..(16)
<223> OTHER INFORMATION: Lys, Gln, Ser, Ala or Phe
<220> FEATURE:
<221> NAME/KEY: MOD_RES
<222> LOCATION: (19)..(19)
<223> OTHER INFORMATION: Glu, Gln, Asp, Leu, Asn or glutamyl-4-
      aminobutane
<220> FEATURE:
<221> NAME/KEY: MOD_RES
<222> LOCATION: (20)..(20)
<223> OTHER INFORMATION: Gly, Gln or Pro
<220> FEATURE:
<221> NAME/KEY: MOD_RES
<222> LOCATION: (21)..(21)
<223> OTHER INFORMATION: Met or Phe
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
<223> OTHER INFORMATION: Arg, Thr or N-omega methyl-L-arginine
<220> FEATURE:
<221> NAME/KEY: MOD_RES
<222> LOCATION: (28)..(28)
<223> OTHER INFORMATION: Lys or Arg
<220> FEATURE:
<221> NAME/KEY: MOD_RES
<222> LOCATION: (32)..(32)
<223> OTHER INFORMATION: Trp or Leu

<400> SEQUENCE: 432

Xaa Xaa Xaa Cys Xaa Xaa Trp Xaa Gln Xaa Cys Xaa Xaa Xaa Xaa
1               5                  10                  15

Cys Cys Xaa Xaa Xaa Xaa Cys Xaa Leu Trp Cys Xaa Lys Lys Leu Xaa
            20                  25                  30

<210> SEQ ID NO 433
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Gln, Arg, Lys, Ala or Ser
<220> FEATURE:
<221> NAME/KEY: MOD_RES
<222> LOCATION: (6)..(6)
<223> OTHER INFORMATION: Lys, Ser, Gln or Arg
<220> FEATURE:
<221> NAME/KEY: MOD_RES
<222> LOCATION: (8)..(8)
<223> OTHER INFORMATION: Met or Phe
<220> FEATURE:
<221> NAME/KEY: MOD_RES
<222> LOCATION: (10)..(10)
<223> OTHER INFORMATION: Thr, Ser, Arg, Lys or Gln
<220> FEATURE:
<221> NAME/KEY: MOD_RES
```

```
<222> LOCATION: (12)..(12)
<223> OTHER INFORMATION: Asp or Thr
<220> FEATURE:
<221> NAME/KEY: MOD_RES
<222> LOCATION: (13)..(13)
<223> OTHER INFORMATION: Ser, Ala or Arg
<220> FEATURE:
<221> NAME/KEY: MOD_RES
<222> LOCATION: (14)..(14)
<223> OTHER INFORMATION: Glu, Arg, Asn, Lys, Thr or Gln
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (16)..(16)
<223> OTHER INFORMATION: Lys, Gln, Ser or Ala
<220> FEATURE:
<221> NAME/KEY: MOD_RES
<222> LOCATION: (19)..(19)
<223> OTHER INFORMATION: Glu, Gln or Asp
<220> FEATURE:
<221> NAME/KEY: MOD_RES
<222> LOCATION: (20)..(20)
<223> OTHER INFORMATION: Gly or Gln
<220> FEATURE:
<221> NAME/KEY: MOD_RES
<222> LOCATION: (21)..(21)
<223> OTHER INFORMATION: Phe or Met
<220> FEATURE:
<221> NAME/KEY: MOD_RES
<222> LOCATION: (22)..(22)
<223> OTHER INFORMATION: Val or Ser
<220> FEATURE:
<221> NAME/KEY: MOD_RES
<222> LOCATION: (24)..(24)
<223> OTHER INFORMATION: Arg or Thr
<220> FEATURE:
<221> NAME/KEY: MOD_RES
<222> LOCATION: (28)..(28)
<223> OTHER INFORMATION: Lys or Arg

<400> SEQUENCE: 433

Gly Pro Gln Cys Xaa Xaa Trp Xaa Gln Xaa Cys Xaa Xaa Xaa Xaa Xaa
1               5                   10                  15

Cys Cys Xaa Xaa Xaa Xaa Cys Xaa Leu Trp Cys Xaa Lys Lys Leu Leu
            20                  25                  30

<210> SEQ ID NO 434
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Gly Pro Tyr Cys Gln Lys Trp Met Trp Thr Cys Asp Ser Arg Arg Lys
1               5                   10                  15

Cys Cys Glu Gly Met Val Cys Arg Leu Trp Cys Lys Lys Lys Leu Trp
            20                  25                  30

<210> SEQ ID NO 435
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435
```

Gly Pro Tyr Cys Gln Lys Trp Met Trp Thr Cys Asp Ser Thr Arg Lys
1               5                   10                  15
Cys Cys Glu Gly Met Val Cys Arg Leu Trp Cys Lys Lys Lys Leu Trp
            20                  25                  30

<210> SEQ ID NO 436
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Gly Pro Tyr Cys Gln Lys Trp Met Trp Thr Cys Asp Asn Glu Arg Lys
1               5                   10                  15
Cys Cys Glu Gly Met Val Cys Arg Leu Trp Cys Lys Lys Lys Leu Trp
            20                  25                  30

<210> SEQ ID NO 437
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Gly Pro Tyr Cys Gln Lys Trp Met Trp Phe Cys Asp Ser Glu Arg Lys
1               5                   10                  15
Cys Cys Glu Gly Met Val Cys Arg Leu Trp Cys Lys Lys Lys Leu Trp
            20                  25                  30

<210> SEQ ID NO 438
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Gly Pro Tyr Cys Gln Lys Trp Met Trp Thr Cys Asp Thr Glu Arg Lys
1               5                   10                  15
Cys Cys Glu Gly Met Val Cys Arg Leu Trp Cys Lys Lys Lys Leu Trp
            20                  25                  30

<210> SEQ ID NO 439
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Gly Pro Asn Cys Gln Lys Trp Met Trp Thr Cys Asp Ser Glu Arg Lys
1               5                   10                  15
Cys Cys Glu Gly Met Val Cys Arg Leu Trp Cys Lys Lys Lys Leu Trp
            20                  25                  30

<210> SEQ ID NO 440
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 440

Gly Pro Tyr Cys Gln Lys Trp Met Trp Thr Cys Asp Ser Glu Arg Lys
1               5                   10                  15

Cys Cys Ala Gly Met Val Cys Arg Leu Trp Cys Lys Lys Lys Leu Trp
            20                  25                  30

<210> SEQ ID NO 441
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Gly Pro Tyr Cys Gln Lys Trp Met Trp Thr Cys Asp Ser Glu Arg Lys
1               5                   10                  15

Cys Cys Asp Gly Met Val Cys Arg Leu Trp Cys Lys Lys Lys Leu Trp
            20                  25                  30

<210> SEQ ID NO 442
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Gly Pro Ile Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 443
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Gly Pro Ser Cys Gln Lys Trp Met Gln Thr Cys Asp Ile Arg Arg Lys
1               5                   10                  15

Cys Cys Glu Gly Phe Ser Cys Arg Leu Trp Cys Lys Lys Lys Leu Trp
            20                  25                  30

<210> SEQ ID NO 444
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Gly Pro Tyr Cys Gln Lys Trp Met Trp Thr Cys Asp Ile Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 445
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Tryptophanol

<400> SEQUENCE: 445

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 446
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Gly Pro Tyr Cys Gln Lys Trp Met Trp Thr Cys Asp Ser Glu Arg Pro
1               5                   10                  15

Cys Cys Glu Gly Met Val Cys Arg Leu Trp Cys Lys Lys Lys Leu Trp
            20                  25                  30

<210> SEQ ID NO 447
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Gly Pro Lys Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 448
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Gly Pro Tyr Cys Gln Lys Trp Met Trp Thr Cys Asp Ser Val Arg Lys
1               5                   10                  15

Cys Cys Glu Gly Met Val Cys Arg Leu Trp Cys Lys Lys Lys Leu Trp
            20                  25                  30

<210> SEQ ID NO 449
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 449

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 450
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Gly Pro Tyr Cys Gln Lys Trp Met Trp Thr Cys Asp Leu Glu Arg Lys
1               5                   10                  15

Cys Cys Glu Gly Met Val Cys Arg Leu Trp Cys Lys Lys Lys Leu Trp
            20                  25                  30

<210> SEQ ID NO 451
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Gly Pro Tyr Cys Gln Lys Trp Met Trp Thr Cys Asp Ser Glu Arg Lys
1               5                   10                  15

Cys Cys Pro Gly Met Val Cys Arg Leu Trp Cys Lys Lys Lys Leu Trp
            20                  25                  30

<210> SEQ ID NO 452
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Gly Pro Tyr Cys Gln Lys Trp Met Trp Tyr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 453
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Gly Pro Leu Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 454
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gly Pro Val Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 455
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Gly Pro Ser Cys Gln Lys Trp Met Gln Thr Cys Asp Ala Arg Arg Lys
1               5                   10                  15

Cys Cys Leu Gly Phe Ser Cys Arg Leu Trp Cys Lys Lys Lys Leu Trp
            20                  25                  30

<210> SEQ ID NO 456
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Gly Pro Tyr Cys Gln Lys Trp Met Trp Leu Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 457
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Gly Pro Tyr Cys Gln Lys Trp Met Trp Thr Cys Asp Ser Glu Arg Lys
1               5                   10                  15

Cys Cys Glu Gly Met Ile Cys Arg Leu Trp Cys Lys Lys Lys Leu Trp
            20                  25                  30

<210> SEQ ID NO 458
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

```
Gly Pro Tyr Cys Gln Lys Trp Met Trp Lys Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 459
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

```
Gly Pro Tyr Cys Gln Lys Trp Met Trp Thr Cys Asp Ser His Arg Lys
1               5                   10                  15

Cys Cys Glu Gly Met Val Cys Arg Leu Trp Cys Lys Lys Lys Leu Trp
            20                  25                  30
```

<210> SEQ ID NO 460
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

```
Gly Pro Tyr Cys Gln Glu Trp Met Trp Thr Cys Asp Ser Glu Arg Lys
1               5                   10                  15

Cys Cys Arg Gly Met Val Cys Arg Leu Trp Cys Lys Lys Lys Leu Trp
            20                  25                  30
```

<210> SEQ ID NO 461
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

```
Gly Pro Tyr Cys Gln Lys Trp Met Trp Gly Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 462
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

```
Gly Pro Tyr Cys Gln Glu Phe Leu Trp Thr Cys Asp Ser Thr Arg Lys
1               5                   10                  15

Cys Cys Glu Gly Met Val Cys Arg Leu Trp Cys Lys Lys Lys Leu Trp
            20                  25                  30
```

<210> SEQ ID NO 463
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 463

Gly Pro Tyr Cys Gln Lys Trp Met Trp Thr Cys Asp Ser Glu Arg His
1               5                   10                  15

Cys Cys Glu Gly Met Val Cys Arg Leu Trp Cys Lys Lys Lys Leu Trp
            20                  25                  30

<210> SEQ ID NO 464
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gly Pro Tyr Cys Gln Lys Trp Met Trp Thr Cys Asp Ser Glu Arg Lys
1               5                   10                  15

Cys Cys Arg Gly Met Val Cys Arg Leu Trp Cys Lys Lys Lys Leu Trp
            20                  25                  30

<210> SEQ ID NO 465
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Gly Pro Tyr Cys Gln Lys Trp Met Trp Thr Cys Asp Ser Glu Arg Val
1               5                   10                  15

Cys Cys Glu Gly Met Val Cys Arg Leu Trp Cys Lys Lys Lys Leu Trp
            20                  25                  30

<210> SEQ ID NO 466
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Gly Pro Ser Cys Gln Lys Trp Phe Trp Thr Cys Asp Arg Thr Arg Lys
1               5                   10                  15

Cys Cys Glu Gly Leu Val Cys Arg Leu Trp Cys Lys Lys Lys Leu Trp
            20                  25                  30

<210> SEQ ID NO 467
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Gly Pro Tyr Cys Gln Lys Trp Met Trp Thr Cys Asp Ser Glu Arg Lys
1               5                   10                  15

Cys Cys Lys Gly Met Val Cys Arg Leu Trp Cys Lys Lys Lys Leu Trp
            20                  25                  30
```

<210> SEQ ID NO 468
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Gly Pro Gln Cys Gln Lys Trp Met Gln Thr Cys Asp Ala Thr Arg Lys
1               5                   10                  15

Cys Cys Glu Gly Phe Val Cys Arg Leu Trp Cys Lys Lys Lys Leu Trp
            20                  25                  30

<210> SEQ ID NO 469
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Gly Pro Tyr Cys Gln Lys Trp Met Trp Thr Cys Asp Ser Tyr Arg Lys
1               5                   10                  15

Cys Cys Glu Gly Met Val Cys Arg Leu Trp Cys Lys Lys Lys Leu Trp
            20                  25                  30

<210> SEQ ID NO 470
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Gly Pro Gln Cys Gln Lys Trp Met Gln Thr Cys Asp Ile Thr Arg Lys
1               5                   10                  15

Cys Cys Glu Gly Phe Val Cys Arg Leu Trp Cys Lys Lys Lys Leu Trp
            20                  25                  30

<210> SEQ ID NO 471
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gly Pro Phe Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 472
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gly Pro Tyr Cys Gln Lys Trp Met Trp Thr Cys Asp Ser Glu Arg Lys
1               5                   10                  15

Cys Cys Ser Gly Met Val Cys Arg Leu Trp Cys Lys Lys Lys Leu Trp
            20                  25                  30

<210> SEQ ID NO 473
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Gly Pro Tyr Cys Gln Lys Trp Met Trp Val Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 474
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gly Pro Thr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 475
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Gly Pro Tyr Cys Gln Lys Trp Met Trp Thr Cys Asp Ser Ile Arg Lys
1               5                   10                  15

Cys Cys Glu Gly Met Val Cys Arg Leu Trp Cys Lys Lys Lys Leu Trp
            20                  25                  30

<210> SEQ ID NO 476
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gly Pro Tyr Cys Gln Lys Trp Met Trp Thr Cys Asp Ser Leu Arg Lys
1               5                   10                  15

Cys Cys Glu Gly Met Val Cys Arg Leu Trp Cys Lys Lys Lys Leu Trp
            20                  25                  30

<210> SEQ ID NO 477
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 477

Gly Pro Tyr Cys Gln Arg Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 478
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Gly Pro Tyr Cys Gln Lys Trp Met Trp Thr Cys Asp Ser Glu Arg Phe
1               5                   10                  15

Cys Cys Glu Gly Met Val Cys Arg Leu Trp Cys Lys Lys Lys Leu Trp
            20                  25                  30

<210> SEQ ID NO 479
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Gly Pro Ser Cys Gln Lys Trp Phe Trp Thr Cys Asp Ala Asn Arg Lys
1               5                   10                  15

Cys Cys Glu Gly Leu Val Cys Arg Leu Trp Cys Lys Lys Lys Leu Trp
            20                  25                  30

<210> SEQ ID NO 480
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Gly Pro Tyr Cys Gln Lys Trp Met Trp Thr Cys Asp Ser Glu Arg Tyr
1               5                   10                  15

Cys Cys Glu Gly Met Val Cys Arg Leu Trp Cys Lys Lys Lys Leu Trp
            20                  25                  30

<210> SEQ ID NO 481
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Gly Pro Tyr Cys Gln Lys Trp Leu Trp Thr Cys Asp Ser Glu Arg Lys
1               5                   10                  15

Cys Cys Glu Gly Met Val Cys Arg Leu Trp Cys Lys Lys Lys Leu Trp
```

<210> SEQ ID NO 482
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gly Pro Tyr Cys Gln Lys Trp Met Trp Thr Cys Asp Ser Glu Arg Lys
1               5                   10                  15

Cys Cys Phe Gly Met Val Cys Arg Leu Trp Cys Lys Lys Lys Leu Trp
            20                  25                  30

<210> SEQ ID NO 483
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Gly Pro Tyr Cys Gln Lys Tyr Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 484
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Gly Pro Tyr Cys Gln Lys Trp Met Trp Thr Cys Arg Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 485
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Gly Pro Tyr Cys Gln Lys Trp Met Trp Thr Cys Asp Ser Glu Arg Arg
1               5                   10                  15

Cys Cys Glu Gly Met Val Cys Arg Leu Trp Cys Lys Lys Lys Leu Trp
            20                  25                  30

<210> SEQ ID NO 486
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Gly Pro Tyr Cys Gln Lys Trp Met Trp Thr Cys Asp Ser Asp Arg Lys
1               5                   10                  15

Cys Cys Glu Gly Met Val Cys Arg Leu Trp Cys Lys Lys Lys Leu Trp
            20                  25                  30

<210> SEQ ID NO 487
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Gly Pro Tyr Cys Gln Lys Trp Met Trp Thr Cys Asp Asp Glu Arg Lys
1               5                   10                  15

Cys Cys Glu Gly Met Val Cys Arg Leu Trp Cys Lys Lys Lys Leu Trp
            20                  25                  30

<210> SEQ ID NO 488
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Palmitoyl-Lys

<400> SEQUENCE: 488

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Lys

<210> SEQ ID NO 489
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

Gly Pro Tyr Cys Gln Lys Trp Met Trp Ala Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 490
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Gly Pro Ser Cys Gln Lys Trp Phe Trp Thr Cys Asp Arg Glu Arg Lys
1               5                   10                  15

Cys Cys Glu Gly Leu Val Cys Arg Leu Trp Cys Lys Lys Lys Leu Trp
            20                  25                  30

<210> SEQ ID NO 491
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Gly Pro Gln Cys Gln Glu Phe Leu Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 492
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Gly Pro Tyr Cys Gln Lys Trp Met Trp Thr Cys Asp Ser Glu Arg Lys
1               5                   10                  15

Cys Cys Asn Gly Met Val Cys Arg Leu Trp Cys Lys Lys Lys Leu Trp
            20                  25                  30

<210> SEQ ID NO 493
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gly Pro Tyr Cys Gln Lys Trp Met Trp Thr Cys Asp Ser Glu Arg Lys
1               5                   10                  15

Cys Cys Glu Gly Met Val Cys Ser Leu Trp Cys Lys Lys Lys Leu Trp
            20                  25                  30

<210> SEQ ID NO 494
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Gly Pro Tyr Cys Gln Lys Trp Met Trp Thr Cys Asp Ser Glu Arg Lys
1               5                   10                  15

Cys Cys Thr Gly Met Val Cys Arg Leu Trp Cys Lys Lys Lys Leu Trp
            20                  25                  30

<210> SEQ ID NO 495
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Gly Pro Ser Cys Gln Lys Trp Phe Trp Thr Cys Asp Ala Thr Arg Lys
1               5                   10                  15

Cys Cys Glu Gly Leu Val Cys Arg Leu Trp Cys Lys Lys Lys Leu Trp
                20                  25                  30

<210> SEQ ID NO 496
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
                20                  25                  30

Gly Gly Gly Gly Gly
        35

<210> SEQ ID NO 497
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Gly Pro Tyr Cys Gln Lys Trp Met Trp Thr Cys Asp Ser Glu Arg Lys
1               5                   10                  15

Cys Cys Glu Gly Met Val Cys Arg Phe Trp Cys Lys Lys Lys Leu Trp
                20                  25                  30

<210> SEQ ID NO 498
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

Gly Pro Tyr Cys Gln Lys Trp Met Trp Thr Cys Asp Ser Glu Arg Lys
1               5                   10                  15

Cys Cys Glu Gly Met Val Cys His Leu Trp Cys Lys Lys Lys Leu Trp
                20                  25                  30

<210> SEQ ID NO 499
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Gly Pro Tyr Cys Gln Glu Phe Leu Trp Thr Cys Asp Arg Thr Arg Lys
1               5                   10                  15

Cys Cys Glu Gly Met Val Cys Arg Leu Trp Cys Lys Lys Lys Leu Trp
                20                  25                  30

<210> SEQ ID NO 500
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Gly Pro Tyr Cys Gln Lys Trp Met Trp Thr Cys Asp Ser Gly Arg Lys
1               5                   10                  15

Cys Cys Glu Gly Met Val Cys Arg Leu Trp Cys Lys Lys Lys Leu Trp
            20                  25                  30

<210> SEQ ID NO 501
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Gly Pro Asp Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 502
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Gly Pro Tyr Cys Gln Asp Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 503
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gly Pro Tyr Cys Gln Lys Trp Met Trp His Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 504
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

```
Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Tyr Lys Lys Leu Trp
            20                  25                  30
```

<210> SEQ ID NO 505
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

```
Gly Pro Tyr Cys Gln Lys Trp Met Trp Thr Cys Asp Ser Glu Arg Lys
1               5                   10                  15

Cys Cys Glu Pro Met Val Cys Arg Leu Trp Cys Lys Lys Lys Leu Trp
            20                  25                  30
```

<210> SEQ ID NO 506
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30
```

<210> SEQ ID NO 507
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

```
Gly Pro Tyr Cys Gln Lys Trp Met Trp Thr Cys Asp Ser Glu Arg Lys
1               5                   10                  15

Cys Cys His Gly Met Val Cys Arg Leu Trp Cys Lys Lys Lys Leu Trp
            20                  25                  30
```

<210> SEQ ID NO 508
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

```
Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys His Trp
            20                  25                  30
```

<210> SEQ ID NO 509
<211> LENGTH: 32
<212> TYPE: PRT

-continued

<210> SEQ ID NO 510
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Gly Pro Tyr Cys Gln Lys Trp Met Trp Thr Cys Asp Ser Glu Arg Lys
1               5                   10                  15

Cys Cys Glu Lys Met Val Cys Arg Leu Trp Cys Lys Lys Lys Leu Trp
            20                  25                  30

<210> SEQ ID NO 510
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Gly Pro Tyr Cys Gln Lys Trp Met Trp Thr Cys Asp Ser Glu Arg Ser
1               5                   10                  15

Cys Cys Glu Gly Met Val Cys Arg Leu Trp Cys Lys Lys Lys Leu Trp
            20                  25                  30

<210> SEQ ID NO 511
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Ser Cys Gln Lys Trp Met Gln Thr Cys Asp Ala Glu Arg Lys Cys Cys
1               5                   10                  15

Glu Gly Phe Val Cys Arg Leu Trp Cys Lys Lys Lys Leu Trp
            20                  25                  30

<210> SEQ ID NO 512
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Gly Pro Tyr Cys Gln Lys Trp Met Trp Thr Cys Asp Ser Glu Arg Gln
1               5                   10                  15

Cys Cys Glu Gly Met Val Cys Arg Leu Trp Cys Lys Lys Lys Leu Trp
            20                  25                  30

<210> SEQ ID NO 513
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Gly Pro Tyr Cys Gln Lys Trp Met Trp Thr Cys Asp Ser Glu Arg Lys
1               5                   10                  15

Cys Cys Glu Gly Met Thr Cys Arg Leu Trp Cys Lys Lys Lys Leu Trp

<210> SEQ ID NO 514
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

Gly Pro Tyr Cys Gln Thr Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 515
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Gly Pro Tyr Cys Gln Lys Trp Met Trp Thr Cys Asp Ser Glu Arg Lys
1               5                   10                  15

Cys Cys Glu Gly Met Val Cys Asn Leu Trp Cys Lys Lys Lys Leu Trp
            20                  25                  30

<210> SEQ ID NO 516
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Gly Pro Tyr Cys Gln Lys Trp Met Trp Thr Cys Asp Ser Glu Arg Lys
1               5                   10                  15

Cys Cys Glu Gly Met Val Cys Arg Leu His Cys Lys Lys Lys Leu Trp
            20                  25                  30

<210> SEQ ID NO 517
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Gly Pro Gln Cys Gln Lys Trp Met Gln Thr Cys Asp Arg Thr Arg Lys
1               5                   10                  15

Cys Cys Glu Gly Phe Val Cys Arg Leu Trp Cys Lys Lys Lys Leu Trp
            20                  25                  30

<210> SEQ ID NO 518
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 518

Gly Pro Tyr Cys Gln Lys Trp Met Trp Thr Cys Asp Ser Glu Arg Lys
1               5                   10                  15
Cys Cys Glu Gly Met Val Cys Arg Leu Trp Cys Lys Lys Lys Val Trp
            20                  25                  30

<210> SEQ ID NO 519
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Gly Pro Gln Cys Gln Lys Trp Met Gln Thr Cys Asp Ala Glu Arg Lys
1               5                   10                  15
Cys Cys Leu Gly Phe Val Cys Arg Leu Trp Cys Lys Lys Lys Leu Trp
            20                  25                  30

<210> SEQ ID NO 520
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Gly Pro Gln Cys Gln Lys Trp Met Gln Thr Cys Asp Ala Glu Arg Lys
1               5                   10                  15
Cys Cys Glu Gly Phe Val Cys Arg Leu Trp Cys Lys Lys Lys Leu Trp
            20                  25                  30
Gly

<210> SEQ ID NO 521
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Gly Pro Gln Cys Gln Lys Trp Met Gln Thr Cys Asp Ile Glu Arg Lys
1               5                   10                  15
Cys Cys Glu Gly Phe Val Cys Arg Leu Trp Cys Lys Lys Lys Leu Trp
            20                  25                  30

<210> SEQ ID NO 522
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

Gly Pro Tyr Cys Gln Lys Trp Met Trp Thr Cys Asp Ser Glu Arg Lys
1               5                   10                  15
Cys Cys Glu Gly Met Val Cys Arg Leu Trp Cys Lys Ala Lys Leu Trp
            20                  25                  30
```

```
<210> SEQ ID NO 523
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Gly Pro Tyr Cys Gln Lys Trp Met Trp Thr Cys Asp Ser Glu Arg Ile
1               5                   10                  15

Cys Cys Glu Gly Met Val Cys Arg Leu Trp Cys Lys Lys Lys Leu Trp
            20                  25                  30

<210> SEQ ID NO 524
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Gly Pro Tyr Cys Gln Lys Leu Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 525
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Gly Pro Tyr Cys Gln Lys Trp Met Trp Thr Cys Asp Val Glu Arg Lys
1               5                   10                  15

Cys Cys Glu Gly Met Val Cys Arg Leu Trp Cys Lys Lys Lys Leu Trp
            20                  25                  30

<210> SEQ ID NO 526
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

Gly Pro Tyr Cys Gln Lys Trp Met Trp Thr Cys Asp Ser Glu Arg Lys
1               5                   10                  15

Cys Cys Glu Gly Met His Cys Arg Leu Trp Cys Lys Lys Lys Leu Trp
            20                  25                  30

<210> SEQ ID NO 527
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Gly Pro Tyr Cys Gln Lys Trp Met Trp Thr Cys Asp Ser Glu Tyr Lys
```

```
                1               5                  10                  15
Cys Cys Glu Gly Met Val Cys Arg Leu Trp Cys Lys Lys Lys Leu Trp
                20                  25                  30

<210> SEQ ID NO 528
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Gly Pro Tyr Cys Gln Lys Trp Met Trp Thr Cys Asp Ser Glu Arg Lys
1               5                   10                  15
Cys Cys Glu Gly Met Lys Cys Arg Leu Trp Cys Lys Lys Lys Leu Trp
                20                  25                  30

<210> SEQ ID NO 529
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Gly Pro Tyr Cys Gln Lys Trp Met Trp Thr Cys Asp His Glu Arg Lys
1               5                   10                  15
Cys Cys Glu Gly Met Val Cys Arg Leu Trp Cys Lys Lys Lys Leu Trp
                20                  25                  30

<210> SEQ ID NO 530
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

Gly Pro Tyr Cys Gln Lys Trp Met Trp Thr Cys Asp Ser Glu Arg Lys
1               5                   10                  15
Cys Cys Glu Gly Met Val Cys Arg Leu Trp Cys Lys Gly Lys Leu Trp
                20                  25                  30

<210> SEQ ID NO 531
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Gly Pro Tyr Cys Gln Lys Trp Met Trp Thr Cys Asp Ser Glu His Lys
1               5                   10                  15
Cys Cys Glu Gly Met Val Cys Arg Leu Trp Cys Lys Lys Lys Leu Trp
                20                  25                  30

<210> SEQ ID NO 532
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 532

Gly Pro Tyr Cys Gln Lys Trp Met Trp Pro Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 533
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Gly Pro Tyr Cys Gln Asn Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 534
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Gly Pro Tyr Cys Gln Glu Trp Met Trp Thr Cys Asp Ser Glu Arg Lys
1               5                   10                  15

Cys Cys Lys Gly Met Val Cys Arg Leu Trp Cys Lys Lys Lys Leu Trp
            20                  25                  30

<210> SEQ ID NO 535
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Gly Pro Tyr Cys Gln Lys Trp Met Trp Thr Cys Asp Ser Glu Arg Gly
1               5                   10                  15

Cys Cys Glu Gly Met Val Cys Arg Leu Trp Cys Lys Lys Lys Leu Trp
            20                  25                  30

<210> SEQ ID NO 536
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Gly Pro Tyr Cys Gln Lys Trp Met Trp Thr Cys Asp Ser Glu Arg Thr
1               5                   10                  15

Cys Cys Glu Gly Met Val Cys Arg Leu Trp Cys Lys Lys Lys Leu Trp
            20                  25                  30
```

<210> SEQ ID NO 537
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Ser Trp
            20                  25                  30

<210> SEQ ID NO 538
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Gly Pro Tyr Cys Gln Lys Trp Met Trp Gln Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 539
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Gly Pro Tyr Cys Gln Lys Trp Met Trp Thr Cys Asp Ser Glu Lys Lys
1               5                   10                  15

Cys Cys Glu Gly Met Val Cys Arg Leu Trp Cys Lys Lys Lys Leu Trp
            20                  25                  30

<210> SEQ ID NO 540
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Palmitoyl-Lys

<400> SEQUENCE: 540

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Lys

<210> SEQ ID NO 541
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 541

Gly Pro Tyr Cys Gln Lys Trp Met Trp Thr Cys Asp Ser Glu Arg Lys
1               5                   10                  15

Cys Cys Glu Gly Met Val Cys Tyr Leu Trp Cys Lys Lys Lys Leu Trp
            20                  25                  30

<210> SEQ ID NO 542
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542

Gly Pro Tyr Cys Gln Lys Trp Met Trp Thr Cys Asp Ser Glu Arg Lys
1               5                   10                  15

Cys Cys Glu Tyr Met Val Cys Arg Leu Trp Cys Lys Lys Lys Leu Trp
            20                  25                  30

<210> SEQ ID NO 543
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Gly Pro Tyr Cys Gln Glu Phe Leu Trp Thr Cys Asp Ser Glu Arg Lys
1               5                   10                  15

Cys Cys Glu Gly Met Val Cys Arg Leu Trp Cys Arg Lys Lys Leu Trp
            20                  25                  30

<210> SEQ ID NO 544
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gly Pro Tyr Cys Gln Lys Trp Met Ser Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 545
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Gly Pro Tyr Cys Gln Gly Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 546
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Gly Pro Tyr Cys Gln Lys Trp Met Arg Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 547
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Thr Lys Lys Leu Trp
            20                  25                  30

<210> SEQ ID NO 548
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Gly Pro Tyr Cys Gln Lys Trp Met Trp Thr Cys Asp Ser Glu Arg Lys
1               5                   10                  15

Cys Cys Glu Gly Met Val Cys Val Leu Trp Cys Lys Lys Lys Leu Trp
            20                  25                  30

<210> SEQ ID NO 549
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Gly Pro Tyr Cys Gln Lys Trp Met Trp Thr Cys Asp Ser Glu Arg Lys
1               5                   10                  15

Cys Cys Glu Gly Met Glu Cys Arg Leu Trp Cys Lys Lys Lys Leu Trp
            20                  25                  30

<210> SEQ ID NO 550
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Gly Pro Tyr Cys Gln Lys Trp Met Trp Thr Cys Phe Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 551
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys His Lys Leu Trp
            20                  25                  30

<210> SEQ ID NO 552
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

Gly Pro Tyr Cys Gln Ser Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 553
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Asn Leu Trp
            20                  25                  30

<210> SEQ ID NO 554
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Gly Pro Tyr Cys Gln Lys Glu Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 555
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 555

Gly Pro Tyr Cys Gln Lys Trp Met Trp Thr Cys Asp Ser Glu Arg Lys
1               5                   10                  15

Cys Cys Glu Gly Met Arg Cys Arg Leu Trp Cys Lys Lys Lys Leu Trp
            20                  25                  30

<210> SEQ ID NO 556
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Gly Pro Tyr Cys Gln Lys Trp Met Trp Glu Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 557
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Gly Pro Tyr Cys Gln Lys Trp Met Trp Thr Cys Asp Ser Glu Arg Glu
1               5                   10                  15

Cys Cys Glu Gly Met Val Cys Arg Leu Trp Cys Lys Lys Lys Leu Trp
            20                  25                  30

<210> SEQ ID NO 558
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Gly Pro Tyr Cys Gln Lys Trp Met Trp Thr Cys Asp Ser Glu Arg Lys
1               5                   10                  15

Cys Cys Glu Gly Met Val Cys Gly Leu Trp Cys Lys Lys Lys Leu Trp
            20                  25                  30

<210> SEQ ID NO 559
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 559

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Val Leu Trp
```

```
                  20                  25                  30

<210> SEQ ID NO 560
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

Gly Pro Tyr Cys Gln Lys Trp Met Trp Thr Cys Arg Ser Arg Arg Lys
1               5                   10                  15

Cys Cys Glu Gly Met Val Cys Arg Leu Trp Cys Lys Lys Lys Leu Trp
            20                  25                  30

<210> SEQ ID NO 561
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Gly Pro Gln Cys Gln Lys Trp Met Gln Thr Cys Asp Ala Glu Arg Lys
1               5                   10                  15

Cys Cys Phe Gly Phe Val Cys Arg Leu Trp Cys Lys Lys Lys Leu Trp
            20                  25                  30

<210> SEQ ID NO 562
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Gly Pro Tyr Cys Gln Lys Trp Met Trp Thr Cys Val Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 563
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

Gly Pro Gln Cys Gln Lys Trp Met Gln Thr Cys Asp Ala Glu Arg Lys
1               5                   10                  15

Cys Cys Glu Gly Phe Val Cys Thr Leu Trp Cys Arg Lys Lys Leu Trp
            20                  25                  30

Asp

<210> SEQ ID NO 564
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 564

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Ser Lys Lys Leu Trp
            20                  25                  30

<210> SEQ ID NO 565
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 565

Gly Pro Ser Cys Gln Lys Trp Phe Trp Thr Cys Asp Ala Glu Arg Lys
1               5                   10                  15

Cys Cys Glu Gly Leu Val Cys Arg Leu Trp Cys Arg Lys Lys Leu Trp
            20                  25                  30

<210> SEQ ID NO 566
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 566

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys His Leu Trp
            20                  25                  30

<210> SEQ ID NO 567
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 567

Gly Pro Tyr Cys Gln Lys Trp Met Trp Thr Cys Asp Thr Glu Arg Lys
1               5                   10                  15

Cys Cys Glu Gly Met Val Cys Arg Leu Trp Cys Lys Lys Lys Leu Trp
            20                  25                  30

<210> SEQ ID NO 568
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 568

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Asp Leu Trp
            20                  25                  30

```
<210> SEQ ID NO 569
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 569

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Thr Lys Leu Trp
            20                  25                  30

<210> SEQ ID NO 570
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 570

Gly Pro Tyr Cys Gln Lys Trp Met Trp Thr Cys Asp Ser Glu Arg Lys
1               5                   10                  15

Cys Cys Glu Gly Met Val Cys Gln Leu Trp Cys Lys Lys Lys Leu Trp
            20                  25                  30

<210> SEQ ID NO 571
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 571

Gly Pro Tyr Cys Gln Lys Trp Met Trp Thr Cys Asp Ser Glu Arg Asn
1               5                   10                  15

Cys Cys Glu Gly Met Val Cys Arg Leu Trp Cys Lys Lys Lys Leu Trp
            20                  25                  30

<210> SEQ ID NO 572
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Gly Pro Tyr Cys Gln Lys Trp Met His Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 573
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Gly Pro Tyr Cys Gln Pro Trp Met Trp Thr Cys Asp Ser Glu Arg Lys
```

```
                1               5                  10                  15
Cys Cys Glu Gly Met Val Cys Arg Leu Trp Cys Lys Lys Lys Leu Trp
            20                  25                  30

<210> SEQ ID NO 574
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 574

Gly Pro Tyr Cys Gly Lys Trp Met Trp Thr Cys Asp Ser Glu Arg Lys
1               5                  10                  15
Cys Cys Glu Gly Met Val Cys Arg Leu Trp Cys Lys Lys Lys Leu Trp
            20                  25                  30

<210> SEQ ID NO 575
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 575

Gly Pro Tyr Cys Gln Lys Trp Met Trp Thr Cys Gln Ser Glu Arg Lys
1               5                  10                  15
Cys Cys Glu Gly Met Val Cys Arg Leu Trp Cys Lys Lys Lys Leu Trp
            20                  25                  30

<210> SEQ ID NO 576
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Gly Pro Ser Cys Gln Glu Phe Leu Trp Thr Cys Asp Ala Glu Arg Lys
1               5                  10                  15
Cys Cys Glu Gly Leu Val Cys Arg Leu Trp Cys Lys Lys Lys Leu Trp
            20                  25                  30

<210> SEQ ID NO 577
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Gly Pro Tyr Cys Gln Lys Trp Met Trp Thr Cys Asp Ser Glu Arg Lys
1               5                  10                  15
Cys Cys Glu Gly Met Val Cys Arg Leu Trp Cys Lys Leu Lys Leu Trp
            20                  25                  30

<210> SEQ ID NO 578
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 578

Gly Pro Tyr Cys Gln Lys Trp Met Trp Thr Cys Asp Ser Glu Arg Lys
1               5                   10                  15

Cys Cys Glu Gly Met Tyr Cys Arg Leu Trp Cys Lys Lys Lys Leu Trp
            20                  25                  30

<210> SEQ ID NO 579
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Asn Trp
            20                  25                  30

<210> SEQ ID NO 580
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

Gly Pro Tyr Cys Gln Lys Trp Met Trp Thr Cys Ala Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 581
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

Gly Pro Tyr Cys Gln Lys Trp Met Trp Thr Cys Asp Ser Glu Arg Lys
1               5                   10                  15

Cys Cys Glu Gly Met Leu Cys Arg Leu Trp Cys Lys Lys Lys Leu Trp
            20                  25                  30

<210> SEQ ID NO 582
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 582

Gly Pro Tyr Cys Phe Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 583
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 583

Gly Pro Tyr Cys Gln Lys Trp Met Trp Thr Cys Asp Ser Glu Arg Lys
1               5                   10                  15

Cys Cys Glu Gly Met Ala Cys Arg Leu Trp Cys Lys Lys Lys Leu Trp
            20                  25                  30

<210> SEQ ID NO 584
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 584

Gly Pro Tyr Cys Gln Lys Trp Met Trp Thr Cys Asp Tyr Glu Arg Lys
1               5                   10                  15

Cys Cys Glu Gly Met Val Cys Arg Leu Trp Cys Lys Lys Lys Leu Trp
            20                  25                  30

<210> SEQ ID NO 585
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 585

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Val Trp
            20                  25                  30

<210> SEQ ID NO 586
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 586

Gly Pro Tyr Cys Gln Lys Trp Met Trp Thr Cys Asp Ser Glu Leu Lys
1               5                   10                  15

Cys Cys Glu Gly Met Val Cys Arg Leu Trp Cys Lys Lys Lys Leu Trp
            20                  25                  30

<210> SEQ ID NO 587
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 587

```
Gly Pro Tyr Cys Gln Lys Trp Met Trp Thr Cys Arg Ser Arg Glu Lys
1               5                   10                  15

Cys Cys Glu Gly Met Val Cys Arg Leu Trp Cys Lys Lys Lys Leu Trp
            20                  25                  30
```

<210> SEQ ID NO 588
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

```
Gly Pro Tyr Cys Gln Glu Trp Met Trp Thr Cys Asp Ser Glu Arg Lys
1               5                   10                  15

Cys Cys Arg Gly Met Val Cys Arg Leu Trp Cys Lys Lys Lys Leu Trp
            20                  25                  30
```

<210> SEQ ID NO 589
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: L-aspartyl-4-aminobutane
<220> FEATURE:
<221> NAME/KEY: MOD_RES
<222> LOCATION: (14)..(14)
<223> OTHER INFORMATION: glutamyl-4-aminobutane
<220> FEATURE:
<221> NAME/KEY: MOD_RES
<222> LOCATION: (19)..(19)
<223> OTHER INFORMATION: glutamyl-4-aminobutane

<400> SEQUENCE: 589

```
Gly Pro Gln Cys Gln Lys Trp Met Gln Thr Cys Asn Ala Gln Arg Lys
1               5                   10                  15

Cys Cys Gln Gly Phe Val Cys Arg Leu Trp Cys Lys Lys Lys Leu Trp
            20                  25                  30
```

<210> SEQ ID NO 590
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 590

```
Gly Pro Tyr Cys Gln Lys Trp Met Trp Ile Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 591
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 591

Gly Pro Tyr Cys Gln Asp Trp Met Trp Thr Cys Asp Ser Glu Arg Lys
1               5                   10                  15

Cys Cys Arg Gly Met Val Cys Arg Leu Trp Cys Lys Lys Lys Leu Trp
            20                  25                  30

<210> SEQ ID NO 592
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 592

Tyr Cys Gln Lys Trp Met Gln Thr Cys Asp Ile Glu Arg Lys Cys Cys
1               5                   10                  15

Glu Gly Phe Val Cys Arg Leu Trp Cys Lys Lys Lys Leu Trp
            20                  25                  30

<210> SEQ ID NO 593
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 593

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Thr Leu Trp
            20                  25                  30

<210> SEQ ID NO 594
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 594

Gly Pro Tyr Cys Gln Lys Trp Met Trp Thr Cys Gly Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 595
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Gly Pro Tyr Cys Gln Lys Trp Met Trp Thr Cys Asp Ser Glu Arg Lys
1               5                   10                  15

Cys Cys Glu His Met Val Cys Arg Leu Trp Cys Lys Lys Lys Leu Trp
            20                  25                  30

<210> SEQ ID NO 596
<211> LENGTH: 30
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 596

Tyr Cys Gln Lys Trp Met Gln Thr Cys Asp Ile Glu Arg Lys Cys Cys
1               5                   10                  15

Glu Gly Met Val Cys Arg Leu Trp Cys Lys Lys Lys Leu Trp
            20                  25                  30

<210> SEQ ID NO 597
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 597

Gly Pro Tyr Cys Gln Lys Trp Met Trp Thr Cys Asp Phe Glu Arg Lys
1               5                   10                  15

Cys Cys Glu Gly Met Val Cys Arg Leu Trp Cys Lys Lys Lys Leu Trp
            20                  25                  30

<210> SEQ ID NO 598
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 598

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Phe Lys Leu Trp
            20                  25                  30

<210> SEQ ID NO 599
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: N-omega-methyl-L-Arg

<400> SEQUENCE: 599

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 600
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Phe Trp
            20                  25                  30

<210> SEQ ID NO 601
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 601

Gly Pro Tyr Cys Ser Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 602
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: 4-chloro-Phe

<400> SEQUENCE: 602

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 603
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

Gly Pro Tyr Cys Gln Lys Trp Met Trp Thr Cys Asp Ser Gln Arg Lys
1               5                   10                  15

Cys Cys Glu Gly Met Val Cys Arg Leu Trp Cys Lys Lys Lys Leu Trp
            20                  25                  30

<210> SEQ ID NO 604
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

Gly Pro Tyr Cys Tyr Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

-continued

```
<210> SEQ ID NO 605
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Val Lys Leu Trp
            20                  25                  30

<210> SEQ ID NO 606
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 606

Gly Pro Tyr Cys Gln Lys Trp Met Trp Thr Cys Asp Ser Glu Arg Lys
1               5                   10                  15

Cys Cys Val Gly Met Val Cys Arg Leu Trp Cys Lys Lys Lys Leu Trp
            20                  25                  30

<210> SEQ ID NO 607
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607

Gly Pro Tyr Cys Gln Lys Trp Met Trp Thr Cys Asp Ile Glu Arg Lys
1               5                   10                  15

Cys Cys Glu Gly Met Val Cys Arg Leu Trp Cys Lys Lys Lys Leu Trp
            20                  25                  30

<210> SEQ ID NO 608
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

Gly Pro Tyr Cys Gln Lys Trp Met Trp Thr Cys Asp Ser Glu Arg Lys
1               5                   10                  15

Cys Cys Glu Arg Met Val Cys Arg Leu Trp Cys Lys Lys Lys Leu Trp
            20                  25                  30

<210> SEQ ID NO 609
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 609

Gly Pro Tyr Cys Gln Lys Trp Met Trp Thr Cys Asp Ser Glu Arg Lys
```

```
                1               5                  10                  15
Cys Cys Glu Gly Met Val Cys Arg Leu Trp Cys Lys Lys Lys Val Trp
                20                  25                  30

<210> SEQ ID NO 610
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 610

Gly Pro Tyr Cys Gln Lys Trp Met Trp Thr Cys Asp Ser Glu Arg Lys
1               5                   10                  15
Cys Cys Glu Gly Met Val Cys Arg Leu Trp Cys Lys Ile Lys Leu Trp
                20                  25                  30

<210> SEQ ID NO 611
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 611

Tyr Cys Gln Lys Trp Met Trp Thr Cys Asp Ile Glu Arg Lys Cys Cys
1               5                   10                  15
Glu Gly Met Val Cys Arg Leu Trp Cys Lys Lys Lys Leu Trp
                20                  25                  30

<210> SEQ ID NO 612
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

Gly Pro Gln Cys Gln Lys Trp Met Gln Thr Cys Asp Ile Glu Arg Lys
1               5                   10                  15
Cys Cys Leu Gly Phe Val Cys Arg Leu Trp Cys Lys Lys Lys Leu Trp
                20                  25                  30

<210> SEQ ID NO 613
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Gly Pro Gln Cys Gln Lys Trp Met Gln Thr Cys Asp Ile Glu Arg Lys
1               5                   10                  15
Cys Cys Glu Gly Phe Val Cys Arg Leu Trp Cys Lys Lys Lys Val Trp
                20                  25                  30

<210> SEQ ID NO 614
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 614

Gly Pro Gln Cys Gln Lys Trp Met Gln Thr Cys Asp Ala Glu Arg Lys
1               5                   10                  15

Cys Cys Leu Gly Phe Val Cys Arg Leu Trp Cys Lys Lys Lys Val Trp
            20                  25                  30

<210> SEQ ID NO 615
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 615

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Val Trp
            20                  25                  30

<210> SEQ ID NO 616
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 616

Gly Pro Gln Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 617
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 617

Gly Pro Ser Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 618
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 618

Gly Pro Arg Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 619
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 619

Gly Pro Tyr Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 620
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Gly Pro Ala Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 621
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Gly Pro Tyr Cys Gln Lys Trp Met Trp Ser Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 622
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Gly Pro Tyr Cys Gln Lys Trp Met Trp Thr Cys Asp Arg Glu Arg Lys
1               5                   10                  15

Cys Cys Glu Gly Met Val Cys Arg Leu Trp Cys Lys Lys Lys Leu Trp
            20                  25                  30

<210> SEQ ID NO 623
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Gly Pro Tyr Cys Gln Lys Trp Phe Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 624
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 624

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 625
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625

Gly Pro Tyr Cys Gln Lys Trp Met Trp Thr Cys Asp Ser Glu Arg Lys
1               5                   10                  15

Cys Cys Glu Gly Met Val Cys Arg Thr Trp Cys Lys Lys Lys Leu Trp
            20                  25                  30

<210> SEQ ID NO 626
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 626

Gly Pro Tyr Cys Gln Lys Trp Met Trp Thr Cys Ser Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 627
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Ser
            20                  25                  30

<210> SEQ ID NO 628
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 628

Gly Pro Tyr Cys Gln Lys Trp Met Trp Thr Cys Asp Ser Glu Arg Ala
1               5                   10                  15

Cys Cys Glu Gly Met Val Cys Arg Leu Trp Cys Lys Lys Lys Leu Trp
            20                  25                  30

<210> SEQ ID NO 629
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Gly Pro Tyr Cys Gln Lys Trp Met Trp Thr Cys Asp Ser Glu Arg Lys
1               5                   10                  15

Cys Cys Glu Gly Ser Val Cys Arg Leu Trp Cys Lys Lys Lys Leu Trp
            20                  25                  30

<210> SEQ ID NO 630
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 630

Gly Pro Tyr Cys Gln Lys Trp Met Trp Thr Cys Asp Ser Glu Arg Lys
1               5                   10                  15

Cys Cys Glu Gly Met Ser Cys Arg Leu Trp Cys Lys Lys Lys Leu Trp
            20                  25                  30

<210> SEQ ID NO 631
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 631

Gly Pro Tyr Cys Gln Lys Trp Met Trp Thr Cys Asp Ser Glu Arg Asp
1               5                   10                  15

Cys Cys Glu Gly Met Val Cys Arg Leu Trp Cys Lys Lys Lys Leu Trp
            20                  25                  30

<210> SEQ ID NO 632
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 632

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Arg Lys Leu Trp
            20                  25                  30
```

<210> SEQ ID NO 633
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 633

Gly Pro Tyr Cys Gln Lys Trp Met Trp Thr Cys Asp Ser Ser Arg Lys
1               5                   10                  15

Cys Cys Glu Gly Met Val Cys Arg Leu Trp Cys Lys Lys Lys Leu Trp
            20                  25                  30

<210> SEQ ID NO 634
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 634

Gly Pro Tyr Cys Gln Lys Trp Met Trp Thr Cys Asp Ser Glu Arg Lys
1               5                   10                  15

Cys Cys Glu Gly Met Val Cys Lys Leu Trp Cys Lys Lys Lys Leu Trp
            20                  25                  30

<210> SEQ ID NO 635
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 635

Gly Pro Tyr Cys Gln Lys Trp Met Trp Arg Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 636
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

Gly Pro Tyr Cys Gln Lys Trp Met Trp Thr Cys Asp Pro Glu Arg Lys
1               5                   10                  15

Cys Cys Glu Gly Met Val Cys Arg Leu Trp Cys Lys Lys Lys Leu Trp
            20                  25                  30

<210> SEQ ID NO 637
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Arg Leu Trp
            20                  25                  30

<210> SEQ ID NO 638
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 638

Gly Pro Tyr Cys Gln Lys Trp Met Trp Thr Cys Asp Ser Glu Arg Lys
1               5                   10                  15

Cys Cys Glu Gly Tyr Val Cys Arg Leu Trp Cys Lys Lys Lys Leu Trp
            20                  25                  30

<210> SEQ ID NO 639
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 639

Gly Pro Tyr Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 640
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 640

Gly Pro Tyr Cys Gln Lys Trp Met Trp Thr Cys Asp Ser Glu Arg Lys
1               5                   10                  15

Cys Cys Glu Gly Met Val Cys Arg Arg Trp Cys Lys Lys Lys Leu Trp
            20                  25                  30

<210> SEQ ID NO 641
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 641

Gly Pro Tyr Cys Gln Lys Trp Met Trp Thr Cys Asp Ser Glu Asn Lys
1               5                   10                  15

Cys Cys Glu Gly Met Val Cys Arg Leu Trp Cys Lys Lys Lys Leu Trp
            20                  25                  30

<210> SEQ ID NO 642
<211> LENGTH: 32
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 642

Gly Pro Tyr Cys Gln Lys Trp Met Trp Thr Cys Asp Ser Glu Arg Lys
1               5                   10                  15
Cys Cys Glu Gly Met Val Cys Arg Lys Trp Cys Lys Lys Lys Leu Trp
            20                  25                  30

<210> SEQ ID NO 643
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 643

Gly Pro Tyr Cys Gln Lys Trp Met Trp Thr Cys Asp Ser Glu Arg Lys
1               5                   10                  15
Cys Cys Glu Gly Arg Val Cys Arg Leu Trp Cys Lys Lys Lys Leu Trp
            20                  25                  30

<210> SEQ ID NO 644
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: N-omega,N-omega-dimethyl(asymmetric)-L-Arg

<400> SEQUENCE: 644

Gly Pro Tyr Cys Gln Lys Trp Met Gln Thr Cys Asp Ser Glu Arg Lys
1               5                   10                  15
Cys Cys Glu Gly Met Val Cys Arg Leu Trp Cys Lys Lys Lys Leu Leu
            20                  25                  30

<210> SEQ ID NO 645
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 645

Gly Pro Tyr Cys Gln Lys Trp Met Trp Thr Cys Asp Ser Glu Arg Lys
1               5                   10                  15
Cys Cys Glu Gly Asn Val Cys Arg Leu Trp Cys Lys Lys Lys Leu Trp
            20                  25                  30

<210> SEQ ID NO 646
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Gly Pro Tyr Cys Gln Gln Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 647
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 647

Gly Pro Tyr Cys Gln Lys Trp Met Trp Thr Cys Asp Ser Glu Arg Lys
1               5                   10                  15

Cys Cys Glu Asn Met Val Cys Arg Leu Trp Cys Lys Lys Lys Leu Trp
            20                  25                  30

<210> SEQ ID NO 648
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Gly Pro Tyr Cys Gln Lys Trp Met Trp Thr Cys Asp Ser Glu Arg Lys
1               5                   10                  15

Cys Cys Gly Gly Met Val Cys Arg Leu Trp Cys Lys Lys Lys Leu Trp
            20                  25                  30

<210> SEQ ID NO 649
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 649

Gly Pro Tyr Cys Gln Lys Trp Met Trp Thr Cys Asp Gly Glu Arg Lys
1               5                   10                  15

Cys Cys Glu Gly Met Val Cys Arg Leu Trp Cys Lys Lys Lys Leu Trp
            20                  25                  30

<210> SEQ ID NO 650
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Gly Pro Tyr Cys Gln Lys Trp Met Trp Thr Cys Asp Ser Glu Arg Lys
1               5                   10                  15

Cys Cys Glu Gly Met Phe Cys Arg Leu Trp Cys Lys Lys Lys Leu Trp
            20                  25                  30

<210> SEQ ID NO 651
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 651

Gly Pro Tyr Cys Gln Lys Trp Met Trp Thr Cys Thr Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 652
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Gln Leu Trp
            20                  25                  30

<210> SEQ ID NO 653
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 653

Gly Pro Tyr Cys Gln Lys Trp Met Trp Thr Cys Asp Glu Glu Arg Lys
1               5                   10                  15

Cys Cys Glu Gly Met Val Cys Arg Leu Trp Cys Lys Lys Lys Leu Trp
            20                  25                  30

<210> SEQ ID NO 654
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Gly Pro Tyr Cys Gln His Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 655
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 655

Gly Pro Tyr Cys Gln Lys Trp Met Trp Thr Cys Asp Ser Glu Arg Lys
1               5                   10                  15

Cys Cys Glu Gly His Val Cys Arg Leu Trp Cys Lys Lys Lys Leu Trp
            20                  25                  30
```

<210> SEQ ID NO 656
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 656

Gly Pro Tyr Cys Gln Lys Trp Met Trp Thr Cys Asp Ser Glu Arg Lys
1               5                   10                  15

Cys Cys Glu Gly Met Val Cys Arg Ile Trp Cys Lys Lys Lys Leu Trp
            20                  25                  30

<210> SEQ ID NO 657
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 657

Gly Pro Tyr Cys Arg Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 658
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 658

Gly Pro His Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 659
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 659

Gly Pro Gly Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 660
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 660

Gly Pro Tyr Cys Gln Lys Trp Met Trp Thr Cys Asp Ser Glu Arg Lys
1               5                   10                  15

Cys Cys Glu Gly Met Val Cys Arg Leu Gly Cys Lys Lys Lys Leu Trp
            20                  25                  30

<210> SEQ ID NO 661
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 661

Gly Pro Tyr Cys Gln Lys Trp Lys Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 662
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 662

Gly Pro Tyr Cys Gln Lys Trp Met Trp Thr Cys Asp Gln Glu Arg Lys
1               5                   10                  15

Cys Cys Glu Gly Met Val Cys Arg Leu Trp Cys Lys Lys Lys Leu Trp
            20                  25                  30

<210> SEQ ID NO 663
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 663

Ser His Ser Asn Thr Gln Thr Leu Ala Lys Ala Pro Glu His Thr Gly
1               5                   10                  15

Ala Pro Ala Pro Ala Pro Ala Pro Ala Pro Tyr Cys Gln Lys Trp Met
            20                  25                  30

Gln Thr Cys Asp Ser Glu Arg Lys Cys Cys Glu Gly Met Val Cys Arg
        35                  40                  45

Leu Trp Cys Lys Lys Lys Leu Leu
    50                  55

<210> SEQ ID NO 664
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

Tyr Cys Gln Lys Trp Met Gln Thr Cys Asp Ser Tyr Arg Phe Cys Cys
1               5                   10                  15

Glu Gly Met Val Cys Arg Leu Trp Cys Lys Lys Lys Leu Leu 20              25              30

<210> SEQ ID NO 665
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 665

Gly Pro Tyr Cys Gln Glu Trp Met Gln Thr Cys Asp Ser Glu Arg Lys
1               5                   10                  15

Cys Cys Arg Gly Met Val Cys Arg Leu Trp Cys Lys Lys Lys Leu Leu
            20                  25                  30

<210> SEQ ID NO 666
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: 4-guanidino-L-Phe

<400> SEQUENCE: 666

Tyr Cys Gln Lys Trp Met Gln Thr Cys Asp Ser Glu Arg Lys Cys Cys
1               5                   10                  15

Leu Gly Met Val Cys Phe Leu Trp Cys Lys Lys Lys Leu Leu
            20                  25                  30

<210> SEQ ID NO 667
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: 4-guanidino-L-Phe

<400> SEQUENCE: 667

Tyr Cys Gln Lys Trp Met Gln Thr Cys Asp Ser Glu Arg Lys Cys Cys
1               5                   10                  15

Glu Gly Met Val Cys Phe Leu Trp Cys Lys Lys Lys Leu Leu
            20                  25                  30

<210> SEQ ID NO 668
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Tyr Cys Gln Lys Trp Met Gln Thr Cys Asp Val Glu Arg Lys Cys Cys
1               5                   10                  15

Leu Gly Met Val Cys Arg Leu Trp Cys Lys Lys Lys Leu Leu
            20                  25                  30

```
<210> SEQ ID NO 669
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 669

Tyr Cys Gln Lys Trp Met Gln Thr Cys Asp Ser Glu Arg Lys Cys Cys
1               5                   10                  15

Leu Pro Met Val Cys Arg Leu Trp Cys Lys Lys Lys Leu Leu
            20                  25                  30

<210> SEQ ID NO 670
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: N-omega-methyl-L-Arg

<400> SEQUENCE: 670

Tyr Cys Gln Lys Trp Met Gln Thr Cys Asp Ser Glu Arg Lys Cys Cys
1               5                   10                  15

Leu Gly Met Val Cys Arg Leu Trp Cys Lys Lys Lys Leu Leu
            20                  25                  30

<210> SEQ ID NO 671
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: N-omega,N-omega-dimethyl(asymmetric)-L-Arg

<400> SEQUENCE: 671

Tyr Cys Gln Lys Trp Met Gln Thr Cys Asp Ser Glu Arg Lys Cys Cys
1               5                   10                  15

Leu Gly Met Val Cys Arg Leu Trp Cys Lys Lys Lys Leu Leu
            20                  25                  30

<210> SEQ ID NO 672
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: N-omega-methyl-L-Arg

<400> SEQUENCE: 672

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Leu
            20                  25                  30
```

<210> SEQ ID NO 673
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 673

Tyr Cys Tyr Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 674
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Tyr Cys Gln Lys Trp Met Gln Thr Cys Asp Ser Glu Arg Lys Cys Cys
1               5                   10                  15

Glu Pro Met Val Cys Arg Leu Trp Cys Lys Lys Lys Leu Leu
            20                  25                  30

<210> SEQ ID NO 675
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Tyr Cys Gln Lys Trp Met Gln Thr Cys Asp Ser Glu Arg Lys Cys Cys
1               5                   10                  15

Leu Gly Met Val Cys Arg Leu Trp Cys Lys Lys Lys Leu Leu
            20                  25                  30

<210> SEQ ID NO 676
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Tyr Cys Gln Lys Trp Met Gln Thr Cys Asp Ser Glu Arg Lys Cys Cys
1               5                   10                  15

Gln Gly Met Val Cys Arg Leu Trp Cys Lys Lys Lys Leu Leu
            20                  25                  30

<210> SEQ ID NO 677
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)

<223> OTHER INFORMATION: Glutamyl-4-aminobutane

<400> SEQUENCE: 677

Tyr Cys Gln Lys Trp Met Gln Thr Cys Asp Ser Glu Arg Lys Cys Cys
1               5                   10                  15

Gln Gly Met Val Cys Arg Leu Trp Cys Lys Lys Lys Leu Leu
            20                  25                  30

<210> SEQ ID NO 678
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 678

Tyr Cys Gln Lys Trp Met Gln Thr Cys Asp Ser Tyr Arg Lys Cys Cys
1               5                   10                  15

Glu Gly Met Val Cys Arg Leu Trp Cys Lys Lys Lys Leu Leu
            20                  25                  30

<210> SEQ ID NO 679
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 679

Gly Pro Tyr Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Leu
            20                  25                  30

<210> SEQ ID NO 680
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

His Leu Asn Ile Leu Ser Thr Leu Trp Lys Tyr Arg Gly Pro Tyr Cys
1               5                   10                  15

Gln Lys Trp Met Gln Thr Cys Asp Ser Glu Arg Lys Cys Cys Glu Gly
            20                  25                  30

Met Val Cys Arg Leu Trp Cys Lys Lys Lys Leu Leu
            35                  40

<210> SEQ ID NO 681
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 681

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu

<210> SEQ ID NO 682
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 682

Tyr Cys Gln Lys Trp Met Gln Thr Cys Asp Ser Glu Arg Phe Cys Cys
1               5                   10                  15

Glu Gly Met Val Cys Arg Leu Trp Cys Lys Lys Lys Leu Leu
            20                  25                  30

<210> SEQ ID NO 683
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (12)..(12)
<223> OTHER INFORMATION: Glutamyl-4-aminobutane

<400> SEQUENCE: 683

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 684
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (10)..(10)
<223> OTHER INFORMATION: Asparagyl-4-aminobutane

<400> SEQUENCE: 684

Tyr Cys Gln Lys Trp Met Gln Thr Cys Asn Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 685
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 685

Tyr Cys Gln Lys Trp Met Gln Thr Cys Asp Ser Glu Arg Phe Cys Cys
1               5                   10                  15

Leu Gly Met Val Cys Arg Leu Trp Cys Lys Lys Lys Leu Leu
            20                  25                  30

<210> SEQ ID NO 686
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 687
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-Lys(N-epsilon-(N-alpha-Palmitoyl-L-gamma-
      glutamyl)

<400> SEQUENCE: 687

Lys Gly Gly Gly Gly Ser Tyr Cys Gln Lys Trp Met Gln Thr Cys Asp
1               5                   10                  15

Ser Glu Arg Lys Cys Cys Glu Gly Met Val Cys Arg Leu Trp Cys Lys
            20                  25                  30

Lys Lys Leu Leu
        35

<210> SEQ ID NO 688
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Tyr Cys Gln Lys Trp Met Gln Thr Cys Asp Ser Glu Arg Phe Cys Cys
1               5                   10                  15

Glu Gly Met Val Cys Arg Leu Trp Cys Lys Lys Lys Leu Leu
            20                  25                  30

<210> SEQ ID NO 689
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-Lys(N-epsilon-(N-alpha-Palmitoyl-L-gamma-
      glutamyl)

<400> SEQUENCE: 689

Lys Gly Gly Gly Gly Ser Tyr Cys Gln Lys Trp Met Gln Thr Cys Asp
1               5                   10                  15

Ser Glu Arg Phe Cys Cys Glu Gly Met Val Cys Arg Leu Trp Cys Lys
            20                  25                  30

Lys Lys Leu Leu
        35

<210> SEQ ID NO 690
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Asparagyl-4-aminobutane

<400> SEQUENCE: 690

Tyr Cys Gln Lys Trp Met Gln Thr Cys Asn Ser Glu Arg Phe Cys Cys
1               5                   10                  15

Glu Gly Met Val Cys Arg Leu Trp Cys Lys Lys Lys Leu Leu
            20                  25                  30

<210> SEQ ID NO 691
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Tyr Cys Gln Lys Trp Met Gln Thr Cys Asp Ser Glu Arg Lys Cys Cys
1               5                   10                  15

Glu Pro Met Val Cys Arg Leu Trp Cys Lys Lys Lys Leu Leu
            20                  25                  30

<210> SEQ ID NO 692
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-bromo-L-Phe

<400> SEQUENCE: 692

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 693
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: 5-bromo-L-Trp

<400> SEQUENCE: 693

Tyr Cys Gln Lys Trp Cys Gln Lys Trp Met Gln Thr Cys Asp Ser Glu

-continued

```
1               5                   10                  15
Arg Lys Cys Cys Glu Gly Met Val Cys Arg Leu Trp Cys Lys Lys
            20                  25                  30
Leu Leu

<210> SEQ ID NO 694
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: 5-bromo-L-Trp

<400> SEQUENCE: 694

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 695
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-chloro-L-Phe

<400> SEQUENCE: 695

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 696
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 3-chloro-L-Tyr

<400> SEQUENCE: 696

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 697
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 697

Tyr Cys Gln Lys Trp Met Gln Thr Cys Asp Ser Lys Arg Ala Cys Cys
1               5                   10                  15

Glu Gly Leu Glu Cys Lys Leu Trp Cys Arg Lys Ile Trp Leu
            20                  25                  30

<210> SEQ ID NO 698
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Tyr Cys Gln Lys Trp Met Gln Thr Cys Asp Ser Lys Arg Lys Cys Cys
1               5                   10                  15

Glu Asp Met Val Cys Gln Leu Trp Cys Lys Lys Arg Leu Leu
            20                  25                  30

<210> SEQ ID NO 699
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Tyr Cys Gln Lys Trp Met Gln Thr Cys Asp Ser Glu Arg Lys Cys Cys
1               5                   10                  15

Glu Asp Met Val Cys Glu Leu Trp Cys Lys Lys Arg Leu Leu
            20                  25                  30

<210> SEQ ID NO 700
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Tyr Cys Gln Lys Trp Met Gln Thr Cys Asp Ser Lys Arg Ala Cys Cys
1               5                   10                  15

Glu Gly Leu Arg Cys Lys Leu Trp Cys Arg Lys Ile Ile Leu
            20                  25                  30

<210> SEQ ID NO 701
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Tyr Cys Gln Lys Trp Met Gln Thr Cys Asp Ser Ala Arg Lys Cys Cys
1               5                   10                  15

Glu Gly Leu Val Cys Arg Leu Trp Cys Lys Lys Ile Ile Leu
            20                  25                  30

<210> SEQ ID NO 702
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Tyr Cys Gln Lys Trp Met Gln Thr Cys Asp Glu Glu Arg Lys Cys Cys
1               5                   10                  15

Glu Gly Leu Val Cys Arg Leu Trp Cys Lys Arg Ile Ile Leu Met
            20                  25                  30

<210> SEQ ID NO 703
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Tyr Cys Gln Lys Trp Met Gln Thr Cys Asp Glu Glu Arg Lys Cys Cys
1               5                   10                  15

Glu Gly Leu Val Cys Arg Leu Trp Cys Lys Lys Lys Ile Leu Glu Gly
            20                  25                  30

<210> SEQ ID NO 704
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Tyr Cys Gln Lys Trp Met Gln Thr Cys Asp Glu Glu Arg Lys Cys Cys
1               5                   10                  15

Glu Gly Leu Val Cys Arg Leu Trp Cys Lys Lys Lys Ile Leu Trp
            20                  25                  30

<210> SEQ ID NO 705
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 705

Tyr Cys Gln Lys Trp Met Gln Thr Cys Asp Glu Glu Arg Lys Cys Cys
1               5                   10                  15

Glu Gly Leu Val Cys Arg Leu Trp Cys Lys Lys Lys Asn Leu Val Val
            20                  25                  30

Ile Ser Gly Glu Asp Thr Lys Leu Pro Thr Leu Lys Ile Gln Leu Met
        35                  40                  45

Lys Ser Asn Ile Thr Asp Ile
    50                  55

<210> SEQ ID NO 706
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 706

Tyr Cys Gln Lys Trp Met Gln Thr Cys Asp Ser Glu Arg Lys Cys Cys
1               5                   10                  15

Glu Gly Tyr Val Cys Glu Leu Trp Cys Lys Tyr Asn Leu Leu
            20                  25                  30

<210> SEQ ID NO 707
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Tyr Cys Gln Lys Trp Met Gln Thr Cys Asp Ser Glu Arg Lys Cys Cys
1               5                   10                  15

Glu Gly Tyr Val Cys Glu Leu Trp Cys Lys Tyr Asn Met Leu
            20                  25                  30

<210> SEQ ID NO 708
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-Lys(N-epsilon-(N-alpha-Palmitoyl-L-gamma-
      glutamyl)

<400> SEQUENCE: 708

Lys Tyr Cys Gln Lys Trp Met Gln Thr Cys Asp Ser Glu Arg Lys Cys
1               5                   10                  15

Cys Glu Gly Met Val Cys Arg Leu Trp Cys Lys Lys Lys Leu Leu
            20                  25                  30

<210> SEQ ID NO 709
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: beta-chloro-L-Ala

<400> SEQUENCE: 709

Tyr Cys Gln Lys Trp Met Gln Thr Cys Asp Ala Glu Arg Lys Cys Cys
1               5                   10                  15

Glu Gly Met Val Cys Arg Leu Trp Cys Lys Lys Lys Leu Leu
            20                  25                  30

<210> SEQ ID NO 710
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

```
Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
                20                  25                  30
```

<210> SEQ ID NO 711
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: L-Lys(N-epsilon-(N-alpha-Palmitoyl-L-gamma-
      glutamyl)

<400> SEQUENCE: 711

```
Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu Gly Gly
                20                  25                  30

Gly Gly Ser Lys
        35
```

<210> SEQ ID NO 712
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-bromo-L-Phe
<220> FEATURE:
<221> NAME/KEY: MOD_RES
<222> LOCATION: (11)..(11)
<223> OTHER INFORMATION: beta-chloro-L-Ala

<400> SEQUENCE: 712

```
Phe Cys Gln Lys Trp Met Gln Thr Cys Asp Ala Glu Arg Lys Cys Cys
1               5                   10                  15

Glu Gly Met Val Cys Arg Leu Trp Cys Lys Lys Lys Leu Leu
                20                  25                  30
```

<210> SEQ ID NO 713
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-bromo-L-Phe
<220> FEATURE:
<221> NAME/KEY: MOD_RES
<222> LOCATION: (11)..(11)
<223> OTHER INFORMATION: beta-chloro-L-Ala
<220> FEATURE:
<221> NAME/KEY: MOD_RES
<222> LOCATION: (24)..(24)
<223> OTHER INFORMATION: 5-bromo-L-Trp

<400> SEQUENCE: 713

```
Phe Cys Gln Lys Trp Met Gln Thr Cys Asp Ala Glu Arg Lys Cys Cys
1               5                   10                  15

Glu Gly Met Val Cys Arg Leu Trp Cys Lys Lys Lys Leu Leu
                20                  25                  30

<210> SEQ ID NO 714
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: beta-chloro-L-Ala
<220> FEATURE:
<221> NAME/KEY: MOD_RES
<222> LOCATION: (24)..(24)
<223> OTHER INFORMATION: 5-bromo-L-Trp

<400> SEQUENCE: 714

Tyr Cys Gln Lys Trp Met Gln Thr Cys Asp Ala Glu Arg Lys Cys Cys
1               5                   10                  15

Glu Gly Met Val Cys Arg Leu Trp Cys Lys Lys Lys Leu Leu
                20                  25                  30

<210> SEQ ID NO 715
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Lys(N-epsilon-(N-alpha-Palmitoyl-L-gamma-
      glutamyl)

<400> SEQUENCE: 715

Tyr Cys Gln Lys Trp Met Gln Thr Cys Asp Lys Glu Arg Lys Cys Cys
1               5                   10                  15

Glu Gly Met Val Cys Arg Leu Trp Cys Lys Lys Lys Leu Leu
                20                  25                  30

<210> SEQ ID NO 716
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Lys(N-epsilon-(N-alpha-Palmitoyl-L-gamma-
      glutamyl)

<400> SEQUENCE: 716

Tyr Cys Gln Lys Trp Met Gln Thr Cys Asp Ser Lys Arg Lys Cys Cys
1               5                   10                  15

Glu Gly Met Val Cys Arg Leu Trp Cys Lys Lys Lys Leu Leu
                20                  25                  30

<210> SEQ ID NO 717
<211> LENGTH: 30
```

-continued

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Lys(N-epsilon-(N-alpha-Palmitoyl-L-gamma-
      glutamyl)

<400> SEQUENCE: 717

Tyr Cys Gln Lys Trp Met Gln Thr Cys Asp Ser Glu Arg Lys Cys Cys
1               5                   10                  15

Lys Gly Met Val Cys Arg Leu Trp Cys Lys Lys Lys Leu Leu
            20                  25                  30

<210> SEQ ID NO 718
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: L-asparagyl-4-aminobutane
<220> FEATURE:
<221> NAME/KEY: MOD_RES
<222> LOCATION: (12)..(12)
<223> OTHER INFORMATION: L-glutamyl-4-aminobutane
<220> FEATURE:
<221> NAME/KEY: MOD_RES
<222> LOCATION: (17)..(17)
<223> OTHER INFORMATION: L-glutamyl-4-aminobutane

<400> SEQUENCE: 718

Tyr Cys Gln Lys Trp Met Gln Thr Cys Asp Ser Gln Arg Lys Cys Cys
1               5                   10                  15

Gln Gly Met Val Cys Arg Leu Trp Cys Lys Lys Lys Leu Leu
            20                  25                  30

<210> SEQ ID NO 719
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-bromo-L-Phe
<220> FEATURE:
<221> NAME/KEY: MOD_RES
<222> LOCATION: (5)..(5)
<223> OTHER INFORMATION: 5-bromo-L-Trp
<220> FEATURE:
<221> NAME/KEY: MOD_RES
<222> LOCATION: (24)..(24)
<223> OTHER INFORMATION: 5-bromo-L-Trp

<400> SEQUENCE: 719

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 720
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-bromo-L-Phe
<220> FEATURE:
<221> NAME/KEY: MOD_RES
<222> LOCATION: (24)..(24)
<223> OTHER INFORMATION: 5-bromo-Trp

<400> SEQUENCE: 720

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 721
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 3,4-dichloro-L-Phe

<400> SEQUENCE: 721

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 722
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 3,5-dibromo-L-Tyr

<400> SEQUENCE: 722

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 723
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 3,4,5-trifluoro-L-Phe

<400> SEQUENCE: 723
```

Phe Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 724
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-cyano-beta-Ala

<400> SEQUENCE: 724

Ala Tyr Cys Gln Lys Trp Met Gln Thr Cys Asp Ser Glu Arg Lys Cys
1               5                   10                  15

Cys Glu Gly Met Val Cys Arg Leu Trp Cys Lys Lys Lys Leu Leu
            20                  25                  30

<210> SEQ ID NO 725
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Propargylglycine

<400> SEQUENCE: 725

Gly Tyr Cys Gln Lys Trp Met Gln Thr Cys Asp Ser Glu Arg Lys Cys
1               5                   10                  15

Cys Glu Gly Met Val Cys Arg Leu Trp Cys Lys Lys Lys Leu Leu
            20                  25                  30

<210> SEQ ID NO 726
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-norvaline

<400> SEQUENCE: 726

Xaa Tyr Cys Gln Lys Trp Met Gln Thr Cys Asp Ser Glu Arg Lys Cys
1               5                   10                  15

Cys Glu Gly Met Val Cys Arg Leu Trp Cys Lys Lys Lys Leu Leu
            20                  25                  30

<210> SEQ ID NO 727
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 727

Tyr Cys Gln Phe Lys Met Gln Thr Cys Asp Ser Glu Arg Lys Cys Cys
1               5                   10                  15

Glu Asp Met Val Cys Arg Leu Trp Cys Lys Leu Asn Leu Leu
            20                  25                  30

<210> SEQ ID NO 728
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 728

Tyr Cys Gln Lys Trp Leu Gln Thr Cys Asp Ser Glu Arg Lys Cys Cys
1               5                   10                  15

Glu Asp Met Val Cys Arg Leu Trp Cys Lys Lys Arg Leu Leu
            20                  25                  30

<210> SEQ ID NO 729
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Tyr Cys Gln Glu Phe Leu Gln Thr Cys Asp Glu Glu Arg Lys Cys Cys
1               5                   10                  15

Gly Asp Met Val Cys Arg Leu Trp Cys Lys Lys Arg Leu Leu
            20                  25                  30

<210> SEQ ID NO 730
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

Tyr Cys Gln Lys Phe Leu Gln Thr Cys Asp Thr Glu Arg Lys Cys Cys
1               5                   10                  15

Glu Asp Met Val Cys Glu Leu Trp Cys Lys Leu Glu Lys Leu
            20                  25                  30

<210> SEQ ID NO 731
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

Tyr Cys Gln Lys Phe Leu Gln Thr Cys Asp Thr Glu Arg Lys Cys Cys
1               5                   10                  15

Glu Asp Met Val Cys Glu Leu Trp Cys Lys Tyr Lys Glu Leu
            20                  25                  30

<210> SEQ ID NO 732
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 732

Tyr Cys Gln Lys Trp Met Gln Thr Cys Asp Ser Tyr Arg Lys Cys Cys
1               5                   10                  15

Glu Gly Met Val Cys Arg Leu Trp Cys Lys Lys Lys Leu Leu
            20                  25                  30

<210> SEQ ID NO 733
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

Tyr Cys Tyr Lys Trp Met Gln Thr Cys Asp Ser Glu Arg Lys Cys Cys
1               5                   10                  15

Glu Gly Met Val Cys Arg Leu Trp Cys Lys Lys Lys Leu Leu
            20                  25                  30

<210> SEQ ID NO 734
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 734

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Tyr
            20                  25                  30

<210> SEQ ID NO 735
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 735

Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Phe
            20                  25                  30

<210> SEQ ID NO 736
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: L-norvaline

<400> SEQUENCE: 736
```

-continued

```
Tyr Cys Gln Lys Trp Met Gln Thr Cys Asp Ser Glu Arg Lys Cys Cys
1               5                   10                  15

Glu Gly Met Val Cys Arg Leu Trp Cys Lys Lys Lys Leu Xaa
            20                  25                  30

<210> SEQ ID NO 737
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Pro, Ala or absent
<220> FEATURE:
<221> NAME/KEY: MOD_RES
<222> LOCATION: (2)..(2)
<223> OTHER INFORMATION: Pro, Ala or absent
<220> FEATURE:
<221> NAME/KEY: MOD_RES
<222> LOCATION: (3)..(3)
<223> OTHER INFORMATION: Ser, Gln, Ala, Arg or Tyr
<220> FEATURE:
<221> NAME/KEY: MOD_RES
<222> LOCATION: (13)..(13)
<223> OTHER INFORMATION: Ser, Ala, Arg, Ile or Val
<220> FEATURE:
<221> NAME/KEY: MOD_RES
<222> LOCATION: (14)..(14)
<223> OTHER INFORMATION: Glu, Arg, Asn, Lys, Thr, Gln, Tyr or glutamyl-
      4-aminobutane
<220> FEATURE:
<221> NAME/KEY: MOD_RES
<222> LOCATION: (16)..(16)
<223> OTHER INFORMATION: Lys, Gln, Ser, Ala or Phe
<220> FEATURE:
<221> NAME/KEY: MOD_RES
<222> LOCATION: (19)..(19)
<223> OTHER INFORMATION: Glu, Gln, Asp, Leu, Asn or glutamyl-4-
      aminobutane
<220> FEATURE:
<221> NAME/KEY: MOD_RES
<222> LOCATION: (20)..(20)
<223> OTHER INFORMATION: Gly, Gln or Pro
<220> FEATURE:
<221> NAME/KEY: MOD_RES
<222> LOCATION: (21)..(21)
<223> OTHER INFORMATION: Met or Phe
<220> FEATURE:
<221> NAME/KEY: MOD_RES
<222> LOCATION: (31)..(31)
<223> OTHER INFORMATION: Leu or Val
<220> FEATURE:
<221> NAME/KEY: MOD_RES
<222> LOCATION: (32)..(32)
<223> OTHER INFORMATION: Trp or Leu

<400> SEQUENCE: 737

Xaa Xaa Xaa Cys Gln Lys Trp Met Gln Thr Cys Asp Xaa Xaa Arg Xaa
1               5                   10                  15

Cys Cys Xaa Xaa Xaa Val Cys Arg Leu Trp Cys Lys Lys Lys Xaa Xaa
            20                  25                  30

<210> SEQ ID NO 738
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 738

Tyr Cys Gln Lys Trp Met Trp Thr Cys Asp Ser Lys Arg Lys Cys Cys
1               5                   10                  15

Glu Asp Met Val Cys Gln Leu Trp Cys Lys Lys Arg Leu
            20                  25

<210> SEQ ID NO 739
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 739

Tyr Cys Gln Lys Trp Met Trp Thr Cys Asp Ser Lys Arg Lys Cys Cys
1               5                   10                  15

Glu Asp Met Val Cys Gln Leu Trp Cys Lys Lys Arg Leu Gly
            20                  25                  30

<210> SEQ ID NO 740
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 740

Tyr Cys Gln Lys Trp Met Trp Thr Cys Asp Ser Glu Arg Lys Cys Cys
1               5                   10                  15

Glu Asp Met Val Cys Glu Leu Trp Cys Lys Lys Arg Leu Trp
            20                  25                  30

<210> SEQ ID NO 741
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Tyr Cys Gln Lys Trp Met Trp Thr Cys Asp Ser Lys Arg Ala Cys Cys
1               5                   10                  15

Glu Gly Leu Arg Cys Lys Leu Trp Cys Arg Lys Ile Ile
            20                  25

<210> SEQ ID NO 742
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile Ile
            20                  25

<210> SEQ ID NO 743
<211> LENGTH: 31

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 743

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Arg Ile Ile Asn Met
            20                  25                  30

<210> SEQ ID NO 744
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 744

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Arg Ile Ile Asn Met
            20                  25                  30

<210> SEQ ID NO 745
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Lys Ile Glu Glu Gly
            20                  25                  30

<210> SEQ ID NO 746
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 746

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Lys Ile Glu Trp
            20                  25                  30

<210> SEQ ID NO 747
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 747

Tyr Cys Gln Lys Trp Met Trp Thr Cys Asp Glu Glu Arg Lys Cys Cys
1               5                   10                  15
```

-continued

Glu Gly Leu Val Cys Arg Leu Trp Cys Lys Lys Asn Arg Val Val
            20                  25                  30

Ile Ser Gly Glu Asp Thr Lys Leu Pro Thr Leu Lys Ile Gln Leu Met
        35                  40                  45

Lys Ser Asn Ile Thr Asp Ile
    50                  55

<210> SEQ ID NO 748
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Tyr Cys Gln Lys Trp Met Trp Thr Cys Asp Ser Glu Arg Lys Cys Cys
1               5                   10                  15

Glu Gly Tyr Val Cys Glu Leu Trp Cys Lys Tyr Asn Leu
            20                  25

<210> SEQ ID NO 749
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 749

Tyr Cys Gln Lys Trp Met Trp Thr Cys Asp Ser Glu Arg Lys Cys Cys
1               5                   10                  15

Glu Gly Tyr Val Cys Glu Leu Trp Cys Lys Tyr Asn Met Gly
            20                  25                  30

<210> SEQ ID NO 750
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Tyr Cys Gln Phe Lys Met Trp Thr Cys Asp Ser Glu Arg Lys Cys Cys
1               5                   10                  15

Glu Asp Met Val Cys Arg Leu Trp Cys Lys Leu Asn Leu
            20                  25

<210> SEQ ID NO 751
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Tyr Cys Gln Lys Trp Leu Trp Thr Cys Asp Ser Glu Arg Lys Cys Cys
1               5                   10                  15

Glu Asp Met Val Cys Arg Leu Trp Cys Lys Lys Arg Leu
            20                  25

<210> SEQ ID NO 752

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 752

Tyr Cys Gln Lys Trp Leu Trp Thr Cys Asp Ser Glu Arg Lys Cys Cys
1               5                   10                  15

Glu Asp Met Val Cys Arg Leu Trp Cys Lys Lys Arg Leu Gly
            20                  25                  30

<210> SEQ ID NO 753
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Tyr Cys Gln Glu Phe Leu Trp Thr Cys Asp Glu Glu Arg Lys Cys Cys
1               5                   10                  15

Gly Asp Met Val Cys Arg Leu Trp Cys Lys Lys Arg Leu
            20                  25

<210> SEQ ID NO 754
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Tyr Cys Gln Lys Phe Leu Trp Thr Cys Asp Thr Glu Arg Lys Cys Cys
1               5                   10                  15

Glu Asp Met Val Cys Glu Leu Trp Cys Lys Leu Glu Lys
            20                  25

<210> SEQ ID NO 755
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Tyr Cys Gln Lys Phe Leu Trp Thr Cys Asp Thr Glu Arg Lys Cys Cys
1               5                   10                  15

Glu Asp Met Val Cys Glu Leu Trp Cys Lys Tyr Lys Glu
            20                  25
```